United States Patent
Miller et al.

(10) Patent No.: US 11,883,104 B2
(45) Date of Patent: Jan. 30, 2024

(54) EYE CENTER OF ROTATION DETERMINATION, DEPTH PLANE SELECTION, AND RENDER CAMERA POSITIONING IN DISPLAY SYSTEMS

(71) Applicant: Magic Leap, Inc., Plantation, FL (US)

(72) Inventors: Samuel A. Miller, Hollywood, FL (US); Lomesh Agarwal, Fremont, CA (US); Lionel Ernest Edwin, Hollywood, FL (US); Ivan Li Chuen Yeoh, Wesley Chapel, FL (US); Daniel Farmer, Verdi, NV (US); Sergey Fyodorovich Prokushkin, Campbell, CA (US); Yonatan Munk, Fort Lauderdale, FL (US); Edwin Joseph Selker, Palo Alto, CA (US); Bradley Vincent Stuart, Fort Lauderdale, FL (US); Jeffrey Scott Sommers, Mountain View, CA (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 17/465,715

(22) Filed: Sep. 2, 2021

(65) Prior Publication Data
US 2022/0057862 A1    Feb. 24, 2022

Related U.S. Application Data

(63) Continuation of application No. 16/250,931, filed on Jan. 17, 2019, now Pat. No. 11,112,863.
(Continued)

(51) Int. Cl.
*A61B 3/113*     (2006.01)
*G06F 3/01*      (2006.01)
(Continued)

(52) U.S. Cl.
CPC ............. *A61B 3/113* (2013.01); *A61B 3/111* (2013.01); *G02B 27/0081* (2013.01);
(Continued)

(58) Field of Classification Search
CPC ... G06F 3/013; G06F 3/04815; H04N 13/383; H04N 13/344; G02B 30/40;
(Continued)

(56) References Cited

U.S. PATENT DOCUMENTS

| 5,280,312 A | 1/1994 | Yamada et al. |
| 5,844,656 A | 12/1998 | Ronzani et al. |

(Continued)

FOREIGN PATENT DOCUMENTS

| CA | 3004271 A1 | 5/2017 |
| JP | 2003307774 A | 10/2003 |

(Continued)

OTHER PUBLICATIONS

International Search Report and Written Opinion for PCT Application No. PCT/US2019/014052, dated Jan. 23, 2018.
(Continued)

*Primary Examiner* — Jin Ge
(74) *Attorney, Agent, or Firm* — Tobias Intellectual Property Law, PLLC

(57) ABSTRACT

A display system can include a head-mounted display configured to project light to an eye of a user to display virtual image content at different amounts of divergence and collimation. The display system can include an inward-facing imaging system images the user's eye and processing electronics that are in communication with the inward-facing imaging system and that are configured to obtain an estimate of a center of rotation of the user's eye. The display system
(Continued)

may render virtual image content with a render camera positioned at the determined position of the center of rotation of said eye.

20 Claims, 53 Drawing Sheets

Related U.S. Application Data

(60) Provisional application No. 62/702,849, filed on Jul. 24, 2018, provisional application No. 62/618,559, filed on Jan. 17, 2018.

(51) Int. Cl.
| | |
|---|---|
| A61B 3/11 | (2006.01) |
| G06V 40/18 | (2022.01) |
| H04N 13/383 | (2018.01) |
| H04N 13/344 | (2018.01) |
| G02B 30/40 | (2020.01) |
| G02B 27/00 | (2006.01) |
| G02B 27/01 | (2006.01) |
| G06F 3/04815 | (2022.01) |
| G06T 3/40 | (2006.01) |
| G06V 10/60 | (2022.01) |

(52) U.S. Cl.
CPC ..... *G02B 27/0093* (2013.01); *G02B 27/0172* (2013.01); *G02B 27/0176* (2013.01); *G02B 30/40* (2020.01); *G06F 3/013* (2013.01); *G06F 3/04815* (2013.01); *G06V 40/193* (2022.01); *H04N 13/344* (2018.05); *H04N 13/383* (2018.05); *G02B 2027/0134* (2013.01); *G02B 2027/0138* (2013.01); *G02B 2027/0174* (2013.01); *G06T 3/40* (2013.01); *G06V 10/60* (2022.01)

(58) Field of Classification Search
CPC ............ G02B 27/0081; G02B 27/0093; G02B 27/0172; G02B 27/0176; G02B 2027/0134; G02B 2027/0138; G02B 2027/0174; G06V 40/193; G06V 10/467; G06V 10/42; G06V 10/60; A61B 3/111; A61B 3/113; G06T 3/40
USPC ........................................................ 345/633
See application file for complete search history.

(56) References Cited

U.S. PATENT DOCUMENTS

| | | |
|---|---|---|
| 6,433,760 B1 | 8/2002 | Vaissie et al. |
| 6,611,283 B1 | 8/2003 | Isonuma |
| 6,771,424 B1 | 8/2004 | Amafuji et al. |
| 6,850,221 B1 | 2/2005 | Tickle |
| 8,928,558 B2 | 1/2015 | Lewis et al. |
| 8,929,589 B2 | 1/2015 | Publicover et al. |
| 9,081,426 B2 | 7/2015 | Armstrong |
| 9,213,163 B2 | 12/2015 | Lewis et al. |
| 9,215,293 B2 | 12/2015 | Miller |
| 9,264,803 B1 | 2/2016 | Johnson et al. |
| 9,348,143 B2 | 5/2016 | Gao et al. |
| 9,417,452 B2 | 8/2016 | Schowengerdt et al. |
| 9,470,906 B2 | 10/2016 | Kaji et al. |
| 9,529,428 B1 | 12/2016 | Bhattacharya et al. |
| 9,547,174 B2 | 1/2017 | Gao et al. |
| 9,671,566 B2 | 6/2017 | Abovitz et al. |
| 9,727,991 B2 | 8/2017 | Guenter et al. |
| 9,740,006 B2 | 8/2017 | Gao |
| 9,791,700 B2 | 10/2017 | Schowengerdt |
| 9,851,563 B2 | 12/2017 | Gao et al. |
| 9,857,591 B2 | 1/2018 | Welch et al. |
| 9,874,749 B2 | 1/2018 | Bradski |
| 10,089,526 B2 | 10/2018 | Amayeh et al. |
| 10,146,997 B2 | 12/2018 | Kaehler |
| 10,296,792 B2 | 5/2019 | Spizhevoy et al. |
| 10,338,677 B2 | 7/2019 | Guenter et al. |
| 10,521,025 B2 | 12/2019 | Powderly et al. |
| 10,573,042 B2 | 2/2020 | Kaehler et al. |
| 10,917,634 B2 | 2/2021 | Edwin et al. |
| 10,951,882 B2 | 3/2021 | Oonishi |
| 11,112,863 B2 | 9/2021 | Miller et al. |
| 11,290,706 B2 | 3/2022 | Edwin et al. |
| 11,567,336 B2 | 1/2023 | Xu et al. |
| 2002/0181115 A1 | 12/2002 | Massof et al. |
| 2003/0030597 A1 | 2/2003 | Geist |
| 2003/0184868 A1 | 10/2003 | Geist |
| 2004/0174496 A1 | 9/2004 | Ji et al. |
| 2006/0028436 A1 | 2/2006 | Armstrong |
| 2006/0250322 A1 | 11/2006 | Hall et al. |
| 2007/0081123 A1 | 4/2007 | Lewis |
| 2007/0120986 A1 | 5/2007 | Nunomaki |
| 2007/0273983 A1 | 11/2007 | Hebert |
| 2008/0002262 A1 | 1/2008 | Chirieleison |
| 2008/0106489 A1 | 5/2008 | Brown et al. |
| 2008/0117289 A1 | 5/2008 | Schowengerdt et al. |
| 2009/0160872 A1 | 6/2009 | Gibbons |
| 2009/0167673 A1 | 7/2009 | Kerofsky |
| 2010/0045932 A1 | 2/2010 | Shelhamer et al. |
| 2010/0149073 A1 | 6/2010 | Chaum et al. |
| 2010/0283969 A1 | 11/2010 | Cooperstock et al. |
| 2011/0075257 A1 | 3/2011 | Hua et al. |
| 2012/0022220 A1 | 1/2012 | Kozlowski et al. |
| 2012/0033179 A1* | 2/2012 | Kratzer .................. A61B 3/111 351/205 |
| 2012/0068913 A1 | 3/2012 | Bar-Zeev et al. |
| 2012/0127062 A1 | 5/2012 | Bar-Zeev et al. |
| 2012/0139817 A1 | 6/2012 | Freeman |
| 2012/0162549 A1 | 6/2012 | Gao et al. |
| 2012/0212484 A1 | 8/2012 | Haddick et al. |
| 2012/0293407 A1 | 11/2012 | Lee |
| 2013/0022220 A1 | 1/2013 | Dong et al. |
| 2013/0038510 A1 | 2/2013 | Brin et al. |
| 2013/0050070 A1 | 2/2013 | Lewis et al. |
| 2013/0050833 A1 | 2/2013 | Lewis et al. |
| 2013/0082922 A1 | 4/2013 | Miller |
| 2013/0083003 A1 | 4/2013 | Perez et al. |
| 2013/0083976 A1* | 4/2013 | Ragland ............... G06V 40/168 382/117 |
| 2013/0093791 A1 | 4/2013 | Arnold et al. |
| 2013/0114043 A1 | 5/2013 | Balan et al. |
| 2013/0114850 A1 | 5/2013 | Publicover et al. |
| 2013/0117377 A1 | 5/2013 | Miller |
| 2013/0125027 A1 | 5/2013 | Abovitz |
| 2013/0128364 A1 | 5/2013 | Wheeler et al. |
| 2013/0208234 A1 | 8/2013 | Lewis |
| 2013/0242262 A1 | 9/2013 | Lewis |
| 2013/0285885 A1 | 10/2013 | Nowatzyk et al. |
| 2013/0286053 A1 | 10/2013 | Fleck et al. |
| 2013/0321925 A1 | 12/2013 | Jacobs et al. |
| 2013/0339433 A1 | 12/2013 | Li et al. |
| 2014/0002442 A1 | 1/2014 | Lamb et al. |
| 2014/0071539 A1 | 3/2014 | Gao |
| 2014/0104143 A1 | 4/2014 | Benson et al. |
| 2014/0146394 A1 | 5/2014 | Tout et al. |
| 2014/0177023 A1 | 6/2014 | Gao et al. |
| 2014/0218468 A1 | 8/2014 | Gao et al. |
| 2014/0232988 A1 | 8/2014 | Kersting et al. |
| 2014/0267420 A1 | 9/2014 | Schowengerdt |
| 2014/0306866 A1 | 10/2014 | Miller et al. |
| 2014/0354514 A1 | 12/2014 | Aronsson |
| 2014/0354948 A1 | 12/2014 | Kratzer et al. |
| 2014/0375540 A1 | 12/2014 | Ackerman et al. |
| 2014/0375680 A1 | 12/2014 | Ackerman et al. |
| 2015/0015461 A1 | 1/2015 | Morimoto |
| 2015/0016777 A1 | 1/2015 | Abovitz et al. |
| 2015/0035744 A1 | 2/2015 | Robbins et al. |
| 2015/0049013 A1 | 2/2015 | Rahman et al. |
| 2015/0077416 A1 | 3/2015 | Villmer |
| 2015/0103306 A1 | 4/2015 | Kaji et al. |
| 2015/0156716 A1 | 6/2015 | Raffle et al. |

(56) References Cited

U.S. PATENT DOCUMENTS

| | | |
|---|---|---|
| 2015/0178939 A1 | 6/2015 | Bradski et al. |
| 2015/0189266 A1 | 7/2015 | Zhou |
| 2015/0205126 A1 | 7/2015 | Schowengerdt |
| 2015/0220779 A1 | 8/2015 | Publicover et al. |
| 2015/0222883 A1 | 8/2015 | Welch |
| 2015/0222884 A1 | 8/2015 | Cheng |
| 2015/0268415 A1 | 9/2015 | Schowengerdt et al. |
| 2015/0278642 A1 | 10/2015 | Chertok et al. |
| 2015/0287206 A1 | 10/2015 | Ebisawa |
| 2015/0302652 A1 | 10/2015 | Miller et al. |
| 2015/0309263 A2 | 10/2015 | Abovitz et al. |
| 2015/0326570 A1 | 11/2015 | Publicover et al. |
| 2015/0346490 A1 | 12/2015 | TeKolste et al. |
| 2015/0346495 A1 | 12/2015 | Welch et al. |
| 2016/0007934 A1 | 1/2016 | Arnold et al. |
| 2016/0011419 A1 | 1/2016 | Gao |
| 2016/0026253 A1 | 1/2016 | Bradski et al. |
| 2016/0041048 A1 | 2/2016 | Blum et al. |
| 2016/0055822 A1 | 2/2016 | Bell |
| 2016/0109709 A1 | 4/2016 | Osterhout |
| 2016/0131902 A1 | 5/2016 | Ambrus et al. |
| 2016/0196465 A1 | 7/2016 | Wu et al. |
| 2016/0198949 A1 | 7/2016 | Spitzer |
| 2016/0209648 A1 | 7/2016 | Haddick et al. |
| 2016/0270656 A1 | 9/2016 | Samec et al. |
| 2017/0053165 A1 | 2/2017 | Kaehler |
| 2017/0053166 A1 | 2/2017 | Amayeh et al. |
| 2017/0092235 A1 | 3/2017 | Osman et al. |
| 2017/0122725 A1 | 5/2017 | Yeoh et al. |
| 2017/0123526 A1 | 5/2017 | Trail et al. |
| 2017/0123744 A1 | 5/2017 | Park et al. |
| 2017/0124713 A1 | 5/2017 | Jurgenson et al. |
| 2017/0124928 A1 | 5/2017 | Edwin et al. |
| 2017/0160518 A1 | 6/2017 | Lanman et al. |
| 2017/0206412 A1 | 7/2017 | Kaehler |
| 2017/0212351 A1 | 7/2017 | Schowengerdt et al. |
| 2017/0237974 A1 | 8/2017 | Samec et al. |
| 2017/0261610 A1 | 9/2017 | Scally et al. |
| 2017/0263007 A1 | 9/2017 | Cavin et al. |
| 2017/0276948 A1 | 9/2017 | Welch et al. |
| 2017/0285343 A1 | 10/2017 | Belenkii et al. |
| 2018/0004002 A1 | 1/2018 | Rong et al. |
| 2018/0018515 A1* | 1/2018 | Spizhevoy ........... G06V 10/245 |
| 2018/0032133 A1 | 2/2018 | Cho et al. |
| 2018/0095295 A1* | 4/2018 | Chene ................ A61B 3/14 |
| 2018/0098056 A1 | 4/2018 | Bohn |
| 2018/0308288 A1 | 10/2018 | Harscoet et al. |
| 2019/0019023 A1 | 1/2019 | Konttori et al. |
| 2019/0094981 A1 | 3/2019 | Bradski et al. |
| 2019/0137765 A1 | 5/2019 | Chang et al. |
| 2019/0141847 A1 | 5/2019 | Chang et al. |
| 2019/0156100 A1* | 5/2019 | Rougeaux ................. G06T 7/73 |
| 2019/0187482 A1 | 6/2019 | Lanman |
| 2019/0222830 A1 | 7/2019 | Edwin et al. |
| 2019/0243448 A1 | 8/2019 | Miller et al. |
| 2019/0279407 A1 | 9/2019 | McHugh et al. |
| 2019/0302882 A1 | 10/2019 | Blixt et al. |
| 2020/0051320 A1 | 2/2020 | Laffont et al. |
| 2020/0218087 A1* | 7/2020 | Grand-Clement ... A61B 3/0025 |
| 2021/0105456 A1 | 4/2021 | Edwin et al. |
| 2021/0271091 A1 | 9/2021 | Xu et al. |
| 2022/0253135 A1 | 8/2022 | Cohen |

FOREIGN PATENT DOCUMENTS

| | | |
|---|---|---|
| JP | 2013195924 A | 9/2013 |
| JP | 2016528533 A | 9/2016 |
| JP | 2016207145 A | 12/2016 |
| WO | 2016129156 A1 | 8/2016 |
| WO | 2017127366 A1 | 7/2017 |
| WO | 2017139667 A1 | 8/2017 |
| WO | 2018091770 A1 | 5/2018 |
| WO | 2019143864 A1 | 7/2019 |
| WO | WO 2019/143844 | 7/2019 |
| WO | 2020023542 A1 | 1/2020 |
| WO | WO 2021/0011686 | 1/2021 |
| WO | WO 2022/015847 | 1/2022 |

OTHER PUBLICATIONS

International Preliminary Report for Patentability for PCT Application No. PCT/US2019/014052, dated Jul. 21,2020.

ARToolKit: https://web.archive.org/web/20051013062315/http://www.hitl.washington.edu:80/artoolkit/documentation/hardware.htm, archived Oct. 13, 2005.

Atchison, "Optical models for human myopic eyes," Vision Research (4614), 2236-50, 2006.

Atchison, "Schematic eyes," Handbook of Visual Optics, vol. 1, Chapter 16, Fundamentals and Eye Optics, pp. 235-248, 2007.

Atchison, "Thomas Young's contribution to visual optics: The Bakerian lecture 'On the mechanism of the eye,'"Journal of Vision, 10(12), 1-16, 2010.

Atchison, et al., "Age-related changes in opitcal and biometric characteristics of emmetropic eyes," Journal of Vision, 8(4):29, 1-20, 2008.

Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.

Azuma, "Predictive Tracking for Augmented Realty," TR95-007, Department of Computer Science, UNC-Chapel Hill, NC, Feb. 1995.

Benes, et al., "Corneal Shap and Eccentricity in Population," Coll. Antropol. 37 (2103) Suppl. 1: 117-120.

Bimber, et al., "Spatial Augmented Reality—Merging Real and Virtual Worlds," 2005 https://web.media.mit.edu/~raskar/book/BimberRaskarAugmentedRealityBook.pdf.

Carney, et al., "Corneal Topography and Myopia," Investigative Ophthalmology & Visual Science, Feb. 1997, vol. 38, No. 2.

Cook, et al., "Ocular Growth and Refractice Error Development in Premature Infants without Retinopathy of Prematurity," Investigative Opthalmology & Visual Science, Mar. 2003, vol. 44, No. 3.

Fedtke, et al., "The entrance pupil of the human eye: a three-dimensional model as a function of viewing angle," Optics Express, Oct. 11, 2010, vol. 18, No. 21.

Fry, et al., "The Center of Rotation of the Eye" American Journal of Optometry and Archives of American Academy of Optometry, vol. 39, No. 11, Nov. 1962.

Fry, et al., "The Mechanics of Elevating the Eye," American Journal of Optometry and Archives of American Academy of Optometry, vol. 40, No. 12, Dec. 1963.

Gale, "Research Note—A Nove on the Remote Oculometer Technique for Recording Eye Movements," Vision Research vol. 22, pp. 201-202, 1982.

Grolman, "The Sighting Center," American Academy of Optometry, Annual Meeting Miami Beach, FL Dec. 10, 1962. American Journal of Optometry and Archives of American Academy of Optometry.

Guestrin, et al., "General Theory of Remote Gaze Estimation Using the Pupil Center and Corneal Reflections," IEEE Transactions on Biomedical Engineering, vol. 53, No. 6, Jun. 2006.

Hansen, D. et al., "In the Eye of the Beholder: A Survey of Models for Eyes and Gaze", IEEE Transactions on Pattern Analysis and Machine Intelligence, vol. 32, No. 3, Mar. 2010, in 23 pages.

Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Kiely, et al., "The mean shape of the human cornea," Optica Acta, 1982, vol. 29, No. 8, 1027-1040.

Kooijman, "Light distribution on the retina of a wide-angle theoretical eye," J. Opt. Soc. Am./vol. 73, No. 11 /Nov. 1983.

Koretz, et al., "Accommodation and Presbyopia in the Human Eye—Changes in the Anterior Segment and Crystalline Lens With Focus," Investigative Ophthalmology & Visual Science, Mar. 1997, vol. 38, No. 3.

(56) References Cited

OTHER PUBLICATIONS

Liou, et al., "Anatomically accurate, finite model eye for optical modeling," J. Opt. Soc. Am. A/vol. 14, No. 8/Aug. 1997.
Logan, et al., "Posterior Retinal Contour in Adult Human Anisomyopia," Investigative Ophthalmology & Visual Science, Jul. 2004, vol. 45, No. 7.
Lotmar_Theoretical Eye Model with Aspherics, Journal of The Optical Society of America, vol. 61, No. 11, Nov. 1971.
Mainstone, et al., "Corneal shape in hyperipia," Clinical and Experimental Optometry 81.3 May-Jun. 1998.
Mashige, "A review of corneal diameter, curvature and thickness values and influencing factors," S Afr Optom 2013 72(4) 185-194.
Morimoto, et al., "Eye gaze tracking techniques for interactive applications," Computer Vision and Image Understanding 98 (2005) 4-24.
Nagamatsu, et al., "Gaze Estimation Method Involving Corneal Reflection-Based Modeling of the Eye as a General Surface of Revolution about the Optical Axis of the Eye," IEICE Trans. Inf. & Syst., vol. E95-D, No. Jun. 6, 2012.
Navarro, et al., "Accommodation-dependent model of the human eye with aspherics," J. Opt. Soc. Am. A vol. 2, No. 8, Aug. 1985.
Shih, et al., "A Novel Approach to 3-D Gaze Tracking Using Stereo Cameras," in 27 pages, TR-M3LAB-2002-001, Feb. 2004 (available at http://erdos.csie.ncnu.edu.tw/~stone/publication/TR-M3LAB-2002-001.pdf) and corresponding article IEEE Transactions on Systems, Man, and Cybernetics—Part B: Cybernetics, vol. 34, No. 1, Feb. 2004.
Taba, "Improving Eye-Gaze Tracking Accuracy Through Personalized Calibration of a User's Aspherical Corneal Model," MS Thesis, University of British Columbia, Jan. 2012.
Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).
Xiong, et al., The analysis of corneal asphericity (Q value) and its related factors of 1,683 Chinese eyes older than 30 years, PLoS ONE 12(5): e0176913. May 2017.
Bennett, et al., "The eye as an opitcal system," In Visual Optics and the Optical Space Sense, vol. 4: The Eye, pp. 101-131, 1962.
Jian-Nan et al., "Key Techniqus of Eye Gaze Tracking Based on Pupil Corneal Reflection," Intelligent Systems, 2009, GCIS '09. WRI Global Congress ON, IEEE, May 19, 2009, pp. 133-138.
Nagamatsu, et al., "One-point calibration gaze tracking based on eyeball kinematics using stereo cameras," Eye Tracking Research & Applications: Proceedings; ETRA 2008: [Eye Tracking Research and Applications Symposium], Mar. 26-28, 2008.
Nair, et al., "RIT-Eyes: Rendering of near-eye images for eye-tracking applications," In Proceedings of ACM Conferences, Washington, DC, USA, Jul. 2017 (Coference '17), 10 pages.
Navarro, "The Optical Design of the Human Eye: a Critical Review," J Optom 2009; 2:3-18.
Zhu, et al., "Novel Eye Gaze Tracking Techniques Under Natural Head Movement," IEEE Transactions on Biomedical Engineering, vo. 54, No. 12, Dec. 1, 2007.
IL275822 Office Action dated Dec. 29, 2022.
JP2020-536814 Official Action dated Jan. 27, 2023.
JP2020-539042 Official Action dated Jan. 20, 2023.
U.S. Appl. No. 17/706,429 Office Action dated Feb. 24, 2023.
U.S. Appl. No. 17/962,289 Office Action dated Feb. 19, 2023.
EP19844174.3 Examination Report dated Jul. 11, 2023.
JP2021-503169 Office Action dated Jul. 26, 2023.
U.S. Appl. No. 17/706,429 Office Action dated Jun. 9, 2023.
U.S. Appl. No. 17/962,289 Office Action dated Aug. 16, 2023.
U.S. Appl. No. 18/155,515 Office Action dated May 10, 2023.

\* cited by examiner

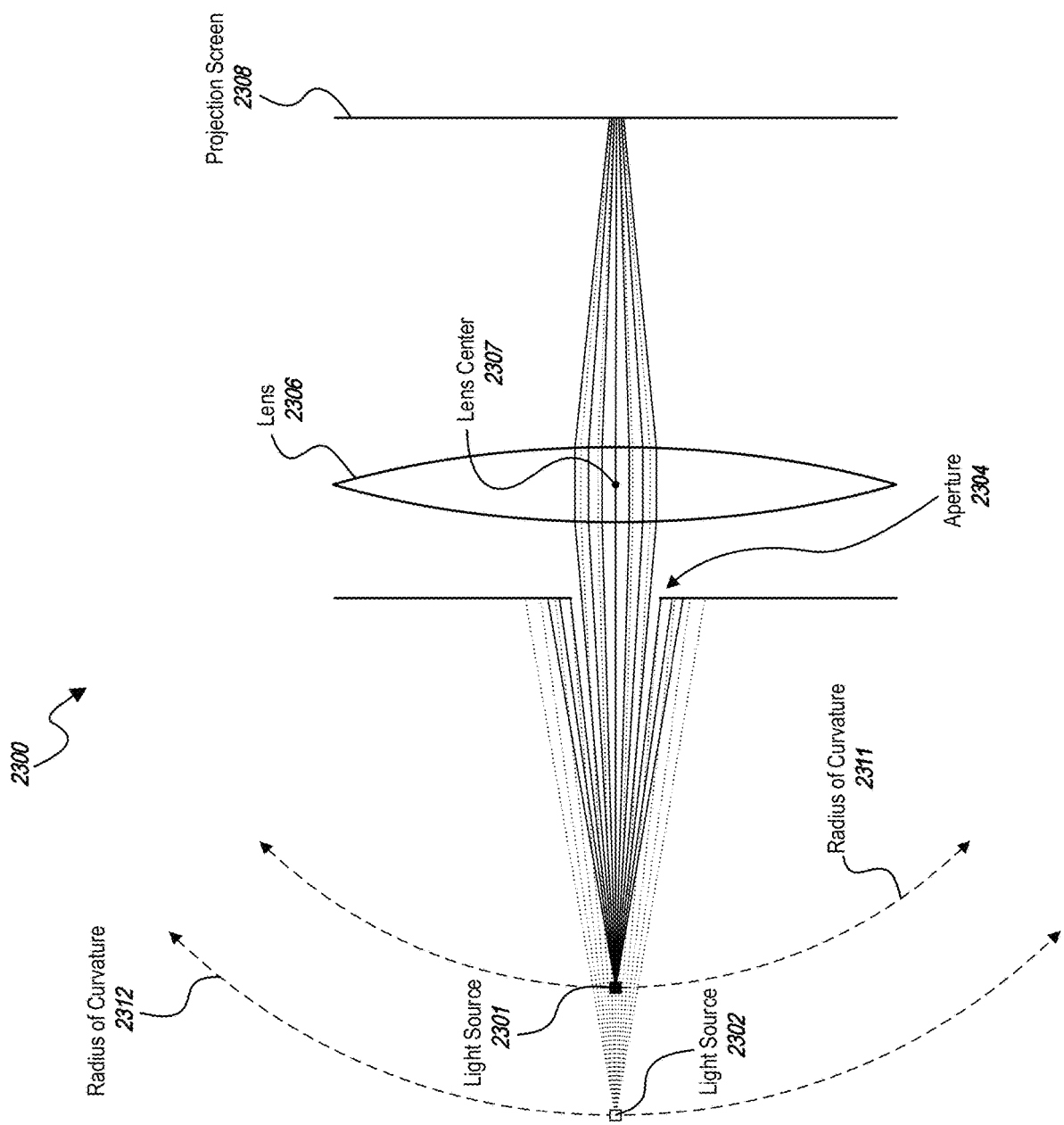

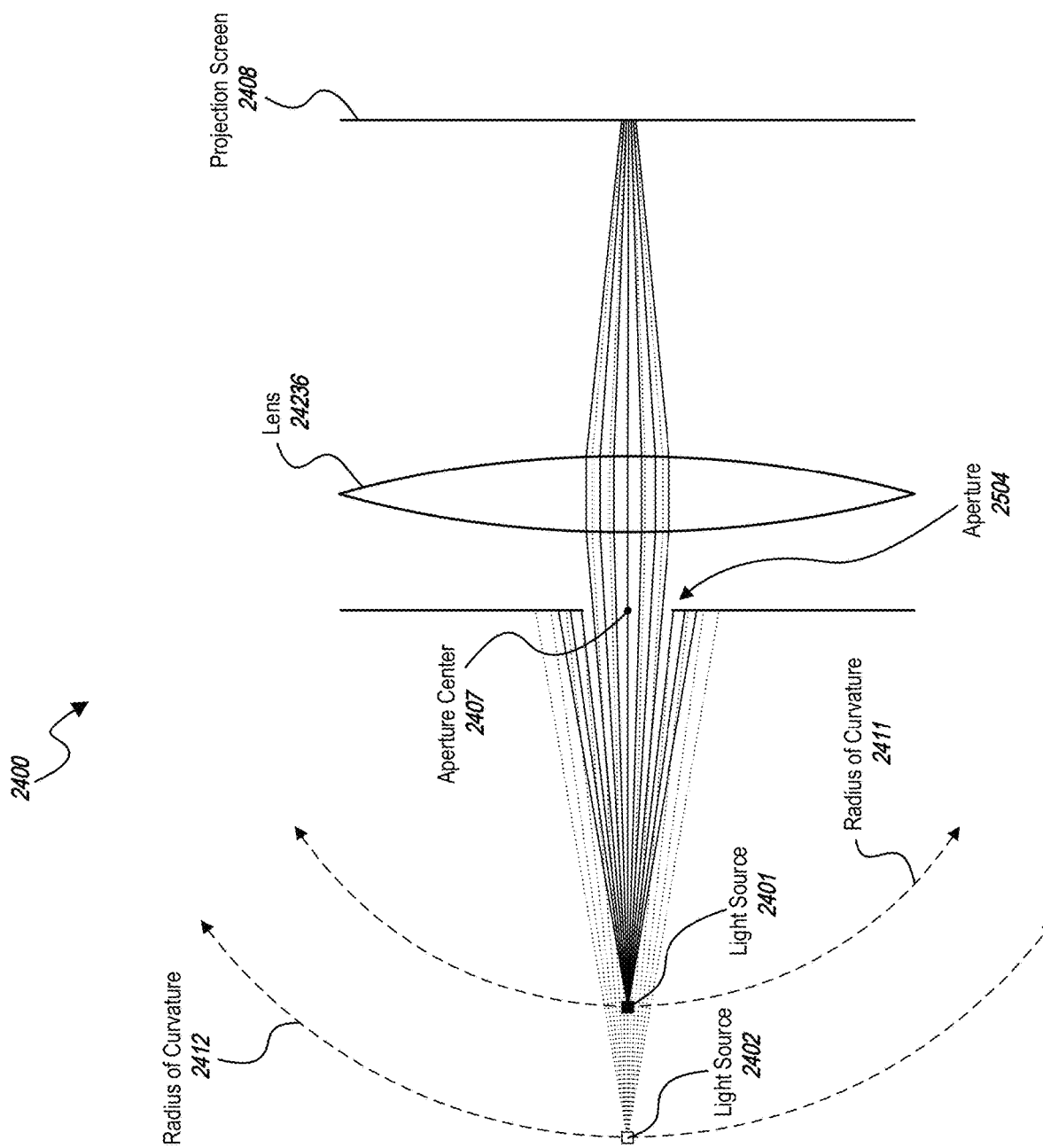

EYE CENTER OF ROTATION DETERMINATION, DEPTH PLANE SELECTION, AND RENDER CAMERA POSITIONING IN DISPLAY SYSTEMS

CROSS-REFERENCE TO RELATED APPLICATIONS

This application is a continuation application of U.S. patent application Ser. No. 16/250,931, which is titled "EYE CENTER OF ROTATION DETERMINATION, DEPTH PLANE SELECTION, AND RENDER CAMERA POSITIONING IN DISPLAY SYSTEMS" and was filed on Jan. 17, 2019; which claims priority to U.S. Patent Prov. App. 62/618,559, which is titled "EYE CENTER OF ROTATION DETERMINATION, DEPTH PLANE SELECTION, AND RENDER CAMERA POSITIONING IN DISPLAY SYSTEMS" and was filed on Jan. 17, 2018. This application further claims priority to U.S. Patent Prov. App. 62/702,849, which is titled "EYE CENTER OF ROTATION DETERMINATION, DEPTH PLANE SELECTION, AND RENDER CAMERA POSITIONING IN DISPLAY SYSTEMS" and was filed on Jul. 24, 2018. Each of the above-recited applications is incorporated herein by reference in its entirety.

This application further incorporates by reference U.S. Patent Pub. 2018/0018515, which is titled "IRIS BOUNDARY ESTIMATION USING CORNEA CURVATURE" and was published on Jan. 18, 2018.

FIELD

The present disclosure relates to display systems, virtual reality, and augmented reality imaging and visualization systems and, more particularly, to depth plane selection based in part on a user's interpupillary distance.

BACKGROUND

Modern computing and display technologies have facilitated the development of systems for so called "virtual reality", "augmented reality", or "mixed reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; a mixed reality, or "MR", related to merging real and virtual worlds to produce new environments where physical and virtual objects co-exist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR and MR technology.

SUMMARY

Various examples of depth plane selection in a mixed reality system are disclosed.

A display system can be configured to project light to an eye of a user to display virtual image content in a vision field of said user. The user's eye may have a cornea, an iris, a pupil, a lens, a retina, and an optical axis extending through said lens, pupil, and cornea. The display system can include a frame configured to be supported on a head of the user, a head-mounted display disposed on the frame, said display configured to project light into said user's eye to display virtual image content to the user's vision field at different amounts of at least one of divergence and collimation and thus the displayed virtual image content appears to originate from different depths at different periods of time, one or more eye tracking cameras configured to image the user's eye, and processing electronics in communication with the display and the one or more eye tracking cameras, the processing electronics configured to obtain an estimate of a center of rotation of said eye based on images of said eye obtained with said one or more eye tracking cameras.

Various examples of display systems that project light to one or more eyes of a user to display virtual image content in a vision field of said user are described herein such as the examples enumerated below:

Example 1: A display system configured to project light to an eye of a user to display virtual image content in a vision field of said user, said eye having a cornea, an iris, a pupil, a lens, a retina, and an optical axis extending through said lens, pupil, and cornea, said display system comprising:

a frame configured to be supported on a head of the user;

a head-mounted display disposed on the frame, said display configured to project light into said user's eye to display virtual image content to the user's vision field at different amounts of at least one of divergence and collimation and thus the displayed virtual image content appears to originate from different depths at different periods of time;

one or more eye tracking cameras configured to image the user's eye; and processing electronics in communication with the display and the one or more eye tracking cameras, the processing electronics configured to obtain an estimate of a center of rotation of said eye based on images of said eye obtained with said one or more eye tracking cameras.

Example 2: The display system of Example 1, further comprising one or more light sources disposed on said frame with respect to said user's eye to illuminate said user's eye, said one or more eye tracking cameras forming images of said eye using said light from said one or more light sources.

Example 3: The display system of Example 1 or 2, wherein said one or more light sources comprises at least two light sources disposed on said frame with respect to said user's eye to illuminate said user's eye.

Example 4: The display system of Example 1 or 3, wherein said one or more light sources comprises infrared light emitters.

Example 5: The display system of any of the Examples 1 to 4, wherein one or more light sources form one or more glints on said eye and said processing electronics is configured to determine a location of said cornea based on said one or more glints.

Example 6: The display system of any of the Examples 1 to 5, wherein said cornea has associated therewith a cornea sphere having a center of curvature and said processing electronics is configured to determine a location of said center of curvature of said cornea sphere.

Example 7: The display system of Example 5, wherein said cornea has associated therewith a cornea sphere having a center of curvature and said processing electronics is configured to determine a location of said center of curvature of said cornea sphere based on said one or more glints.

Example 8: The display system of any of the Examples above, wherein said one or more eye tracking camera is configured to image said pupil of said eye.

Example 9: The display system of any of the Examples above, wherein said processing electronics is configured to determine the location of said center of said pupil.

Example 10: The display system of any of the Examples above, wherein said processing electronics is configured to determine at least a portion of a boundary between said iris and said pupil.

Example 11: The display system of Example 10, wherein said processing electronics is configured to determine a center of said boundary between said iris and said pupil.

Example 12: The display system of any of the Examples above, wherein said processing electronics is configured to determine a location of said center of said pupil in three-dimensional space with respect to a center of curvature of said cornea.

Example 13: The display system of any of the Examples above, wherein said processing electronics is configured to determine a location and orientation of said optical axis.

Example 14: The display system of Example 12, wherein said processing electronics is configured to determine a location and orientation of said optical axis based on a location of said center of said pupil in three-dimensional space.

Example 15: The display system of any of the Examples above, wherein said processing electronics is configured to determine said location and orientation of said optical axis based on a location of said center of said pupil in three-dimensional space with respect to a center of curvature of said cornea.

Example 16: The display system of any of the Examples above, wherein said processing electronics is configured to determine a location of said center of rotation of said eye based on a center of curvature of said cornea.

Example 17: The display system of any of the Examples above, wherein said processing electronics is configured to determine a location of said center of rotation of said eye based on a center of curvature of said cornea and a location and orientation of said optical axis.

Example 18: The display system of Example 17, wherein said processing electronics is configured to determine the location of said center of rotation of said eye by translating a particular distance along said optical axis from said center of curvature of said cornea.

Example 19: The display system of Example 18, wherein said particular distance from said center of curvature to said center of rotation is between 4.0 mm and 6.0 mm Example 20: The display system of Example 18 or 19, wherein said particular distance from said center of curvature to said center of rotation is about 4.7 mm.

Example 21: The display system of Example 18 or 19, wherein said particular distance is fixed.

Example 22: The display system of Example 18 or 19, wherein said processing electronics is configured to determine the particular distance based at least on one or more images of said eye previously obtained with said one or more eye tracking cameras.

Example 23: The display system of any of the Examples above, wherein said processing electronics is configured to determine a location and orientation of a visual axis, offset from said optical axis, based on said location and orientation of said optical axis.

Example 24: The display system of any of the Examples above, wherein said processing electronics is configured to determine a location and orientation of a visual axis based on an angular rotation with respect to said optical axis.

Example 25: The display system of any of the Examples above, wherein said processing electronics is configured to determine a location and orientation of a visual axis based on an angular rotation of between 4.0° and 6.5° with respect to said optical axis.

Example 26: The display system of any of the Examples above, wherein said processing electronics is configured to determine a location and orientation of a visual axis based on an angular rotation of about 5.2° with respect to said optical axis.

Example 27: The display system of any of the Examples above, wherein said processing electronics are configured to determine a location and orientation of a visual axis based at least on one or more images of said eye previously obtained with said one or more eye tracking cameras.

Example 28: The display system of any of the Examples above, wherein said processing electronics is configured to determine a center of rotation of said eye based multiple determinations of said location of said optical axis or visual axis over a period of time during which said eye is rotating.

Example 29: The display system of any of the Examples above, wherein said processing electronics is configured to determine said center of rotation by identifying a region of intersection, convergence, or close proximity of multiple determinations of said location of said optical axis or a visual axis over a period of time during which said eye is rotating.

Example 30: The display system of any of the Examples above, wherein said processing electronics is configured to determine a vergence distance of said user where left and right eyes of a user are gazing based on a determination of the location and orientation of said optical axes for said left and right eyes of the user.

Example 31: The display system of any of the Examples above, wherein said processing electronics is configured to determine a vergence distance of said user where left and right eyes of a user are gazing based on a determination of the location and orientation of said visual axes for said left and right eyes of the user.

Example 32: The display system of any of the Examples above, wherein said processing electronics is configured to determine a vergence distance where left and right eyes of a user are gazing based on identifying a region of intersection, convergence, or close proximity of said visual axes for said left and right eyes of the user.

Example 33: The display system of any of the Examples above, wherein said processing electronics is configured to determine a vergence distance where left and right eyes of a user are gazing by projecting the visual axes for said left and right eyes onto a horizontal plane and identifying a region of intersection, convergence, or close proximity of said projections of the visual axes for said left and right eyes onto a horizontal plane.

Example 34: The display system of any of the Examples above, wherein said processing electronics is configured to determine the relative amounts of at least one of divergence, and collimation to project image content based on a determination of said vergence distance.

Example 35: The display system of any of the Examples above, wherein said processing electronics includes electronics on said frame.

Example 36: The display system of any of the Examples above, wherein said processing electronics includes electronics on said frame and electronics disposed at a location remote from said frame.

Example 37: The display system of any of the Examples above, wherein said processing electronics includes electronics on said frame and electronics on a belt pack.

Example 38: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 39: The display system of any of the Examples above, wherein said head-mounted display receives light from a portion of the environment in front of the user at a first amount of divergence and transmits the light from the portion of the environment in front of the user to the user's eye with a second amount of divergence that is substantially similar to the first amount of divergence.

Example 40: The display system of any of the Examples above, wherein the processing electronics is configured to obtain the estimate of the center of rotation by filtering, averaging, applying a Kalman filter, or any combinations thereof a plurality of estimated center of rotation positions.

Example 41: The display system of any of the Examples above, wherein said processing electronics is configured to present said virtual image content to said user's eye that is rendered as if captured by a camera having an aperture at the determined position of the center of rotation of said user's eye.

Example 42: The display system of any of the Examples above, wherein said processing electronics is configured to use a render camera at said center of rotation to render virtual images to be presented to said eye.

Example 43: The display system of any of the Examples above, wherein said processing electronics is configured to use a render camera configured to render virtual images to be presented to said eye that are rendered as if captured by a camera having an aperture closer to said the center of rotation than said retina of said eye.

Example 44: The display system of any of the Examples above, wherein said processing electronics is configured to use a render camera configured to render virtual images to be presented to said eye that are rendered as if captured by a camera having an aperture at said the center of rotation of said eye.

Example 45: The display system of any of the Examples above, wherein said processing electronics is configured to use a render camera at said center of rotation to render virtual images to be presented to said eye, said render camera modeled with an aperture at said center of rotation of said eye.

Example 46: A display system configured to project light to an eye of a user to display virtual image content in a vision field of said user, said eye having a cornea, an iris, a pupil, a lens, a retina, and an optical axis extending through said lens, pupil, and cornea, said display system comprising:

a frame configured to be supported on a head of the user;

a head-mounted display disposed on the frame, said display configured to project light into said user's eye to display virtual image content to the user's vision field at different amounts of at least one of divergence and collimation, and thus the displayed virtual image content appears to originate from different depths at different periods of time;

one or more eye tracking cameras configured to image the user's eye; and processing electronics in communication with the display and the one or more eye tracking cameras, the processing electronics configured to obtain a position estimate of a center of perspective of said eye based on images of said eye obtained with said one or more eye tracking cameras, said center of perspective being estimated to be proximal said pupil of said eye or between said cornea and said pupil of said eye, wherein said processing electronics is configured to present said virtual image content to said user's eye that are rendered by a render camera located at said center of perspective.

Example 47: The display system of any of the Examples above, wherein said processing electronics is configured to present said virtual image content to said user's eye that are rendered as if captured by a camera having an aperture closer to said center of perspective than said retina.

Example 48: The display system of any of the Examples above, wherein said processing electronics is configured to present said virtual image content to said user's eye that are rendered as if captured by a camera having an aperture closer to said center of perspective than a center of rotation of the eye.

Example 49: The display system of any of the Examples above, wherein said processing electronics is configured to present said virtual image content to said user's eye that are rendered as if captured by a camera having an aperture at said center of perspective.

Example 50: The display system of any of the Examples above, wherein said center of perspective is not located at said pupil of said eye.

Example 51: The display system of any of the Examples above, wherein the processing electronics is configured to obtain an estimate of said user's eye pose over time and wherein the processing electronics adjust the position of the render camera based at least in part upon the user's eye pose.

Example 52: The display system of any of the Examples above, wherein the processing electronics is configured to track said user's eye pose over time and wherein the position of the render camera is adjusted over time in response to changes in said user's eye pose over time.

Example 53: The display system of any of the Examples above, wherein the processing electronics is configured to obtain the estimate of the center of perspective by filtering a plurality of estimated center of perspective positions.

Example 54: The display system of any of the Examples above, wherein the processing electronics is configured to obtain the estimate of the center of perspective by averaging and/or applying a Kalman filter to a plurality of estimated center of perspective positions.

Example 55: The display system of any of the Examples above, wherein the center of perspective comprises a position within the anterior chamber of said user's eye.

Example 56: The display system of any of the Examples above, wherein the center of perspective comprises a position in front of said pupil of said user's eye.

Example 57: The display system of any of the Examples above, wherein the center of perspective comprises a position that is between 1.0 mm and 2.0 mm in front of said pupil of said user's eye.

Example 58: The display system of any of the Examples above, wherein the center of perspective comprises a position that is about 1.0 mm in front of said pupil of said user's eye.

Example 59: The display system of any of the Examples above, wherein the center of perspective comprises a position that is between 0.25 mm and 1.0 mm in front of said pupil of said user's eye.

Example 60: The display system of any of the Examples above, wherein the center of perspective comprises a position that is between 0.5 mm and 1.0 mm in front of said pupil of said user's eye.

Example 61: The display system of any of the Examples above, wherein the center of perspective comprises a position that is between 0.25 mm and 0.5 mm in front of said pupil of said user's eye.

Example 62: The display system of any of the Examples above, wherein the center of perspective lies along the optical axis of said eye and wherein said processing electronics are further configured to obtain the position estimate of the center of perspective by obtaining a position estimate of the optical axis of said eye.

Example 63: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye.

Example 64: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye and a position estimate of a center of rotation of said eye, the cornea of said eye, the iris of said eye, the retina of said eye, and the pupil of said eye or any combinations thereof.

Example 65: The display system of any of the Examples above, wherein said processing electronics includes electronics on said frame.

Example 66: The display system of any of the Examples above, wherein said processing electronics includes electronics on said frame and electronics disposed at a location remote from said frame.

Example 67: The display system of any of the Examples above, wherein said processing electronics includes electronics on said frame and electronics on a belt pack.

Example 68: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 69: The display system of any of the Examples above, further comprising one or more light sources disposed on said frame with respect to said user's eye to illuminate said user's eye, said one or more eye tracking cameras capturing images of said eye using said light from said one or more light sources.

Example 70: The display system of any of the Examples above, wherein said one or more light sources comprises at least two light sources disposed on said frame with respect to said user's eye to illuminate said user's eye.

Example 71: The display system of any of the Examples above, wherein said one or more light sources comprises at least three light sources disposed on said frame with respect to said user's eye to illuminate said user's eye.

Example 72: The display system of any of the Examples above, wherein said one or more light sources comprises infrared light emitters.

Example 73: The display system of any of the Examples above, wherein said one or more light sources form one or more glints on said eye and said processing electronics is configured to determine the position of the center of curvature of said cornea based on said one or more glints.

Example 74: The display system of any of the Examples above, wherein said one or more light sources form one or more glints on said eye and said processing electronics is configured to determine a three-dimensional position of the center of curvature of said cornea based on said one or more glints.

Example 75: The display system of any of the Examples above, wherein said one or more eye-tracking cameras are further configured to image said pupil of the user's eye and wherein said processing electronics are further configured to determine the position of said pupil of said eye based at least on the image of said pupil from the one or more eye-tracking cameras.

Example 76: The display system of any of the Examples above, wherein said one or more eye-tracking cameras are further configured to image said pupil of the user's eye and wherein said processing electronics are further configured to determine a three-dimensional position of said pupil of said eye based at least on the image of said pupil from the one or more eye-tracking cameras.

Example 77: The display system of any of the Examples above, wherein said one or more eye-tracking cameras are further configured to image said pupil of the user's eye and wherein said processing electronics are further configured to determine the position of said pupil of said eye based on the position of the center of curvature of said cornea and based on the image of said pupil from the one or more eye-tracking cameras.

Example 78: The display system of any of the Examples above, wherein said processing electronics is configured to determine the optical axis of said eye based on the three-dimensional position of the center of curvature of said cornea and based on the three-dimensional position of said pupil.

Example 79: The display system of any of the Examples above, wherein said processing electronics is configured to determine a visual axis of said eye based on the optical axis.

Example 80: The display system of any of the Examples above, wherein said processing electronics is configured to determine the visual axis of said eye based on the optical axis and the three-dimensional position of at least one of the center of curvature of said cornea, said pupil or both.

Example 81: The display system of any of the Examples above, wherein said processing electronics is configured to determine a three-dimensional position of the center of rotation of said eye based on the three-dimensional position of the center of curvature of said cornea.

Example 82: The display system of any of the Examples above, wherein said processing electronics is configured to determine a three-dimensional position of the center of rotation of said eye based on the three-dimensional position of the center of curvature of said cornea and based on said optical axis.

Example 83: The display system of any of the Examples above, wherein said processing electronics is configured to determine the distance between said eye and the additional eye of said user based at least on the three-dimensional position of the center of rotation of said eye.

Example 84: The display system of any of the Examples above, wherein said processing electronics is configured to determine an interpupillary distance between said eye and the additional eye of said user based at least on the three-dimensional position of the center of rotation of said eye.

Example 85: The display system of any of the Examples above, wherein said processing electronics is configured to determine the vergence distance of said user based at least on the optical axis of said eye.

Example 86: The display system of any of the Examples above, wherein said processing electronics is configured to determine the vergence distance of said user based at least on the optical axis of said eye and on a determined optical axis of the additional eye of said user.

Example 87: The display system of any of the Examples above, wherein said processing electronics is configured to determine the vergence distance of said user based at least on the visual axis of said eye and on a determined visual axis of the additional eye of said user.

Example 88: The display system of any of the Examples above, wherein said display is configured to project collimated light into said user's eye.

Example 89: The display system of any of the Examples above, wherein said display is configured to project collimated light corresponding to an image pixel into said user's eye at a first period of time and divergent light corresponding to said image pixel into said user's eye at a second period of time.

Example 90: The display system of any of the Examples above, wherein said display is configured to project light corresponding to an image pixel having a first amount of divergence into said user's eye at a first period of time and to project light corresponding to said image pixel having a second amount of divergence, greater than the first amount of divergence, into said user's eye at a second period of time.

Example 91: A method of rendering virtual image content in a display system configured to project light to an eye of a user to display the virtual image content in a vision field of said user, said eye having a cornea, an iris, a pupil, a lens, a retina, and an optical axis extending through said lens, pupil, and cornea, said method comprising:

with one or more eye tracking cameras configured to image said eye of the user to track movements of said eye, determining a position of a center of rotation of said eye;

with a render engine, rendering virtual image content with a render camera at said center of rotation of said eye, said render camera configured to render virtual images to be presented to said eye; and with a head-mounted display, projecting light into said user's eye to display the rendered virtual image content to the user's vision field at different amounts of divergence such that the virtual image content appears to originate from different depths at different periods of time.

Example 92: The method of any of the Examples above, wherein said render camera is configured to render virtual images to be presented to said eye that are rendered as if captured by a camera having an aperture closer to said the center of rotation than said retina of said eye.

Example 93: The method of any of the Examples above, wherein said render camera is configured to render virtual images to be presented to said eye that are rendered as if captured by a camera having an aperture at said the center of rotation.

Example 94: The method of any of the Examples above, wherein said render camera is modeled with an aperture at said center of rotation of said eye.

Example 95: The method of any of the Examples above, wherein said render camera is modeled with an aperture, a lens, and a detector.

Example 96: The method of any of the Examples above, wherein said render camera has an aperture at a position along a line between (i) the determined position of the center of rotation of said eye and (ii) the determined position of the at least one of said iris or pupil.

Example 97: The method of any of the Examples above, further comprising:

with the one or more eye tracking cameras, determining a position of a center of perspective of said user's eye, wherein the center of perspective of said user's eye is located less than approximately 1.0 mm from the pupil of said user's eye; and with the render engine, rendering the virtual image content with the render camera, wherein said render camera has an aperture at the determined position of the center of perspective of said user's eye.

Example 98: The method of any of the Examples above, further comprising:

with the render engine, rendering the virtual image content with the render camera, wherein said render camera has an aperture at a position along a line between (i) the determined position of the center of rotation of said eye and (ii) the determined position of the center of perspective of said user's eye.

Example 99: The method of any of the Examples above, further comprising:

with processing electronics in communication with the one or more eye tracking cameras, determining a measure of change with time of the determined position of the center of perspective of said user's eye; and with the processing electronics, if it is determined that the measure of change with time exceeds a first threshold, directing the render engine to render the virtual content with the render camera, wherein the render camera has an aperture at the determined position of the center of rotation of said eye.

Example 100: The method of any of the Examples above, further comprising:

with the processing electronics, if it is determined that the measure of change with time is below a second threshold, directing the render engine to render the virtual content with the render camera, wherein the render camera has an aperture at the determined position of the center of perspective of said eye, and wherein the first threshold is indicative of a higher level change with time in the determined position of the center of perspective of said user's eye than the second threshold.

Example 101: The method of any of the Examples above, further comprising:

with the processing electronics, if it is determined that the measure of change with time is below a second threshold, directing the render engine to render the virtual content with the render camera, wherein the render camera has an aperture at the determined position of the center of perspective of said eye.

Example 102: The method of any of the Examples above, further comprising:

with the processing electronics, if it is determined that the measure of change with time is between the first and second thresholds, directing the render engine to render the virtual content with the render camera, wherein the render camera has an aperture at a point along a line between (i) the determined position of the center of rotation of said eye and (ii) the determined position of the center of perspective of said eye.

Example 103: The method of any of the Examples above, further comprising:

with at least a portion of said display, said portion being transparent and disposed at a location in front of the user's eye when the user wears said head-mounted display, transmitting light from a portion of the environment in front of the user and said head-mounted display to the user's eye to provide a view of said portion of the environment in front of the user and said head-mounted display.

Example 104: The method of any of the Examples above, further comprising:

with the one or more eye tracking cameras, determining a position of at least one of said iris, pupil, or lens Example 105: The method of any of the Examples above, further comprising:

with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the at least one of said iris or pupil.

Example 106: The method of any of the Examples above, further comprising:

with the one or more eye tracking cameras, determining a position of a center of perspective of said user's eye, wherein the center of perspective of said user's eye is located less than approximately 1.0 mm from the pupil of said user's eye; and with the render engine, rendering the virtual image content with the render camera, said render camera configured to present virtual images to said eye images that are rendered as if captured by a camera having an aperture at the determined position of the center of perspective of said user's eye.

Example 107: The method of any of the Examples above, further comprising:

with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the center of perspective of said user's eye.

Example 108: The method of any of the Examples above, further comprising:

with processing electronics in communication with the one or more eye tracking cameras, determining a measure of change with time of the determined position of the center of perspective of said user's eye; and with the processing electronics, if it is determined that the measure of change with time exceeds a first threshold, directing the render engine to render the virtual content with the render camera as if captured by a camera having an aperture at the determined position of the center of rotation of said eye.

Example 109: The method of any of the Examples above, further comprising:

with the processing electronics, if it is determined that the measure of change with time is below a second threshold, directing the render engine to render the virtual content with the render camera as if captured by a camera having an aperture at the determined position of the center of perspective of said eye, wherein the first threshold is indicative of a higher level change with time in the determined position of the center of perspective of said user's eye than the second threshold.

Example 110: The method of any of the Examples above, further comprising:

with the processing electronics, if it is determined that the measure of change with time is below a second threshold, directing the render engine to render the virtual content with the render camera as if captured by a camera having an aperture at the determined position of the center of perspective of said eye.

Example 111: The method of any of the Examples above, further comprising:

with the processing electronics, if it is determined that the measure of change with time is between the first and second thresholds, directing the render engine to render the virtual content with the render camera as if captured by a camera having an aperture at a point along a line between (i) the determined position of the center of rotation of said eye and (ii) the determined position of the center of perspective of said eye.

Example 112: A display system configured to project light to an eye of a user to display virtual image content in a vision field of said user, said eye having a cornea, an iris, a pupil, a lens, and a retina, and an optical axis extending through said lens, pupil, and cornea, said display system comprising:

a frame configured to be supported on a head of the user;

a head-mounted display disposed on the frame, said display configured to project light into said user's eye to display virtual image content to the user's vision field at different amounts of divergence and thus the displayed virtual image content appears to originate from different depths at different periods of time, wherein said head-mounted display is configured to project light into said user's eye having a first amount of divergence at a first period of time and is configured to project light into said user's eye having a second amount of divergence at a second period of time, wherein the first amount of divergence is different from the second amount of divergence;

one or more eye tracking cameras configured to image the user's eye; and processing electronics in communication with the display and the one or more eye tracking cameras, the processing electronics configured to obtain an estimate of a center of rotation of said eye based on images of said eye obtained with said one or more eye tracking cameras, obtain an estimate of a vergence distance of said user based on images of said eye obtained with said one or more eye tracking cameras, and shift from projecting light into said user's eye at the first amount of divergence to projecting light into said user's eye at the second amount of divergence based on the estimated vergence distance of said user.

Example 113: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 114: The display system of any of the Examples above, wherein said processing electronics is further configured to, based on images of said eye obtained with said one or more eye tracking cameras, detect a blink of said eye.

Example 115: The display system of any of the Examples above, wherein said processing electronics is further configured to, based on images of said eye obtained with said one or more eye tracking cameras, detect a saccade of said eye.

Example 116: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected the blink of said eye.

Example 117: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected the saccade of said eye.

Example 118: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected at least one of the saccade or the blink of said eye.

Example 119: The display system of any of the Examples above, wherein said first amount of divergence is associated with vergence distances in a first range and wherein said second amount of divergence is associated with vergence distances in a second range.

Example 120: The display system of any of the Examples above, wherein said first amount of divergence is associated with vergence distances in a first range, wherein said second amount of divergence is associated with vergence distances in a second range and wherein the first and second ranges overlap but are not equal.

Example 121: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range.

Example 122: The display system of any of the Examples above, wherein said processing electronics is configured to shift from projecting light into said user's eye at the first amount of divergence to projecting light into said user's eye at the second amount of divergence upon determining the vergence distance of said user lies outside the second range and lies within the first range.

Example 123: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range and also detecting a blink of said eye.

Example 124: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range and also detecting a saccade of said eye.

Example 125: The display system of any of the Examples above, wherein said processing electronics is configured to shift from projecting light into said user's eye at the first amount of divergence to projecting light into said user's eye at the second amount of divergence upon determining the vergence distance of said user has been outside the first range and within the second range for longer than a predetermined period of time.

Example 126: The display system of any of the Examples above, wherein said processing electronics is configured to shift from projecting light into said user's eye at the first amount of divergence to projecting light into said user's eye at the second amount of divergence upon determining the vergence distance of said user has been outside the first range and within the second range for longer than a predetermined period of time of at least 10 seconds.

Example 127: The display system of any of the Examples above, wherein said head-mounted display comprises a first display element configured to project light having the first amount of divergence and a second display element configured to project light having the second amount of divergence.

Example 128: The display system of any of the Examples above, wherein said display is configured to project light into said user's eye to display virtual image content in a discrete display mode in which the display is configured to project light associated with a plurality of sequential frames using only one of the first display element.

Example 129: The display system of any of the Examples above, wherein said display is configured to project light into said user's eye to display virtual image content in a blended display mode in which the display is configured to project light associated with a plurality of sequential frames using both of the first and second display elements for each of the frames.

Example 130: The display system of any of the Examples above, wherein said display is configured to project light into said user's eye to display virtual image content in a blended display mode in which the display is configured to project light associated with a plurality of sequential frames using both of the first and second display elements for each of the frames and wherein, in the blended display mode, the display is configured to project light, using the first and second display elements, that is perceived by a user as having a given amount of divergence that is between the first and second amounts of divergence.

Example 131: The display system of any of the Examples above, wherein said display is configured to project light into said user's eye to display virtual image content in a multi-focus display mode in which the display is configured to project light associated with a plurality of sequential frames using both of the first and second display elements for each of the frames, wherein, in the multi-focus display mode, the display is configured to project light associated with first virtual image content at a third amount of divergence and to project light associated with second virtual image content at a fourth amount of divergence, and wherein the third amount of divergence is different from the fourth amount of divergence.

Example 132: The display system of any of the Examples above, wherein third and fourth amounts of divergence are each between the first and second amounts of divergence.

Example 133: The display system of any of the Examples above, wherein at least one of the third and fourth amounts of divergence are between the first and second amounts of divergence.

Example 134: The display system of any of the Examples above, wherein the third and fourth amounts of divergence are respectively equal to the first and second amounts of divergence.

Example 135: The display system of any of the Examples above, wherein the display is configured to project light associated with the first virtual image in a first region of the user's vision field and to project light associated with the second virtual image in a second region of the user's vision field and wherein the first and second regions are different.

Example 136: The display system of any of the Examples above, wherein the display is configured to project light associated with the first virtual image in a first region of the user's vision field and to project light associated with the second virtual image in a second region of the user's vision field and wherein the first and second regions do not overlap.

Example 137: A display system configured to project light to left and right eyes of a user to display virtual image content in a vision field of said user, each of said eyes having a cornea, an iris, a pupil, a lens, a retina, and an optical axis extending through said lens, pupil, and cornea, said display system comprising:
 a frame configured to be supported on a head of the user;
 a head-mounted display disposed on the frame, said display configured to project light into said user's left and right eyes to display virtual image content to the user's vision field at different amounts of at least one of divergence and collimation and thus the displayed virtual image content appears to originate from different distances from the user's left and right eyes at different periods of time;
 a first eye tracking camera configured to image the user's left eye;
 a second eye tracking camera configured to image the user's right eye; and
 processing electronics in communication with the display and the first and second eye tracking cameras, the processing electronics configured to obtain an estimate of an interpupillary distance between the user's left and right eyes based on images of said left and right eyes obtained with said first and second eye tracking cameras.

Example 138: The display system of any of the Examples above, further comprising one or more light sources disposed on said frame with respect to said user's eye to illuminate said user's eye, said one or more eye tracking cameras forming images of said eye using said light from said one or more light sources.

Example 139: The display system of any of the Examples above, wherein said one or more light sources comprises at least two light sources disposed on said frame with respect to said user's eye to illuminate said user's eye.

Example 140: The display system of any of the Examples above, wherein said one or more light sources comprises infrared light emitters.

Example 141: The display system of any of the Examples above, wherein one or more light sources form one or more glints on said eye and said processing electronics is configured to determine a location of said cornea based on said one or more glints.

Example 142: The display system of any of the Examples above, wherein said cornea has associated therewith a cornea sphere having a center of curvature and said processing electronics is configured to determine a location of said center of curvature of said cornea sphere.

Example 143: The display system of any of the Examples above, wherein said cornea has associated therewith a cornea sphere having a center of curvature and said processing electronics is configured to determine a location of said center of curvature of said cornea sphere based on said one or more glints.

Example 144: The display system of any of the Examples above, wherein said one or more eye tracking camera is configured to image said pupil of said eye.

Example 145: The display system of any of the Examples above, wherein said processing electronics is configured to determine the location of said center of said pupil.

Example 146: The display system of any of the Examples above, wherein said processing electronics is configured to determine at least a portion of a boundary between said iris and said pupil.

Example 147: The display system of any of the Examples above, wherein said processing electronics is configured to determine a center of said boundary between said iris and said pupil.

Example 148: The display system of any of the Examples above, wherein said processing electronics is configured to determine a location of said center of said pupil in three-dimensional space with respect to a center of curvature of said cornea.

Example 149: The display system of any of the Examples above, wherein said processing electronics is configured to determine a location and orientation of said optical axis.

Example 150: The display system of any of the Examples above, wherein said processing electronics is configured to determine a location and orientation of said optical axis based on a location of said center of said pupil in three-dimensional space.

Example 151: The display system of any of the Examples above, wherein said processing electronics is configured to determine said location and orientation of said optical axis based on a location of said center of said pupil in three-dimensional space with respect to a center of curvature of said cornea.

Example 152: The display system of any of the Examples above, wherein said processing electronics is configured to determine a location of said center of rotation of said eye based on a center of curvature of said cornea.

Example 153: The display system of any of the Examples above, wherein said processing electronics is configured to determine a location of said center of rotation of said eye based on a center of curvature of said cornea and a location and orientation of said optical axis.

Example 154: The display system of any of the Examples above, wherein said processing electronics is configured to determine the location of said center of rotation of said eye by translating a particular distance along said optical axis from said center of curvature of said cornea.

Example 155: A method of rendering virtual image content in a display system configured to project light to left and right eyes of a user to display the virtual image content in a vision field of said user, each of said eyes having a cornea, an iris, a pupil, a lens, a retina, and an optical axis extending through said lens, pupil, and cornea, said method comprising:
 with one or more eye tracking cameras configured to image said eyes of the user to track movements of said eyes, determining a position of a center of rotation of said left eye and a position of a center of rotation of said right eye;
 with processing electronics in communication with the one or more eye tracking cameras, estimating said user's interpupillary distance based on the determined positions of the center of rotation of said left and right eyes;

with the one or more eye tracking cameras, determining a current left eye pose and a current right eye pose; and with the processing electronics, estimating said user's current vergence distance by comparing said estimated interpupillary distance and said determined current left eye pose and said determined current right eye pose.

Example 156: The method of any of the Examples above, wherein determining said current left and right eye poses comprises, with the one or more eye tracking cameras, estimating a position of said pupil of said user's left eye and a position of said pupil of said user's right eye.

Example 157: The method of any of the Examples above, wherein determining said current left and right eye poses comprises, with the one or more eye tracking cameras, estimating a position of said cornea of said user's left eye and a position of said cornea of said user's right eye.

Example 158: The method of any of the Examples above, wherein determining said current left and right eye poses comprises, with the one or more eye tracking cameras, estimating a position of said iris of said user's left eye and a position of said iris of said user's right eye.

Example 159: The method of any of the Examples above, wherein determining said current left and right eye poses comprises, with the one or more eye tracking cameras, estimating a position of said lens of said user's left eye and a position of said lens of said user's right eye.

Example 160: The method of any of the Examples above, wherein estimating said user's current vergence distance comprises:

with processing electronics, estimating a distance between said positions of said irises of said user's left and right eyes; and with the processing electronics, estimating said user's current vergence distance based on a comparison of said estimated interpupillary distance and said estimated distance between said positions of said irises of said user's left and right eyes.

Example 161: The method of any of the Examples above, further comprising: with a head-mounted display, projecting light into said user's eye to display the rendered virtual image content to the user's vision field at different amounts of divergence such that the virtual image content appears to originate from different depths at different periods of time.

Example 162: The method of any of the Examples above, further comprising: with at least a portion of said display, said portion being transparent and disposed at a location in front of the user's eye when the user wears said head-mounted display, transmitting light from a portion of the environment in front of the user and said head-mounted display to the user's eye to provide a view of said portion of the environment in front of the user and said head-mounted display.

Example 163: A display system configured to project light to an eye of a user to display virtual image content in a vision field of said user, said eye having a cornea, an iris, a pupil, a lens, a retina, and an optical axis extending through said lens, pupil, and cornea, said display system comprising:

a frame configured to be supported on a head of the user;

a head-mounted display disposed on the frame, said display configured to project light into said user's eye to display virtual image content to the user's vision field at different amounts of at least one of divergence and collimation and thus the displayed virtual image content appears to originate from different depths at different periods of time;

one or more eye tracking cameras configured to image the user's eye; and processing electronics in communication with the display and the one or more eye tracking cameras, the processing electronics configured to obtain a position estimate of a center of rotation of said eye based on images of said eye obtained with said one or more eye tracking cameras and configured to obtain a direction estimate of the optical axis of said eye based on said images, wherein said processing electronics is configured to present said virtual image content to said user's eye that are rendered as if captured by a camera having an aperture disposed along the optical axis and spaced apart from the estimated position of the center of rotation of said eye by between 6.0 mm and 13.0 mm in a direction away from said retina.

Example 164: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 7.0 mm and 12.0 mm in a direction away from said retina.

Example 165: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 8.0 mm and 11.0 mm in a direction away from said retina.

Example 166: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 9.0 mm and 10.0 mm in a direction away from said retina.

Example 167: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 9.5 mm and 10.0 mm in a direction away from said retina.

Example 168: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by approximately 9.7 mm.

Example 169: The display system of any of the Examples above, wherein said processing electronics includes electronics on said frame.

Example 170: The display system of any of the Examples above, wherein said processing electronics includes electronics on said frame and electronics disposed at a location remote from said frame.

Example 171: The display system of any of the Examples above, wherein said processing electronics includes electronics on said frame and electronics on a belt pack.

Example 172: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 173: The display system of any of the Examples above, further comprising one or more light sources disposed on said frame with respect to said user's eye to illuminate said user's eye, said one or more eye tracking cameras capturing images of said eye using said light from said one or more light sources.

Example 174: The display system of any of the Examples above, wherein said one or more light sources comprises at least two light sources disposed on said frame with respect to said user's eye to illuminate said user's eye.

Example 175: The display system of any of the Examples above, wherein said one or more light sources comprises at least three light sources disposed on said frame with respect to said user's eye to illuminate said user's eye.

Example 176: The display system of any of the Examples above, wherein said one or more light sources comprises infrared light emitters.

Example 177: A display system configured to project light to an eye of a user to display virtual image content in a vision field of said user, said eye having a cornea, an iris, a pupil, a lens, a retina, and an optical axis extending through said lens, pupil, and cornea, said display system comprising:
    a frame configured to be supported on a head of the user;
    a head-mounted display disposed on the frame, said display configured to project light into said user's eye to display virtual image content to the user's vision field at different amounts of at least one of divergence and collimation and thus the displayed virtual image content appears to originate from different depths at different periods of time;
    one or more eye tracking cameras configured to image the user's eye; and
    processing electronics in communication with the display and the one or more eye tracking cameras,
    wherein said processing electronics is configured to present said virtual image content to said user's eye that are rendered by a render camera located at the pupil of the eye or between the pupil and the cornea of the eye.

Example 178: The display system of any of the Examples above, wherein the render camera is located at a position that is between 1.0 mm and 2.0 mm in front of said pupil of said user's eye.

Example 179: The display system of any of the Examples above, wherein the render camera is located a position that is about 1.0 mm in front of said pupil of said user's eye.

Example 180: The display system of any of the Examples above, wherein the render camera is located at a position that is between 0.25 mm and 1.0 mm in front of said pupil of said user's eye.

Example 181: The display system of any of the Examples above, wherein the render camera is located at a position that is between 0.5 mm and 1.0 mm in front of said pupil of said user's eye.

Example 182: The display system of any of the Examples above, wherein the render camera is located at position that is between 0.25 mm and 0.5 mm in front of said pupil of said user's eye.

Example 183: The display system of any of the Examples above, wherein the render camera is located at the pupil of the eye.

Example 184: The display system of any of the Examples above, wherein the render camera is not located at the pupil of the eye.

Example 185: Any of the Examples above, wherein the camera comprises a pinhole camera.

Example 186: Any of the Examples above, wherein the aperture comprises a pinhole of a pinhole camera.

Example 187: A method of rendering virtual image content in a display system configured to project light to an eye of a user to display the virtual image content in a vision field of said user, said eye having a cornea, an iris, a pupil, a lens, a retina, and an optical axis extending through said lens, pupil, and cornea, said method comprising:
    with one or more eye cameras configured to image said eye of the user, determining a position based on said imaging of said eye with said one or more cameras;
    with a render engine, rendering virtual image content with a render camera at a location based on said determined position, said render camera configured to render virtual images to be presented to said eye; and with a head-mounted display, projecting light into said user's eye to display the rendered virtual image content to the user's vision field.

Example 188: The method of any of the Examples above, wherein said position is a center of rotation of said eye.

Example 189: The method of any of the Examples above, wherein said location of said render camera is at said center of rotation of said eye.

Example 190: The method of any of the Examples above, wherein said position is a center of perspective of said eye.

Example 191: The method of any of the Examples above, wherein said location of said render camera is at said center of perspective of said eye.

Example 192: The method of any of the Examples above, wherein said render camera is configured to render virtual images to be presented to said eye that are rendered as if captured by a camera having an aperture closer to said the center of rotation than said retina of said eye.

Example 193: The method of any of the Examples above, wherein said render camera is configured to render virtual images to be presented to said eye that are rendered as if captured by a camera having an aperture at said the center of rotation.

Example 194: The method of any of the Examples above, wherein said render camera is modeled with an aperture at said center of rotation of said eye.

Example 195: The method of any of the Examples above, wherein said render camera is modeled with an aperture, a lens, and a detector.

Example 196: The method of any of the Examples above, wherein said render camera has an aperture at a position along a line between (i) the determined position of the center of rotation of said eye and (ii) the determined position of the at least one of said iris or pupil.

Example 197: The method of any of the Examples above, further comprising:
    with the one or more cameras, determining a position of a center of perspective of said user's eye, wherein the center of perspective of said user's eye is located less than approximately 1.0 mm from the pupil of said user's eye; and with the render engine, rendering the virtual image content with the render camera, wherein said render camera has an aperture at the determined position of the center of perspective of said user's eye.

Example 198: The method of any of the Examples above, further comprising:
    with the render engine, rendering the virtual image content with the render camera, wherein said render camera has an aperture at a position along a line between (i) the determined position of the center of rotation of said eye and (ii) the determined position of the center of perspective of said user's eye.

Example 199: The method of any of the Examples above, further comprising:

with processing electronics in communication with the one or more cameras, determining a measure of change with time of the determined position of the center of perspective of said user's eye; and with the processing electronics, if it is determined that the measure of change with time exceeds a first threshold, directing the render engine to render the virtual content with the render camera, wherein the render camera has an aperture at the determined position of the center of rotation of said eye.

Example 200: The method of any of the Examples above, further comprising:

with the processing electronics, if it is determined that the measure of change with time is below a second threshold, directing the render engine to render the virtual content with the render camera, wherein the render camera has an aperture at the determined position of the center of perspective of said eye, and wherein the first threshold is indicative of a higher level change with time in the determined position of the center of perspective of said user's eye than the second threshold.

Example 201: The method of any of the Examples above, further comprising:

with the processing electronics, if it is determined that the measure of change with time is below a second threshold, directing the render engine to render the virtual content with the render camera, wherein the render camera has an aperture at the determined position of the center of perspective of said eye.

Example 202: The method of any of the Examples above, further comprising:

with the processing electronics, if it is determined that the measure of change with time is between the first and second thresholds, directing the render engine to render the virtual content with the render camera, wherein the render camera has an aperture at a point along a line between (i) the determined position of the center of rotation of said eye and (ii) the determined position of the center of perspective of said eye.

Example 203: The method of any of the Examples above, further comprising:

with at least a portion of said display, said portion being transparent and disposed at a location in front of the user's eye when the user wears said head-mounted display, transmitting light from a portion of the environment in front of the user and said head-mounted display to the user's eye to provide a view of said portion of the environment in front of the user and said head-mounted display.

Example 204: The method of any of the Examples above, further comprising:

with the one or more cameras, determining a position of at least one of said iris, pupil, or lens Example 205: The method of any of the Examples above, further comprising:

with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the at least one of said iris or pupil.

Example 206: The method of any of the Examples above, further comprising:

with the one or more cameras, determining a position of a center of perspective of said user's eye, wherein the center of perspective of said user's eye is located less than approximately 1.0 mm from the pupil of said user's eye; and with the render engine, rendering the virtual image content with the render camera, said render camera configured to present virtual images to said eye images that are rendered as if captured by a camera having an aperture at the determined position of the center of perspective of said user's eye.

Example 207: The method of any of the Examples above, further comprising:

with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the center of perspective of said user's eye.

Example 208: The method of any of the Examples above, wherein with said head-mounted display, projecting light into said user's eye to display the rendered virtual image content to the user's vision field comprises projecting light into said user's eye to display the rendered virtual image content to the user's vision field at different amounts of divergence such that the virtual image content appears to originate from different depths at different periods of time.

Example 209: The method of any of the Examples above, wherein said different amount of divergence includes zero divergence.

Example 210: The method of any of the Examples above, wherein said different amount of divergence includes collimation.

Example 211: A display system configured to project light to an eye of a user to display virtual image content in a vision field of said user, said eye having a cornea, an iris, a pupil, a lens, a retina, and an optical axis extending through said lens, pupil, and cornea, said display system comprising:

a frame configured to be supported on a head of the user;

a head-mounted display disposed on the frame, said display configured to project light into said user's eye to display virtual image content to the user's vision field;

one or more cameras configured to image the user's eye; and processing electronics in communication with the display and the one or more cameras, the processing electronics configured to obtain a position of said eye based on images of said eye obtained with said one or more cameras, wherein said processing electronics is configured to present said virtual image content to said user's eye that are rendered by a render camera located at location based on said determined position.

Example 212: The display system of any of the Examples above, wherein said position is an estimate of a center of rotation of said eye.

Example 213: The display system of any of the Examples above, wherein said location of said render camera is at said estimated center of rotation of said eye.

Example 214: The display system of any of the Examples above, wherein said position is an estimate of a center of perspective of said eye.

Example 215: The display system of any of the Examples above, wherein said location of said render camera is at said estimated center of perspective of said eye.

Example 216: The display system of any of the Examples above, wherein said processing electronics is configured to present said virtual image content to said user's eye that are rendered as if captured by a camera having an aperture closer to said center of perspective than said retina.

Example 217: The display system of any of the Examples above, wherein said processing electronics is configured to present said virtual image content to said user's eye that are rendered as if captured by a camera having an aperture closer to said center of rotation than said retina.

Example 218: The display system of any of the Examples above, wherein said processing electronics is configured to present said virtual image content to said user's eye that are rendered as if captured by a camera having an aperture at said center of rotation.

Example 219: The display system of any of the Examples above, wherein said processing electronics is configured to present said virtual image content to said user's eye that are rendered as if captured by a camera having an aperture closer to said center of rotation than said center of perspective.

Example 220: The display system of any of the Examples above, wherein said processing electronics is configured to present said virtual image content to said user's eye that are rendered as if captured by a camera having an aperture closer to said center of perspective than said retina.

Example 221: The display system of any of the Examples above, wherein said processing electronics is configured to present said virtual image content to said user's eye that are rendered as if captured by a camera having an aperture closer to said center of perspective than a center of rotation of the eye.

Example 222: The display system of any of the Examples above, wherein said processing electronics is configured to present said virtual image content to said user's eye that are rendered as if captured by a camera having an aperture at said center of perspective.

Example 223: The display system of any of the Examples above, wherein said center of perspective is not located at said pupil of said eye.

Example 224: The display system of any of the Examples above, wherein the processing electronics is configured to obtain an estimate of said user's eye pose over time and wherein the processing electronics adjust the position of the render camera based at least in part upon the user's eye pose.

Example 225: The display system of any of the Examples above, wherein the processing electronics is configured to track said user's eye pose over time and wherein the position of the render camera is adjusted over time in response to changes in said user's eye pose over time.

Example 226: The display system of any of the Examples above, wherein the processing electronics is configured to obtain the estimate of the center of perspective by filtering a plurality of estimated center of perspective positions.

Example 227: The display system of any of the Examples above, wherein the processing electronics is configured to obtain the estimate of the center of perspective by averaging and/or applying a Kalman filter to a plurality of estimated center of perspective positions.

Example 228: The display system of any of the Examples above, wherein the center of perspective comprises a position within the anterior chamber of said user's eye.

Example 229: The display system of any of the Examples above, wherein the center of perspective comprises a position in front of said pupil of said user's eye.

Example 230: The display system of any of the Examples above, wherein the center of perspective comprises a position that is between 1.0 mm and 2.0 mm in front of said pupil of said user's eye.

Example 231: The display system of any of the Examples above, wherein the center of perspective comprises a position that is about 1.0 mm in front of said pupil of said user's eye.

Example 232: The display system of any of the Examples above, wherein the center of perspective comprises a position that is between 0.25 mm and 1.0 mm in front of said pupil of said user's eye.

Example 233: The display system of any of the Examples above, wherein the center of perspective comprises a position that is between 0.5 mm and 1.0 mm in front of said pupil of said user's eye.

Example 234: The display system of any of the Examples above, wherein the center of perspective comprises a position that is between 0.25 mm and 0.5 mm in front of said pupil of said user's eye.

Example 235: The display system of any of the Examples above, wherein the center of perspective lies along the optical axis of said eye and wherein said processing electronics are further configured to obtain the position estimate of the center of perspective by obtaining a position estimate of the optical axis of said eye.

Example 236: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye.

Example 237: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye and a position estimate of a center of rotation of said eye, the cornea of said eye, the iris of said eye, the retina of said eye, and the pupil of said eye or any combinations thereof.

Example 238: The display system of any of the Examples above, wherein said processing electronics includes electronics on said frame.

Example 239: The display system of any of the Examples above, wherein said processing electronics includes electronics on said frame and electronics disposed at a location remote from said frame.

Example 240: The display system of any of the Examples above, wherein said processing electronics includes electronics on said frame and electronics on a belt pack.

Example 241: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 242: The display system of any of the Examples above, further comprising one or more light sources disposed on said frame with respect to said user's eye to illuminate said user's eye, said one or more cameras capturing images of said eye using said light from said one or more light sources.

Example 243: The display system of any of the Examples above, wherein said one or more light sources comprises at least two light sources disposed on said frame with respect to said user's eye to illuminate said user's eye.

Example 244: The display system of any of the Examples above, wherein said one or more light sources comprises at least three light sources disposed on said frame with respect to said user's eye to illuminate said user's eye.

Example 245: The display system of any of the Examples above, wherein said one or more light sources comprises infrared light emitters.

Example 246: The display system of any of the Examples above, wherein said one or more light sources form one or more glints on said eye and said processing electronics is configured to determine the position of the center of curvature of said cornea based on said one or more glints.

Example 247: The display system of any of the Examples above, wherein said one or more light sources form one or more glints on said eye and said processing electronics is configured to determine a three-dimensional position of the center of curvature of said cornea based on said one or more glints.

Example 248: The display system of any of the Examples above, wherein said one or more cameras are further configured to image said pupil of the user's eye and wherein said processing electronics are further configured to determine the position of said pupil of said eye based at least on the image of said pupil from the one or more cameras.

Example 249: The display system of any of the Examples above, wherein said one or more cameras are further configured to image said pupil of the user's eye and wherein said processing electronics are further configured to determine a three-dimensional position of said pupil of said eye based at least on the image of said pupil from the one or more cameras.

Example 250: The display system of any of the Examples above, wherein said one or more cameras are further configured to image said pupil of the user's eye and wherein said processing electronics are further configured to determine the position of said pupil of said eye based on the position of the center of curvature of said cornea and based on the image of said pupil from the one or more cameras.

Example 251: The display system of any of the Examples above, wherein said processing electronics is configured to determine the optical axis of said eye based on the three-dimensional position of the center of curvature of said cornea and based on the three-dimensional position of said pupil.

Example 252: The display system of any of the Examples above, wherein said processing electronics is configured to determine a visual axis of said eye based on the optical axis.

Example 253: The display system of any of the Examples above, wherein said processing electronics is configured to determine the visual axis of said eye based on the optical axis and the three-dimensional position of at least one of the center of curvature of said cornea, said pupil or both.

Example 254: The display system of any of the Examples above, wherein said processing electronics is configured to determine a three-dimensional position of the center of rotation of said eye based on the three-dimensional position of the center of curvature of said cornea.

Example 255: The display system of any of the Examples above, wherein said processing electronics is configured to determine a three-dimensional position of the center of rotation of said eye based on the three-dimensional position of the center of curvature of said cornea and based on said optical axis.

Example 256: The display system of any of the Examples above, wherein said processing electronics is configured to determine the distance between said eye and the additional eye of said user based at least on the three-dimensional position of the center of rotation of said eye.

Example 257: The display system of any of the Examples above, wherein said processing electronics is configured to determine an interpupillary distance between said eye and the additional eye of said user based at least on the three-dimensional position of the center of rotation of said eye.

Example 258: The display system of any of the Examples above, wherein said processing electronics is configured to determine the vergence distance of said user based at least on the optical axis of said eye.

Example 259: The display system of any of the Examples above, wherein said processing electronics is configured to determine the vergence distance of said user based at least on the optical axis of said eye and on a determined optical axis of the additional eye of said user.

Example 260: The display system of any of the Examples above, wherein said processing electronics is configured to determine the vergence distance of said user based at least on the visual axis of said eye and on a determined visual axis of the additional eye of said user.

Example 261: The display system of any of the Examples above, wherein said display is configured to project collimated light into said user's eye.

Example 262: The display system of any of the Examples above, wherein said display is configured to project collimated light corresponding to an image pixel into said user's eye at a first period of time and divergent light corresponding to said image pixel into said user's eye at a second period of time.

Example 263: The display system of any of the Examples above, wherein said display is configured to project light corresponding to an image pixel having a first amount of divergence into said user's eye at a first period of time and to project light corresponding to said image pixel having a second amount of divergence, greater than the first amount of divergence, into said user's eye at a second period of time.

Example 264: The display system of any of the Examples above, wherein center of perspective is estimated to be proximal said pupil of said eye Example 265: The display system of any of the Examples above, wherein center of perspective is estimated to be between said cornea and said pupil of said eye.

Example 266: The display system of any of the Examples above, wherein said display is configured to project light into said user's eye to display virtual image content to the user's vision field at different amounts of at least one of divergence and collimation and thus the displayed virtual image content appears to originate from different depths at different periods of time.

Example 267: A display system configured to project light to an eye of a user to display virtual image content in a vision field of said user, said eye having a cornea, an iris, a pupil, a lens, a retina, said display system comprising:

a frame configured to be supported on a head of the user;

a head-mounted display disposed on the frame, said display configured to project light into said user's eye to display virtual image content to the user's vision field at different amounts of at least one of divergence and collimation and thus the displayed virtual image content appears to originate from different depths at different periods of time;

one or more eye tracking cameras configured to image the user's eye; and processing electronics in communication with the display and the one or more eye tracking cameras, the processing electronics configured to:

obtain a position and orientation estimate of an optical axis extending through the lens, pupil, and cornea of the user's eye based on images of said eye obtained with one or more eye tracking cameras;

identify a particular location along an axis in render space that is registered to said optical axis of said eye; and present said virtual image content to said user's eye as rendered by a virtual render camera located at the particular location in render space.

Example 268: The display system of Examples 267, wherein said head-mounted display is configured to project light into said user's eye having a first amount of divergence at a first period of time and is configured to project light into said user's eye having a second amount of divergence at a second period of time, wherein the first amount of divergence is different from the second amount of divergence, and wherein the processing electronics are further configured to obtain an estimate of a vergence distance of said user based on images of said eye obtained with said one or more eye tracking cameras, and shift from projecting light into said user's eye at the first amount of divergence to projecting light into said user's eye at the second amount of divergence based on the estimated vergence distance of said user.

Example 269: The display system of Examples 267, wherein said head-mounted display is configured to project light into said user's eye having a first amount of divergence at a first period of time and is configured to project light into said user's eye having a second amount of divergence at a second period of time, wherein the first amount of divergence is different from the second amount of divergence, and wherein the processing electronics are further configured to obtain an estimate of a vergence distance of said user based on images of said eye obtained with said one or more eye tracking cameras, and shift from projecting light into said user's eye at the first amount of divergence to projecting light into said user's eye at the second amount of divergence based on the estimated vergence distance of said user.

Example 270: The display system of Example 267, wherein the processing electronics are further configured to determine a position along the optical axis at which a center of rotation of said eye is estimated to be located based on images of said eye obtained with one or more eye tracking cameras, and wherein the processing electronics are configured to identify the particular location along the axis in render space that is registered to said optical axis of said eye based on said position along the optical axis at which the center of rotation of said eye is estimated to be located.

Example 271: The display system of Examples 267, wherein the particular location along the axis in render space comprises a location along the axis in render space at which parallax shifts in the render space are determined to be reduced.

Example 272: The display system of Examples 267, wherein the particular location along the axis in render space comprises a location along the axis in render space at which parallax shifts in the render space are determined to be minimized.

Example 273: The display system of any of the Examples above, wherein said processing electronics are configured to obtain the estimate of the center of rotation of said eye based on determination of multiple gaze directions of the user's eye over a period of time during which said eye is rotating based on images of said eye obtained by said one or more eye tracking cameras.

Example 274: The display system of Example 273, wherein said processing electronics are configured to determine said gaze direction based on variations of the shape of one or more of the pupil, iris, or limbus of the user's eye in images obtained with said one or more eye tracking cameras over a period of time during which said eye is rotating.

Example 275: The display system of any of the Examples above, wherein said processing electronics are configured to determine an array of positions based on a plurality of spatial locations on an image of the user's eye obtained with said one or more eye tracking cameras.

Example 276: The display system of Example 275, wherein said array of positions corresponds to at least a portion of an ellipse.

Example 277: The display system of any of Examples 275 or 276, wherein said processing electronics are configured to determine said array of positions by fitting a curve to said plurality of spatial locations on said image of the user's eye.

Example 278: The display system of Example 277, wherein said curve comprises an ellipse.

Example 279: The display system of any of Examples 275 to 278, wherein said plurality of spatial locations on said image comprises spatial locations on the limbus of said user's eye in said image.

Example 280: The display system of any of Examples 275 to 279, wherein said plurality of spatial locations on said image comprises spatial locations on a boundary between the iris and the sclera of said user's eye in said image.

Example 281: The display system of any of Examples 275 to 279, wherein said plurality of spatial locations on said image comprises spatial locations on a boundary between the cornea and the sclera of said user's eye in said image obtained with said one or more eye tracking cameras.

Example 282: The display system of any of Examples 275 to 281, wherein said processing electronics are configured to determine a plurality of linear paths extending from a location on a first side of said array of positions through said array of positions to a second opposite side of said array of positions.

Example 283: The display system of Example 282, wherein said processing electronics are configured to determine a circular region based on said plurality of linear paths, said circular region having a radius, R.

Example 284: The display system of Example 283, wherein said radius, R, corresponds to an average radius of a limbus.

Example 285: The display system of Example 283, wherein said radius, R, corresponds to a measured radius of the limbus of the user's eye.

Example 286: The display system of Example 283, wherein said radius, R, corresponds to an average radius of a pupil.

Example 287: The display system of Example 283, wherein said radius, R, corresponds to a measured radius of the pupil of the user's eye.

Example 288: The display system of any of Examples 282 to 287, wherein said processing electronics are configured to determine the location and direction of a normal through a central portion of said circular region.

Example 289: The display system of any of Examples 282 to 288, wherein said processing electronics are configured to determine respective locations and directions of a plurality of normals through central portions of respective circular regions based on a plurality of images of said eye previously obtained with said one or more eye tracking cameras.

Example 290: The display system of Example 289, wherein said processing electronics are configured to determine a position where said plurality of normals converge or intersect.

Example 291: The display system of Example 289, wherein said processing electronics are configured to obtain the estimate of the center of rotation of said user's eye by identifying a region of intersection, convergence, or close proximity of multiple of said normals determined based on images of the user's eye obtained over a period of time during which said eye is rotating.

Example 292: The display system of Example 289, wherein said processing electronics are configured to obtain the estimate of the center of rotation of said user's eye based on the locations and directions of multiple of said plurality of normals determined based on images of the user's eye obtained over a period of time during which said eye is rotating.

Example 293: The display system of any of Examples 282-292, wherein the location on the first side of said array positions corresponds to an origin of a coordinate system of one of said one or more eye tracking cameras.

Example 294: The display system of any of the Examples above, wherein the processing electronics is configured to obtain the estimate of the center of rotation by filtering, averaging, applying a Kalman filter, or any combinations thereof to a plurality of estimated center of rotation positions.

Various additional examples of display systems that project light to one or more eyes of a user to display virtual image content in a vision field of said user are described herein such as the additional examples enumerated below:

Additional Example 1: A display system configured to project light to an eye of a user to display virtual image content in a vision field of said user, said eye having a cornea, an iris, a pupil, a lens, a retina, and an optical axis extending through said lens, pupil, and cornea, said display system comprising:
  a frame configured to be supported on a head of the user;
  a head-mounted display disposed on the frame, said display configured to project light into said user's eye to display virtual image content to the user's vision field, at least a portion of said display being transparent and disposed at a location in front of the user's eye when the user wears the frame such that said transparent portion transmits light from a portion of the environment in front of the user and said head-mounted display to the user's eye to provide a view of said portion of the environment in front of the user and said head-mounted display;
  an inward-facing imaging system configured to image the user's eye; and
  processing electronics in communication with the inward-facing imaging system, the processing electronics configured to obtain an estimate of a center of rotation of said eye based on multiple images of said eye obtained with said inward-facing imaging system, said processing electronics configured to a determine a variation in calculated values of center of rotation and select a statistically determined estimate of center of rotation based on said variation.

Additional Example 2: The display system of Additional Example 1, wherein reduced variation is used to identify said statistically determined center of rotation.

Additional Example 3: The display system of Additional Example 1 or 2, wherein a first set of estimates of center of rotation are calculated based on a first value of a parameter used to calculate the center of rotation and a first variation is determined from said first set of estimates.

Additional Example 4: The display system of Additional Example 3, wherein a second set of estimates of center of rotation are calculated based on a second value of said parameter and a second variation is determined from said second set of estimates.

Additional Example 5: The display system of Additional Example 4, wherein said first and second variations are compared to determine which set has reduced variation, said determination of said statistically determined estimate of the center of rotation being based on this comparison.

Additional Example 6: The display system of Additional Example 1 or 2, wherein multiple sets of values of centers of rotation are calculated based on multiple respective values of a parameter and respective variations determined for the different respective sets.

Additional Example 7: The display system of Additional Example 6, wherein the respective variations are compared to determine which set has reduced variation and said determination of said statistically determined estimate of said center of rotation is based on said comparison.

Additional Example 8: The display system of Additional Example 6 or 7, wherein the value of the parameter for said set having the lowest variation is used in calculating said statistically determined estimate of said center of rotation.

Additional Example 9: The display system of Additional Example 6, 7, or 8, wherein said set having the lowest the variation is used in calculating said statistically determined estimate of said center of rotation.

Additional Example 10: The display system of any of Additional Examples 3 to 9, wherein said parameter comprises distance to said center of rotation from the center of curvature of said cornea.

Additional Example 11: The display system of any of Additional Examples 3 to 9, wherein said parameter comprises distance along the optical axis from the center of curvature of said cornea to said center of rotation.

Additional Example 12: The display system of any of the Additional Examples above, wherein said variation comprises variance and/or standard deviation.

Additional Example 13: The display system of any of the Additional Examples above, further comprising one or more light sources disposed on said frame with respect to said user's eye to illuminate said user's eye, said inward-facing imaging system forming images of said eye using said light from said one or more light sources.

Additional Example 14: The display system of Additional Example 13, wherein said one or more light sources comprises at least two light sources disposed on said frame with respect to said user's eye to illuminate said user's eye.

Additional Example 15: The display system of Additional Example 13 or 14, wherein said one or more light sources comprises infrared light emitters.

Additional Example 16: The display system of any of the Additional Examples 13 to 15, wherein one or more light sources form one or more glints on said eye and said processing electronics is configured to determine a location of said cornea based on said one or more glints.

Additional Example 17: The display system of any of the Additional Examples 13 to 16, wherein said cornea has associated therewith a cornea sphere having a center of curvature and said processing electronics is configured to determine a location of said center of curvature of said cornea sphere.

Additional Example 18: The display system of Additional Example 17, wherein said cornea has associated therewith a cornea sphere having a center of curvature and said processing electronics is configured to determine a location of said center of curvature of said cornea sphere based on said one or more glints.

Additional Example 19: The display system of any of the Additional Examples above, wherein said inward-facing imaging system is configured to image said pupil of said eye.

Additional Example 20: The display system of any of the Additional Examples above, wherein said processing electronics is configured to determine the location of said center of said pupil.

Additional Example 21: The display system of any of the Additional Examples above, wherein said processing electronics is configured to determine at least a portion of a boundary between said iris and said pupil.

Additional Example 22: The display system of Additional Example 21, wherein said processing electronics is configured to determine a center of said boundary between said iris and said pupil.

Additional Example 23: The display system of any of the Additional Examples above, wherein said processing electronics is configured to determine a location of said center of said pupil in three-dimensional space with respect to a center of curvature of said cornea.

Additional Example 24: The display system of any of the Additional Examples above, wherein said processing electronics is configured to determine a location and orientation of said optical axis.

Additional Example 25: The display system of Additional Example 24, wherein said processing electronics is configured to determine a location and orientation of said optical axis based on a location of said center of said pupil in three-dimensional space.

Additional Example 26: The display system of any of the Additional Examples above, wherein said processing electronics is configured to determine said location and orientation of said optical axis based on a location of said center of said pupil in three-dimensional space with respect to a center of curvature of said cornea.

Additional Example 27: The display system of any of the Additional Examples above, wherein said processing electronics is configured to determine a location of said center of rotation of said eye based on a center of curvature of said cornea.

Additional Example 28: The display system of any of the Additional Examples above, wherein said processing electronics is configured to determine a location of said center of rotation of said eye based on a center of curvature of said cornea and a location and orientation of said optical axis.

Additional Example 29: The display system of Additional Example 28, wherein said processing electronics is configured to determine the location of said center of rotation of said eye by translating a particular distance along said optical axis from said center of curvature of said cornea.

Additional Example 30: The display system of Additional Example 29, wherein said particular distance from said center of curvature to said center of rotation is between 4.0 mm and 6.0 mm Additional Example 31: The display system of Additional Example 29 or 30, wherein said particular distance from said center of curvature to said center of rotation is about 4.7 mm.

Additional Example 32: The display system of Additional Example 20 or 30, wherein said processing electronics is configured to determine the particular distance based at least on one or more images of said eye previously obtained with said inward-facing imaging system.

Additional Example 33: The display system of any of the Additional Examples above, wherein said processing electronics includes electronics on said frame.

Additional Example 34: The display system of any of the Additional Examples above, wherein said processing electronics includes electronics on said frame and electronics disposed at a location remote from said frame.

Additional Example 35: The display system of any of the Additional Examples above, wherein said processing electronics includes electronics on said frame and electronics on a belt pack.

Additional Example 36: The display system of any of the Additional Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Additional Example 37: The display system of any of the Additional Examples above, wherein said head-mounted display receives light from a portion of the environment in front of the user at a first amount of divergence and transmits the light from the portion of the environment in front of the user to the user's eye with a second amount of divergence that is substantially similar to the first amount of divergence.

Additional Example 38: The display system of any of the Additional Examples above, wherein the processing electronics is configured to obtain the estimate of the center of rotation by filtering, averaging, applying a Kalman filter, or any combinations thereof a plurality of estimated center of rotation positions.

Additional Example 39: The display system of any of the Additional Examples above, wherein said processing electronics is configured to present said virtual image content to said user's eye that is rendered as if captured by a camera having an aperture at the determined position of the center of rotation of said user's eye.

Additional Example 40: The display system of any of the Additional Examples above, wherein said processing electronics is configured to use a render camera at said center of rotation to render virtual images to be presented to said eye.

Additional Example 41: The display system of any of the Additional Examples above, wherein said processing electronics is configured to use a render camera configured to render virtual images to be presented to said eye that are rendered as if captured by a camera having an aperture closer to said the center of rotation than said retina of said eye.

Additional Example 42: The display system of any of the Additional Examples above, wherein said processing electronics is configured to use a render camera configured to render virtual images to be presented to said eye that are rendered as if captured by a camera having an aperture at said the center of rotation of said eye.

Additional Example 43: The display system of any of the Additional Examples above, wherein said processing electronics is configured to use a render camera at said center of rotation to render virtual images to be presented to said eye, said render camera modeled with an aperture at said center of rotation of said eye.

Additional Example 44: The display system of any of Additional Examples 1 to 9, wherein said processing electronics is configured to select the statistically-determined estimate of center of rotation based on said variation during a calibration procedure.

Additional Example 45: The display system of any of the Examples or Additional Examples above, wherein said processing electronics are configured to obtain the estimate of the center of rotation of said eye based on determination of multiple gaze directions of the user's eye over a period of time during which said eye is rotating based on images of said eye obtained by said one or more eye tracking cameras.

Additional Example 46: The display system of any of the Examples or Additional Examples above, wherein said processing electronics are configured to determine said gaze direction based on variations of the shape of one or more of the pupil, iris, or limbus of the user's eye in images obtained with said one or more eye tracking cameras over a period of time during which said eye is rotating.

Additional Example 47: The display system of any of the Examples or Additional Examples above, wherein said processing electronics are configured to determine an array of positions based on a plurality of spatial locations on an image of the user's eye obtained with said one or more eye tracking cameras.

Additional Example 48: The display system of any of the Examples or Additional Examples above, wherein said array of positions corresponds to at least a portion of an ellipse.

Additional Example 49: The display system of any of the Examples or Additional Examples above, wherein said processing electronics are configured to determine said array of positions by fitting a curve to said plurality of spatial locations on said image of the user's eye.

Additional Example 50: The display system of any of the Examples or Additional Examples above, wherein said curve comprises an ellipse.

Additional Example 51: The display system of any of the Examples or Additional Examples above, wherein said plurality of spatial locations on said image comprises spatial locations on the limbus of said user's eye in said image.

Additional Example 52: The display system of any of the Examples or Additional Examples above, wherein said plurality of spatial locations on said image comprises spatial locations on a boundary between the iris and the sclera of said user's eye in said image.

Additional Example 53: The display system of any of the Examples or Additional Examples above, wherein said plurality of spatial locations on said image comprises spatial locations on a boundary between the cornea and the sclera of said user's eye in said image obtained with said one or more eye tracking cameras.

Additional Example 54: The display system of any of the Examples or Additional Examples above, wherein said processing electronics are configured to determine a plurality of linear paths extending from a location on a first side of said array of positions through said array of positions to a second opposite side of said array of positions.

Additional Example 55: The display system of any of the Examples or Additional Examples above, wherein said processing electronics are configured to determine a circular region based on said plurality of linear paths, said circular region having a radius, R.

Additional Example 56: The display system of any of the Examples or Additional Examples above, wherein said radius, R, corresponds to an average radius of a limbus.

Additional Example 57: The display system of any of the Examples or Additional Examples above, wherein said radius, R, corresponds to a measured radius of the limbus of the user's eye.

Additional Example 58: The display system of any of the Examples or Additional Examples above, wherein said radius, R, corresponds to an average radius of a pupil.

Additional Example 59: The display system of any of the Examples or Additional Examples above, wherein said radius, R, corresponds to a measured radius of the pupil of the user's eye.

Additional Example 60: The display system of any of the Examples or Additional Examples above, wherein said processing electronics are configured to determine the location and direction of a normal through a central portion of said circular region.

Additional Example 61: The display system of any of the Examples or Additional Examples above, wherein said processing electronics are configured to determine respective locations and directions of a plurality of normals through central portions of respective circular regions based on a plurality of images of said eye previously obtained with said one or more eye tracking cameras.

Additional Example 62: The display system of any of the Examples or Additional Examples above, wherein said processing electronics are configured to determine a position where said plurality of normals converge or intersect.

Additional Example 63: The display system of any of the Examples or Additional Examples above, wherein said processing electronics are configured to obtain the estimate of the center of rotation of said user's eye by identifying a region of intersection, convergence, or close proximity of multiple of said normals determined based on images of the user's eye obtained over a period of time during which said eye is rotating.

Additional Example 64: The display system of any of the Examples or Additional Examples above, wherein said processing electronics are configured to obtain the estimate of the center of rotation of said user's eye based on the locations and directions of multiple of said plurality of normals determined based on images of the user's eye obtained over a period of time during which said eye is rotating.

Additional Example 65: The display system of any of the Examples or Additional Examples above, wherein the location on the first side of said array positions corresponds to an origin of a coordinate system of one of said one or more eye tracking cameras.

Additional Example 66: The display system of any of the Examples or Additional Examples above, wherein the processing electronics is configured to obtain the estimate of the center of rotation by filtering, averaging, applying a Kalman filter, or any combinations thereof to a plurality of estimated center of rotation positions.

Any of the above Examples or Additional Examples can be combined. Additionally, any of the above Examples or Additional Examples can be integrated with a head mounted display. In addition, any of the above Examples or Additional Examples can be implemented with a single depth plane and/or with one or more variable depth planes (e.g., one or more elements with variable focusing power that provide accommodation cues that vary over time).

Furthermore, apparatus and methods for determining a variety of values, parameters, etc., such as, but not limited to, anatomical, optical, and geometric features, locations, and orientations, etc., are disclosed herein. Examples of such parameters include, for example, the center of rotation of the eye, the center of curvature of the cornea, the center of the pupil, the boundary of the pupil, the center of the iris, the boundary of the iris, the boundary of the limbus, the optical axis of the eye, the visual axis of the eye, the center of perspective, but are not limited to these. Determinations of such values, parameters, etc., as recited herein include estimations thereof and need not necessarily coincide precisely with the actual values. For example, determinations of the center of rotation of the eye, the center of curvature of the cornea, the center or boundary of the pupil or iris, the boundary of the limbus, the optical axis of the eye, the visual axis of the eye, the center of perspective, etc., may be estimations, approximations, or values close to, but not the same as, the actual (e.g., anatomical, optical, or geometric) values or parameters. In some cases, for example, root mean square estimation techniques are used to obtain estimates of such values. As an example, certain techniques described herein relate to identifying a location or point at which rays or vectors intersect. Such rays or vectors, however, may not intersect. In this example, the location or point may be estimated. For example, the location or point may be determined based on root mean square, or other, estimation techniques (e.g., the location or point may be estimated to be close to or the closest to the rays or vectors). Other processes may also be used to estimate, approximate or otherwise provide a value that may not coincide with the actual value. Accordingly, the term determining and estimating, or determined and estimated, are used interchangeably herein. Reference to such determined values may therefore include estimates, approximations, or values close to the actual value. Accordingly, reference to determining a parameter or value above, or elsewhere herein should not be limited precisely to the actual value but may include estimations, approximations or values close thereto.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIG. 5A schematically illustrates an example coordinate system for determining an eye pose of an eye

FIG. 23A illustrates an embodiment of an optical system in a first stage.

FIG. 24A illustrates another embodiment of an optical system in a first stage.

Figure 1:
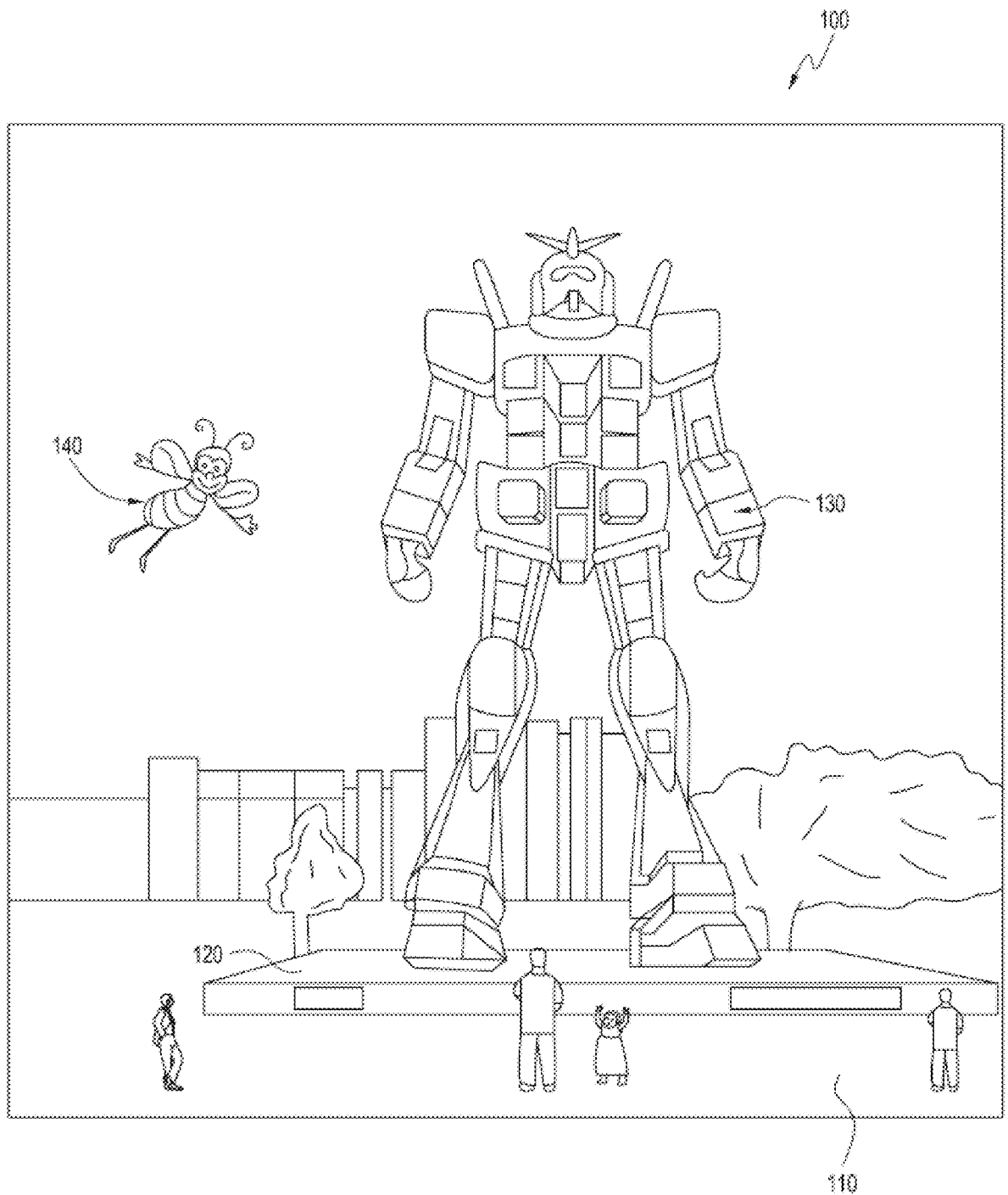
FIG. 1 depicts an illustration of a mixed reality scenario with certain virtual reality objects, and certain physical objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

Reference will now be made to the drawings, in which like reference numerals refer to like parts throughout. Unless indicated otherwise, the drawings are schematic not necessarily drawn to scale.

Examples of 3D Display of a Wearable System

A wearable system (also referred to herein as an augmented reality (AR) system) can be configured to present 2D or 3D virtual images to a user. The images may be still images, frames of a video, or a video, in combination or the like. At least a portion of the wearable system can be implemented on a wearable device that can present a VR, AR, or MR environment, alone or in combination, for user interaction. The wearable device can be used interchangeably as an AR device (ARD). Further, for the purpose of the present disclosure, the term "AR" is used interchangeably with the term "MR".

FIG. 1 depicts an illustration of a mixed reality scenario with certain virtual reality objects, and certain physical objects viewed by a person. In FIG. 1, an MR scene 100 is depicted wherein a user of an MR technology sees a real-world park-like setting 110 featuring people, trees, buildings in the background, and a concrete platform 120. In addition to these items, the user of the MR technology also perceives that he "sees" a robot statue 130 standing upon the real-world platform 120, and a cartoon-like avatar character 140 flying by which seems to be a personification of a bumble bee, even though these elements do not exist in the real world.

In order for the 3D display to produce a true sensation of depth, and more specifically, a simulated sensation of surface depth, it may be desirable for each point in the display's visual field to generate an accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

VR, AR, and MR experiences can be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth plane or based on observing different image features on different depth planes being out of focus. As discussed elsewhere herein, such depth cues provide credible perceptions of depth.

Figure 2:
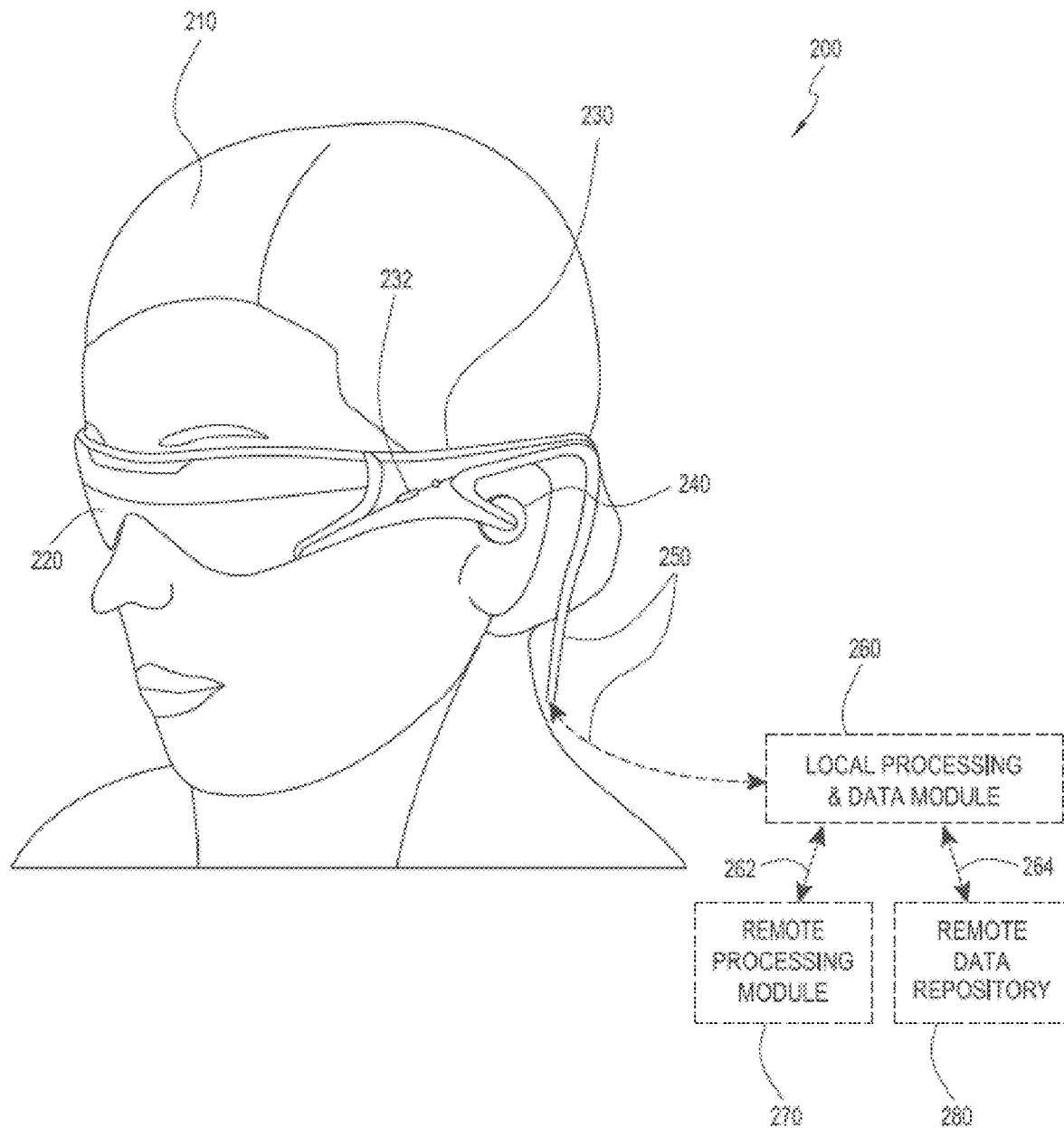
FIG. 2 schematically illustrates an example of a wearable system.

FIG. 2 illustrates an example of wearable system 200 which can be configured to provide an AR/VR/MR scene. The wearable system 200 can also be referred to as the AR system 200. The wearable system 200 includes a display 220, and various mechanical and electronic modules and systems to support the functioning of display 220. The display 220 may be coupled to a frame 230, which is wearable by a user, wearer, or viewer 210. The display 220 can be positioned in front of the eyes of the user 210. The display 220 can present AR/VR/MR content to a user. The display 220 can comprise a head mounted display (HMD) that is worn on the head of the user.

In some embodiments, a speaker 240 is coupled to the frame 230 and positioned adjacent the ear canal of the user (in some embodiments, another speaker, not shown, is positioned adjacent the other ear canal of the user to provide for stereo/shapeable sound control). The display 220 can include an audio sensor (e.g., a microphone) 232 for detecting an audio stream from the environment and capture ambient sound. In some embodiments, one or more other audio sensors, not shown, are positioned to provide stereo sound reception. Stereo sound reception can be used to determine the location of a sound source. The wearable system 200 can perform voice or speech recognition on the audio stream.

The wearable system 200 can include an outward-facing imaging system 464 (shown in FIG. 4) which observes the world in the environment around the user. The wearable system 200 can also include an inward-facing imaging system 462 (shown in FIG. 4) which can track the eye movements of the user. The inward-facing imaging system may track either one eye's movements or both eyes' movements. The inward-facing imaging system 462 may be attached to the frame 230 and may be in electrical communication with the processing modules 260 or 270, which may process image information acquired by the inward-facing imaging system to determine, e.g., the pupil diameters or orientations of the eyes, eye movements or eye pose of the user 210. The inward-facing imaging system 462 may include one or more cameras. For example, at least one camera may be used to image each eye. The images acquired by the cameras may be used to determine pupil size or eye pose for each eye separately, thereby allowing presentation of image information to each eye to be dynamically tailored to that eye.

As an example, the wearable system 200 can use the outward-facing imaging system 464 or the inward-facing imaging system 462 to acquire images of a pose of the user. The images may be still images, frames of a video, or a video.

The display 220 can be operatively coupled 250, such as by a wired lead or wireless connectivity, to a local data processing module 260 which may be mounted in a variety of configurations, such as fixedly attached to the frame 230, fixedly attached to a helmet or hat worn by the user, embedded in headphones, or otherwise removably attached to the user 210 (e.g., in a backpack-style configuration, in a belt-coupling style configuration).

The local processing and data module 260 may comprise a hardware processor, as well as digital memory, such as non-volatile memory (e.g., flash memory), both of which may be utilized to assist in the processing, caching, and storage of data. The data may include data a) captured from sensors (which may be, e.g., operatively coupled to the frame 230 or otherwise attached to the user 210), such as image capture devices (e.g., cameras in the inward-facing imaging system or the outward-facing imaging system), audio sensors (e.g., microphones), inertial measurement units (IMUs), accelerometers, compasses, global positioning system (GPS) units, radio devices, or gyroscopes; orb) acquired or processed using remote processing module 270 or remote data repository 280, possibly for passage to the display 220 after such processing or retrieval. The local processing and data module 260 may be operatively coupled by communication links 262 or 264, such as via wired or wireless communication links, to the remote processing module 270 or remote data repository 280 such that these remote modules are available as resources to the local processing and data module 260. In addition, remote processing module 280 and remote data repository 280 may be operatively coupled to each other.

In some embodiments, the remote processing module 270 may comprise one or more processors configured to analyze and process data or image information. In some embodiments, the remote data repository 280 may comprise a digital data storage facility, which may be available through the internet or other networking configuration in a "cloud" resource configuration. In some embodiments, all data is stored and all computations are performed in the local processing and data module, allowing fully autonomous use from a remote module.

Example Components of a Wearable System

Figure 3:
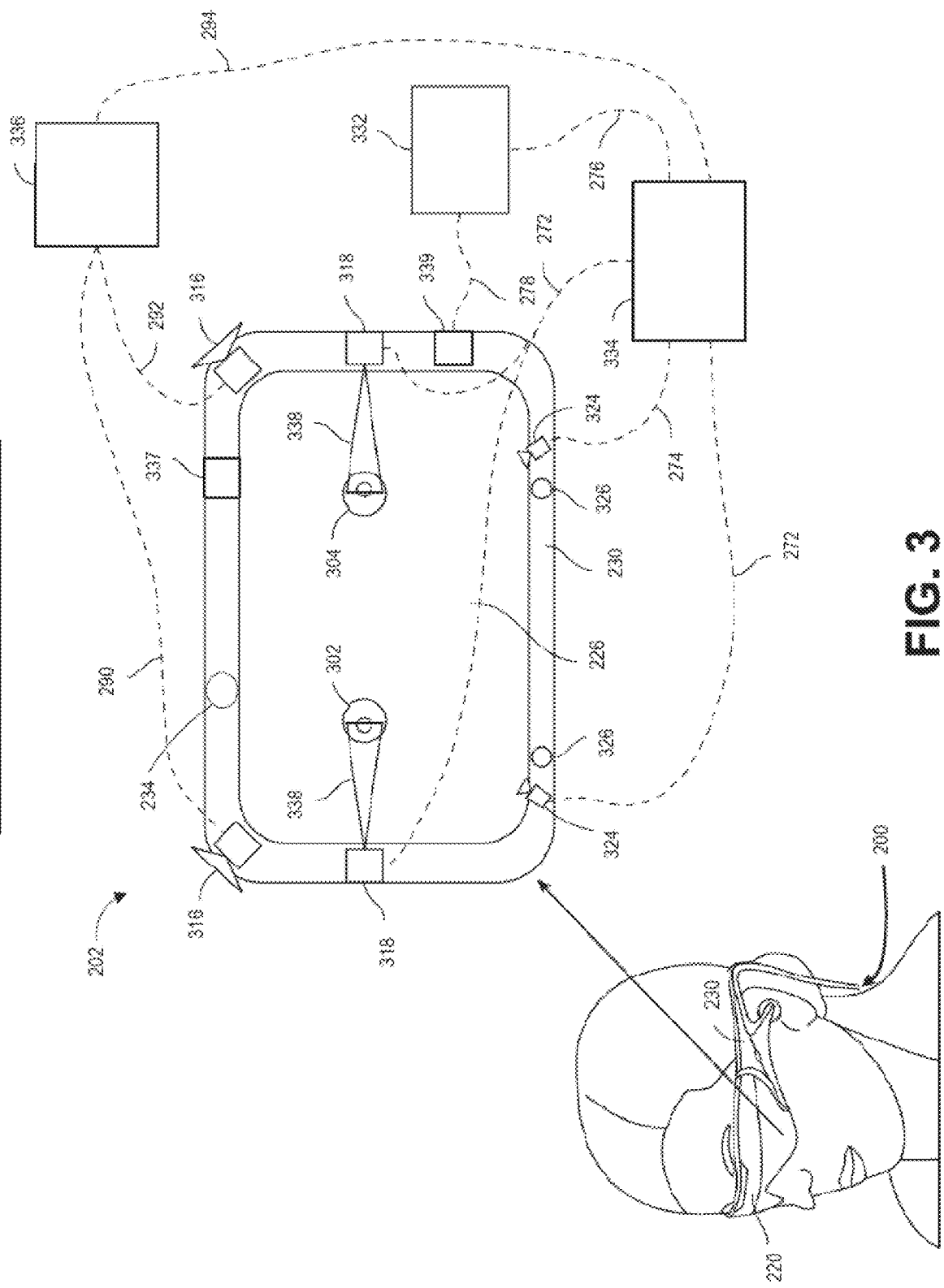
FIG. 3 schematically illustrates example components of a wearable system.

FIG. 3 schematically illustrates example components of a wearable system. FIG. 3 shows a wearable system 200 which can include a display 220 and a frame 230. A blown-up view 202 schematically illustrates various components of the wearable system 200. In certain implements, one or more of the components illustrated in FIG. 3 can be part of the display 220. The various components alone or in combination can collect a variety of data (such as e.g., audio or visual data) associated with the user of the wearable system 200 or the user's environment. It should be appreciated that other embodiments may have additional or fewer components depending on the application for which the wearable system is used. Nevertheless, FIG. 3 provides a basic idea of some of the various components and types of data that may be collected, analyzed, and stored through the wearable system.

FIG. 3 shows an example wearable system 200 which can include the display 220. The display 220 can comprise a display lens 226 that may be mounted to a user's head or a housing or frame 230, which corresponds to the frame 230. The display lens 226 may comprise one or more transparent mirrors positioned by the housing 230 in front of the user's eyes 302, 304 and may be configured to bounce projected light 338 into the eyes 302, 304 and facilitate beam shaping, while also allowing for transmission of at least some light from the local environment. The wavefront of the projected light beam 338 may be bent or focused to coincide with a desired focal distance of the projected light. As illustrated, two wide-field-of-view machine vision cameras 316 (also referred to as world cameras) can be coupled to the housing 230 to image the environment around the user. These cameras 316 can be dual capture visible light/non-visible (e.g., infrared) light cameras. The cameras 316 may be part of the outward-facing imaging system 464 shown in FIG. 4. Image acquired by the world cameras 316 can be processed by the pose processor 336. For example, the pose processor 336 can implement one or more object recognizers 708 (e.g., shown in FIG. 7) to identify a pose of a user or another person in the user's environment or to identify a physical object in the user's environment.

With continued reference to FIG. 3, a pair of scanned-laser shaped-wavefront (e.g., for depth) light projector modules with display mirrors and optics configured to project light 338 into the eyes 302, 304 are shown. The depicted view also shows two miniature infrared cameras 324 paired with infrared light sources 326 (such as light emitting diodes "LED"s), which are configured to be able to track the eyes 302, 304 of the user to support rendering and user input. The cameras 324 may be part of the inward-facing imaging system 462 shown in FIG. 4. The wearable system 200 can further feature a sensor assembly 339, which may comprise X, Y, and Z axis accelerometer capability as well as a magnetic compass and X, Y, and Z axis gyro capability, preferably providing data at a relatively high frequency, such as 200 Hz. The sensor assembly 339 may be part of the IMU described with reference to FIG. 2A The depicted system 200 can also comprise a head pose processor 336, such as an ASIC (application specific integrated circuit), FPGA (field programmable gate array), or ARM processor (advanced reduced-instruction-set machine), which may be configured to calculate real or near-real time user head pose from wide field of view image information output from the capture devices 316. The head pose processor 336 can be a hardware processor and can be implemented as part of the local processing and data module 260 shown in FIG. 2A.

The wearable system can also include one or more depth sensors 234. The depth sensor 234 can be configured to measure the distance between an object in an environment to a wearable device. The depth sensor 234 may include a laser scanner (e.g., a lidar), an ultrasonic depth sensor, or a depth sensing camera. In certain implementations, where the cameras 316 have depth sensing ability, the cameras 316 may also be considered as depth sensors 234.

Also shown is a processor 332 configured to execute digital or analog processing to derive pose from the gyro, compass, or accelerometer data from the sensor assembly 339. The processor 332 may be part of the local processing and data module 260 shown in FIG. 2. The wearable system 200 as shown in FIG. 3 can also include a position system such as, e.g., a GPS 337 (global positioning system) to assist with pose and positioning analyses. In addition, the GPS may further provide remotely-based (e.g., cloud-based) information about the user's environment. This information may be used for recognizing objects or information in user's environment.

The wearable system may combine data acquired by the GPS 337 and a remote computing system (such as, e.g., the remote processing module 270, another user's ARD, etc.) which can provide more information about the user's environment. As one example, the wearable system can determine the user's location based on GPS data and retrieve a world map (e.g., by communicating with a remote processing module 270) including virtual objects associated with the user's location. As another example, the wearable system 200 can monitor the environment using the world cameras 316 (which may be part of the outward-facing imaging system 464 shown in FIG. 4). Based on the images acquired by the world cameras 316, the wearable system 200 can detect objects in the environment (e.g., by using one or more object recognizers 708 shown in FIG. 7). The wearable system can further use data acquired by the GPS 337 to interpret the characters.

The wearable system 200 may also comprise a rendering engine 334 which can be configured to provide rendering information that is local to the user to facilitate operation of the scanners and imaging into the eyes of the user, for the user's view of the world. The rendering engine 334 may be implemented by a hardware processor (such as, e.g., a central processing unit or a graphics processing unit). In some embodiments, the rendering engine is part of the local processing and data module 260. The rendering engine 334 can be communicatively coupled (e.g., via wired or wireless links) to other components of the wearable system 200. For example, the rendering engine 334, can be coupled to the eye cameras 324 via communication link 274, and be coupled to a projecting subsystem 318 (which can project light into user's eyes 302, 304 via a scanned laser arrangement in a manner similar to a retinal scanning display) via the communication link 272. The rendering engine 334 can also be in communication with other processing units such as, e.g., the sensor pose processor 332 and the image pose processor 336 via links 276 and 294 respectively.

The cameras 324 (e.g., mini infrared cameras) may be utilized to track the eye pose to support rendering and user input. Some example eye poses may include where the user is looking or at what depth he or she is focusing (which may be estimated with eye vergence). The GPS 337, gyros, compass, and accelerometers 339 may be utilized to provide coarse or fast pose estimates. One or more of the cameras 316 can acquire images and pose, which in conjunction with data from an associated cloud computing resource, may be utilized to map the local environment and share user views with others.

The example components depicted in FIG. 3 are for illustration purposes only. Multiple sensors and other functional modules are shown together for ease of illustration and description. Some embodiments may include only one or a subset of these sensors or modules. Further, the locations of these components are not limited to the positions depicted in FIG. 3. Some components may be mounted to or housed within other components, such as a belt-mounted component, a hand-held component, or a helmet component. As one example, the image pose processor 336, sensor pose processor 332, and rendering engine 334 may be positioned in a beltpack and configured to communicate with other components of the wearable system via wireless communication, such as ultra-wideband, Wi-Fi, Bluetooth, etc., or via wired communication. The depicted housing 230 preferably is head-mountable and wearable by the user. However, some components of the wearable system 200 may be worn to other portions of the user's body. For example, the speaker 240 may be inserted into the ears of a user to provide sound to the user.

Regarding the projection of light 338 into the eyes 302, 304 of the user, in some embodiment, the cameras 324 may be utilized to measure where the centers of a user's eyes are geometrically verged to, which, in general, coincides with a position of focus, or "depth of focus", of the eyes. A 3-dimensional surface of all points the eyes verge to can be referred to as the "horopter". The focal distance may take on a finite number of depths, or may be infinitely varying. Light projected from the vergence distance appears to be focused to the subject eye 302, 304, while light in front of or behind the vergence distance is blurred. Examples of wearable devices and other display systems of the present disclosure are also described in U.S. Patent Publication No. 2016/0270656, which is incorporated by reference herein in its entirety.

The human visual system is complicated and providing a realistic perception of depth is challenging. Viewers of an object may perceive the object as being three-dimensional due to a combination of vergence and accommodation. Vergence movements (e.g., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic and comfortable simulations of three-dimensional imagery.

Further spatially coherent light with a beam diameter of less than about 0.7 millimeters can be correctly resolved by the human eye regardless of where the eye focuses. Thus, to create an illusion of proper focal depth, the eye vergence may be tracked with the cameras 324, and the rendering engine 334 and projection subsystem 318 may be utilized to render all objects on or close to the horopter in focus, and all other objects at varying degrees of defocus (e.g., using intentionally-created blurring). Preferably, the system 220 renders to the user at a frame rate of about 60 frames per second or greater. As described above, preferably, the cameras 324 may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system 220 may be integrated with a localization system, which may involve GPS elements, optical tracking, compass, accelerometers, or other data sources, to assist with position and pose determination; localization information may be utilized to facilitate accurate rendering in the user's view of the pertinent world (e.g., such information would facilitate the glasses to know where they are with respect to the real world).

In some embodiments, the wearable system 200 is configured to display one or more virtual images based on the accommodation of the user's eyes. Unlike prior 3D display approaches that force the user to focus where the images are being projected, in some embodiments, the wearable system is configured to automatically vary the focus of projected virtual content to allow for a more comfortable viewing of one or more images presented to the user. For example, if the user's eyes have a current focus of 1 m, the image may be projected to coincide with the user's focus. If the user shifts focus to 3 m, the image is projected to coincide with the new focus. Thus, rather than forcing the user to a predetermined focus, the wearable system 200 of some embodiments allows the user's eye to a function in a more natural manner.

Such a wearable system 200 may eliminate or reduce the incidences of eye strain, headaches, and other physiological symptoms typically observed with respect to virtual reality devices. To achieve this, various embodiments of the wearable system 200 are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, wearable system 200 may employ eye tracking to determine a vergence of the user's eyes, determine the user's current focus, and project the virtual image at the determined focus. In other embodiments, wearable system 200 comprises a light modulator that variably projects, through a fiber scanner, or other light generating source, light beams of varying focus in a raster pattern across the retina. Thus, the ability of the display of the wearable system 200 to project images at varying focal distances not only eases accommodation for the user to view objects in 3D, but may also be used to compensate for user ocular anomalies, as further described in U.S. Patent Publication No. 2016/0270656, which is incorporated by reference herein in its entirety. In some other embodiments, a spatial light modulator may project the images to the user through various optical components. For example, as described further below, the spatial light modulator may project the images onto one or more waveguides, which then transmit the images to the user.

Waveguide Stack Assembly

Figure 4:
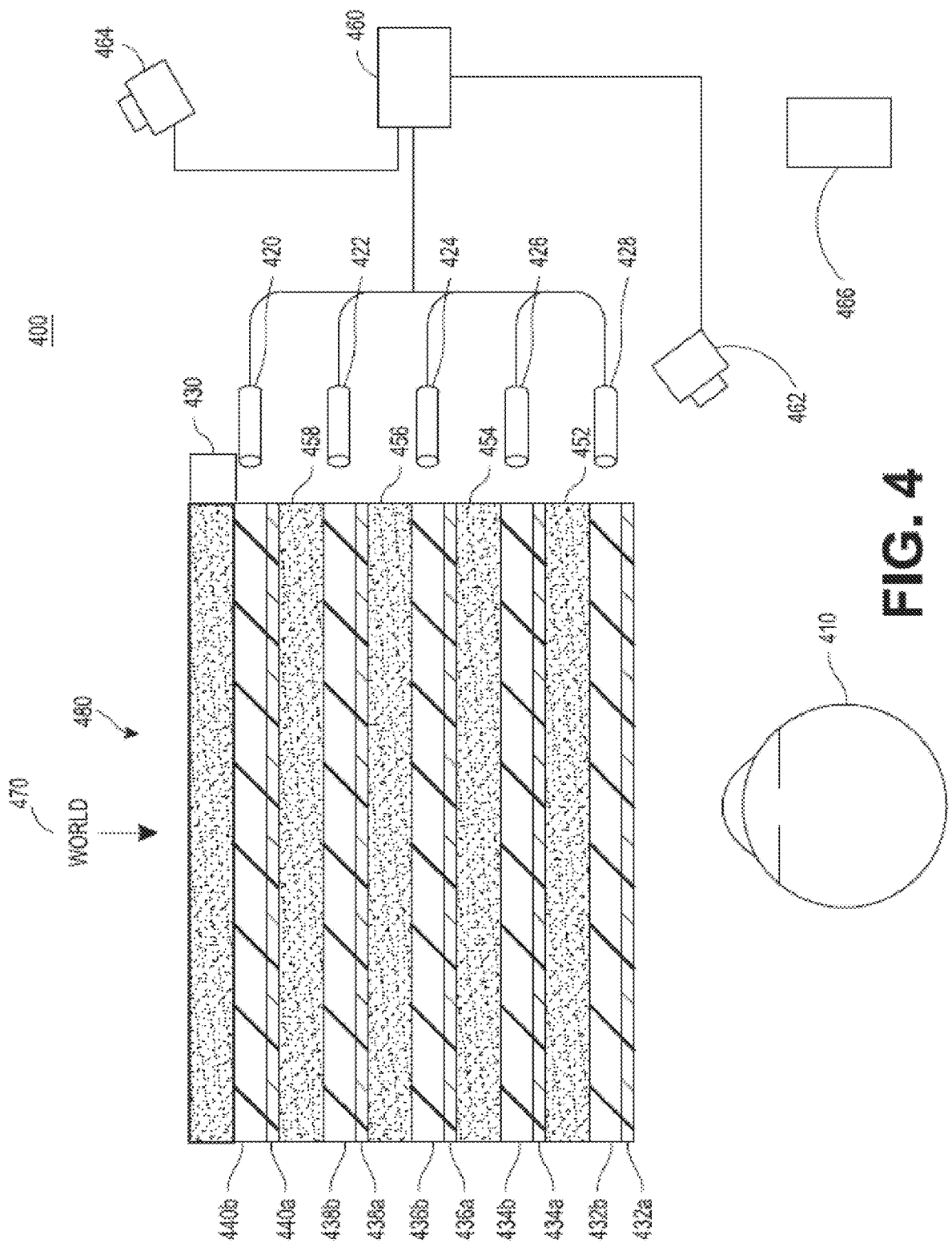
FIG. 4 schematically illustrates an example of a waveguide stack of a wearable device for outputting image information to a user.

FIG. 4 illustrates an example of a waveguide stack for outputting image information to a user. A wearable system 400 includes a stack of waveguides, or stacked waveguide assembly 480 that may be utilized to provide three-dimensional perception to the eye/brain using a plurality of waveguides 432b, 434b, 436b, 438b, 4400b. In some embodiments, the wearable system 400 may correspond to wearable system 200 of FIG. 2, with FIG. 4 schematically showing some parts of that wearable system 200 in greater detail. For example, in some embodiments, the waveguide assembly 480 may be integrated into the display 220 of FIG. 2.

With continued reference to FIG. 4, the waveguide assembly 480 may also include a plurality of features 458, 456, 454, 452 between the waveguides. In some embodiments, the features 458, 456, 454, 452 may be lenses. In other embodiments, the features 458, 456, 454, 452 may not be lenses. Rather, they may simply be spacers (e.g., cladding layers or structures for forming air gaps).

The waveguides 432b, 434b, 436b, 438b, 440b or the plurality of lenses 458, 456, 454, 452 may be configured to send image information to the eye with various levels of wavefront curvature or light ray divergence. Each waveguide level may be associated with a particular depth plane and may be configured to output image information corresponding to that depth plane. Image injection devices 420, 422, 424, 426, 428 may be utilized to inject image information into the waveguides 440b, 438b, 436b, 434b, 432b, each of which may be configured to distribute incoming light across each respective waveguide, for output toward the eye 410. Light exits an output surface of the image injection devices 420, 422, 424, 426, 428 and is injected into a corresponding input edge of the waveguides 440b, 438b, 436b, 434b, 432b. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 420, 422, 424, 426, 428 are discrete displays that each produce image information for injection into a corresponding waveguide 440b, 438b, 436b, 434b, 432b, respectively. In some other embodiments, the image injection devices 420, 422, 424, 426, 428 are the output ends of a single multiplexed display which may, e.g., pipe image information via one or more optical conduits (such as fiber optic cables) to each of the image injection devices 420, 422, 424, 426, 428.

A controller 460 controls the operation of the stacked waveguide assembly 480 and the image injection devices 420, 422, 424, 426, 428. The controller 460 includes programming (e.g., instructions in a non-transitory computer-readable medium) that regulates the timing and provision of image information to the waveguides 440b, 438b, 436b, 434b, 432b. In some embodiments, the controller 460 may be a single integral device, or a distributed system connected by wired or wireless communication channels. The controller 460 may be part of the processing modules 260 or 270 (illustrated in FIG. 2) in some embodiments.

The waveguides 440b, 438b, 436b, 434b, 432b may be configured to propagate light within each respective waveguide by total internal reflection (TIR). The waveguides 440b, 438b, 436b, 434b, 432b may each be planar or have another shape (e.g., curved), with major top and bottom surfaces and edges extending between those major top and bottom surfaces. In the illustrated configuration, the waveguides 440b, 438b, 436b, 434b, 432b may each include light extracting optical elements 440a, 438a, 436a, 434a, 432a that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (440a, 438a, 436a, 434a, 432a) may, for example, be reflective or diffractive optical features. While illustrated disposed at the bottom major surfaces of the waveguides 440b, 438b, 436b, 434b, 432b for ease of description and drawing clarity, in some embodiments, the light extracting optical elements 440a, 438a, 436a, 434a, 432a may be disposed at the top or bottom major surfaces, or may be disposed directly in the volume of the waveguides 440b, 438b, 436b, 434b, 432b. In some embodiments, the light extracting optical elements 440a, 438a, 436a, 434a, 432a may be formed in a layer of material that is attached to a transparent substrate to form the waveguides 440b, 438b, 436b, 434b, 432b. In some other embodiments, the waveguides 440b, 438b, 436b, 434b, 432b may be a monolithic piece of material and the light extracting optical elements 440a, 438a, 436a, 434a, 432a may be formed on a surface or in the interior of that piece of material.

With continued reference to FIG. 4, as discussed herein, each waveguide 440b, 438b, 436b, 434b, 432b is configured to output light to form an image corresponding to a particular depth plane. For example, the waveguide 432b nearest the eye may be configured to deliver collimated light, as injected into such waveguide 432b, to the eye 410. The collimated light may be representative of the optical infinity focal plane. The next waveguide up 434b may be configured to send out collimated light which passes through the first lens 452 (e.g., a negative lens) before it can reach the eye 410. First lens 452 may be configured to create a slight convex wavefront curvature so that the eye/brain interprets light coming from that next waveguide up 434b as coming from a first focal plane closer inward toward the eye 410 from optical infinity. Similarly, the third up waveguide 436b passes its output light through both the first lens 452 and second lens 454 before reaching the eye 410. The combined optical power of the first and second lenses 452 and 454 may be configured to create another incremental amount of wavefront curvature so that the eye/brain interprets light coming from the third waveguide 436b as coming from a second focal plane that is even closer inward toward the person from optical infinity than was light from the next waveguide up 434b.

The other waveguide layers (e.g., waveguides 438b, 440b) and lenses (e.g., lenses 456, 458) are similarly configured, with the highest waveguide 440b in the stack sending its output through all of the lenses between it and the eye for an aggregate focal power representative of the closest focal plane to the person. To compensate for the stack of lenses 458, 456, 454, 452 when viewing/interpreting light coming from the world 470 on the other side of the stacked waveguide assembly 480, a compensating lens layer 430 may be disposed at the top of the stack to compensate for the aggregate power of the lens stack 458, 456, 454, 452 below. (Compensating lens layer 430 and the stacked waveguide assembly 480 as a whole may be configured such that light coming from the world 470 is conveyed to the eye 410 at substantially the same level of divergence (or collimation) as the light had when it was initially received by the stacked waveguide assembly 480.) Such a configuration provides as many perceived focal planes as there are available waveguide/lens pairings. Both the light extracting optical elements of the waveguides and the focusing aspects of the lenses may be static (e.g., not dynamic or electro-active). In some alternative embodiments, either or both may be dynamic using electro-active features.

With continued reference to FIG. 4, the light extracting optical elements 440a, 438a, 436a, 434a, 432a may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 440a, 438a, 436a, 434a, 432a may be volumetric or surface features, which may be configured to output light at specific angles. For example, the light extracting optical elements 440a, 438a, 436a, 434a, 432a may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety.

In some embodiments, the light extracting optical elements 440a, 438a, 436a, 434a, 432a are diffractive features that form a diffraction pattern, or "diffractive optical element" (also referred to herein as a "DOE"). Preferably, the DOE has a relatively low diffraction efficiency so that only a portion of the light of the beam is deflected away toward the eye 410 with each intersection of the DOE, while the rest continues to move through a waveguide via total internal reflection. The light carrying the image information can thus be divided into a number of related exit beams that exit the waveguide at a multiplicity of locations and the result is a fairly uniform pattern of exit emission toward the eye 304 for this particular collimated beam bouncing around within a waveguide.

In some embodiments, one or more DOEs may be switchable between "on" state in which they actively diffract, and "off" state in which they do not significantly diffract. For instance, a switchable DOE may comprise a layer of polymer dispersed liquid crystal, in which microdroplets comprise a diffraction pattern in a host medium, and the refractive index of the microdroplets can be switched to substantially match the refractive index of the host material (in which case the pattern does not appreciably diffract incident light) or the microdroplet can be switched to an index that does not match that of the host medium (in which case the pattern actively diffracts incident light).

In some embodiments, the number and distribution of depth planes or depth of field may be varied dynamically based on the pupil sizes or orientations of the eyes of the viewer. Depth of field may change inversely with a viewer's pupil size. As a result, as the sizes of the pupils of the viewer's eyes decrease, the depth of field increases such that one plane that is not discernible because the location of that plane is beyond the depth of focus of the eye may become discernible and appear more in focus with reduction of pupil size and commensurate with the increase in depth of field. Likewise, the number of spaced apart depth planes used to present different images to the viewer may be decreased with the decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size or orientation, or upon receiving electrical signals indicative of particular pupil size or orientation. For example, if the user's eyes are unable to distinguish between two depth planes associated with two waveguides, then the controller 460 (which may be an embodiment of the local processing and data module 260) can be configured or programmed to cease providing image information to one of these waveguides. Advantageously, this may reduce the processing burden on the system, thereby increasing the responsiveness of the system. In embodiments in which the DOEs for a waveguide are switchable between the on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The wearable system 400 can include an outward-facing imaging system 464 (e.g., a digital camera) that images a portion of the world 470. This portion of the world 470 may be referred to as the field of view (FOV) of a world camera and the imaging system 464 is sometimes referred to as an FOV camera. The FOV of the world camera may or may not be the same as the FOV of a viewer 210 which encompasses a portion of the world 470 the viewer 210 perceives at a given time. For example, in some situations, the FOV of the world camera may be larger than the viewer 210 of the viewer 210 of the wearable system 400. The entire region available for viewing or imaging by a viewer may be referred to as the field of regard (FOR). The FOR may include 4π steradians of solid angle surrounding the wearable system 400 because the wearer can move his body, head, or eyes to perceive substantially any direction in space. In other contexts, the wearer's movements may be more constricted, and accordingly the wearer's FOR may subtend a smaller solid angle. Images obtained from the outward-facing imaging system 464 can be used to track gestures made by the user (e.g., hand or finger gestures), detect objects in the world 470 in front of the user, and so forth.

The wearable system 400 can include an audio sensor 232, e.g., a microphone, to capture ambient sound. As described above, in some embodiments, one or more other audio sensors can be positioned to provide stereo sound reception useful to the determination of location of a speech source. The audio sensor 232 can comprise a directional microphone, as another example, which can also provide such useful directional information as to where the audio source is located. The wearable system 400 can use information from both the outward-facing imaging system 464 and the audio sensor 230 in locating a source of speech, or to determine an active speaker at a particular moment in time, etc. For example, the wearable system 400 can use the voice recognition alone or in combination with a reflected image of the speaker (e.g., as seen in a mirror) to determine the identity of the speaker. As another example, the wearable system 400 can determine a position of the speaker in an environment based on sound acquired from directional microphones. The wearable system 400 can parse the sound coming from the speaker's position with speech recognition algorithms to determine the content of the speech and use voice recognition techniques to determine the identity (e.g., name or other demographic information) of the speaker.

The wearable system 400 can also include an inward-facing imaging system 466 (e.g., a digital camera), which observes the movements of the user, such as the eye movements and the facial movements. The inward-facing imaging system 466 may be used to capture images of the eye 410 to determine the size and/or orientation of the pupil of the eye 304. The inward-facing imaging system 466 can be used to obtain images for use in determining the direction the user is looking (e.g., eye pose) or for biometric identification of the user (e.g., via iris identification). In some embodiments, at least one camera may be utilized for each eye, to separately determine the pupil size or eye pose of each eye independently, thereby allowing the presentation of image information to each eye to be dynamically tailored to that eye. In some other embodiments, the pupil diameter or orientation of only a single eye 410 (e.g., using only a single camera per pair of eyes) is determined and assumed to be similar for both eyes of the user. The images obtained by the inward-facing imaging system 466 may be analyzed to determine the user's eye pose or mood, which can be used by the wearable system 400 to decide which audio or visual content should be presented to the user. The wearable system 400 may also determine head pose (e.g., head position or head orientation) using sensors such as IMUs, accelerometers, gyroscopes, etc.

The wearable system 400 can include a user input device 466 by which the user can input commands to the controller 460 to interact with the wearable system 400. For example, the user input device 466 can include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. A multi-DOF controller can sense user input in some or all possible translations (e.g., left/right, forward/backward, or up/down) or rotations (e.g., yaw, pitch, or roll) of the controller. A multi-DOF controller which supports the translation movements may be referred to as a 3DOF while a multi-DOF controller which supports the translations and rotations may be referred to as 6DOF. In some cases, the user may use a finger (e.g., a thumb) to press or swipe on a touch-sensitive input device to provide input to the wearable system 400 (e.g., to provide user input to a user interface provided by the wearable system 400). The user input device 466 may be held by the user's hand during the use of the wearable system 400. The user input device 466 can be in wired or wireless communication with the wearable system 400.

Other Components of the Wearable System

In many implementations, the wearable system may include other components in addition or in alternative to the components of the wearable system described above. The wearable system may, for example, include one or more haptic devices or components. The haptic devices or components may be operable to provide a tactile sensation to a user. For example, the haptic devices or components may provide a tactile sensation of pressure or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents. In some implementations, haptic devices or components may be worn by the user (e.g., a user wearable glove). In some implementations, haptic devices or components may be held by the user.

The wearable system may, for example, include one or more physical objects which are manipulable by the user to allow input or interaction with the wearable system. These physical objects may be referred to herein as totems. Some totems may take the form of inanimate objects, such as for example, a piece of metal or plastic, a wall, a surface of table. In certain implementations, the totems may not actually have any physical input structures (e.g., keys, triggers, joystick, trackball, rocker switch). Instead, the totem may simply provide a physical surface, and the wearable system may render a user interface so as to appear to a user to be on one or more surfaces of the totem. For example, the wearable system may render an image of a computer keyboard and trackpad to appear to reside on one or more surfaces of a totem. For example, the wearable system may render a virtual computer keyboard and virtual trackpad to appear on a surface of a thin rectangular plate of aluminum which serves as a totem. The rectangular plate does not itself have any physical keys or trackpad or sensors. However, the wearable system may detect user manipulation or interaction or touches with the rectangular plate as selections or inputs made via the virtual keyboard or virtual trackpad. The user input device 466 (shown in FIG. 4) may be an embodiment of a totem, which may include a trackpad, a touchpad, a trigger, a joystick, a trackball, a rocker or virtual switch, a mouse, a keyboard, a multi-degree-of-freedom controller, or another physical input device. A user may use the totem, alone or in combination with poses, to interact with the wearable system or other users.

Examples of haptic devices and totems usable with the wearable devices, HMD, and display systems of the present disclosure are described in U.S. Patent Publication No. 2015/0016777, which is incorporated by reference herein in its entirety.

Example of an Eye Image

Figure 5:
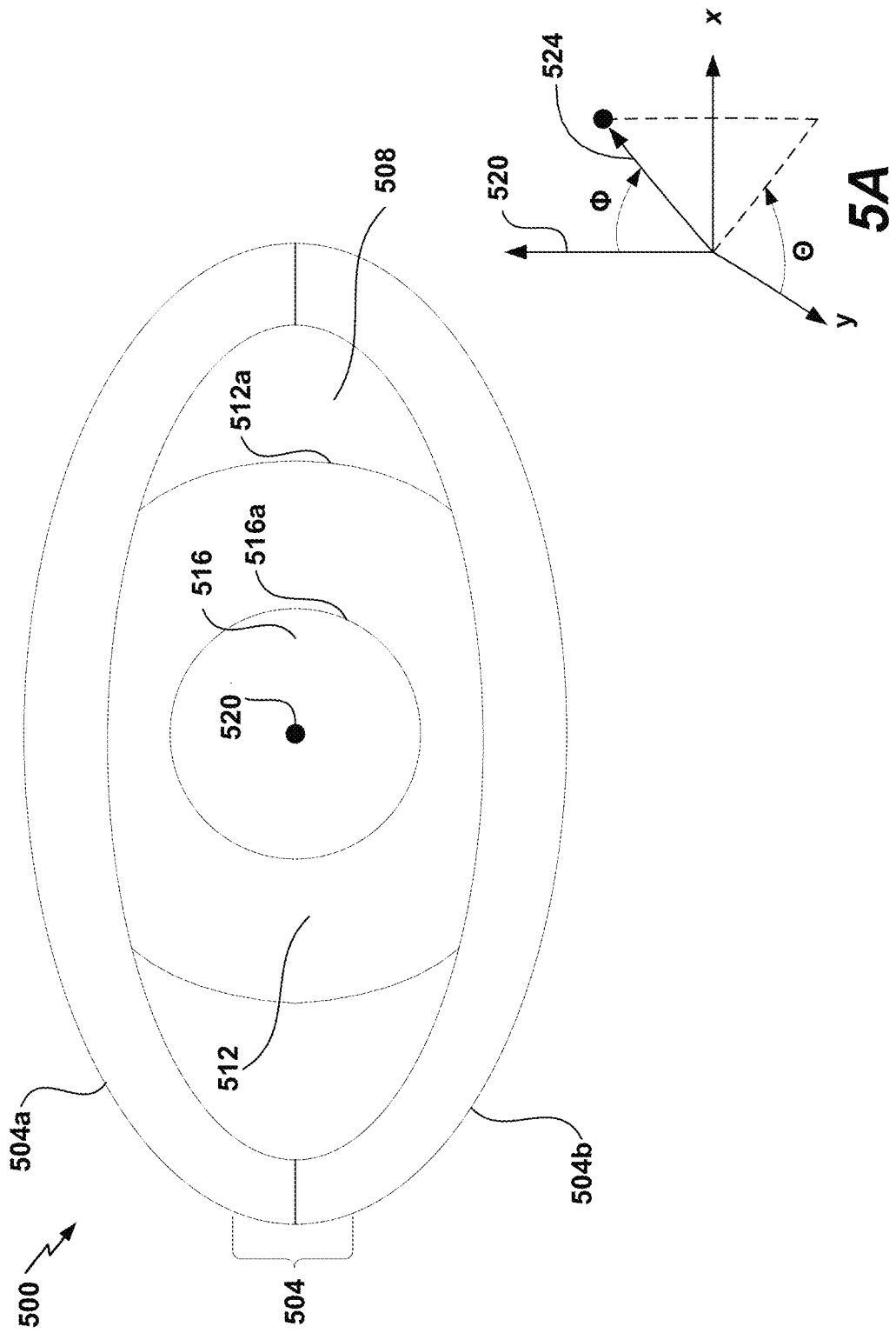
FIG. 5 schematically illustrates an example of an eye.

FIG. 5 illustrates an image of an eye 500 with eyelids 504, sclera 508 (the "white" of the eye), iris 512, and pupil 516. Curve 516a shows the pupillary boundary between the pupil 516 and the iris 512, and curve 512a shows the limbic boundary between the iris 512 and the sclera 508. The eyelids 504 include an upper eyelid 504a and a lower eyelid 504b. The eye 500 is illustrated in a natural resting pose (e.g., in which the user's face and gaze are both oriented as they would be toward a distant object directly ahead of the user). The natural resting pose of the eye 500 can be indicated by a natural resting direction 520, which is a direction orthogonal to the surface of the eye 500 when in the natural resting pose (e.g., directly out of the plane for the eye 500 shown in FIG. 5) and in this example, centered within the pupil 516.

As the eye 500 moves to look toward different objects, the eye pose will change relative to the natural resting direction 520. The current eye pose can be determined with reference to an eye pose direction 524, which is a direction orthogonal to the surface of the eye (and centered in within the pupil 516) but oriented toward the object at which the eye is currently directed. With reference to an example coordinate system shown in FIG. 5A, the pose of the eye 500 can be expressed as two angular parameters indicating an azimuthal deflection and a zenithal deflection of the eye pose direction 524 of the eye, both relative to the natural resting direction 520 of the eye. For purposes of illustration, these angular parameters can be represented as $\theta$ (azimuthal deflection, determined from a fiducial azimuth) and $\phi$ (zenithal deflection, sometimes also referred to as a polar deflection). In some implementations, angular roll of the eye around the eye pose direction 524 can be included in the determination of eye pose, and angular roll can be included in the following analysis. In other implementations, other techniques for determining the eye pose can be used, for example, a pitch, yaw, and optionally roll system.

An eye image can be obtained from a video using any appropriate process, for example, using a video processing algorithm that can extract an image from one or more sequential frames. The pose of the eye can be determined from the eye image using a variety of eye-tracking techniques. For example, an eye pose can be determined by considering the lensing effects of the cornea on light sources that are provided. Any suitable eye tracking technique can be used for determining eye pose in the eyelid shape estimation techniques described herein.

Example of an Eye Tracking System

Figure 6:
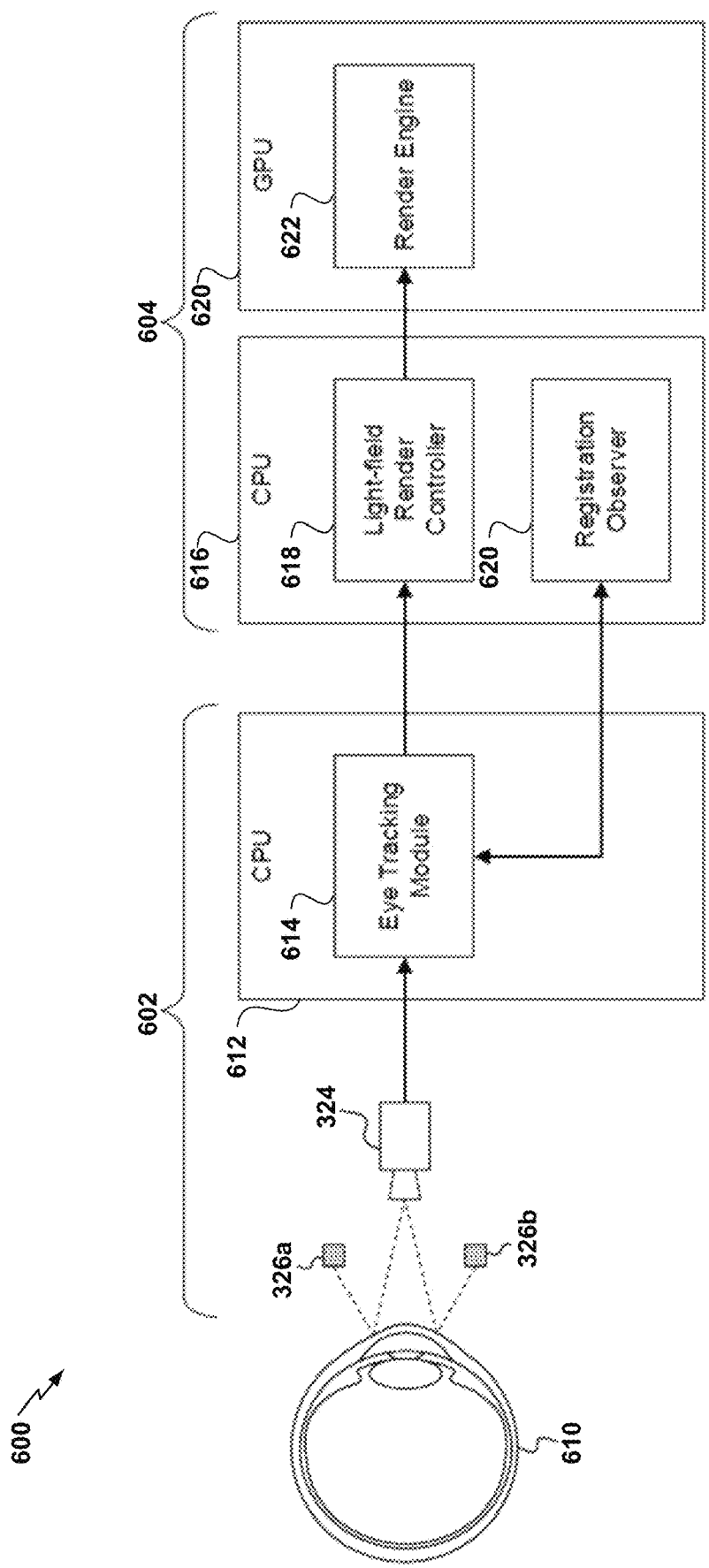
FIG. 6 is a schematic diagram of a wearable system that includes an eye tracking system.

FIG. 6 illustrates a schematic diagram of a wearable system 600 that includes an eye tracking system. The wearable system 600 may, in at least some embodiments, include components located in a head-mounted unit 602 and components located in a non-head-mounted unit 604. Non-head mounted unit 604 may be, as examples, a belt-mounted component, a hand-held component, a component in a backpack, a remote component, etc. Incorporating some of the components of the wearable system 600 in non-head-mounted unit 604 may help to reduce the size, weight, complexity, and cost of the head-mounted unit 602. In some implementations, some or all of the functionality described as being performed by one or more components of head-mounted unit 602 and/or non-head mounted 604 may be provided by way of one or more components included elsewhere in the wearable system 600. For example, some or all of the functionality described below in association with a CPU 612 of head-mounted unit 602 may be provided by way of a CPU 616 of non-head mounted unit 604, and vice versa. In some examples, some or all of such functionality may be provided by way of peripheral devices of wearable system 600. Furthermore, in some implementations, some or all of such functionality may be provided by way of one or more cloud computing devices or other remotely-located computing devices in a manner similar to that which has been described above with reference to FIG. 2.

As shown in FIG. 6, wearable system 600 can include an eye tracking system including a camera 324 that captures images of a user's eye 610. If desired, the eye tracking system may also include light sources 326a and 326b (such as light emitting diodes "LED"s). The light sources 326a and 326b may generate glints (e.g., reflections off of the user's eyes that appear in images of the eye captured by camera 324). The positions of the light sources 326a and 326b relative to the camera 324 may be known and, as a consequence, the positions of the glints within images captured by camera 324 may be used in tracking the user's eyes (as will be discussed in more detail below in connection with FIGS. 7-11). In at least one embodiment, there may be one light source 326 and one camera 324 associated with a single one of the user's eyes 610. In another embodiment, there may be one light source 326 and one camera 324 associated with each of a user's eyes. 610. In yet other embodiments, there may be one or more cameras 324 and one or more light sources 326 associated with one or each of a user's eyes 610. As a specific example, there may be two light sources 326a and 326b and one or more cameras 324 associated with each of a user's eyes 610. As another example, there may be three or more light sources such as light sources 326a and 326b and one or more cameras 324 associated with each of a user's eyes 610.

Eye tracking module 614 may receive images from eye tracking camera(s) 324 and may analyze the images to extract various pieces of information. As examples, the eye tracking module 614 may detect the user's eye poses, a three-dimensional position of the user's eye relative to the eye tracking camera 324 (and to the head-mounted unit 602), the direction one or both of the user's eyes 610 are focused on, the user's vergence depth (e.g., the depth from the user at which the user is focusing on), the positions of the user's pupils, the positions of the user's cornea and cornea sphere, the center of rotation of each of the user's eyes, and the center of perspective of each of the user's eyes. The eye tracking module 614 may extract such information using techniques described below in connection with FIGS. 7-11. As shown in FIG. 6, eye tracking module 614 may be a software module implemented using a CPU 612 in a head-mounted unit 602.

Data from eye tracking module 614 may be provided to other components in the wearable system. As example, such data may be transmitted to components in a non-head-mounted unit 604 such as CPU 616 including software modules for a light-field render controller 618 and a registration observer 620.

Render controller 618 may use information from eye tracking module 614 to adjust images displayed to the user by render engine 622 (e.g., a render engine that may be a software module in GPU 620 and that may provide images to display 220). As an example, the render controller 618 may adjust images displayed to the user based on the user's center of rotation or center of perspective. In particular, the render controller 618 may use information on the user's center of perspective to simulate a render camera (e.g., to simulate collecting images from the user's perspective) and may adjust images displayed to the user based on the simulated render camera.

A "render camera," which is sometimes also referred to as a "pinhole perspective camera" (or simply "perspective camera") or "virtual pinhole camera" (or simply "virtual camera"), is a simulated camera for use in rendering virtual image content possibly from a database of objects in a virtual world. The objects may have locations and orientations relative to the user or wearer and possibly relative to real objects in the environment surrounding the user or wearer. In other words, the render camera may represent a perspective within render space from which the user or wearer is to view 3D virtual contents of the render space (e.g., virtual objects). The render camera may be managed by a render engine to render virtual images based on the database of virtual objects to be presented to said eye. The virtual images may be rendered as if taken from the perspective the user or wearer. For example, the virtual images may be rendered as if captured by a pinhole camera (corresponding to the "render camera") having a specific set of intrinsic parameters (e.g., focal length, camera pixel size, principal point coordinates, skew/distortion parameters, etc.), and a specific set of extrinsic parameters (e.g., translational components and rotational components relative to the virtual world). The virtual images are taken from the perspective of such a camera having a position and orientation of the render camera (e.g., extrinsic parameters of the render camera). It follows that the system may define and/or adjust intrinsic and extrinsic render camera parameters. For example, the system may define a particular set of extrinsic render camera parameters such that virtual images may be rendered as if captured from the perspective of a camera having a specific location with respect to the user's or wearer's eye so as to provide images that appear to be from the perspective of the user or wearer. The system may later dynamically adjust extrinsic render camera parameters on-the-fly so as to maintain registration with said specific location. Similarly, intrinsic render camera parameters may be defined and dynamically adjusted over time. In some implementations, the images are rendered as if captured from the perspective of a camera having an aperture (e.g., pinhole) at a specific location with respect to the user's or wearer's eye (such as the center of perspective or center of rotation, or elsewhere).

In some embodiments, the system may create or dynamically reposition and/or reorient one render camera for the user's left eye, and another render camera for the user's right eye, as the user's eyes are physically separated from one another and thus consistently positioned at different locations. It follows that, in at least some implementations, virtual content rendered from the perspective of a render camera associated with the viewer's left eye may be presented to the user through an eyepiece on the left side of a head-mounted display (e.g., head-mounted unit 602), and that virtual content rendered from the perspective of a render camera associated with the user's right eye may be presented to the user through an eyepiece on the right side of such a head-mounted display. Further details discussing the creation, adjustment, and use of render cameras in rendering processes are provided in U.S. patent application Ser. No. 15/274,823, entitled "METHODS AND SYSTEMS FOR DETECTING AND COMBINING STRUCTURAL FEATURES IN 3D RECONSTRUCTION," which is expressly incorporated herein by reference in its entirety for all purposes.

In some examples, one or more modules (or components) of the system 600 (e.g., light-field render controller 618, render engine 620, etc.) may determine the position and orientation of the render camera within render space based on the position and orientation of the user's head and eyes (e.g., as determined based on head pose and eye tracking data, respectively). That is, the system 600 may effectively map the position and orientation of the user's head and eyes to particular locations and angular positions within a 3D virtual environment, place and orient render cameras at the particular locations and angular positions within the 3D virtual environment, and render virtual content for the user as it would be captured by the render camera. Further details discussing real world to virtual world mapping processes are provided in U.S. patent application Ser. No. 15/296,869, entitled "SELECTING VIRTUAL OBJECTS IN A THREE-DIMENSIONAL SPACE," which is expressly incorporated herein by reference in its entirety for all purposes. As an example, the render controller 618 may adjust the depths at which images are displayed by selecting which depth plane (or depth planes) are utilized at any given time to display the images. In some implementations, such a depth plane switch may be carried out through an adjustment of one or more intrinsic render camera parameters. For example, the light-field render controller 618 may adjust the focal lengths of render cameras when executing a depth plane switch or adjustment. As described in further detail below, depth planes may be switched based on the user's determined vergence or fixation depth.

Registration observer 620 may use information from eye tracking module 614 to identify whether the head-mounted unit 602 is properly positioned on a user's head. As an example, the eye tracking module 614 may provide eye location information, such as the positions of the centers of rotation of the user's eyes, indicative of the three-dimensional position of the user's eyes relative to camera 324 and head-mounted unit 602 and the eye tracking module 614 may use the location information to determine if display 220 is properly aligned in the user's field of view, or if the head-mounted unit 602 (or headset) has slipped or is otherwise misaligned with the user's eyes. As examples, the registration observer 620 may be able to determine if the head-mounted unit 602 has slipped down the user's nose bridge, thus moving display 220 away and down from the user's eyes (which may be undesirable), if the head-mounted unit 602 has been moved up the user's nose bridge, thus moving display 220 closer and up from the user's eyes, if the head-mounted unit 602 has been shifted left or right relative the user's nose bridge, if the head-mounted unit 602 has been lifted above the user's nose bridge, or if the head-mounted unit 602 has been moved in these or other ways away from a desired position or range of positions. In general, registration observer 620 may be able to determine if head-mounted unit 602, in general, and displays 220, in particular, are properly positioned in front of the user's eyes. In other words, the registration observer 620 may determine if a left display in display system 220 is appropriately aligned with the user's left eye and a right display in display system 220 is appropriately aligned with the user's right eye. The registration observer 620 may determine if the head-mounted unit 602 is properly positioned by determining if the head-mounted unit 602 is positioned and oriented within a desired range of positions and/or orientations relative to the user's eyes.

In at least some embodiments, registration observer 620 may generate user feedback in the form of alerts, messages, or other content. Such feedback may be provided to the user to inform the user of any misalignment of the head-mounted unit 602, along with optional feedback on how to correct the misalignment (such as a suggestion to adjust the head-mounted unit 602 in a particular manner).

Example registration observation and feedback techniques, which may be utilized by registration observer 620, are described in U.S. patent application Ser. No. 15/717,747, filed Sep. 27, 2017 and U.S. Provisional Patent Application No. 62/644,321, filed Mar. 16, 2018, both of which are incorporated by reference herein in their entirety.

Example of an Eye Tracking Module

Figure 7A:
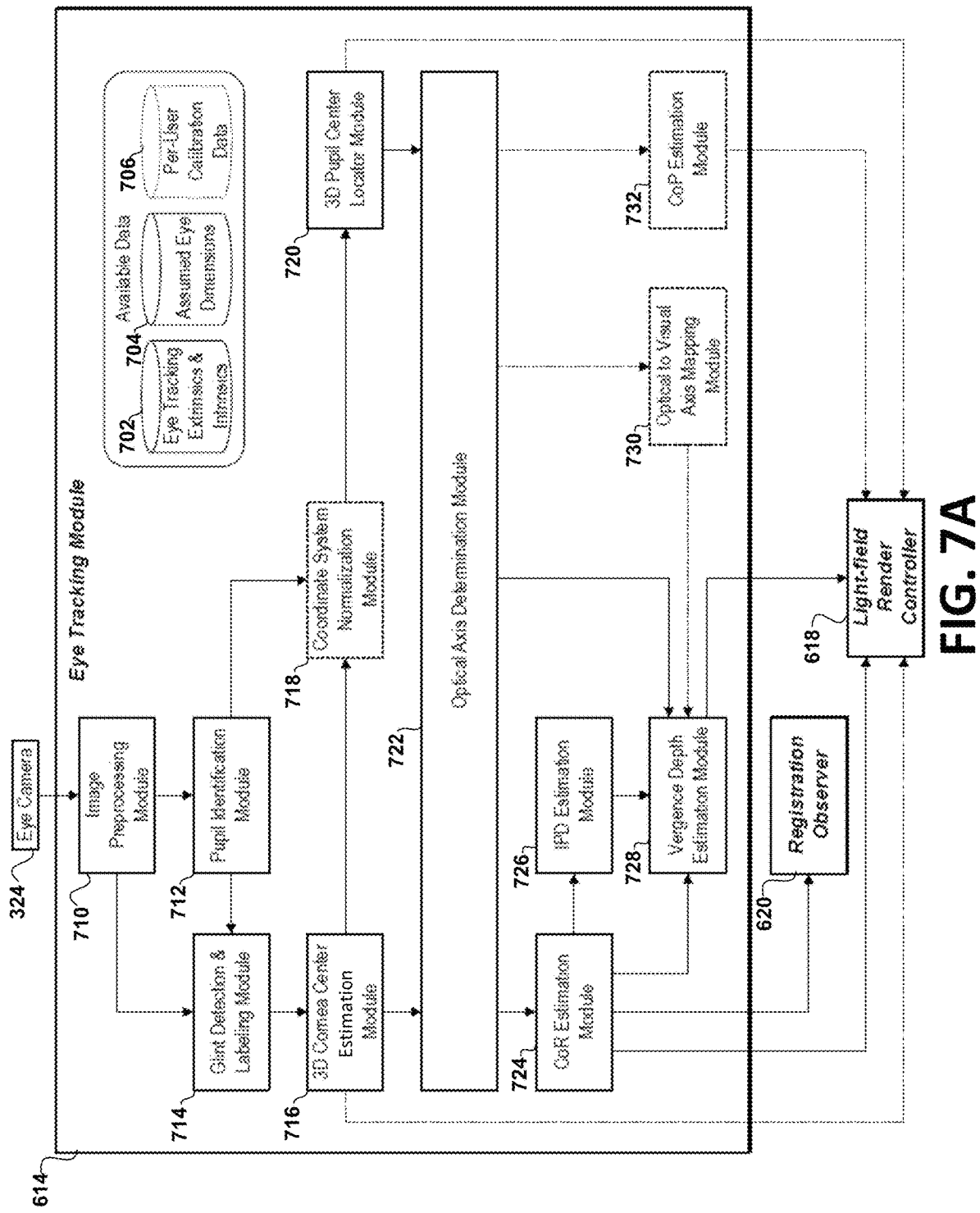
FIG. 7A is a block diagram of a wearable system that may include an eye tracking system.

A detailed block diagram of an example eye tracking module 614 is shown in FIG. 7A. As shown in FIG. 7A, eye tracking module 614 may include a variety of different submodules, may provide a variety of different outputs, and may utilize a variety of available data in tracking the user's eyes. As examples, eye tracking module 614 may utilize available data including eye tracking extrinsics and intrinsics, such as the geometric arrangements of the eye tracking camera 324 relative to the light sources 326 and the head-mounted-unit 602; assumed eye dimensions 704 such as a typical distance of approximately 4.7 mm between a user's center of cornea curvature and the average center of rotation of the user's eye or typical distances between a user's center of rotation and center of perspective; and per-user calibration data 706 such as a particular user's interpupillary distance. Additional examples of extrinsics, intrinsics, and other information that may be employed by the eye tracking module 614 are described in U.S. patent application Ser. No. 15/497,726, filed Apr. 26, 2017, which is incorporated by reference herein in its entirety.

Image preprocessing module 710 may receive images from an eye camera such as eye camera 324 and may perform one or more preprocessing (e.g., conditioning) operations on the received images. As examples, image preprocessing module 710 may apply a Gaussian blur to the images, may down sample the images to a lower resolution, may applying an unsharp mask, may apply an edge sharpening algorithm, or may apply other suitable filters that assist with the later detection, localization, and labelling of glints, a pupil, or other features in the images from eye camera 324. The image preprocessing module 710 may apply a low-pass filter or a morphological filter such as an open filter, which can remove high-frequency noise such as from the pupillary boundary 516a (see FIG. 5), thereby removing noise that can hinder pupil and glint determination. The image preprocessing module 710 may output preprocessed images to the pupil identification module 712 and to the glint detection and labeling module 714.

Pupil identification module 712 may receive preprocessed images from the image preprocessing module 710 and may identify regions of those images that include the user's pupil. The pupil identification module 712 may, in some embodiments, determine the coordinates of the position, or coordinates, of the center, or centroid, of the user's pupil in the eye tracking images from camera 324. In at least some embodiments, pupil identification module 712 may identify contours in eye tracking images (e.g., contours of pupil iris boundary), identify contour moments (e.g., centers of mass), apply a starburst pupil detection and/or a canny edge detection algorithm, reject outliers based on intensity values, identify sub-pixel boundary points, correct for eye-camera distortion (e.g., distortion in images captured by eye camera 324), apply a random sample consensus (RANSAC) iterative algorithm to fit an ellipse to boundaries in the eye tracking images, apply a tracking filter to the images, and identify sub-pixel image coordinates of the user's pupil centroid. The pupil identification module 712 may output pupil identification data, which may indicate which regions of the preprocessing images module 712 identified as showing the user's pupil, to glint detection and labeling module 714. The pupil identification module 712 may provide the 2D coordinates of the user's pupil (e.g., the 2D coordinates of the centroid of the user's pupil) within each eye tracking image to glint detection module 714. In at least some embodiments, pupil identification module 712 may also provide pupil identification data of the same sort to coordinate system normalization module 718.

Pupil detection techniques, which may be utilized by pupil identification module 712, are described in U.S. Patent Publication No. 2017/0053165, published Feb. 23, 2017 and in U.S. Patent Publication No. 2017/0053166, published Feb. 23, 2017, each of which is incorporated by reference herein in its entirety.

Glint detection and labeling module 714 may receive preprocessed images from module 710 and pupil identification data from module 712. Glint detection module 714 may use this data to detect and/or identify glints (e.g., reflections off of the user's eye of the light from light sources 326) within regions of the preprocessed images that show the user's pupil. As an example, the glint detection module 714 may search for bright regions within the eye tracking image, sometimes referred to herein as "blobs" or local intensity maxima, that are in the vicinity of the user's pupil. In at least some embodiments, the glint detection module 714 may rescale (e.g., enlarge) the pupil ellipse to encompass additional glints. The glint detection module 714 may filter glints by size and/or by intensity. The glint detection module 714 may also determine the 2D positions of each of the glints within the eye tracking image.

In at least some examples, the glint detection module 714 may determine the 2D positions of the glints relative to the user's pupil, which may also be referred to as the pupil-glint vectors. Glint detection and labeling module 714 may label the glints and output the preprocessing images with labeled glints to the 3D cornea center estimation module 716. Glint detection and labeling module 714 may also pass along data such as preprocessed images from module 710 and pupil identification data from module 712. In some implementations, the glint detection and labeling module 714 may determine which light source (e.g., from among a plurality of light sources of the system including infrared light sources 326a and 326b) produced each identified glint. In these examples, the glint detection and labeling module 714 may label the glints with information identifying the associated light source and output the preprocessing images with labeled glints to the 3D cornea center estimation module 716.

Pupil and glint detection, as performed by modules such as modules 712 and 714, can use any suitable techniques. As examples, edge detection can be applied to the eye image to identify glints and pupils. Edge detection can be applied by various edge detectors, edge detection algorithms, or filters. For example, a Canny Edge detector can be applied to the image to detect edges such as in lines of the image. Edges may include points located along a line that correspond to the local maximum derivative. For example, the pupillary boundary 516a (see FIG. 5) can be located using a Canny edge detector. With the location of the pupil determined, various image processing techniques can be used to detect the "pose" of the pupil 116. Determining an eye pose of an eye image can also be referred to as detecting an eye pose of the eye image. The pose can also be referred to as the gaze, pointing direction, or the orientation of the eye. For example, the pupil may be looking leftwards towards an object, and the pose of the pupil could be classified as a leftwards pose. Other methods can be used to detect the location of the pupil or glints. For example, a concentric ring can be located in an eye image using a Canny Edge detector. As another example, an integro-differential operator can be used to find the pupillary or limbus boundaries of the iris. For example, the Daugman integro-differential operator, the Hough transform, or other iris segmentation techniques can be used to return a curve that estimates the boundary of the pupil or the iris.

3D cornea center estimation module 716 may receive preprocessed images including detected glint data and pupil identification data from modules 710, 712, 714. 3D cornea center estimation module 716 may use these data to estimate the 3D position of the user's cornea. In some embodiments, the 3D cornea center estimation module 716 may estimate the 3D position of an eye's center of cornea curvature or a user's corneal sphere, e.g., the center of an imaginary sphere having a surface portion generally coextensive with the user's cornea. The 3D cornea center estimation module 716 may provide data indicating the estimated 3D coordinates of the corneal sphere and/or user's cornea to the coordinate system normalization module 718, the optical axis determination module 722, and/or the light-field render controller 618. Further details of the operation of the 3D cornea center estimation module 716 are provided herein in connection with FIGS. 8A-8E. Techniques for estimating the positions of eye features such as a cornea or corneal sphere, which may be utilized by 3D cornea center estimation module 716 and other modules in the wearable systems of the present disclosure are discussed in U.S. patent application Ser. No. 15/497,726, filed Apr. 26, 2017, which is incorporated by reference herein in its entirety.

Coordinate system normalization module 718 may optionally (as indicated by its dashed outline) be included in eye tracking module 614. Coordinate system normalization module 718 may receive data indicating the estimated 3D coordinates of the center of the user's cornea (and/or the center of the user's corneal sphere) from the 3D cornea center estimation module 716 and may also receive data from other modules. Coordinate system normalization module 718 may normalize the eye camera coordinate system, which may help to compensate for slippages of the wearable device (e.g., slippages of the head-mounted component from its normal resting position on the user's head, which may be identified by registration observer 620). Coordinate system normalization module 718 may rotate the coordinate system to align the z-axis (e.g., the vergence depth axis) of the coordinate system with the cornea center (e.g., as indicated by the 3D cornea center estimation module 716) and may translate the camera center (e.g., the origin of the coordinate system) to a predetermined distance away from the cornea center such as 30 mm (e.g., module 718 may enlarge or shrink the eye tracking image depending on whether the eye camera 324 was determined to be nearer or further than the predetermined distance). With this normalization process, the eye tracking module 614 may be able to establish a consistent orientation and distance in the eye tracking data, relatively independent of variations of headset positioning on the user's head. Coordinate system normalization module 718 may provide 3D coordinates of the center of the cornea (and/or corneal sphere), pupil identification data, and preprocessed eye tracking images to the 3D pupil center locator module 720. Further details of the operation of the coordinate system normalization module 718 are provided herein in connection with FIGS. 9A-9C.

3D pupil center locator module 720 may receive data, in the normalized or the unnormalized coordinate system, including the 3D coordinates of the center of the user's cornea (and/or corneal sphere), pupil location data, and preprocessed eye tracking images. 3D pupil center locator module 720 may analyze such data to determine the 3D coordinates of the center of the user's pupil in the normalized or unnormalized eye camera coordinate system. The 3D pupil center locator module 720 may determine the location of the user's pupil in three-dimensions based on the 2D position of the pupil centroid (as determined by module 712), the 3D position of the cornea center (as determined by module 716), assumed eye dimensions 704 such as the size of the a typical user's corneal sphere and the typical distance from the cornea center to the pupil center, and optical properties of eyes such as the index of refraction of the cornea (relative to the index of refraction of air) or any combination of these. Further details of the operation of the 3D pupil center locator module 720 are provided herein in connection with FIGS. 9D-9G. Techniques for estimating the positions of eye features such as a pupil, which may be utilized by 3D pupil center locator module 720 and other modules in the wearable systems of the present disclosure are discussed in U.S. patent application Ser. No. 15/497,726, filed Apr. 26, 2017, which is incorporated by reference herein in its entirety.

Optical axis determination module 722 may receive data from modules 716 and 720 indicating the 3D coordinates of the center of the user's cornea and the user's pupil. Based on such data, the optical axis determination module 722 may identify a vector from the position of the cornea center (e.g., from the center of the corneal sphere) to the center of the user's pupil, which may define the optical axis of the user's eye. Optical axis determination module 722 may provide outputs specifying the user's optical axis to modules 724, 728, 730, and 732, as examples.

Center of rotation (CoR) estimation module 724 may receive data from module 722 including parameters of the optical axis of the user's eye (e.g., data indicating the direction of the optical axis in a coordinate system with a known relation to the head-mounted unit 602). For example, CoR estimation module 724 may estimate the center of rotation of a user's eye. The center of rotation may indicate a point around which the user's eye rotates when the user eye rotates left, right, up, and/or down. While eyes may not rotate perfectly around a singular point, assuming a singular point may be sufficient. In at least some embodiments, CoR estimation module 724 may estimate an eye's center of rotation by moving from the center of the pupil (identified by module 720) or the center of curvature of the cornea (as identified by module 716) toward the retina along the optical axis (identified by module 722) a particular distance. This particular distance may be an assumed eye dimension 704.

As one example, the particular distance between the center of curvature of the cornea and the CoR may be approximately 4.7 mm. This distance may be varied for a particular user based on any relevant data including the user's age, sex, vision prescription, other relevant characteristics, etc. Additional discussion of the value of 4.7 mm as an estimate for the distance between the center of curvature of the cornea and the CoR is provided in Appendix (Part III), which forms part of this application.

In at least some embodiments, the CoR estimation module 724 may refine its estimate of the center of rotation of each of the user's eyes over time. As an example, as time passes, the user will eventually rotate their eyes (to look somewhere else, at something closer, further, or sometime left, right, up, or down) causing a shift in the optical axis of each of their eyes. CoR estimation module 724 may then analyze two (or more) optical axes identified by module 722 and locate the 3D point of intersection of those optical axes. The CoR estimation module 724 may then determine the center of rotation lies at that 3D point of intersection. Such a technique may provide for an estimate of the center of rotation, with an accuracy that improves over time.

Various techniques may be employed to increase the accuracy of the CoR estimation module 724 and the determined CoR positions of the left and right eyes. As an example, the CoR estimation module 724 may estimate the CoR by finding the average point of intersection of optical axes determined for various different eye poses over time. As additional examples, module 724 may filter or average estimated CoR positions over time, may calculate a moving average of estimated CoR positions over time, and/or may apply a Kalman filter and known dynamics of the eyes and eye tracking system to estimate the CoR positions over time. In some implementations, a least-squares approach may be taken to determine one or more points of intersection of optical axes. In such implementations, the system may, at a given point in time, identify a location at which the sum of the squared distances to a given set of optical axes is reduced or minimized as the point of optical axes intersection. As a specific example, module 724 may calculate a weighted average of determined points of optical axes intersection and assumed CoR positions (such as 4.7 mm from an eye's center of cornea curvature), such that the determined CoR may slowly drift from an assumed CoR position (e.g., 4.7 mm behind an eye's center of cornea curvature) to a slightly different location within the user's eye over time as eye tracking data for the user is obtain and thereby enables per-user refinement of the CoR position.

Under ideal conditions, the 3D position of the true CoR of a user's eye relative to the HMD should change a negligible or minimal amount over time as the user moves their eye (e.g., as the user's eye rotates around its center of rotation). In other words, for a given set of eye movements, the 3D position of the true CoR of the user's eye (relative to the HMD) should hypothetically vary less over time than any other point along the optical axis of the user's eye. As such, it follows that the further away a point along the optical axis is from the true CoR of the user's eye, the more variation or variance its 3D position will exhibit over time as the user moves their eye. In some embodiments, the CoR estimation module 724 and/or other submodules of eye tracking module 614 may make use of this statistical relationship to improve CoR estimation accuracy. In such embodiments, the CoR estimation module 724 and/or other submodules of eye tracking module 614 may refine their estimates of the CoR 3D position over time by identifying variations of its CoR estimates having a low variation (e.g., low variance or standard deviation).

As a first example and in embodiments where the CoR estimation module 724 estimates CoR based on intersection of multiple different optical axes (each associated with the user looking in a different direction), the CoR estimation module 724 may make use of this statistical relationship (that the true CoR should have a low variance) by introducing common offsets to the direction of each of the optical axes (e.g., shifting each axis by some uniform amount) and determining if the offset optical axes intersect with each other in an intersection point having a low variation, e.g., low variance or standard deviation. This may correct for minor systemic errors in calculating the directions of the optical axes and help to refine the estimated position of the CoR to be closer to the true CoR.

As a second example and in embodiments where the CoR estimation module 724 estimates CoR by moving along an optical axis (or other axis) by a particular distance (e.g., such as the distance between the center of curvature of the cornea and the CoR), the system may vary, optimize, tune, or otherwise adjust the particular distance between the center of curvature of the cornea and the CoR over time (for example, for a large group of images of the eye captured at different times) in a manner so as to reduce or minimize the variation, for example, variance and/or standard deviation of the estimated CoR position. For example, if the CoR estimation module 724 initially uses a particular distance value of 4.7 mm (from the center of curvature of the cornea and along the optical axis) to obtain CoR position estimates, but the true CoR of a given user's eye may be positioned 4.9 mm behind the eye's center of cornea curvature (along the optical axis), then an initial set of CoR position estimates obtained by the CoR estimation module 724 may exhibit a relatively high amount of variation, e.g., variance or standard deviation. In response to detecting such a relatively high amount of variation (e.g., variance or standard deviation), the CoR estimation module 724 may look for and identify one or more points along the optical axis having a lower amount of variation (e.g., variance or standard deviation), may identify the 4.9 mm distance as having the lowest variation (e.g., variance or standard deviation), and may thus adjust the particular distance value utilized to 4.9 mm.

The CoR estimation module 724 may look for alternative CoR estimations having lower variation (e.g., variance and/or standard deviation) in response to detecting that a current CoR estimate has a relatively high amount of variation (e.g., variance or standard deviation) or may look for alternative CoR estimations having lower variation (e.g. variance or standard deviation) as a matter of course after obtaining initial CoR estimates. In some examples, such an optimization/adjustment can happen gradually over time, while in other examples, such an optimization/adjustment can be made during an initial user calibration session. In examples where such a procedure is conducted during a calibration procedure, the CoR estimation module 724 may not initially subscribe/adhere to any assumed particular distance, but may rather collect a set of eye tracking data over time, perform statistical analysis on the set of eye tracking data, and determine the particular distance value yielding CoR position estimates with the least possible amount (e.g., global minima) of variation (e.g. variance or standard deviation) based on the statistical analysis.

Additional discussion of the statistical relationship described above (e.g., that the true CoR should have low variance or standard deviation), as well as the significance of taking into account corneal refraction in determining pupil position, is provided in Appendix (Part III), which forms part of this application.

Interpupillary distance (IPD) estimation module 726 may receive data from CoR estimation module 724 indicating the estimated 3D positions of the centers of rotation of the user's left and right eyes. IPD estimation module 726 may then estimate a user's IPD by measuring the 3D distance between the centers of rotation of the user's left and right eyes. In general, the distance between the estimated CoR of the user's left eye and the estimated CoR of the user's right eye may be roughly equal to the distance between the centers of a user's pupils, when the user is looking at optical infinity (e.g., the optical axes of the user's eyes are substantially parallel to one another), which is the typical definition of interpupillary distance (IPD). A user's IPD may be used by various components and modules in the wearable system. As example, a user's IPD may be provided to registration observer 620 and used in assessing how well the wearable device is aligned with the user's eyes (e.g., whether the left and right display lenses are properly spaced in accordance with the user's IPD). As another example, a user's IPD may be provided to vergence depth estimation module 728 and be used in determining a user's vergence depth. Module 726 may employ various techniques, such as those discussed in connection with CoR estimation module 724, to increase the accuracy of the estimated IPD. As examples, IPD estimation module 724 may apply filtering, averaging over time, weighted averaging including assumed IPD distances, Kalman filters, etc. as part of estimating a user's IPD in an accurate manner.

Vergence depth estimation module 728 may receive data from various modules and submodules in the eye tracking module 614 (as shown in connection with FIG. 7A). In particular, vergence depth estimation module 728 may employ data indicating estimated 3D positions of pupil centers (e.g., as provided by module 720 described above), one or more determined parameters of optical axes (e.g., as provided by module 722 described above), estimated 3D positions of centers of rotation (e.g., as provided by module 724 described above), estimated IPD (e.g., Euclidean distance(s) between estimated 3D positions of centers of rotations) (e.g., as provided by module 726 described above), and/or one or more determined parameters of optical and/or visual axes (e.g., as provided by module 722 and/or module 730 described below). Vergence depth estimation module 728 may detect or otherwise obtain a measure of a user's vergence depth, which may be the distance from the user at which the user's eyes are focused. As examples, when the user is looking at an object three feet in front of them, the user's left and right eyes have a vergence depth of three feet; and, while when the user is looking at a distant landscape (e.g., the optical axes of the user's eyes are substantially parallel to one another such that the distance between the centers of the user's pupils may be roughly equal to the distance between the centers of rotation of the user's left and right eyes), the user's left and right eyes have a vergence depth of infinity. In some implementations, the vergence depth estimation module 728 may utilize data indicating the estimated centers of the user's pupils (e.g., as provided by module 720) to determine the 3D distance between the estimated centers of the user's pupils. The vergence depth estimation module 728 may obtain a measure of vergence depth by comparing such a determined 3D distance between pupil centers to estimated IPD (e.g., Euclidean distance(s) between estimated 3D positions of centers of rotations) (e.g., as indicated by module 726 described above). In addition to the 3D distance between pupil centers and estimated IPD, the vergence depth estimation module 728 may utilize known, assumed, estimated, and/or determined geometries to calculate vergence depth. As an example, module 728 may combine 3D distance between pupil centers, estimated IPD, and 3D CoR positions in a trigonometric calculation to estimate (e.g., determine) a user's vergence depth. Indeed, an evaluation of such a determined 3D distance between pupil centers against estimated IPD may serve to indicate a measure of the user's current vergence depth relative to optical infinity. In some examples, the vergence depth estimation module 728 may simply receive or access data indicating an estimated 3D distance between the estimated centers of the user's pupils for purposes of obtaining such a measure of vergence depth. In some embodiments, the vergence depth estimation module 728 may estimate vergence depth by comparing a user's left and right optical axis. In particular, vergence depth estimation module 728 may estimate vergence depth by locating the distance from a user at which the user's left and right optical axes intersect (or where projections of the user's left and right optical axes on a plane such as a horizontal plane intersect). Module 728 may utilize a user's IPD in this calculation, by setting the zero depth to be the depth at which the user's left and right optical axes are separated by the user's IPD. In at least some embodiments, vergence depth estimation module 728 may determine vergence depth by triangulating eye tracking data together with known or derived spatial relationships.

In some embodiments, vergence depth estimation module 728 may estimate a user's vergence depth based on the intersection of the user's visual axes (instead of their optical axes), which may provide a more accurate indication of the distance at which the user is focused on. In at least some embodiments, eye tracking module 614 may include optical to visual axis mapping module 730. As discussed in further detail in connection with FIG. 10, a user's optical and visual axis are generally not aligned. A visual axis is the axis along which a person is looking, while an optical axis is defined by the center of that person's lens and pupil, and may go through the center of the person's retina. In particular, a user's visual axis is generally defined by the location of the user's fovea, which may be offset from the center of a user's retina, thereby resulting in different optical and visual axis. In at least some of these embodiments, eye tracking module 614 may include optical to visual axis mapping module 730. Optical to visual axis mapping module 730 may correct for the differences between a user's optical and visual axis and provide information on the user's visual axis to other components in the wearable system, such as vergence depth estimation module 728 and light-field render controller 618. In some examples, module 730 may use assumed eye dimensions 704 including a typical offset of approximately 5.2° inwards (nasally, towards a user's nose) between an optical axis and a visual axis. In other words, module 730 may shift a user's left optical axis (nasally) rightwards by 5.2° towards the nose and a user's right optical axis (nasally) leftwards by 5.2° towards the nose in order to estimate the directions of the user's left and right optical axes. In other examples, module 730 may utilize per-user calibration data 706 in mapping optical axes (e.g., as indicated by module 722 described above) to visual axes. As additional examples, module 730 may shift a user's optical axes nasally by between 4.0° and 6.5°, by between 4.5° and 6.0°, by between 5.0° and 5.4°, etc., or any ranges formed by any of these values. In some arrangements, the module 730 may apply a shift based at least in part upon characteristics of a particular user such as their age, sex, vision prescription, or other relevant characteristics and/or may apply a shift based at least in part upon a calibration process for a particular user (e.g., to determine a particular user's optical-visual axis offset). In at least some embodiments, module 730 may also shift the origins of the left and right optical axes to correspond with the user's CoP (as determined by module 732) instead of the user's CoR.

Optional center of perspective (CoP) estimation module 732, when provided, may estimate the location of the user's left and right centers of perspective (CoP). A CoP may be a useful location for the wearable system and, in at least some embodiments, is a position just in front of a pupil. In at least some embodiments, CoP estimation module 732 may estimate the locations of a user's left and right centers of perspective based on the 3D location of a user's pupil center, the 3D location of a user's center of cornea curvature, or such suitable data or any combination thereof. As an example, a user's CoP may be approximately 5.01 mm in front of the center of cornea curvature (e.g., 5.01 mm from the corneal sphere center in a direction that is towards the eye's cornea and that is along the optical axis) and may be approximately 2.97 mm behind the outer surface of a user's cornea, along the optical or visual axis. A user's center of perspective may be just in front of the center of their pupil. As examples, a user's CoP may be less than approximately 2.0 mm from the user's pupil, less than approximately 1.0 mm from the user's pupil, or less than approximately 0.5 mm from the user's pupil or any ranges between any of these values. As another example, the center of perspective may correspond to a location within the anterior chamber of the eye. As other examples, the CoP may be between 1.0 mm and 2.0 mm, about 1.0 mm, between 0.25 mm and 1.0 mm, between 0.5 mm and 1.0 mm, or between 0.25 mm and 0.5 mm.

The center of perspective described herein (as a potentially desirable position for a pinhole of a render camera and an anatomical position in a user's eye) may be a position that serves to reduce and/or eliminate undesired parallax shifts. In particular, the optical system of a user's eye is very roughly equivalent to theoretical system formed by a pinhole in front of a lens, projecting onto a screen, with the pinhole, lens, and screen roughly corresponding to a user's pupil/iris, lens, and retina, respectively. Moreover, it may be desirable for there to be little or no parallax shift when two point light sources (or objects) at different distances from the user's eye are rigidly rotated about the opening of the pinhole (e.g., rotated along radii of curvature equal to their respective distance from the opening of the pinhole). Thus, it would seem that the CoP should be located at the center of the pupil of an eye (and such a CoP may be used in some embodiments). However, the human eye includes, in addition to the lens and pinhole of the pupil, a cornea that imparts additional optical power to light propagating toward the retina). Thus, the anatomical equivalent of the pinhole in the theoretical system described in this paragraph may be a region of the user's eye positioned between the outer surface of the cornea of the user's eye and the center of the pupil or iris of the user's eye. For instance, the anatomical equivalent of the pinhole may correspond to a region within the anterior chamber of a user's eye. For various reasons discussed herein, it may be desired to set the CoP to such a position within the anterior chamber of the user's eye. The derivation and significance of the CoP are described in more detail below, with respect to FIGS. 22-24B.

As discussed above, eye tracking module 614 may provide data, such as estimated 3D positions of left and right eye centers of rotation (CoR), vergence depth, left and right eye optical axis, 3D positions of a user's eye, 3D positions of a user's left and right centers of cornea curvature, 3D positions of a user's left and right pupil centers, 3D positions of a user's left and right center of perspective, a user's IPD, etc., to other components, such as light-field render controller 618 and registration observer 620, in the wearable system. Eye tracking module 614 may also include other submodules that detect and generate data associated with other aspects of a user's eye. As examples, eye tracking module 614 may include a blink detection module that provides a flag or other alert whenever a user blinks and a saccade detection module that provides a flag or other alert whenever a user's eye saccades (e.g., quickly shifts focus to another point).

Example of a Render Controller

Figure 7B:
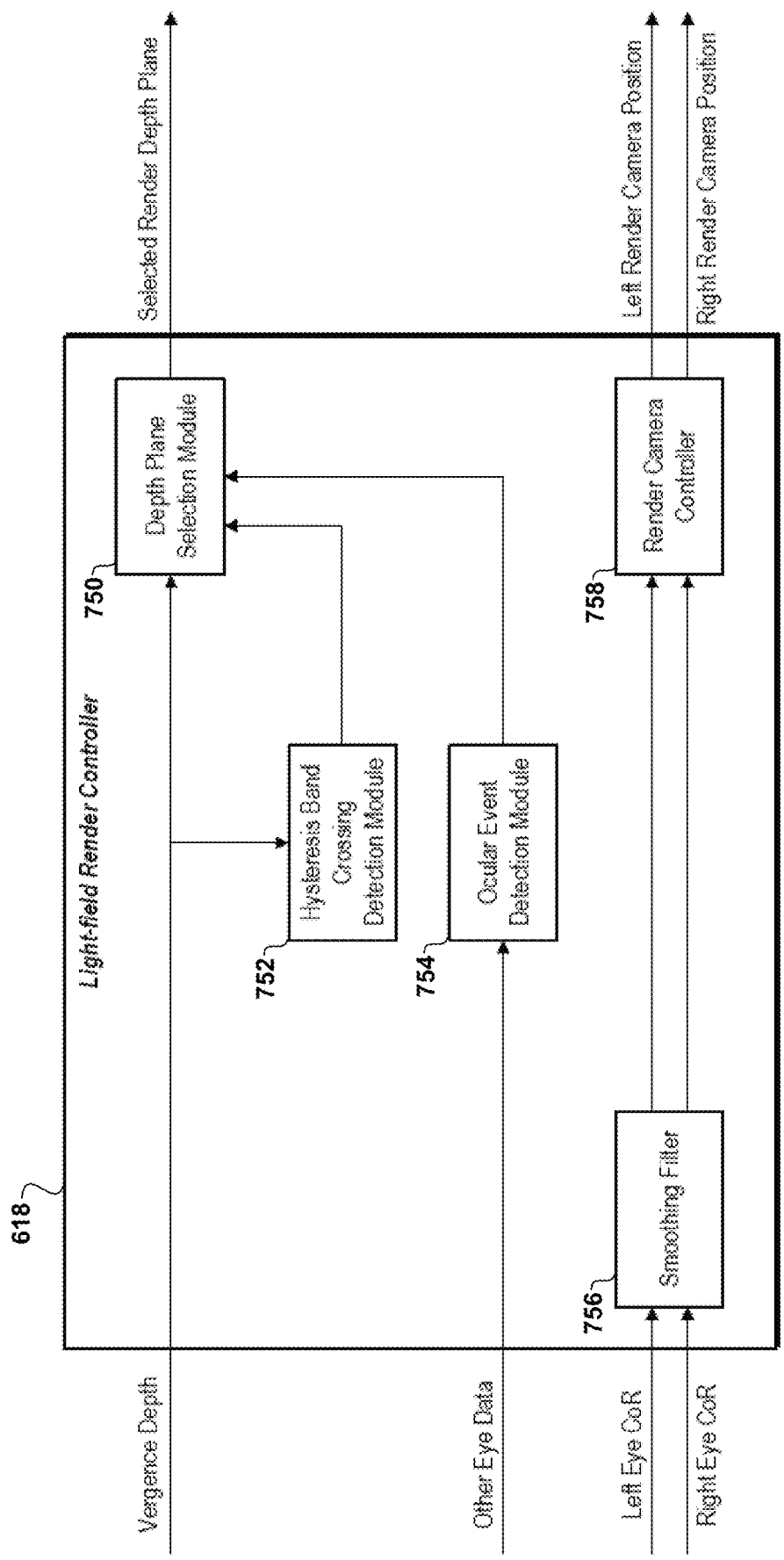
FIG. 7B is a block diagram of a render controller in a wearable system.

A detailed block diagram of an example light-field render controller 618 is shown in FIG. 7B. As shown in FIGS. 6 and 7B, render controller 618 may receive eye tracking information from eye tracking module 614 and may provide outputs to render engine 622, which may generate images to be displayed for viewing by a user of the wearable system. As examples, render controller 618 may receive a vergence depth, left and right eye centers of rotation (and/or centers of perspective), and other eye data such as blink data, saccade data, etc.

Depth plane selection module 750 may receive vergence depth information and other eye data and, based on such data, may cause render engine 622 to convey content to a user with a particular depth plane (e.g., at a particular accommodation or focal distance). As discussed in connection with FIG. 4, a wearable system may include a plurality of discrete depth planes formed by a plurality of waveguides, each conveying image information with a varying level of wavefront curvature. In some embodiments, a wearable system may include one or more variable depth planes, such as an optical element that conveys image information with a level of wavefront curvature that varies over time. In these and other embodiments, depth plane selection module 750 may cause render engine 622 to convey content to a user at a selected depth (e.g., cause render engine 622 to direct display 220 to switch depth planes), based in part of the user's vergence depth. In at least some embodiments, depth plane selection module 750 and render engine 622 may render content at different depths and also generate and/or provide depth plane selection data to display hardware such as display 220. Display hardware such as display 220 may perform an electrical depth plane switching in response to depth plane selection data (which may be control signals) generated by and/or provided by modules such as depth plane selection module 750 and render engine 622.

In general, it may be desirable for depth plane selection module 750 to select a depth plane matching the user's current vergence depth, such that the user is provided with accurate accommodation cues. However, it may also be desirable to switch depth planes in a discreet and unobtrusive manner. As examples, it may be desirable to avoid excessive switching between depth planes and/or it may be desire to switch depth planes at a time when the user is less likely to notice the switch, such as during a blink or eye saccade.

Hysteresis band crossing detection module 752 may help to avoid excessive switching between depth planes, particularly when a user's vergence depth fluctuates at the midpoint or transition point between two depth planes. In particular, module 752 may cause depth plane selection module 750 to exhibit hysteresis in its selection of depth planes. As an example, modules 752 may cause depth plane selection module 750 to switch from a first farther depth plane to a second closer depth plane only after a user's vergence depth passes a first threshold. Similarly, module 752 may cause depth plane selection module 750 (which may in turn direct displays such as display 220) to switch to the first farther depth plane only after the user's vergence depth passes a second threshold that is farther from the user than the first threshold. In the overlapping region between the first and second thresholds, module 750 may cause depth plane selection module 750 to maintain whichever depth plane is currently select as the selected depth plane, thus avoiding excessive switching between depth planes.

Ocular event detection module 750 may receive other eye data from the eye tracking module 614 of FIG. 7A and may cause depth plane selection module 750 to delay some depth plane switches until an ocular event occurs. As an example, ocular event detection module 750 may cause depth plane selection module 750 to delay a planned depth plane switch until a user blink is detected; may receive data from a blink detection component in eye tracking module 614 that indicates when the user is currently blinking; and, in response, may cause depth plane selection module 750 to execute the planned depth plane switch during the blink event (such by causing module 750 to direct display 220 to execute the depth plane switch during the blink event). In at least some embodiments, the wearable system may be able to shift content onto a new depth plane during a blink event such that the user is unlikely to perceive the shift. As another example, ocular event detection module 750 may delay planned depth plane switches until an eye saccade is detected. As discussed in connection with eye blinks, such as an arrangement may facilitate the discretely shifting of depth planes.

If desired, depth plane selection module 750 may delay planned depth plane switches only for a limited period of time before executing the depth plane switch, even in the absence of an ocular event. Similarly, depth plane selection module 750 may execute a depth plane switch when the user's vergence depth is substantially outside of a currently-selected depth plane (e.g., when the user's vergence depth has exceeded a predetermined threshold beyond the regular threshold for a depth plane switch), even in the absence of an ocular event. These arrangements may help ensure that ocular event detection module 754 does not indefinitely delay depth plane switches and does not delay depth plane switches when a large accommodation error is present. Further details of the operation of depth plane selection module 750, and how the module may time depth plane switches, are provided herein in connection with FIG. 12.

Render camera controller 758 may provide information to render engine 622 indicating where the user's left and right eyes are. Render engine 622 may then generate content by simulating cameras at the positions of the user's left and right eyes and generating content based on the perspectives of the simulated cameras. As discussed above, the render camera is a simulated camera for use in rendering virtual image content possibly from a database of objects in a virtual world. The objects may have locations and orientations relative to the user or wearer and possibly relative to real objects in the environment surrounding the user or wearer. The render camera may be included in a render engine to render virtual images based on the database of virtual objects to be presented to said eye. The virtual images may be rendered as if taken from the perspective the user or wearer. For example, the virtual images may be rendered as if captured by a camera (corresponding to the "render camera") having an aperture, lens, and detector viewing the objects in the virtual world. The virtual images are taken from the perspective of such a camera having a position of the "render camera." For example, the virtual images may be rendered as if captured from the perspective of a camera having a specific location with respect to the user's or wearer's eye so as to provide images that appear to be from the perspective of the user or wearer. In some implementations, the images are rendered as if captured from the perspective of a camera having an aperture at a specific location with respect to the user's or wearer's eye (such as the center of perspective or center of rotation as discussed herein, or elsewhere).

Render camera controller 758 may determine the positions of the left and right cameras based on the left and right eye centers of rotation (CoR), determined by CoR estimation module 724, and/or based on the left and right eye centers of perspective (CoP), determined by CoP estimation module 732. In some embodiments, render camera controller 758 may switch between the CoR and CoP locations based on various factors. As examples, the render camera controller 758 may, in various modes, register the render camera to the CoR locations at all times, register the render camera to the CoP locations at all times, toggle or discretely switch between registering the render camera to the CoR locations and registering the render camera to the CoP locations over time based on various factors, or dynamically register the render camera to any of a range of different positions along the optical (or visual) axis between the CoR and CoP locations over time based on various factors. The CoR and CoP positions may optionally pass through smoothing filter 756 (in any of the aforementioned modes for render camera positioning) which may average the CoR and CoP locations over time to reduce noise in these positions and prevent jitter in the render simulated render cameras.

Figure 16A:
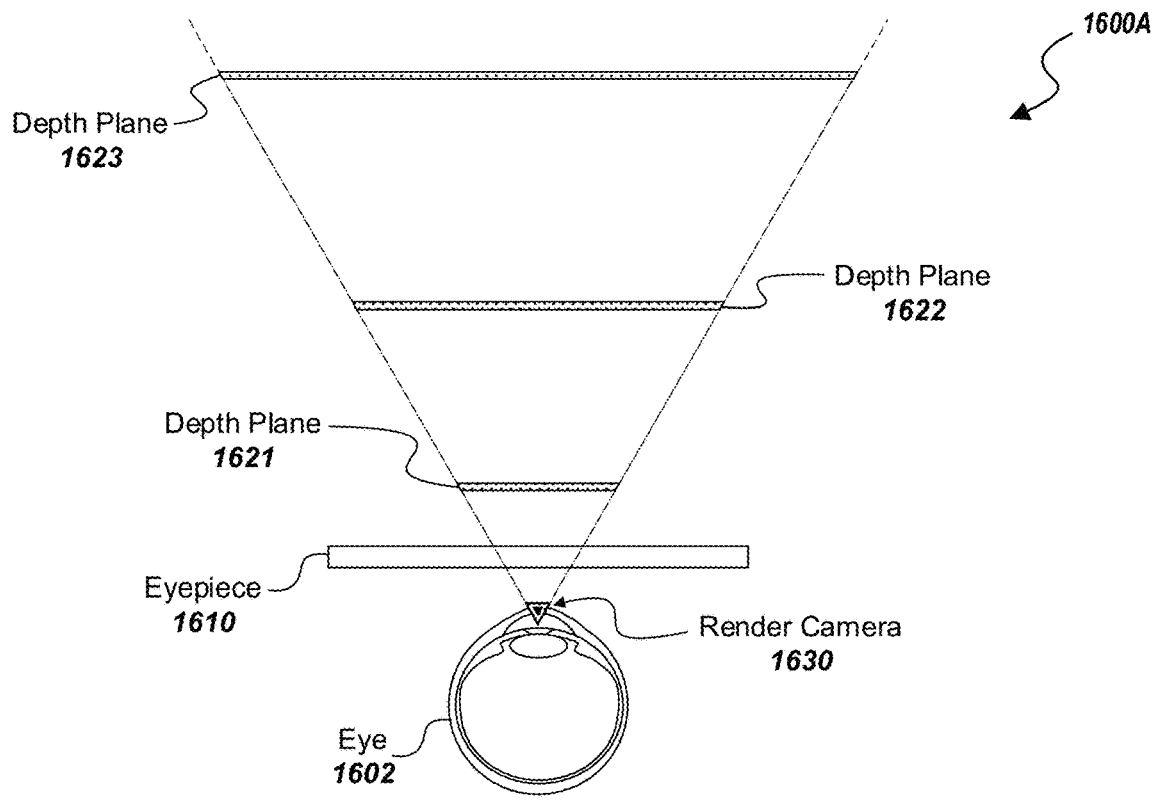
FIGS. 16A and 16B illustrate an example in which the pinhole of a render camera is aligned with an eye's center of perspective or approximately with an eye's pupil.
Figure 16B:
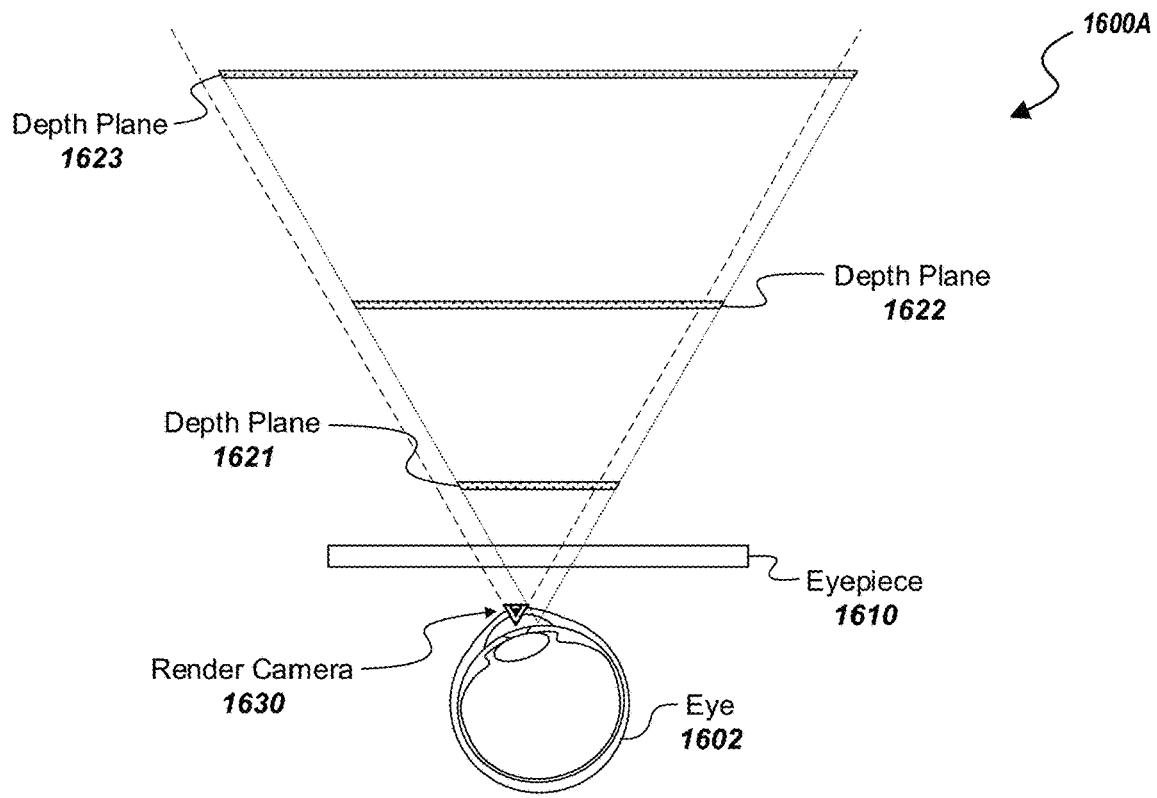

In at least some embodiments, the render camera may be simulated as a pinhole camera with the pinhole disposed at the position of the estimated CoR or CoP identified by eye tracking module 614. As the CoP is offset from the CoR, the location of the render camera and its pinhole both shift as the user's eye rotates, whenever the render camera's position is based on a user's CoP (see, e.g., how the render camera linearly translates with the eye rotation as shown in FIGS. 16A and 16B). In contrast, whenever the render camera's position is based on a user's CoR, the location of the render camera's pinhole does not move with eye rotations, although the render camera (which is behind the pinhole) may, in some embodiments, move with eye rotation. In other embodiments where the render camera's position is based on a user's CoR, the render camera may not move (e.g., rotate) with a user's eye (see, e.g., how the render camera does not move, or linearly translate, with the eye rotation depicted in FIGS. 17A and 17B).

Example of Locating a User's Cornea with an Eye Tracking System

Figure 8A:
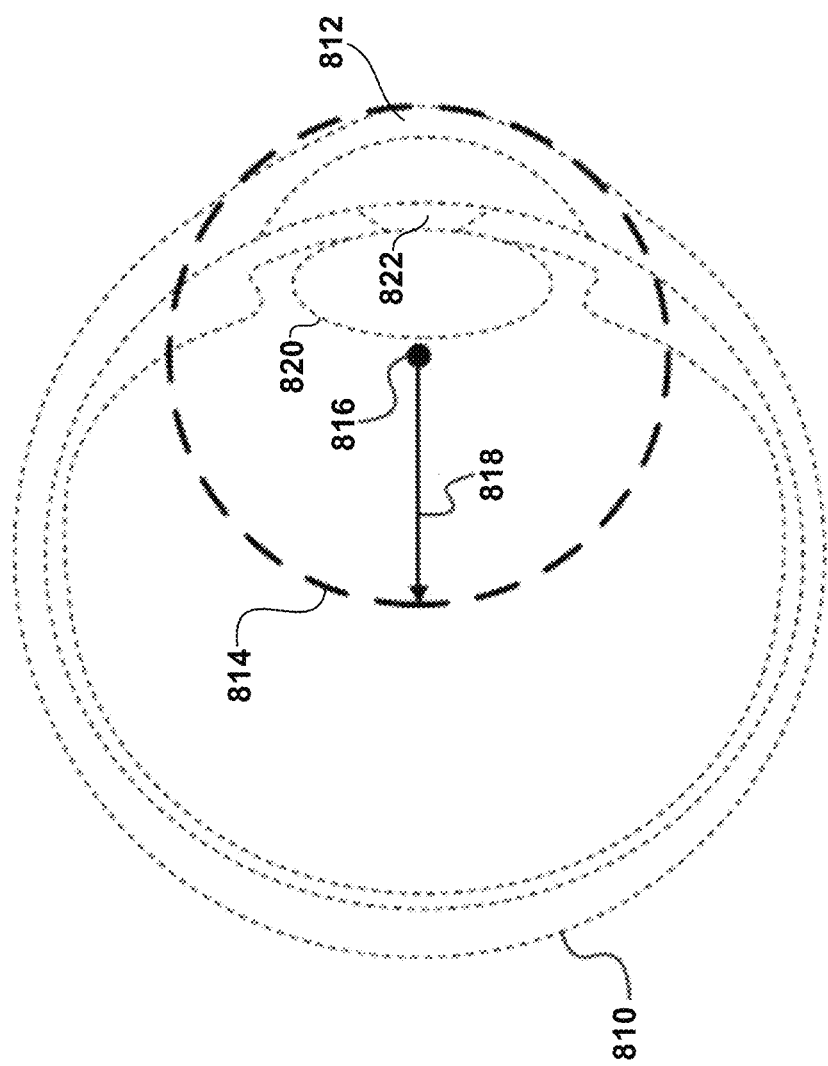
FIG. 8A is a schematic diagram of an eye showing the eye's corneal sphere.

FIG. 8A is a schematic diagram of an eye showing the eye's corneal sphere. As shown in FIG. 8A, a user's eye 810 may have a cornea 812, a pupil 822, and a lens 820. The cornea 812 may have an approximately spherical shape, shown by corneal sphere 814. Corneal sphere 814 may have a center point 816, also referred to as a corneal center, and a radius 818. The semispherical cornea of a user's eye may curve around the corneal center 816.

FIGS. 8B-8E illustrate an example of locating a user's corneal center 816 using 3D cornea center estimation module 716 and eye tracking module 614.

Figure 8B:
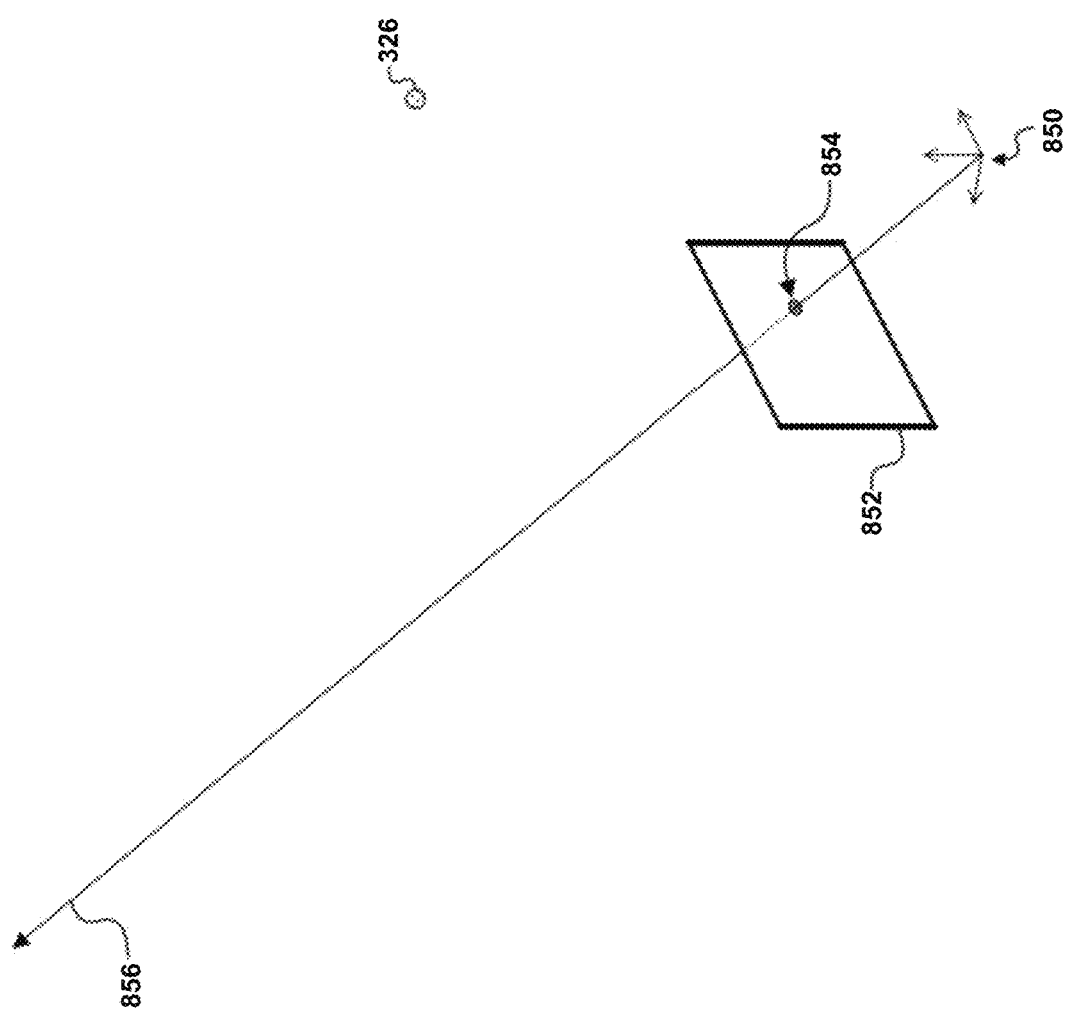
FIG. 8B illustrates an example corneal glint detected by an eye tracking camera.

As shown in FIG. 8B, 3D cornea center estimation module 716 may receive an eye tracking image 852 that includes a corneal glint 854. The 3D cornea center estimation module 716 may then simulate, in an eye camera coordinate system 850, the known 3D positions of the eye camera 324 and light source 326 (which may be based on data in eye tracking extrinsics & intrinsics database 702, assumed eye dimensions database 704, and/or per-user calibration data 706) in order to cast a ray 856 in the eye camera coordinate system. In at least some embodiments, the eye camera coordinate system 850 may have its origin at the 3D position of the eye tracking camera 324.

Figure 8C:
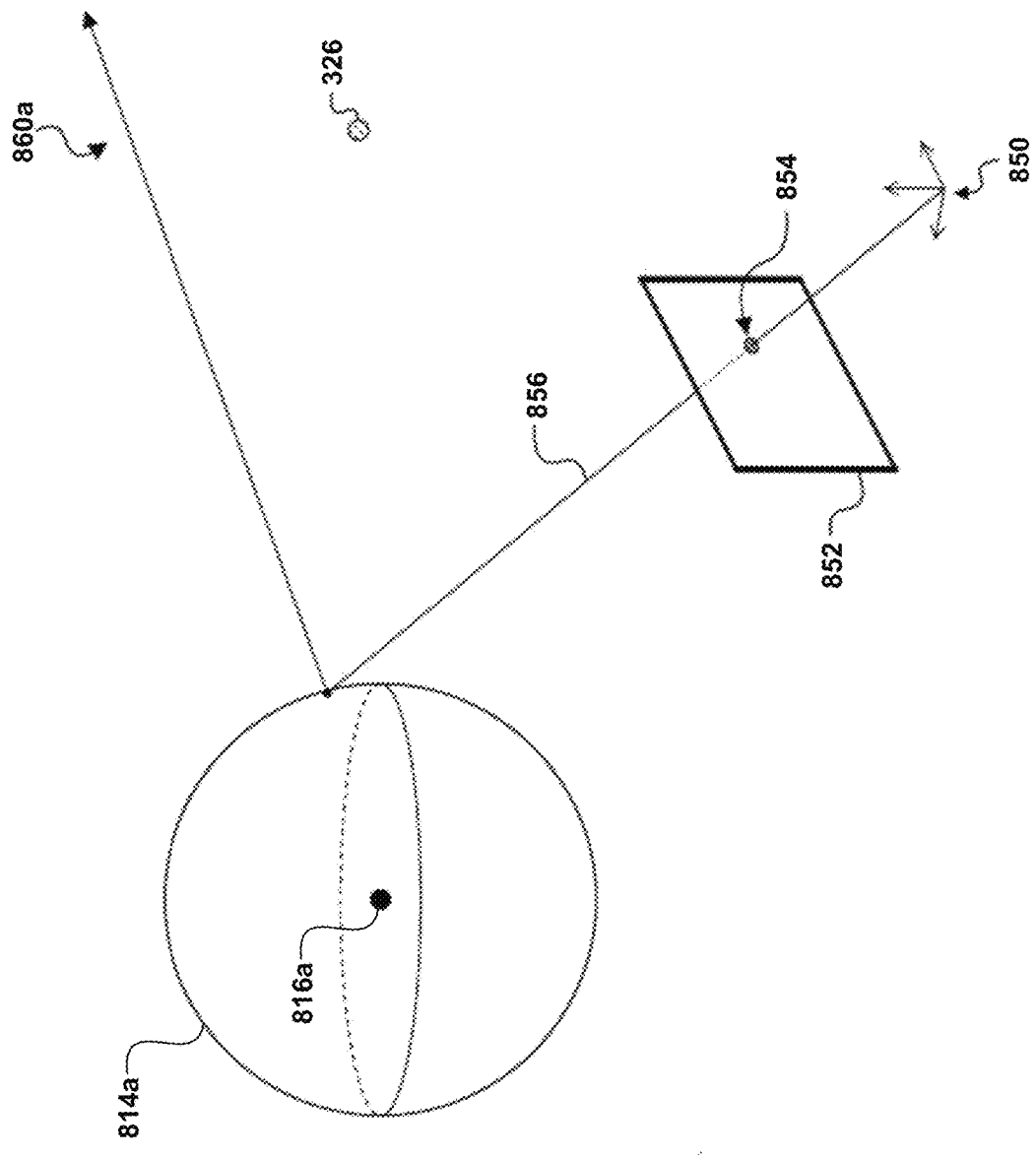
FIGS. 8C-8E illustrate example stages of locating a user's corneal center with an eye tracking module in a wearable system.

In FIG. 8C, 3D cornea center estimation module 716 simulates a corneal sphere 814a (which may be based on assumed eye dimensions from database 704) and corneal curvature center 816a at a first position. The 3D cornea center estimation module 716 may then check to see whether the corneal sphere 814a would properly reflect light from the light source 326 to the glint position 854. As shown in FIG. 8C, the first position is not a match as the ray 860a does not intersect light source 326.

Figure 8D:
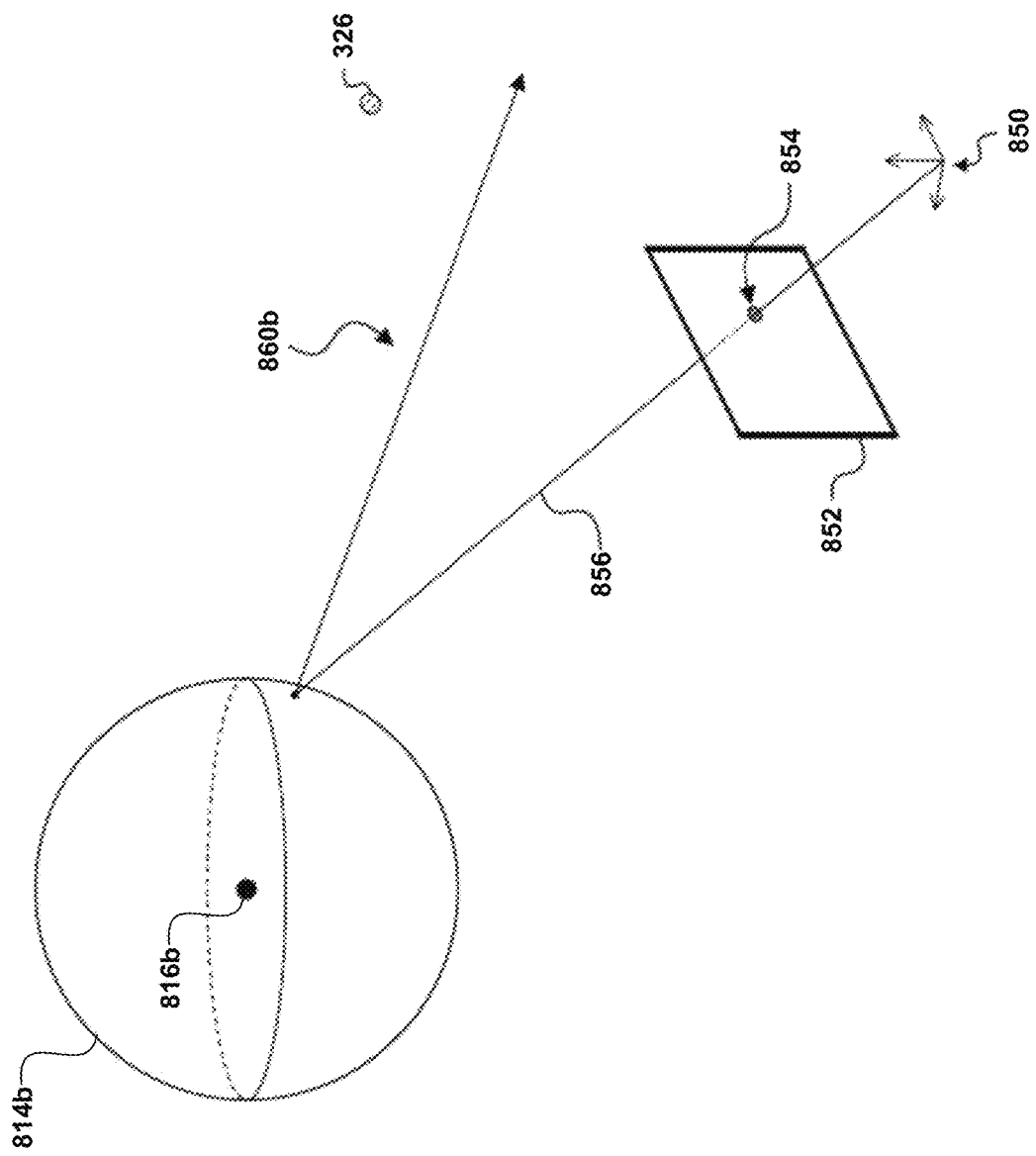

Similarly in FIG. 8D, 3D cornea center estimation module 716 simulates a corneal sphere 814b and corneal curvature center 816b at a second position. The 3D cornea center estimation module 716 then checks to see whether the corneal sphere 814b properly reflects light from the light source 326 to the glint position 854. As shown in FIG. 8D, the second position is also not a match.

Figure 8E:
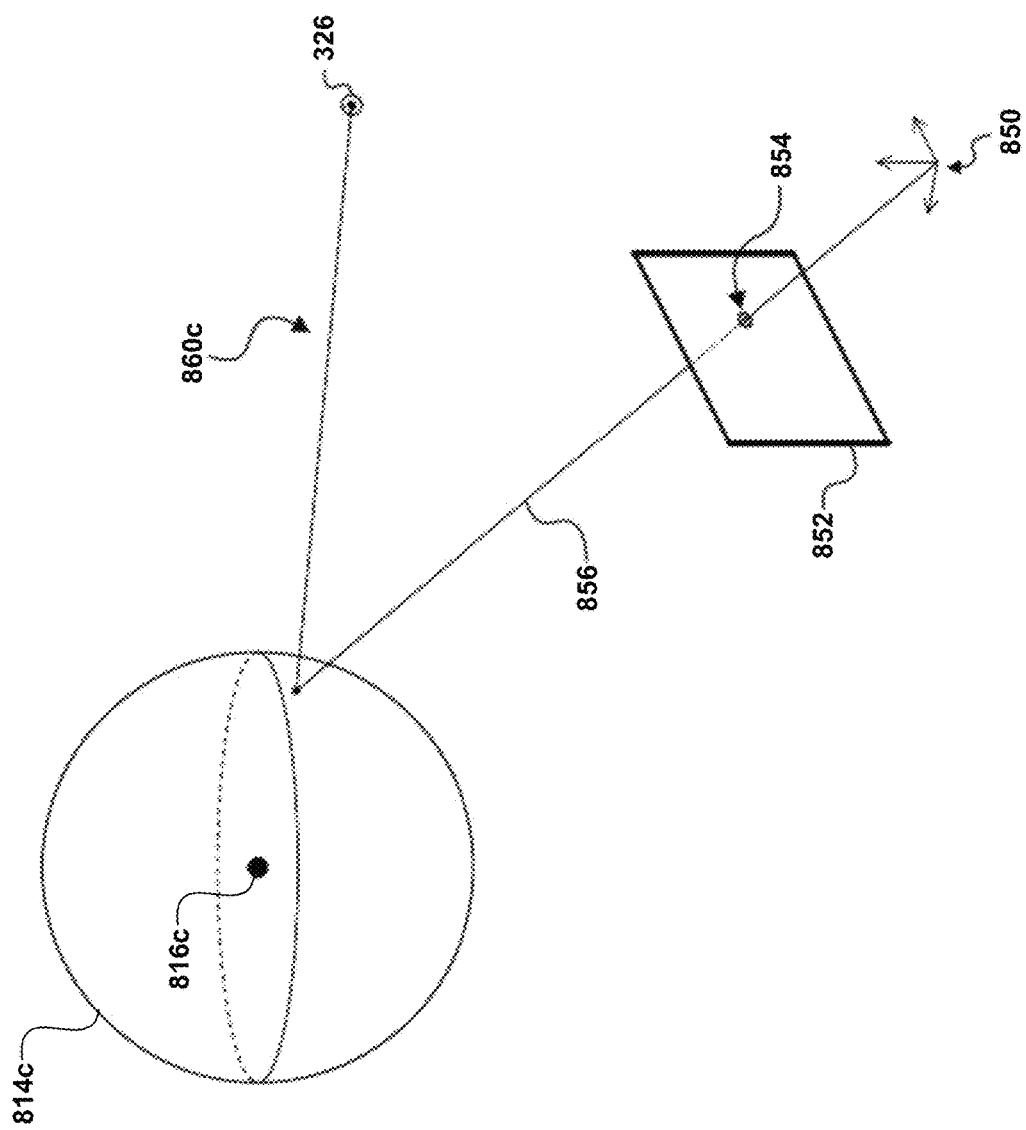

As shown in FIG. 8E, the 3D cornea center estimation module 716 eventually is able to determine the correct position of the corneal sphere is corneal sphere 814c and corneal curvature center 816c. The 3D cornea center estimation module 716 confirms the illustrated position is correct by checking that light from source 326 will properly reflect off of the corneal sphere and be imaged by camera 324 at the correct location of glint 854 on image 852. With this arrangement and with the known 3D positions of the light source 326, the camera 324, and the optical properties of the camera (focal length, etc.), the 3D cornea center estimation module 716 can determine the 3D location of the cornea's center of curvature 816 (relative to the wearable system).

The processes described herein in connection with at least FIGS. 8C-8E may effectively be an iterative, repetitious, or optimization process to identify the 3D position of the user's cornea center. As such, any of a plurality of techniques (e.g., iterative, optimization techniques, etc.) may be used to efficiently and quickly prune or reduce the search space of possible positions. Moreover, in some embodiments, the system may include two, three, four, or more light sources such as light source 326 and some of all of these light sources may be disposed at different positions, resulting in multiple glints such as glint 854 located at different positions on image 852 and multiple rays such as ray 856 having different origins and directions. Such embodiments may enhance the accuracy of the 3D cornea center estimation module 716, as the module 716 may seek to identify a cornea position that results in some or all of the glints & rays being properly reflected between their respective light sources and their respective positions on image 852. In other words and in these embodiments, the positions of some or all of the light sources may be relied upon in the 3D cornea position determination (e.g., iterative, optimization techniques, etc.) processes of FIGS. 8B-8E. In some implementations, the system may determine a vector or ray along which the center of the cornea resides before performing optimization processes (i.e., a 2D cornea center position). In such implementations, the 3D cornea center estimation module 716 may only search for cornea positions along such a vector, which may serve to provide computational and/or time savings when performing optimization processes. In at least some of these implementations, before determining such a vector, the system may initially (i) define a first plane between the origin of the eye camera coordinate system 850, a first light source (e.g., light source 326a), and a first glint (e.g., glint 854a) produced by the first light source, and (ii) define a second plane between the origin of the eye camera coordinate system 850, a second light source (e.g., light source 326b), and a second glint (e.g., glint 854b) produced by the second light source. The system may then simply calculate the cross product of the first plane and the second plane to determine the vector or ray along which the center of the cornea resides (i.e., the 2D cornea center position).

Example of Normalizing the Coordinate System of Eye Tracking Images

Figure 9A:
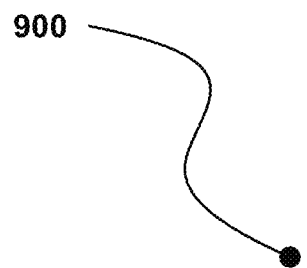
FIGS. 9A-9C illustrate an example normalization of the coordinate system of eye tracking images.
Figure 9A:
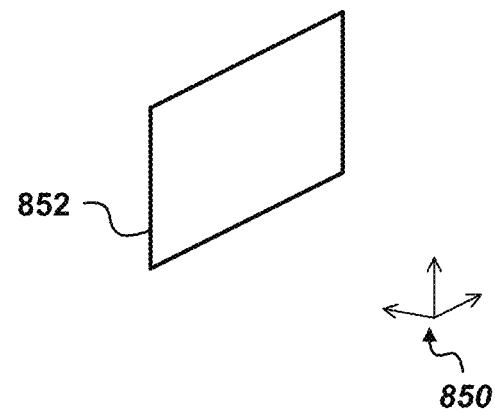
Figure 9B:
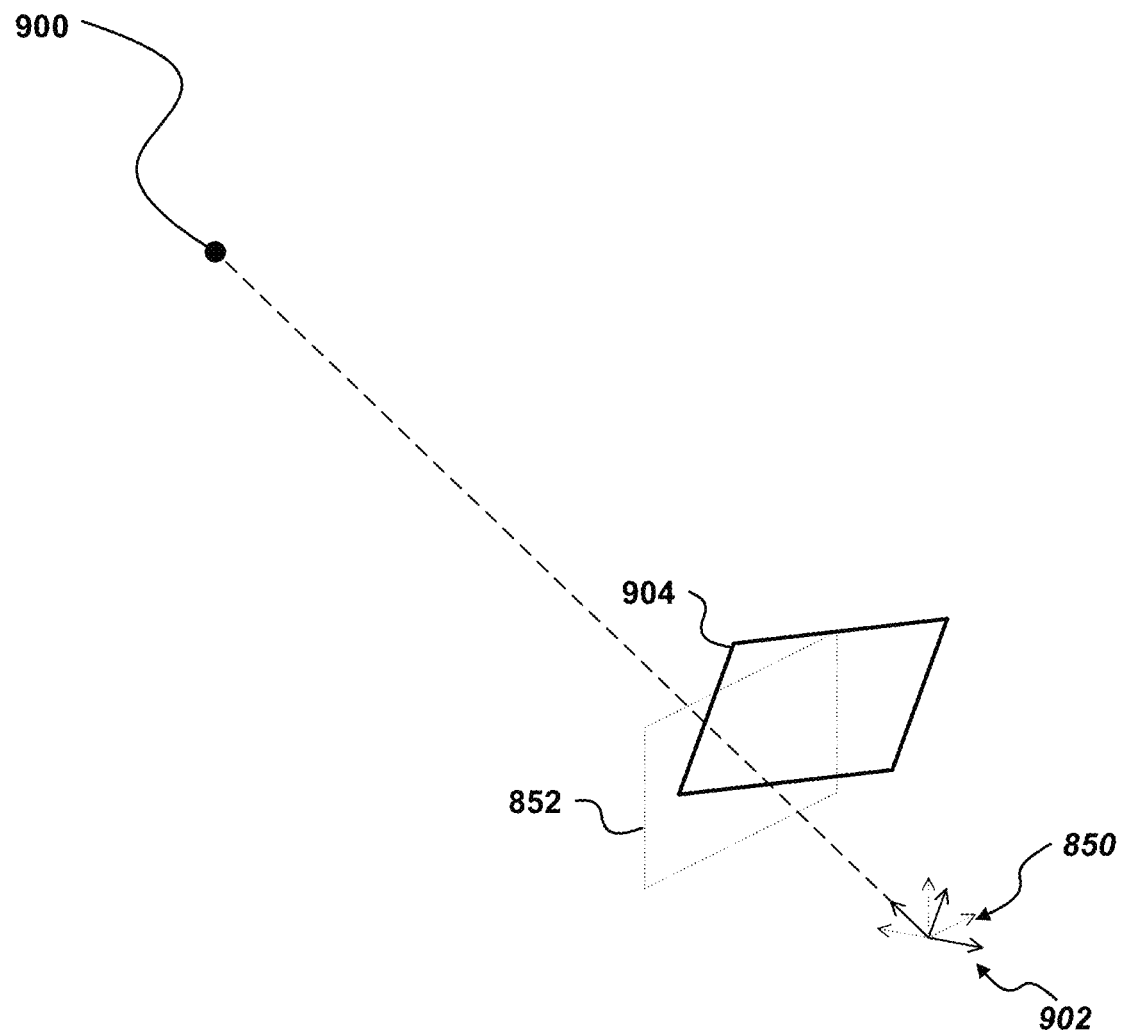
Figure 9C:
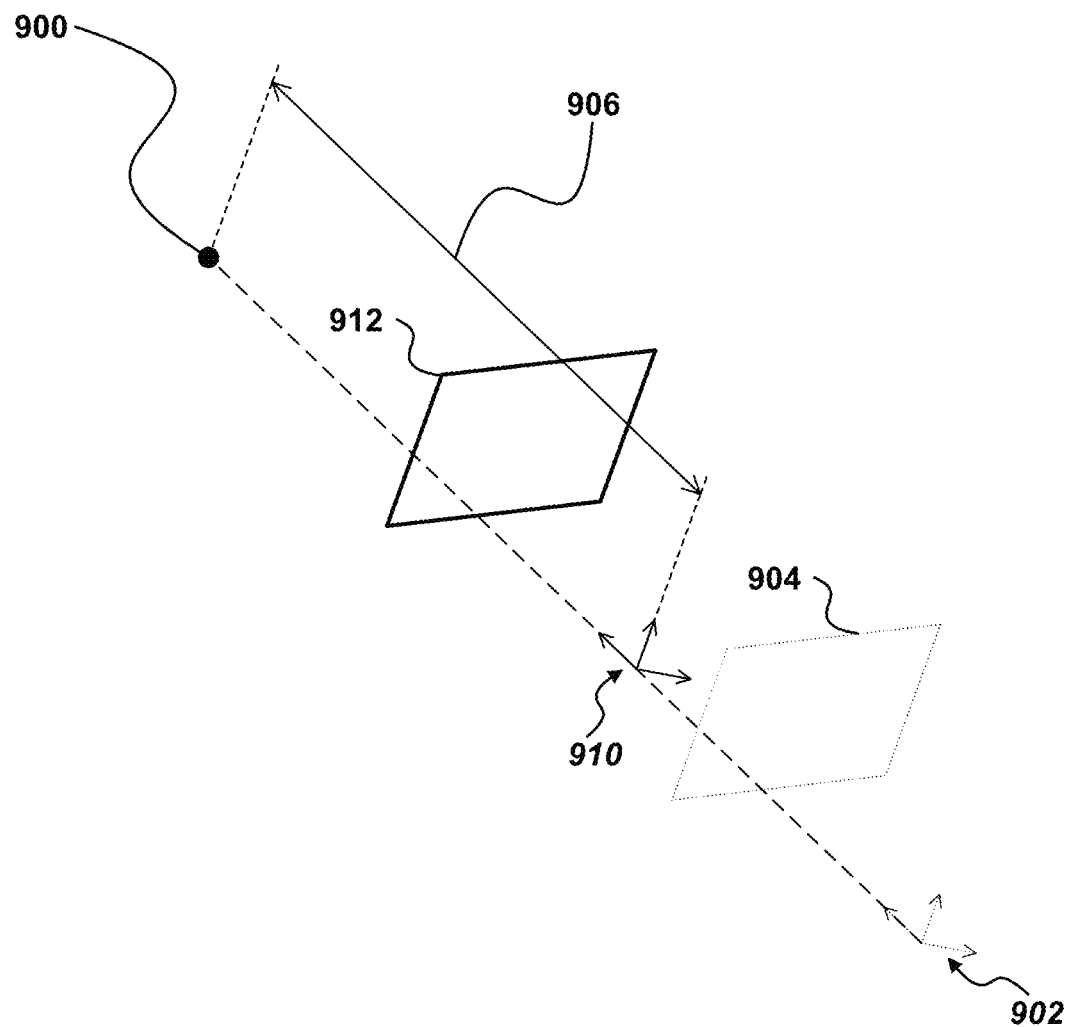

FIGS. 9A-9C illustrate an example normalization of the coordinate system of eye tracking images, by a component in the wearable system such as coordinate system normalization module 718 of FIG. 7A. Normalizing the coordinate system of eye tracking images relative to a user's pupil location may compensate for slippage of the wearable system relative to a user's face (e.g., headset slippage) and such normalization may establish a consistent orientation and distance between eye tracking images and a user's eyes.

As shown in FIG. 9A, coordinate system normalization module 718 may receive estimated 3D coordinates 900 of a user's center of corneal rotation and may receive un-normalized eye tracking images such as image 852. Eye tracking image 852 and coordinates 900 may be in an un-normalized coordinate system 850 that is based on the location of eye tracking camera 324, as an example.

As a first normalization step, coordinate system normalization module 718 may rotate coordinate system 850 into rotated coordinate system 902, such that the z-axis (e.g., the vergence depth axis) of the coordinate system may be aligned with a vector between the origin of the coordinate system and cornea center of curvature coordinates 900, as shown in FIG. 9B. In particular, coordinate system normalization module 718 may rotate eye tracking image 850 into rotated eye tracking image 904, until the coordinates 900 of the user's corneal center of curvature are normal to the plane of the rotated image 904.

As a second normalization step, coordinate system normalization module 718 may translate rotated coordinate system 902 into normalized coordinate system 910, such that cornea center of curvature coordinates 900 are a standard, normalized distance 906 from the origin of normalized coordinate system 910, as shown in FIG. 9C. In particular, coordinate system normalization module 718 may translate rotated eye tracking image 904 into normalized eye tracking image 912. In at least some embodiments, the standard, normalized distance 906 may be approximately 30 millimeters. If desired, the second normalization step may be performed prior to the first normalization step.

Example of Locating a User's Pupil Centroid with an Eye Tracking System

FIGS. 9D-9G illustrate an example of locating a user's pupil center (e.g., the center of a user's pupil 822 as shown in FIG. 8A) using 3D pupil center locator module 720 and eye tracking module 614.

Figure 9D:
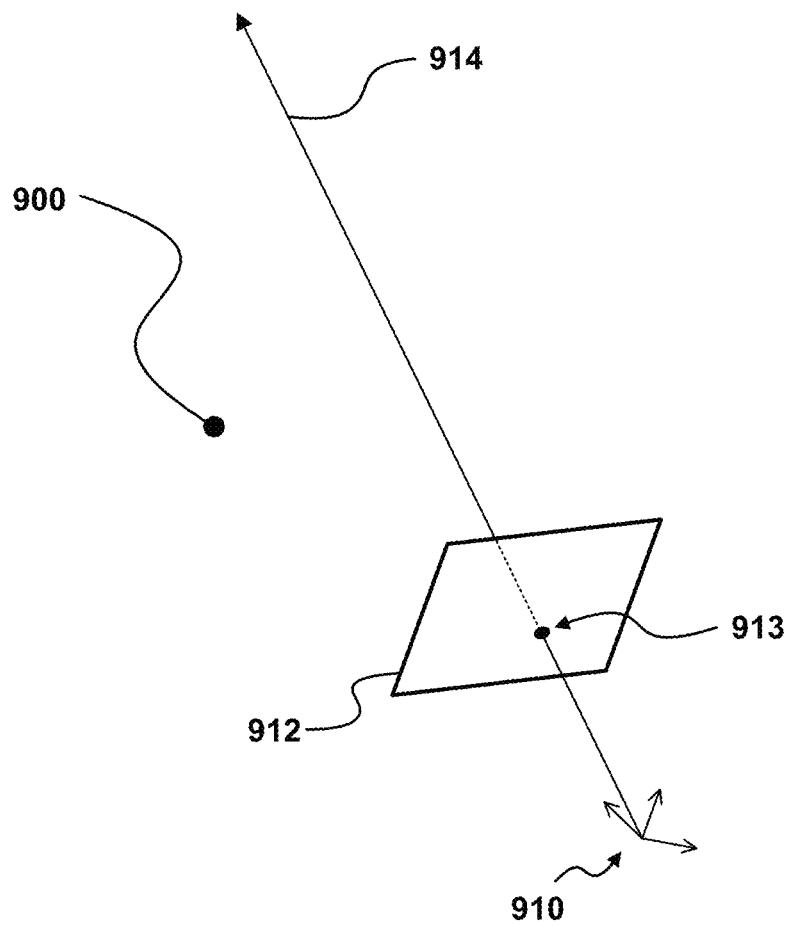
FIGS. 9D-9G illustrate example stages of locating a user's pupil center with an eye tracking module in a wearable system.

As shown in FIG. 9D, 3D pupil center locator module 720 may receive a normalized eye tracking image 912 that includes a pupil centroid 913 (e.g., a center of a user's pupil as identified by pupil identification module 712). The 3D pupil center locator module 720 may then simulate the normalized 3D position 910 of eye camera 324 to cast a ray 914 in the normalized coordinate system 910, through the pupil centroid 913.

Figure 9E:
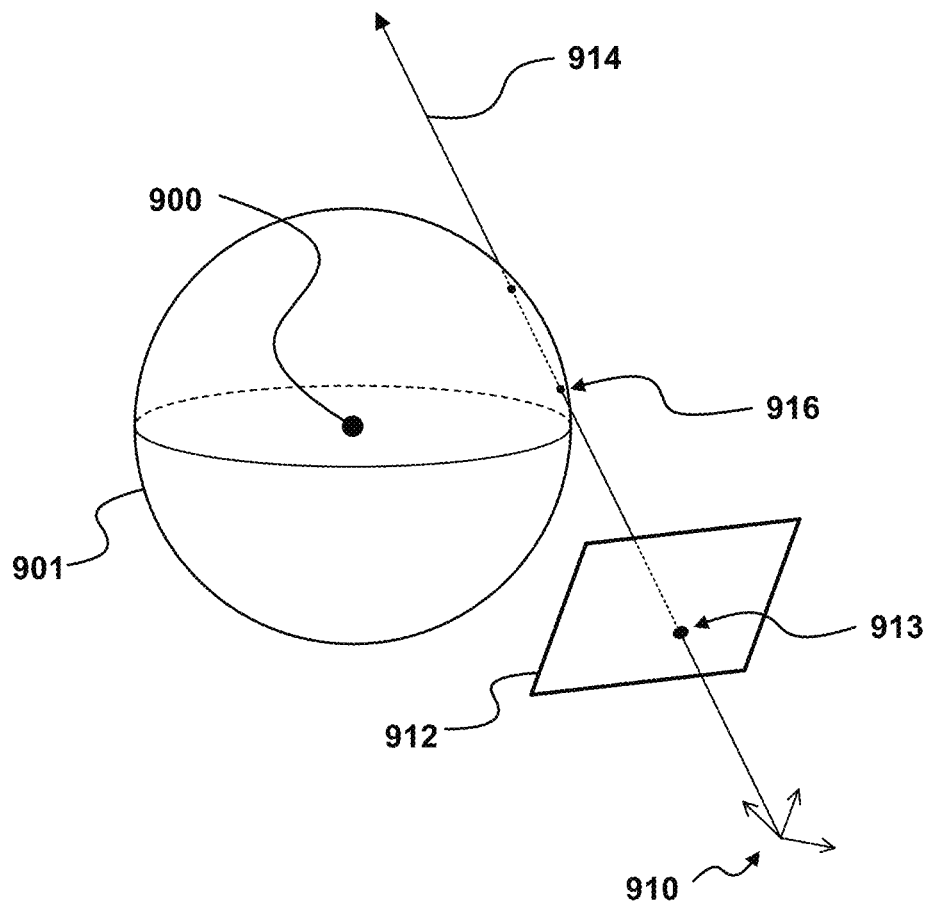

In FIG. 9E, 3D pupil center locator module 720 may simulate a corneal sphere such as corneal sphere 901 having center of curvature 900 based on data from 3D cornea center estimation module 716 (and as discussed in more detail in connection with FIGS. 8B-8E). As an example, the corneal sphere 901 may be positioned in the normalized coordinate system 910 based on the location of the center of curvature 816c identified in connection with FIG. 8E and based on the normalization processes of FIGS. 9A-9C. Additionally, 3D pupil center locator module 720 may identify a first intersection 916 between ray 914 (e.g., a ray between the origin of normalized coordinate system 910 and the normalized location of a user's pupil) and the simulated cornea, as shown in FIG. 9E.

Figure 9F:
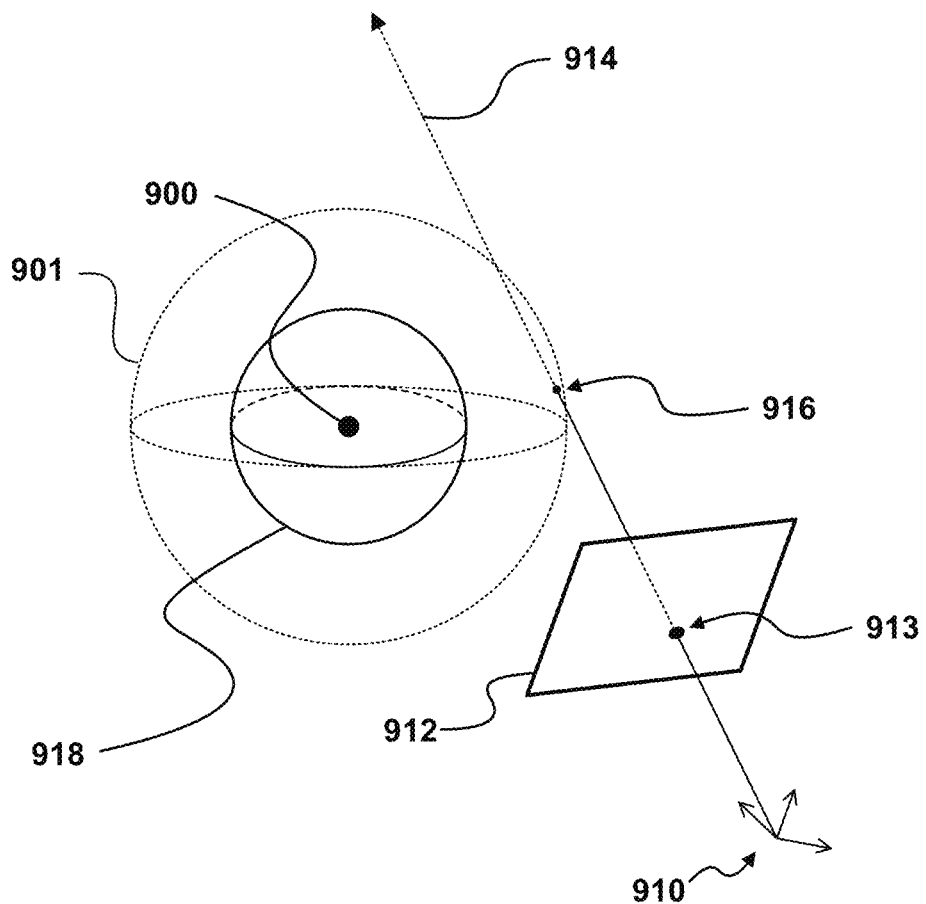

As shown in FIG. 9F, 3D pupil center locator module 720 may determine pupil sphere 918 based on corneal sphere 901. Pupil sphere 918 may share a common center of curvature with corneal sphere 901, but have a smaller radius. 3D pupil center locator module 720 may determine a distance between cornea center 900 and pupil sphere 918 (e.g., a radius of pupil sphere 918) based on a distance between the corneal center and the pupil center. In some embodiments, the distance between a pupil center and a corneal center of curvature may be determined from assumed eye dimensions 704 of FIG. 7A, from eye tracking extrinsics and intrinsics database 702, and/or from per-user calibration data 706. In other embodiments, the distance between a pupil center and a corneal center of curvature may be determined from per-user calibration data 706 of FIG. 7A.

Figure 9G:
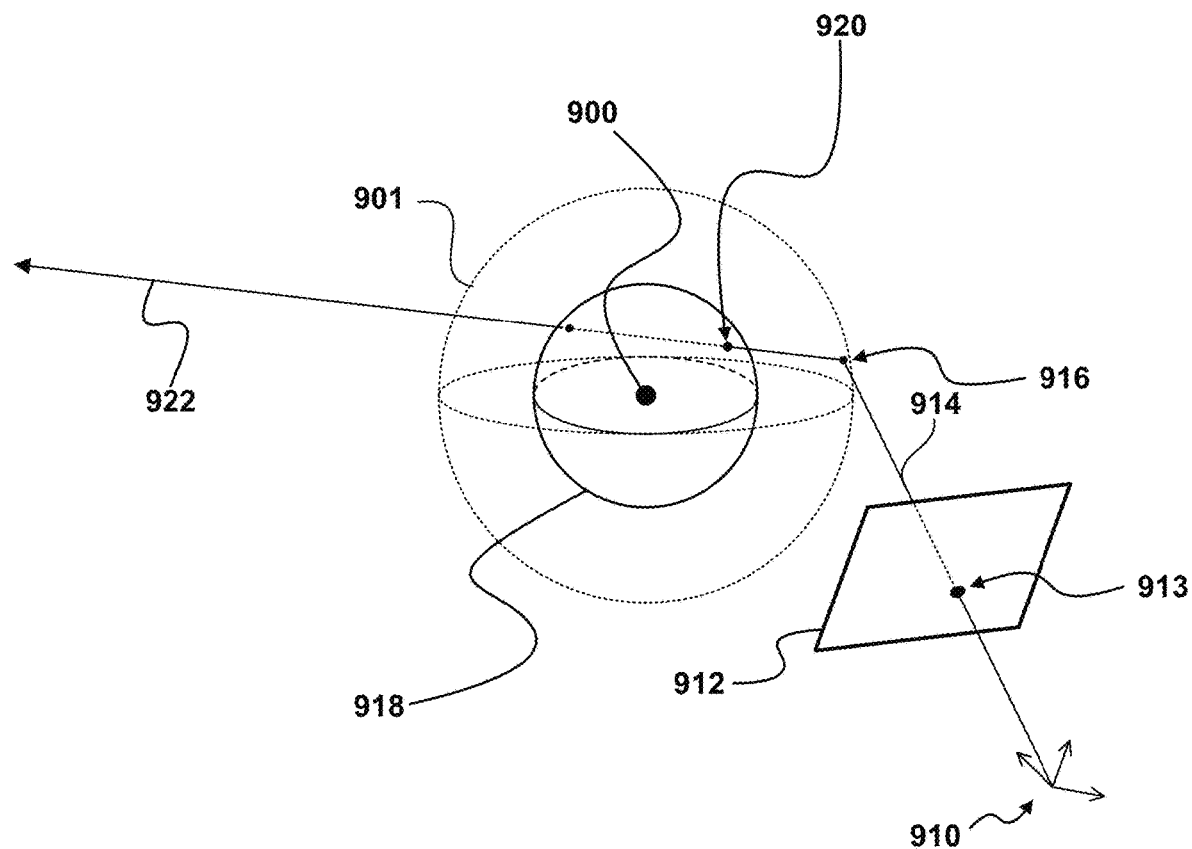

As shown in FIG. 9G, 3D pupil center locator module 720 may locate the 3D coordinates of a user's pupil center based on variety of inputs. As examples, the 3D pupil center locator module 720 may utilize the 3D coordinates and radius of the pupil sphere 918, the 3D coordinates of the intersection 916 between a simulated cornea sphere 901 and a ray 914 associated with a pupil centroid 913 in a normalized eye tracking image 912, information on the index of refraction of a cornea, and other relevant information such as the index of refraction of air (which may be stored in eye tracking extrinsics & intrinsics database 702) to determine the 3D coordinates of the center of a user's pupil. In particular, the 3D pupil center locator module 720 may, in simulation, bend ray 916 into refracted ray 922 based on refraction difference between air (at a first index of refraction of approximately 1.00) and corneal material (at a second index of refraction of approximately 1.38). After taking into account refraction caused by the cornea, 3D pupil center locator module 720 may determine the 3D coordinates of the first intersection 920 between refracted ray 922 and pupil sphere 918. 3D pupil center locator module 720 may determine that a user's pupil center 920 is located at approximately the first intersection 920 between refracted ray 922 and pupil sphere 918. With this arrangement, the 3D pupil center locator module 720 can determine the 3D location of the pupil center 920 (relative to the wearable system), in the normalized coordinate system 910. If desired, the wearable system can un-normalize the coordinates of the pupil center 920 into the original eye camera coordinate system 850. The pupil center 920 may be used together with the corneal curvature center 900 to determine, among other things, a user's optical axis using optical axis determination module 722 and a user's vergence depth by vergence depth estimation module 728.

Taking into account cornea refraction may possibly result in a more stable determined pupil position than one based on the first intersection 916 between ray 914 (i.e., a ray between the origin of normalized coordinate system 910 and the normalized location of a user's pupil) and the simulated cornea, as shown in FIG. 9E. This is true in part because, while simpler to compute, the first intersection 916 may not correspond to a physical feature of the eye and, therefore, may not move together with the eye as a solid body. In contrast, calculating the pupil center 920 by taking into account cornea refraction may correspond better to the physical pupil position of the eye, even if there is still some variation as a result of viewing angle. In various implements, therefore, determining the optical axis of the eye may thus involve a calculation of the true pupil center, not the first intersection 916 between ray 914 and the simulated cornea.

Figure 9H:
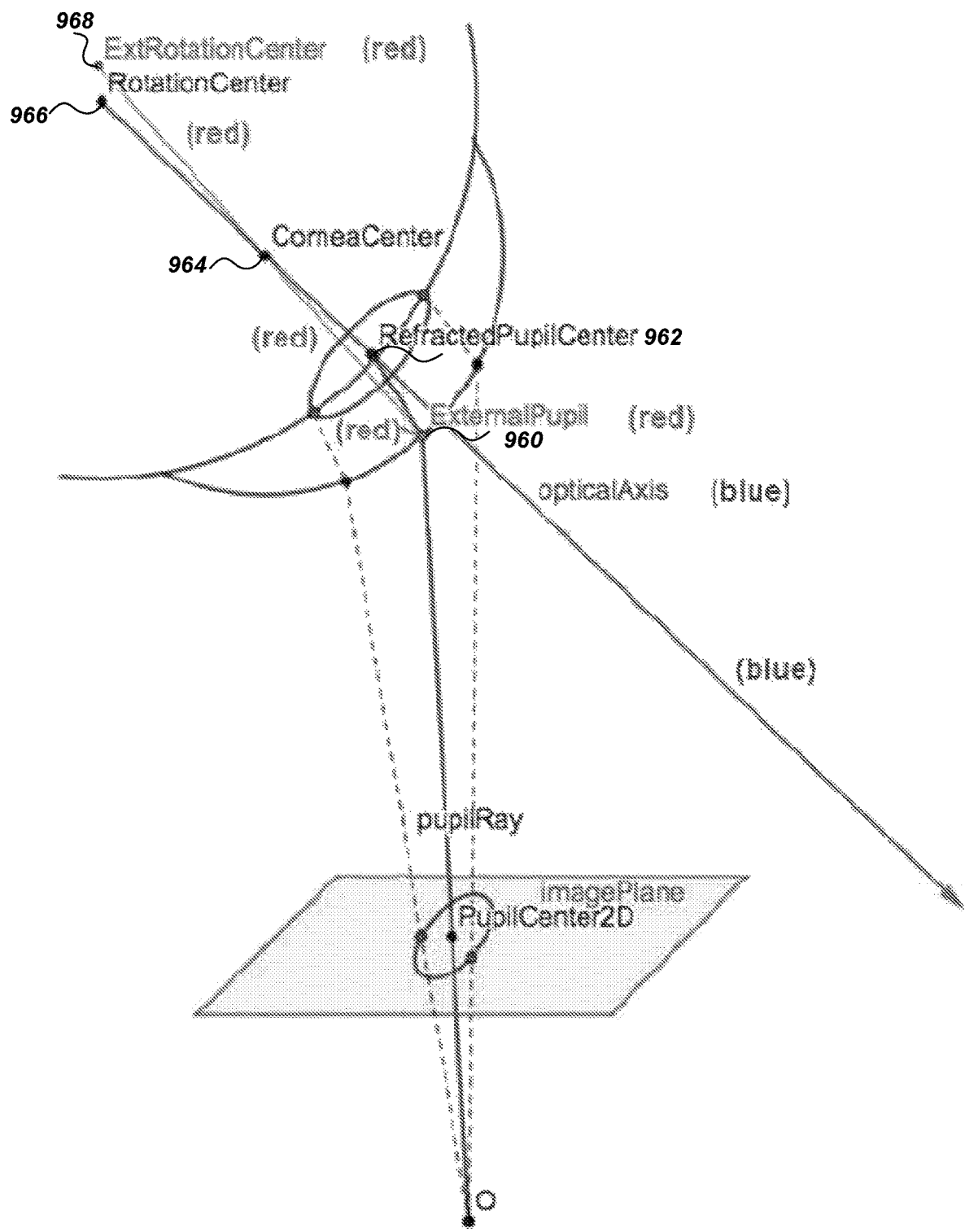
FIG. 9H illustrates example calculated locations of a pupil center that results from both taking into account cornea refraction and not taking into account cornea refraction.

A noticeable benefit in including refraction of the cornea occurs when the center of rotation (CoR) is estimated as a point at a fixed distance from the cornea center along the optical axis of the eye. In particular, including cornea refraction in determining pupil position may significantly reduce variation in calculating the center of rotation for different orientations of the eye. For example, the variation can be caused when the eye as a whole moves in the camera coordinate frame, such as during remount of the headset because the eye as a whole may be oriented differently with respect to the headset on remount. Because the pupil center 920 corresponds better to the physical pupil position of the eye, there may be less variation in the CoR when the eye as a whole moves in the camera coordinate frame. Advantageously, including refraction of the cornea surface may results in a more stable and accurate CoR that can potentially be used in determining when a headset is replaced onto a user's head, may allow for more correct render camera placement, may allow for other novel gaze tracking algorithms or any combination thereof. Additionally, CoR as a stable, slowly changing feature of the eye may potentially be tracked by multi-frame Kalman-type temporal filters to provide a geometric reference location for other applications. FIG. 9H illustrates example calculated locations of a pupil center that results from including cornea refraction and not including cornea refraction. When the pupil center is calculated without including the effect of cornea refraction, an external pupil 960 may be the result. The external pupil center 960 may correspond to the first intersection 916 between ray 914 (i.e., a ray between the origin of normalized coordinate system 910 and the normalized location of a user's pupil) and the simulated cornea, as shown in FIG. 9E. When the pupil center is calculated with taking cornea refraction into account, a refracted pupil center 962 may be the result. The refracted pupil center 962 may correspond to the pupil center 920, as shown in FIG. 9G. The different locations of the external pupil center 960 and the refracted pupil center 962 may result in different calculations of the Center of Rotation of the eye, as determined as a fixed distance from the cornea center 964 along the optical axis of the eye. For example, the external pupil center 960 may result in an external rotation center 968. The external rotation center 968 may vary significantly from the rotation center 966 calculated from the refracted pupil center 962.

FIGS. 9I-9L illustrate example experimental variations of the calculated Center of Rotation of the eye based on different calculated pupil centers using a collection of over 400 datasets. The data selected were only those frames that had four glints and a valid pupil center (i.e. not all three x, y, z coordinate components being equal to zero), to exclude obvious pipeline failure cases. Different center of rotation (CoR) to cornea curvature center distance values (R) were examined, and it was found that R=4.7 mm gives a nearly optimal average result. However, specific user distance values can be adjusted to provide even smaller variations of the CoR coordinates.

Figure 9I:
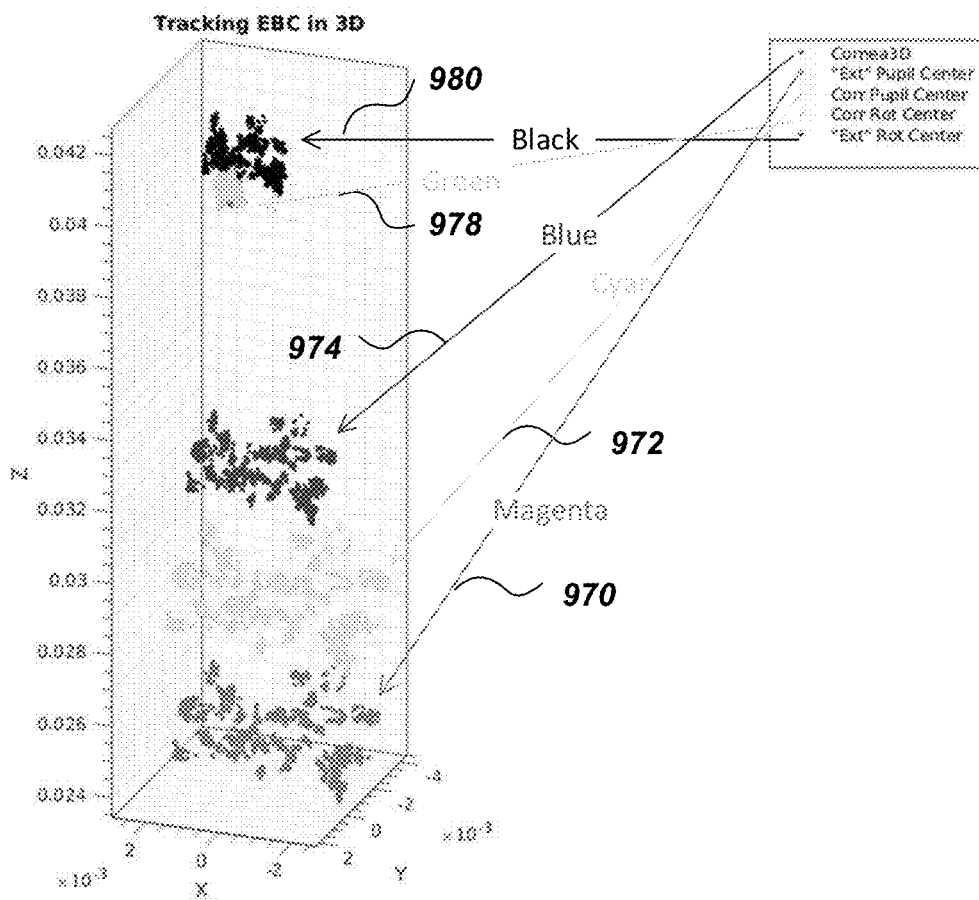
FIGS. 9I-9M illustrate example experimental variations of the calculated Center of Rotation of the eye based on different calculated pupil centers.
Figure 9J:
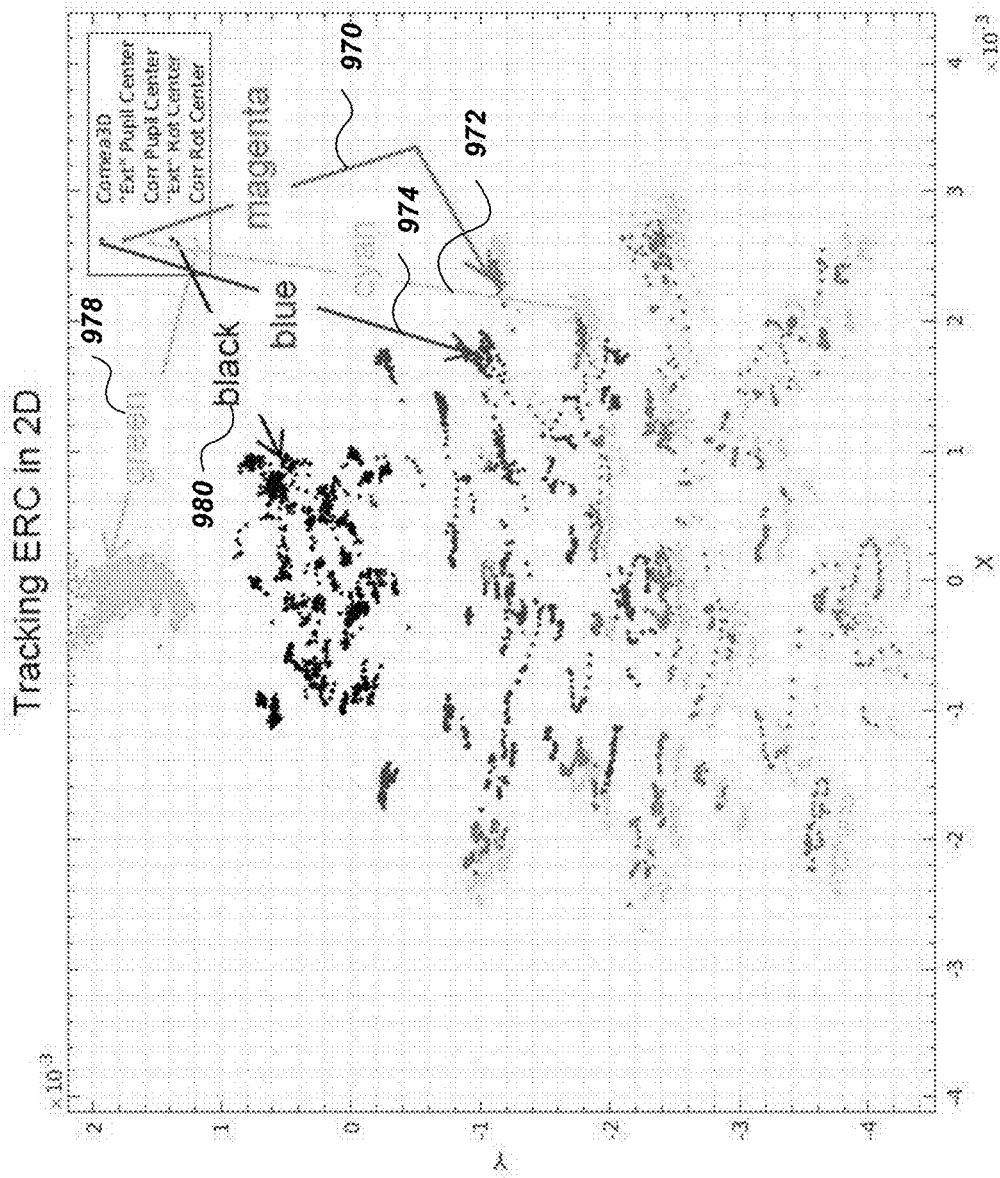

FIG. 9I illustrates a three dimensional graph of the x, y, and z coordinates of the different pupil centers, and corresponding CoRs calculated using the different pupil centers for the dataset described above. FIG. 9J illustrates the data in FIG. 9I in the XY projection. Cluster 970 corresponds to the coordinates for the external pupil center 960, cluster 972 corresponds to the coordinates for the correct, refracted pupil center 962, cluster 974 corresponds to the cornea location (e.g., a three-dimensional cornea center location), cluster 978 corresponds to the CoR using the correct, refracted pupil center 962, and cluster 980 corresponds to the CoR using the external pupil center 960. Cluster 978 is smaller in size, specifically in the x direction than cluster 980, indicating less variation in the CoR using the refracted pupil center 962 than in the CoR using the external pupil center 960.

TABLE 1

| Center of Rotation | Left eye | | | | Right eye | | | |
| --- | --- | --- | --- | --- | --- | --- | --- | --- |
| | mean sigma$_x$ | mean sigma$_y$ | mean sigma$_z$ | mean sigma$_{3d}$ | mean sigma$_x$ | mean sigma$_y$ | mean sigma$_z$ | mean sigma$_{3d}$ |
| 'external' pupil | 0.00056 | 0.00033 | 0.00041 | 0.00080 | 0.00058 | 0.00032 | 0.00037 | 0.00078 |
| 'refracted' pupil | 0.00025 | 0.00027 | 0.00044 | 0.00060 | 0.00027 | 0.00026 | 0.00040 | 0.00058 |

As can be seen from Table 1, the standard deviation (or sigma) of x-component of the CoR is reduced by about half when the refracted pupil center 962 was used for the calculation as compared to when the external pupil center 960. The total three dimensional standard deviation (sigma$_{3d}$) also reduced significantly with the use of the refracted pupil center 962.

Figure 9K:
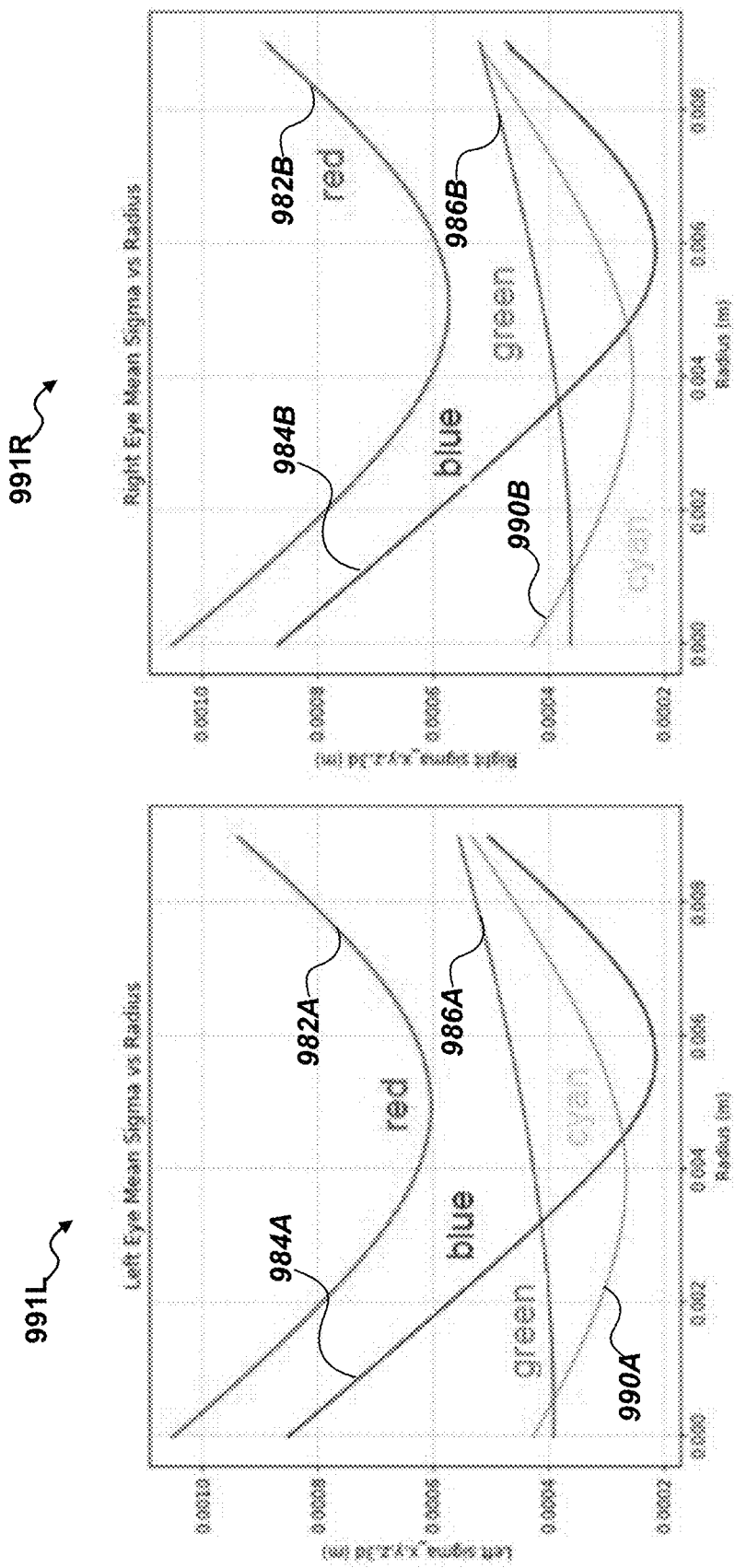
Figure 9L:
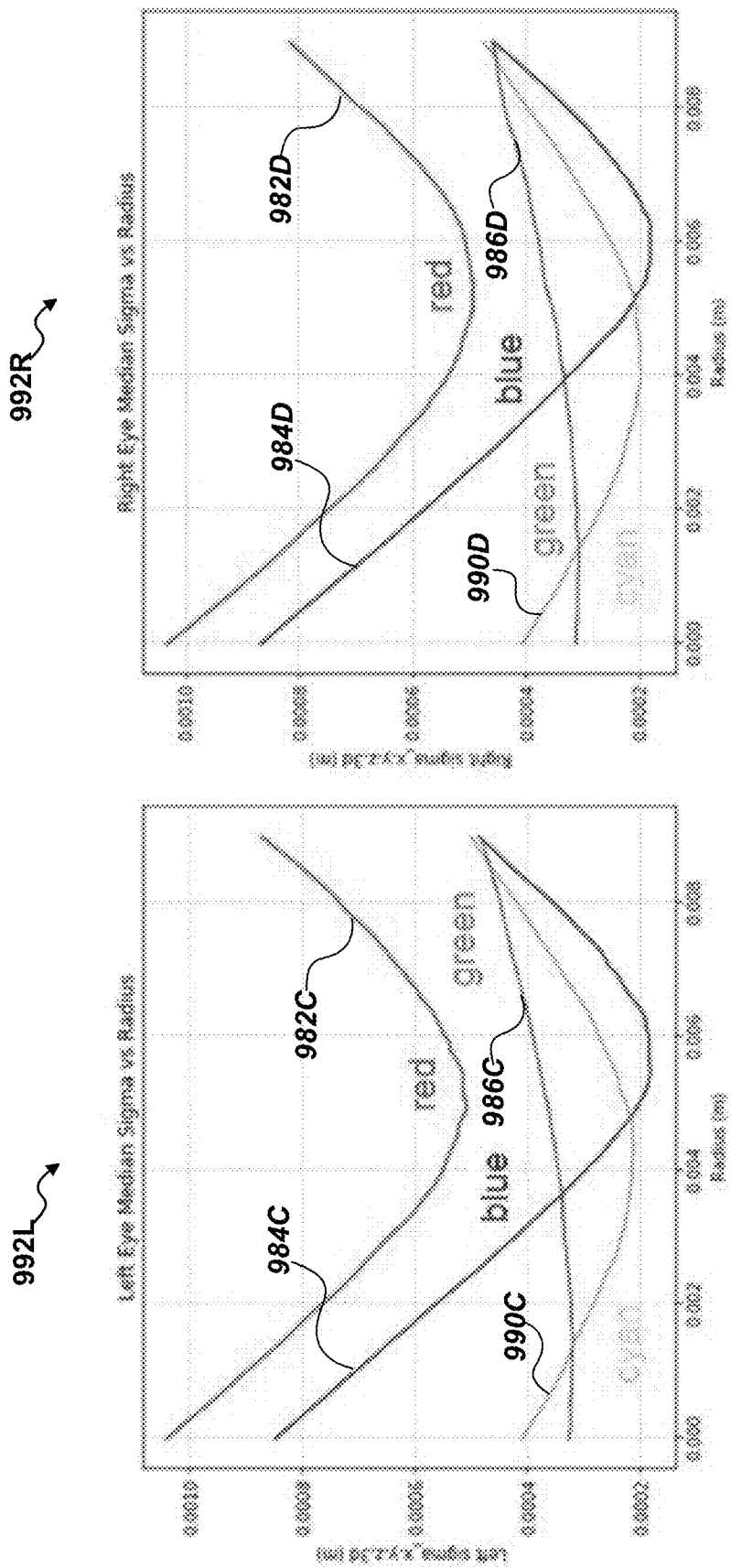

FIGS. 9K and 9L illustrates the mean and median CoR standard deviation, respectively, as a function of the CoR to cornea center of curvature distance for a collection of over 400 datasets. Graphs 991L and 991R illustrate the mean three dimensional CoR standard deviation (sigma$_{3d}$) as a function of the CoR to cornea center of curvature distance for the left and right eye, respectively. Graphs 992L and 992R illustrate the median three dimensional CoR standard deviation (sigma$_{3d}$) of the CoR to cornea center of curvature distance for the left and right eye respectively. Curve 982A corresponds to the total left eye mean sigma$_{3d}$, curve 982B corresponds to the total right eye mean sigma$_{3d}$, curve 982C corresponds to the total left eye median sigma$_{3d}$, curve 982D corresponds to the total right eye median sigma$_{3d}$. Curves 984A-D correspond to the x components of the various sigma$_{3d}$, curves 990A-D correspond to the y components of the various sigma$_{3d}$, and curves 986A-D correspond to the z components of the various sigma$_{3d}$.

Figure 9M:
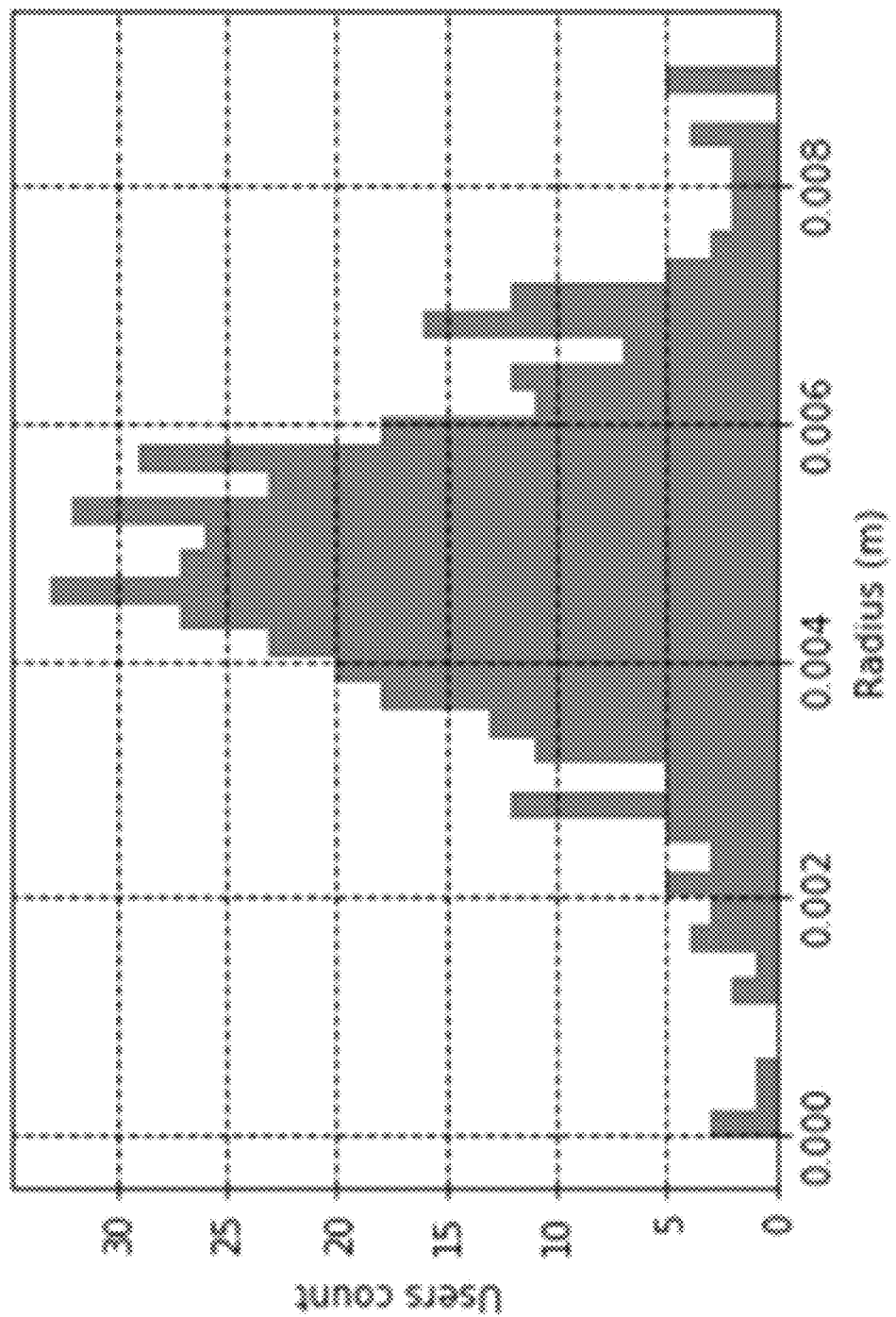
Figure 10:
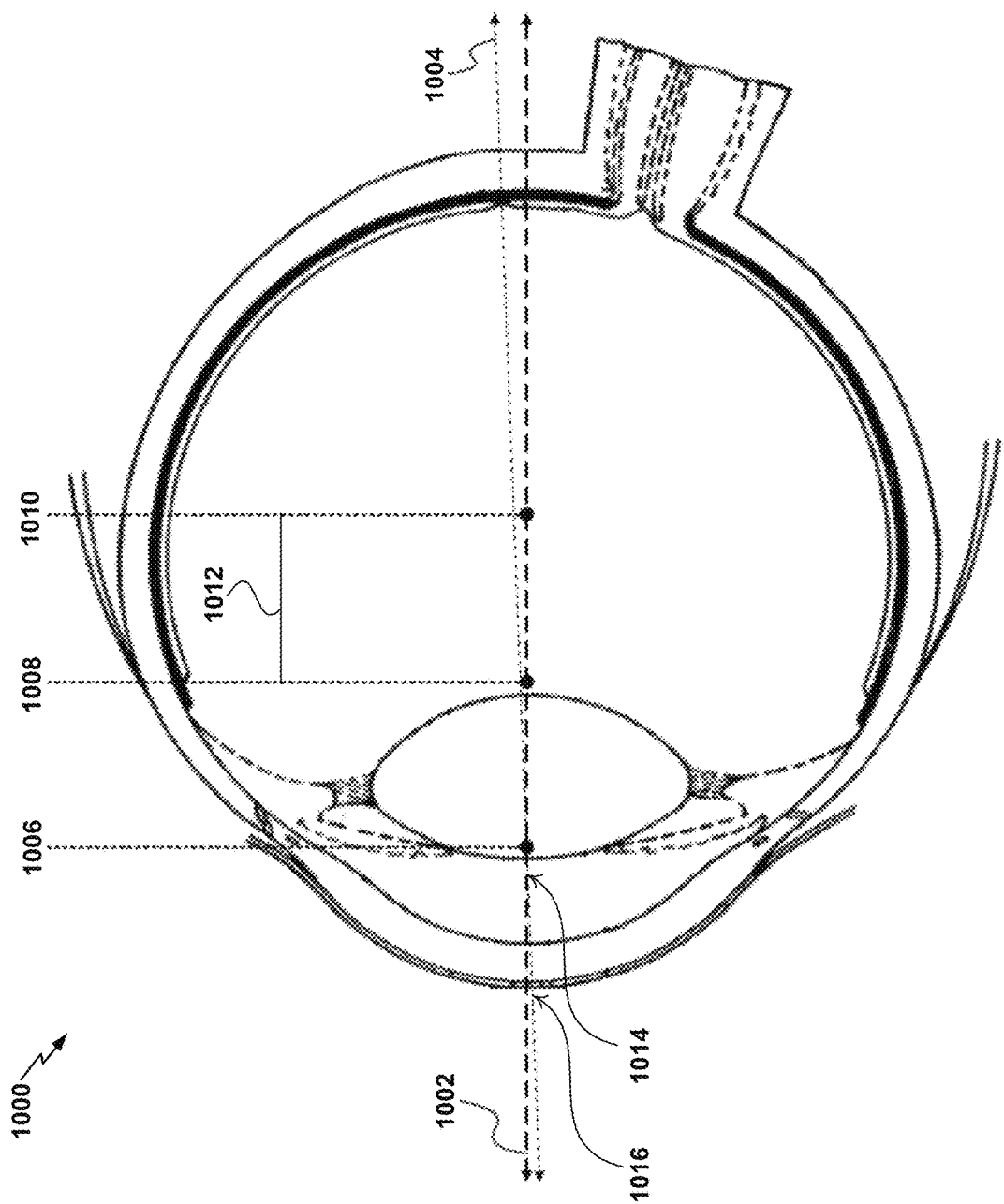
FIG. 10 illustrates an example of an eye including the eye's optical and visual axes and the eye's center of rotation.

FIG. 9M illustrates an example distribution of the optimal radius calculated individually for each user dataset as a value of the CoR to cornea distance that provides a minimum of the sigma$_{3d}$. The mean of the distribution is found to be at R=4.9 mm, with a standard deviation of 1.5 mm. The users with very small radius (R~1 mm) were found to be cases with very bad gaze tracking and so had to be excluded. Example of Differences Between Optical and Visual Axes As discussed in connection with optical to visual mapping module 730 of FIG. 7A, a user's optical and visual axes are generally not aligned, due in part to a user's visual axis being defined by their fovea and that foveae are not generally in the center of a person's retina. Thus, when a person desires to concentrate on a particular object, the person aligns their visual axis with that object to ensure that light from the object falls on their fovea while their optical axis (defined by the center of their pupil and center of curvature of their cornea) is actually slightly offset from that object. FIG. 10 is an example of an eye 1000 illustrating the eye's optical axis 1002, the eye's visual axis 1004, and the offset between these axes. Additionally, FIG. 10 illustrates the eye's pupil center 1006, the eye's center of cornea curvature 1008, and the eye's average center of rotation (CoR) 1010. In at least some populations, the eye's center of cornea curvature 1008 may lie approximately 4.7 mm in front, as indicated by dimension 1012, of the eye's average center of rotation (CoR) 1010. Additionally, the eye's center of perspective 1014 may lie approximately 5.01 mm in front of the eye's center of cornea curvature 1008, about 2.97 mm behind the outer surface 1016 of the user's cornea, and/or just in front of the user's pupil center 1006 (e.g., corresponding to a location within the anterior chamber of eye 1000). As additional examples, dimension 1012 may between 3.0 mm and 7.0 mm, between 4.0 and 6.0 mm, between 4.5 and 5.0 mm, or between 4.6 and 4.8 mm or any ranges between any values and any values in any of these ranges. The eye's center of perspective (CoP) 1014 may be a useful location for the wearable system as, in at least some embodiments, registering a render camera at the CoP may help to reduce or eliminate parallax artifacts.

FIG. 10 also illustrates such a within a human eye 1000 with which the pinhole of a render camera can be aligned. As shown in FIG. 10, the pinhole of a render camera may be registered with a location 1014 along the optical axis 1002 or visual axis 1004 of the human eye 1000 closer to the outer surface of the cornea than both (a) the center of the pupil or iris 1006 and (b) the center of cornea curvature 1008 of the human eye 1000. For example, as shown in FIG. 10, the pinhole of a render camera may be registered with a location 1014 along the optical axis 1002 of the human eye 1000 that is about 2.97 millimeters rearward from the outer surface of the cornea 1016 and about 5.01 millimeters forward from the center of cornea curvature 1008. The location 1014 of the pinhole of the render camera and/or the anatomical region of the human eye 1000 to which the location 1014 corresponds can be seen as representing the center of perspective of the human eye 1000. The optical axis 1002 of the human eye 1000 as shown in FIG. 10 represents the most direct line through the center of cornea curvature 1008 and the center of the pupil or iris 1006. The visual axis 1004 of the human eye 1000 differs from the optical axis 1002, as it represents a line extending from the fovea of the human eye 1000 to the center of the pupil or iris 1006.

Figure 11:
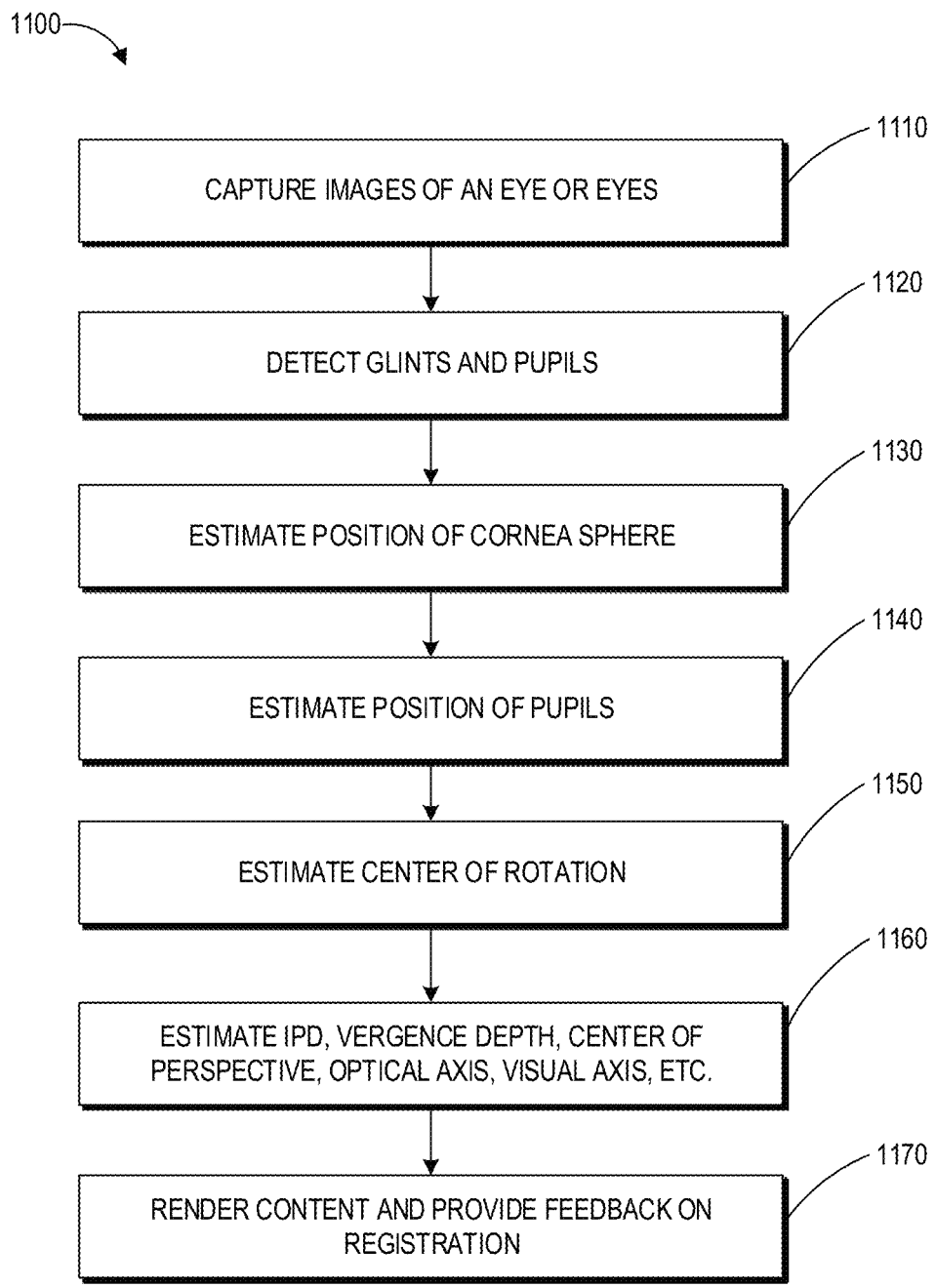
FIG. 11 is a process flow diagram of an example of a method for using eye tracking in rendering content and providing feedback on registration in a wearable device.

Example Processes of Rendering Content and Checking Registration Based on Eye Tracking FIG. 11 is a process flow diagram of an example method 1100 for using eye tracking in rendering content and providing feedback on registration in a wearable device. The method 1100 may be performed by the wearable system described herein. Embodiments of the method 1100 can be used by the wearable system to render content and provide feedback on registration (e.g., fit of the wearable device to the user) based on data from an eye tracking system.

At block 1110, the wearable system may capture images of a user's eye or eyes. The wearable system may capture eye images using one or more eye cameras 324, as shown at least in the example of FIG. 3. If desired, the wearable system may also include one or more light sources 326 configured to shine IR light on a user's eyes and produce corresponding glints in the eye images captured by eye cameras 324. As discussed herein, the glints may be used by an eye tracking module 614 to derive various pieces of information about a user's eye including where the eye is looking.

At block 1120, the wearable system may detect glints and pupils in the eye images captured in block 1110. As an example, block 1120 may include processing the eye images by glint detection & labeling module 714 to identify the two-dimensional positions of glints in the eye images and processing the eye images by pupil identification module 712 to identify the two-dimensional positions of pupils in the eye images.

At block 1130, the wearable system may estimate the three-dimensional positions of a user's left and right corneas relative to the wearable system. As an example, the wearable system may estimate the positions of the center of curvature of a user's left and right corneas as well as the distances between those centers of curvature and the user's left and right corneas. Block 1130 may involve 3D cornea center estimation module 716 identifying the position of the centers of curvature as described herein at least in connection with FIGS. 7A and 8A-8E.

At block 1140, the wearable system may estimate the three-dimensional positions of a user's left and right pupil centers relative to the wearable system. As an example, the wearable system and 3D pupil center locator module 720 in particular, may estimate the positions of the user's left and right pupil centers as described at least in connection with FIGS. 7A and 9D-9G, as part of block 1140.

At block 1150, the wearable system may estimate the three-dimensional positions of a user's left and right centers or rotation (CoR) relative to the wearable system. As an example, the wearable system and CoR estimation module 724 in particular, may estimate the positions of the CoR for the user's left and right eyes as described at least in connection with FIGS. 7A and 10. As a particular example, the wearable system may find the CoR of an eye by walking back along the optical axis from the center of curvature of a cornea towards the retina.

At block 1160, the wearable system may estimate a user's IPD, vergence depth, center of perspective (CoP), optical axis, visual axis, and other desired attributes from eye tracking data. As examples, IPD estimation module 726 may estimate a user's IPD by comparing the 3D positions of the left and right CoRs, vergence depth estimation module 728 may estimate a user's depth by finding an intersection (or near intersection) of the left and right optical axes or an intersection of the left and right visual axes, optical axis determination module 722 may identify the left and right optical axes over time, optical to visual axis mapping module 730 may identify the left and right visual axes over time, and the CoP estimation module 732 may identify the left and right centers of perspective, as part of block 1160.

At block 1170, the wearable system may render content and may, optionally, provide feedback on registration (e.g., fit of the wearable system to the user's head) based in part on the eye tracking data identified in blocks 1120-1160. As an example, the wearable system may identify a suitable location for a render camera and then generate content for a user based on the render camera's location, as discussed in connection with light-field render controller 618, FIG. 7B, and render engine 622. As another example, the wearable system may determine if it is properly fitted to the user, or has slipped from its proper location relative to the user, and may provide optional feedback to the user indicating whether the fit of the device needs adjustment, as discussed in connection with registration observer 620. In some embodiments, the wearable system may adjust rendered content based on improper or less than ideal registration in an attempt to reduce, minimize or compensate for the effects of improper or mis-registration.

Example Graphs of Rendering Content in Response to User Eye Movements

Figure 12:
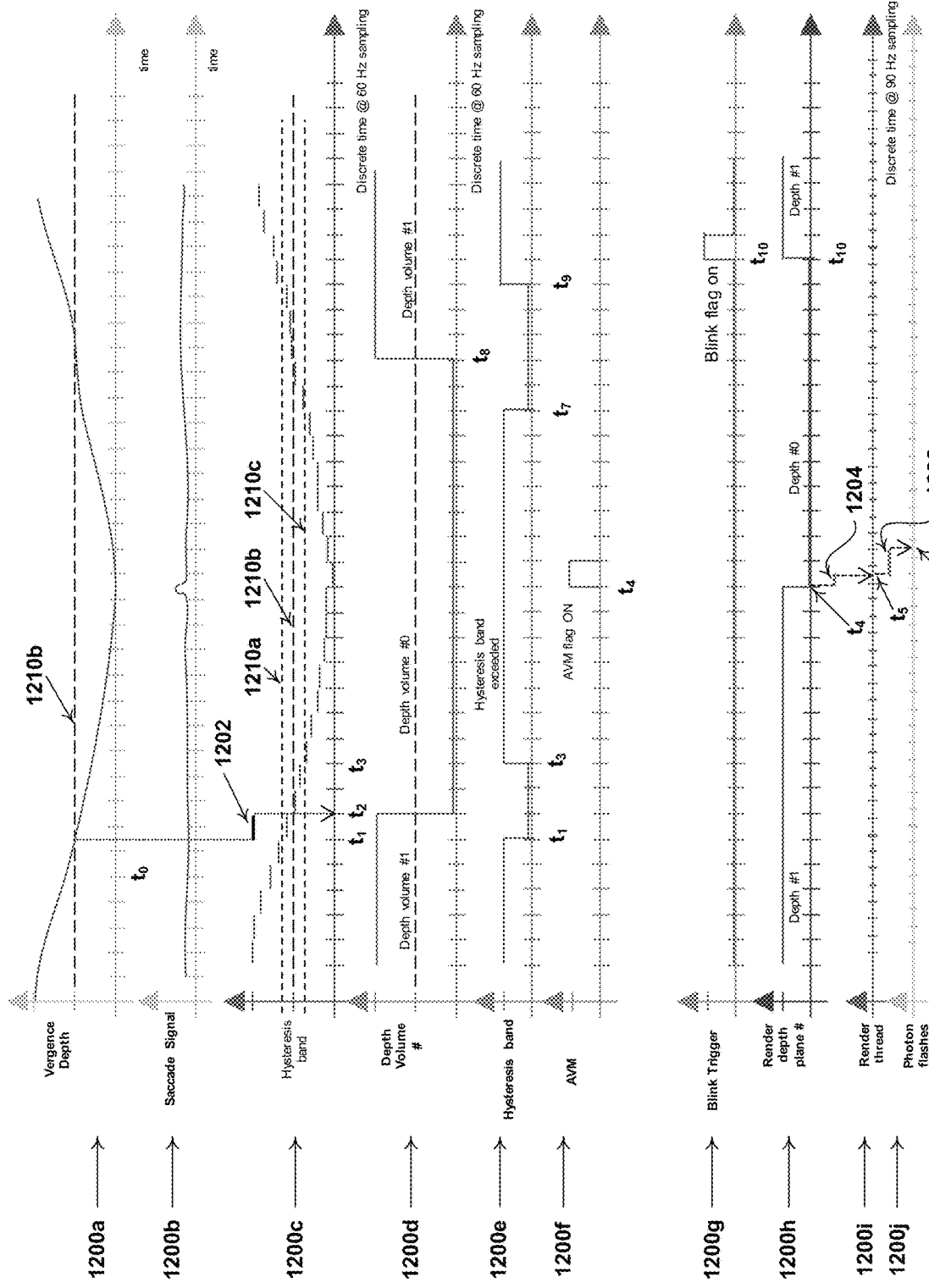
FIG. 12 is a set of example graphs illustrating how the wearable system may switch depth planes in response to the user's eye movements.

FIG. 12 includes a set of example graphs 1200a-1200j which illustrate how the wearable system may switch depth planes in response to the user's eye movements. As discussed herein in connection with FIGS. 4 and 7, the wearable system may include multiple depth planes, where the various depth planes are configured to present content to a user at a different simulated depth or with a different accommodation cue (e.g., with various levels of wavefront curvature or light ray divergence). As an example, the wearable system may include a first depth plane configured to simulate a first range of depths and a second depth plane configured to simulate a second range of depths and, while these two ranges may desirably overlap to facilitate hysteresis in switching, the second range of depths may generally extend to greater distances from the user. In such embodiments, the wearable system may track a user's vergence depth, saccade movements, and blinks to switch between the first and second depth planes in a manner that avoid excessive depth plane switching, excessive accommodation-vergence mismatches, and excessive periods of accommodation-vergence mismatch and that seek to reduce the visibility of depth plane switches (e.g., by shifting depth planes during blinks and saccades).

Graph 1200a illustrates an example of a user's vergence depth over time. Graph 1200b illustrates an example of a user's saccade signal or velocity of eye movements over time.

Graph 1200c may illustrate vergence depth data generated by eye tracking module 614 and, in particular, data generated by vergence depth estimation module 728. As shown in graphs 1200c-1200h, eye tracking data may be sampled within eye tracking module 614 at a rate of approximately 60 Hz. As shown between graphs 1200b and 1200c, eye tracking data within eye tracking module 614 may lag behind a user's actual eye movements by a delay 1202. As an example, at time $t_1$ a user's vergence depth may cross a hysteresis threshold 1210a, but the hysteresis band crossing detection module 752 may not recognize the event until time $t_2$ after delay 1202.

Graph 1200c also illustrates various thresholds 1210a, 1210b, 1210c in a hysteresis band, which may be associated with transitions between first and second depth planes (e.g., depth planes #1 and #0 in FIG. 12). In some embodiments, the wearable system may try to display content with depth plane #1 whenever a user's vergence depth is greater than threshold 1210*b* and to display content with depth plane #0 whenever a user's vergence depth is less than threshold 1210*b*. However, to avoid excessive switching, the wearable system may implement hysteresis, whereby the wearable system will not switch from depth plane #1 to depth plane #0 until the user's vergence depth crosses outer threshold 1210*c*. Similarly, the wearable system may not switch from depth plane #0 to depth plane #1 until the user's vergence depth crosses outer threshold 1210*a*.

Graph 1200*d* illustrates an internal flag that may be generated by depth plane selection module 750, or hysteresis band crossing detection module 752, indicating whether the user's vergence depth is in the volume generally associated with depth plane #1 or the volume generally associated with depth plane #2 (e.g., whether the user's vergence depth is greater or less than threshold 1210*b*).

Graph 1200*e* illustrates an internal hysteresis band flag that may be generated by depth plane section module 750, or hysteresis band crossing detection module 752, indicating whether a user's vergence depth has cross an outer threshold such as threshold 1210*a* or 1210*c*. In particular, graph 1200*e* illustrates a flag indicative of whether the user's vergence depth has completely crossed a hysteresis band and into a region outside of the active depth plane's volume (e.g., into a region associated with a depth plane other than an active depth plane), thus potentially leading to undesirable accommodation-vergence mismatch (AVM).

Graph 1200*f* illustrates an internal AVM flag that may be generated by depth plane selection module 750, or hysteresis band crossing detection module 752, indicating whether a user's vergence has been in outside of the active depth plane's volume for greater than a predetermined time. The AVM flag may therefore identify when the user may have been subjected to an undesirable accommodation-vergence mismatch for a nearly-excessive or excessive period of time. Additionally or alternatively, the internal AVM flag may also indicate whether a user's vergence has gone a predetermined distance beyond the active depth plane's volume, thus creating a potentially-excessive accommodation-vergence mismatches. In other words, the AVM flag may indicate when a user's vergence has exceeded an additional threshold even further from threshold 1210*b* than thresholds 1210*a* and 1210*c*.

Graph 1200*g* illustrates an internal blink flag that may be generated by ocular event detection module 754, which may determine when a user has or is blinking. As noted herein, it may be desired to switch depth planes upon user blink, to reduce the likelihood of the user perceiving the switch in depth planes.

Graph 1200*h* illustrates an example output from depth plane selection module 750. In particular, graph 1200*h* shows that depth plane selection module 750 may output an instruction to utilize a selected depth plane, which may change over time, to a render engine such as render engine 622 (see FIG. 6).

Graphs 1200*i* and 1200*j* illustrate delays that may be present in the wearable system including a delay by render engine 622 to switch depth planes and a delay by the display 220, which may need to provide light associated with a new image frame in a new depth plane to effectuate a change in depth planes.

Reference will now be made to the events illustrated in graphs 1200*a*-1200*j* at various times ($t_0$-$t_{10}$).

Sometime around time $t_0$, a user's vergence depth may cross threshold 1210*a*, which may be an outer hysteresis threshold. After a delay associated with image capture and signal processing, the wearable system may generate a signal, as indicated in graph 1200*e*, that indicates that the user's vergence depth lies within the hysteresis band. In the example of graph 1200*e*, one or more modules of light-field render controller 618 may present a hysteresis band exceeded flag at approximately time $t_1$ in connection with the user's vergence depth crossing threshold 1210*a*.

The user's vergence depth may continue to decrease from time to until approximately time $t_4$ and may thereafter increase.

At time $t_1$, a user's vergence depth may cross threshold 1210*b*, which may be a midpoint between two depth planes such as depth planes #1 and #0. After processing delay 1202, eye tracking module 614 may alter an internal flag indicating that the user's vergence depth has moved from a volume generally associated with depth plane #1 into a volume generally associated with depth plane #0, as illustrated in graph 1200*d*.

At time $t_3$, one or more modules of light-field render controller 618 may determine that the user's vergence depth, as shown in graph 1200*a*, has moved entirely through the hysteresis band and cross outer threshold 1210*c*. As a result, one or more modules of light-field render controller 618 may generate a signal, as indicated in graph 1200*e*, that indicates that the user's vergence depth lies outside the hysteresis band. In at least some embodiments, one or more modules of light-field render controller 618 (e.g., depth plane selection module 750) may switch between first and second depth planes only when a user's vergence depth is outside of the hysteresis band between those two depth planes.

In at least some embodiments, one or more modules of light-field render controller 618 may be configured to switch depth planes at time $t_3$. In particular, one or more modules of light-field render controller 618 may be configured to switch depth planes based on a determination that the vergence depth has moved from the volume of the currently selected depth plane (depth plane #1 as indicated by graph 1200*h*) into the volume of another depth plane (depth plane #0) and entirely crossed a hysteresis band. In other words, one or more modules of light-field render controller 618 may implement a depth plane switch whenever the hysteresis band is exceeded (graph 1200*e* is high) and an accommodation-vergence mismatch based on time or magnitude of mismatch is detected (graph 1200*f* is high). In such embodiments, one or more modules of light-field render controller 618 may provide a signal to render engine 622 instructing render engine 622 to switch to the other depth plane (depth plane #0). In the example of FIG. 12, however, one or more modules of light-field render controller 618 may be configured to delay depth plane switches until at least one other condition has been satisfied. These additional conditions may include, as examples, a blink condition, an accommodation-vergence mismatch timeout condition, and an accommodation-vergence magnitude condition.

At time $t_4$ and in the example of FIG. 12, one or more modules of light-field render controller 618 may be configured to switch depth planes. In particular, one or more modules of light-field render controller 618 may determine that the user's vergence has been in the volume associated with depth plane #0 for longer than a predetermined threshold of time (and optionally, also outside of the hysteresis band for that period of time). Examples of predetermined thresholds of time include 5 seconds, 10 seconds, 20 seconds, 30 seconds, 1 minute, and 90 seconds and any range between any of these values. Upon such a determination, one or more modules of light-field render controller 618 may generate an AVM flag, as indicated in graph 1200*f*, and direct render engine 622 to switch to depth plane #0, as indicated in graph 1200h. In some embodiments, one or more modules of light-field render controller 618 may generate an AVM flag and direct render engine 622 to switch depth planes if the user's vergence depth is detected to be more than a threshold distance from the current selected depth volume.

At time $t_5$ and after delay 1204, the render engine 622 may start rendering content at the newly-selected depth plane #0. After a delay 1206 associated with rendering and conveying light to a user through the display 220, the display 220 may be fully switched to the newly-selected depth plane #0 by time $t_6$.

Thus, graphs 1200a-j illustrates, between times to and $t_6$, how the system may respond to a user's changing vergence and may switch depth planes after the user's vergence has moved away from a prior depth volume for more than a predetermined period of time. Graphs 1200a-j, between times $t_7$ and $t_{10}$, may illustrate how the system responds to a user's changing vergence and may switch depth planes upon detection of the user blinking, which may be prior to the predetermined period of time.

At time $t_7$, one or more modules of light-field render controller 618 may detect that the user's vergence depth has entered the hysteresis region between depth planes #0 and #1 (e.g., that the user's vergence depth has crossed outer threshold 1210c). In response, one or more modules of light-field render controller 618 may alter a hysteresis flag as shown in graph 1200e.

At time $t_8$, one or more modules of light-field render controller 618 may detect that the user's vergence depth has cross threshold 1210b and moved from the volume generally associated with depth plane #0 into the volume generally associated with depth plane #1. As such, one or more modules of light-field render controller 618 may alter a depth volume flag, as shown in graph 1200d.

At time $t_9$, one or more modules of light-field render controller 618 may detect that the user's vergence depth has crossed threshold 1210a and moved out of the hysteresis volume into the volume generally associated exclusively with depth plane #1. In response, one or more modules of light-field render controller 618 may alter a hysteresis flag as shown in graph 1200e.

At around time $t_{10}$, the user may blink and one or more modules of light-field render controller 618 may detect that blink. As one example, ocular event detection module 754 may detect a user's blink. In response, one or more modules of light-field render controller 618 may generate a blink flag, as shown in graph 1200h. In at least some embodiments, one or more modules of light-field render controller 618 may implement a depth plane switch whenever the hysteresis band is exceeded (graph 1200e is high) and a blink is detected (graph 1200g is high). Thus, one or more modules of light-field render controller 618 may instruct render engine 622 to switch depth planes at time $t_{10}$.

Example Rendering Modes in a Mixed Reality System Having Multiple Depth Planes

In mixed reality systems, computer-generated (rendered) scenes may be conveyed to the human eye such that real and virtual objects are spatially aligned (from the perspective of the user). To provide a user with a visual perception of spatial alignment between real and virtual objects, the perspective from which the computer-generated scene is rendered and presented may preferably correspond to the perspective (e.g., the position and orientation) of the user's eye. As an example, user may perceive real and virtual objects to be spatially aligned in a desired manner when a "Real World" frame (within which real objects exist) and a "Render World" frame (within which virtual objects exist) are accurately aligned with one another.

A digital light-field display device, such as wearable system 200 including display 220 of FIG. 2, is an example of a mixed reality system in which a light-field representative of 3D virtual content (virtual objects) may be provided to a user at various depths using one or more depth planes. The depth planes may be compared to one or more virtual screens, at varying distances from the user, onto which virtual content can be projected or displayed, converted into virtual pixels, and provided to a user. As such, a mixed reality system may be optically equivalent to a system having one or more transparent floating screens, located at varying distances from the user. In this manner, a digitized light field is projected through a user's iris onto their retina and an image of the 3D virtual content is formed (e.g., the user perceives the image of the 3D virtual content).

Figure 13:
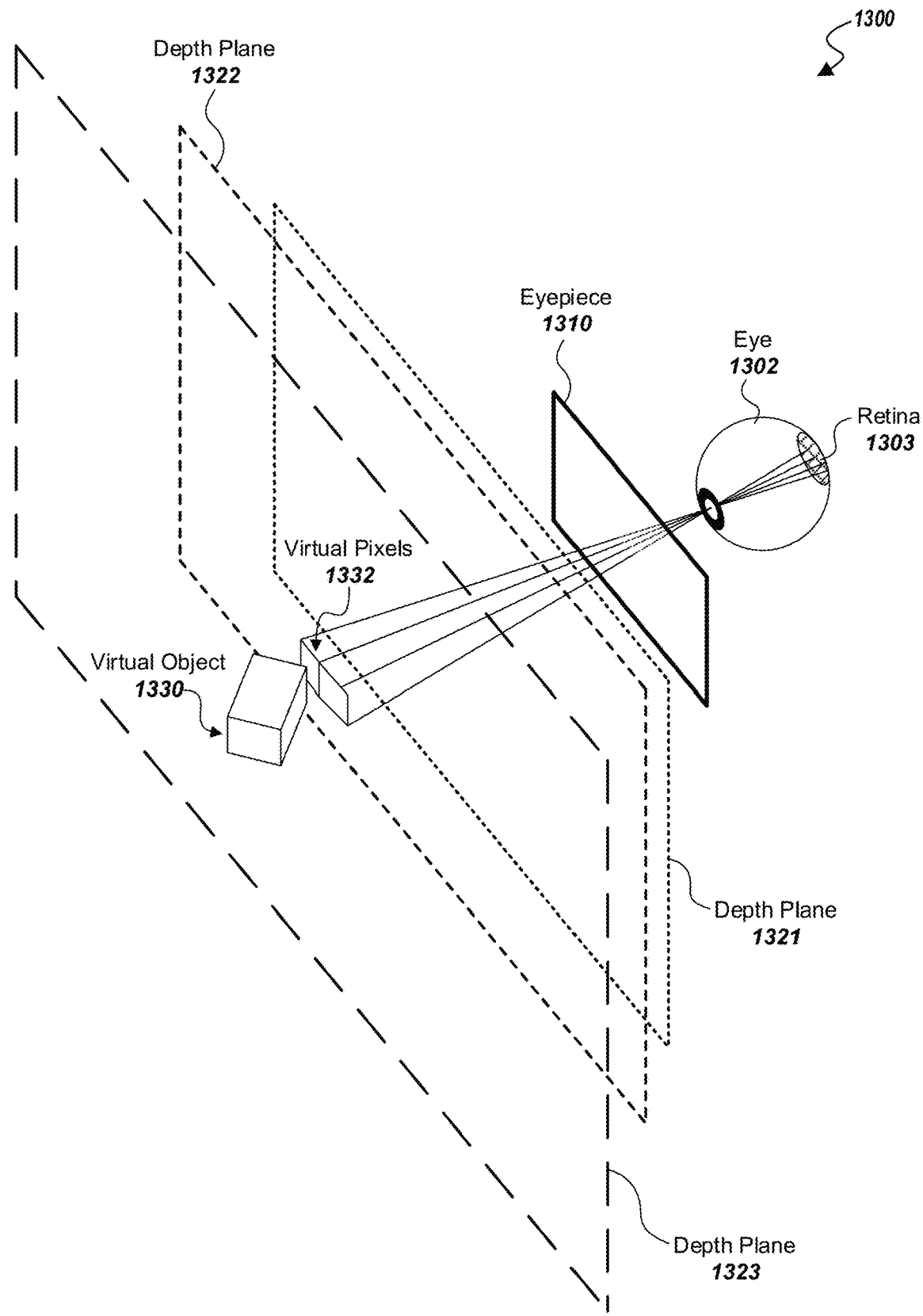
FIG. 13 depicts a mixed reality system in which certain virtual objects may be discretized in depth into one or more depth planes.

FIG. 13 shows a mixed reality system 1300 in which a light-field representative of 3D virtual content including virtual objects is provided to a user's eye using one or more depth planes, which may be optical structures on a wearable device that simulate virtual screens spaced apart from the user and the wearable device at various distances. The mixed reality system 1300 may include an eyepiece 1310, which may represent an eyepiece of a head-worn digital light-field display device, such as display 220 of FIG. 3, or a portion thereof. Such a system may be configured to project a light-field representative of 3D virtual object 1330 through the eyepiece 1310 and onto the retina 1303 of a user's eye 1302.

FIG. 13 also shows depth planes 1321-1323 onto which the virtual object 1330 and other virtual content can be projected or displayed and converted into virtual pixels. In the particular example depicted in FIG. 13, the virtual object 1330 is projected onto depth plane 1322 and thereby converted into virtual pixels 1332. As a result, light generated by eyepiece 1310 (e.g., display 220) may provide accommodation cues to the user's eye 1302 as if the virtual object 1330 were provided on a physical display or projector screen located at the distance from the user of depth plane 1322. The head-worn digital display device may generate a digitized light field representative of the virtual pixels 1332, and may project such a light field through the eyepiece 1310 and onto the retina 1303 of a user's eye 1302.

Figure 14A:
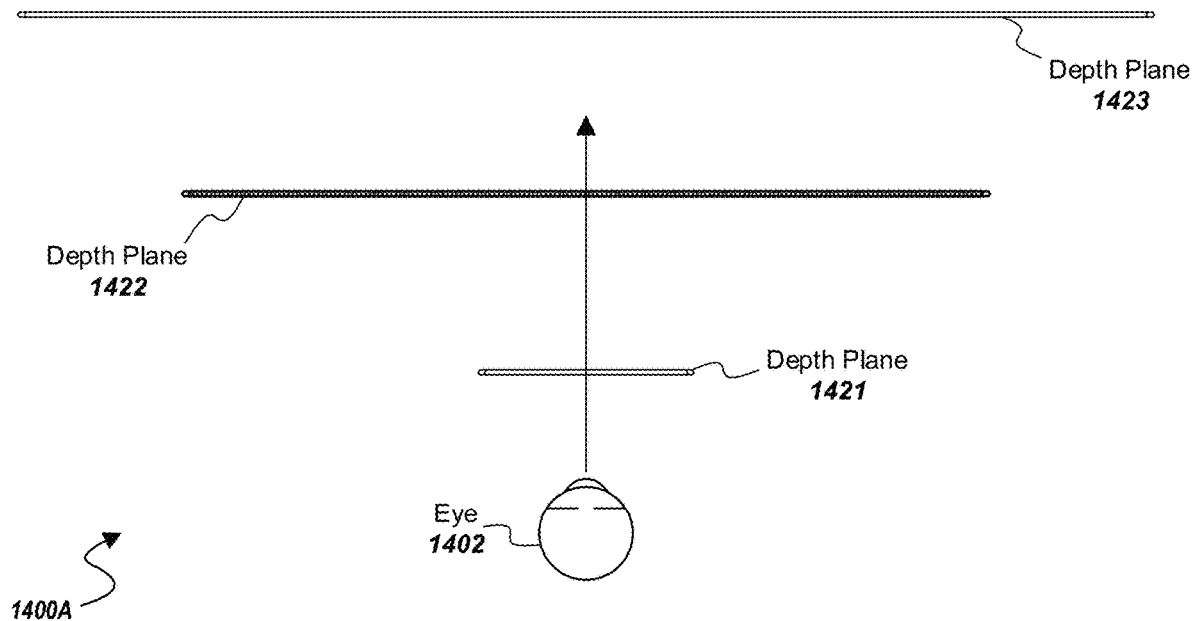
FIGS. 14A and 14B illustrate an example in which a mixed reality system displays virtual objects using a single depth plane.
Figure 14B:
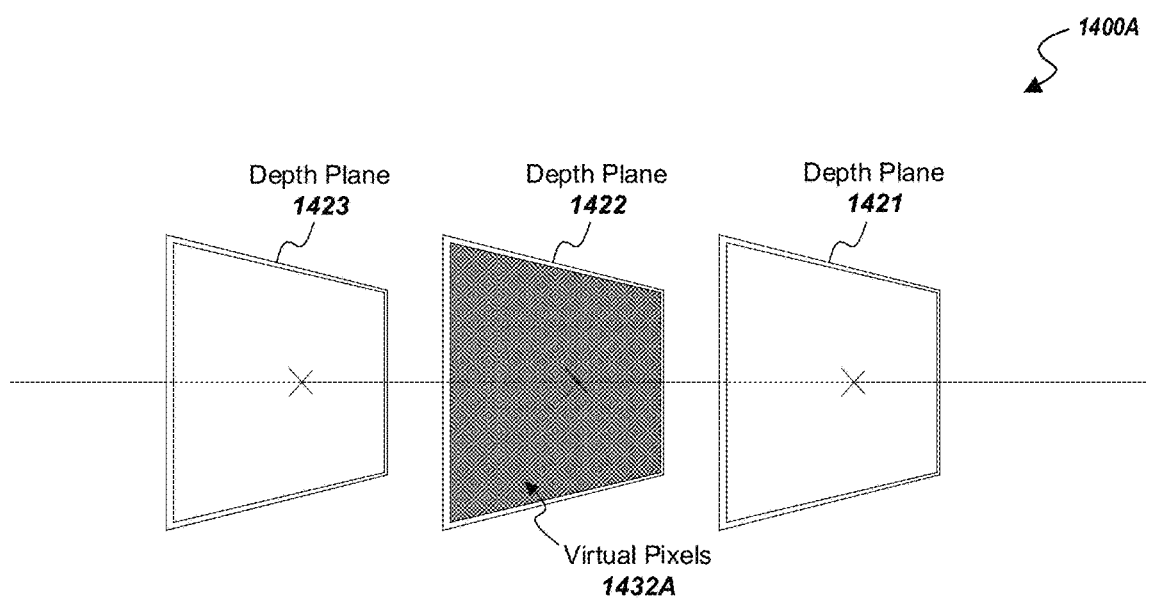
Figure 14C:
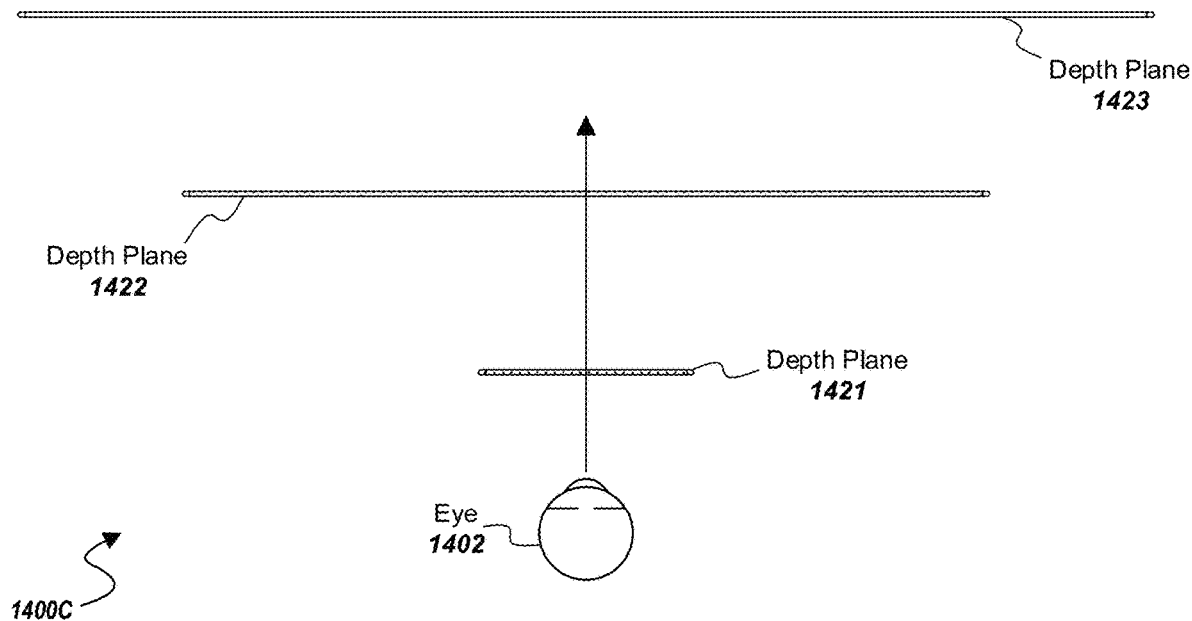
FIGS. 14C and 14D illustrate an example in which a mixed reality system displays virtual objects using two adjacent depth planes to generate accommodation cues between the two adjacent depth planes.
Figure 14D:
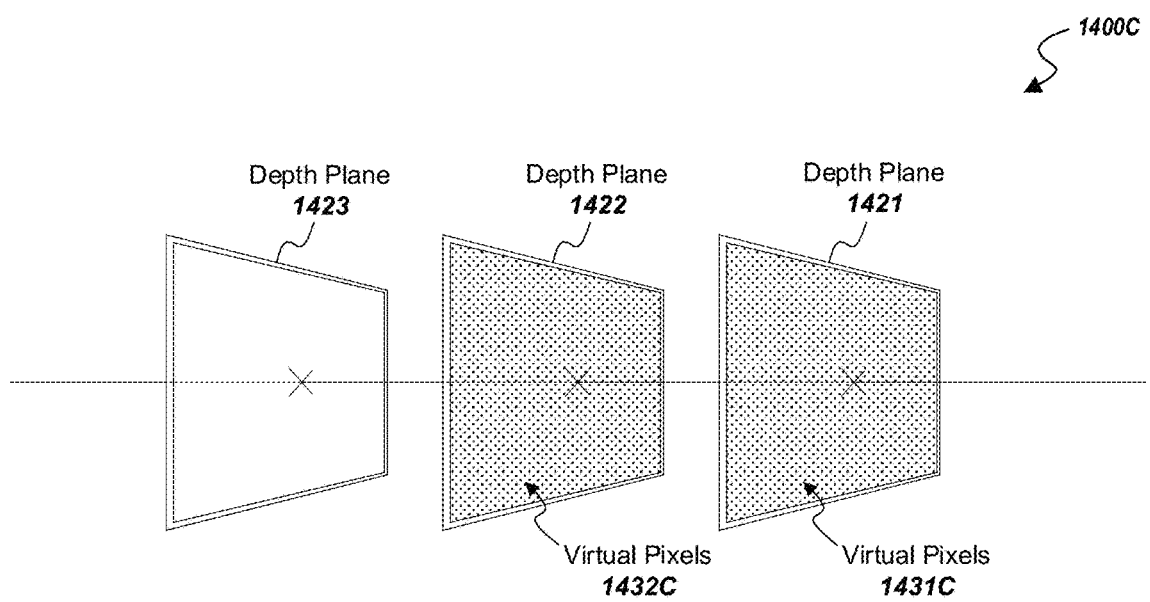
Figure 14E:
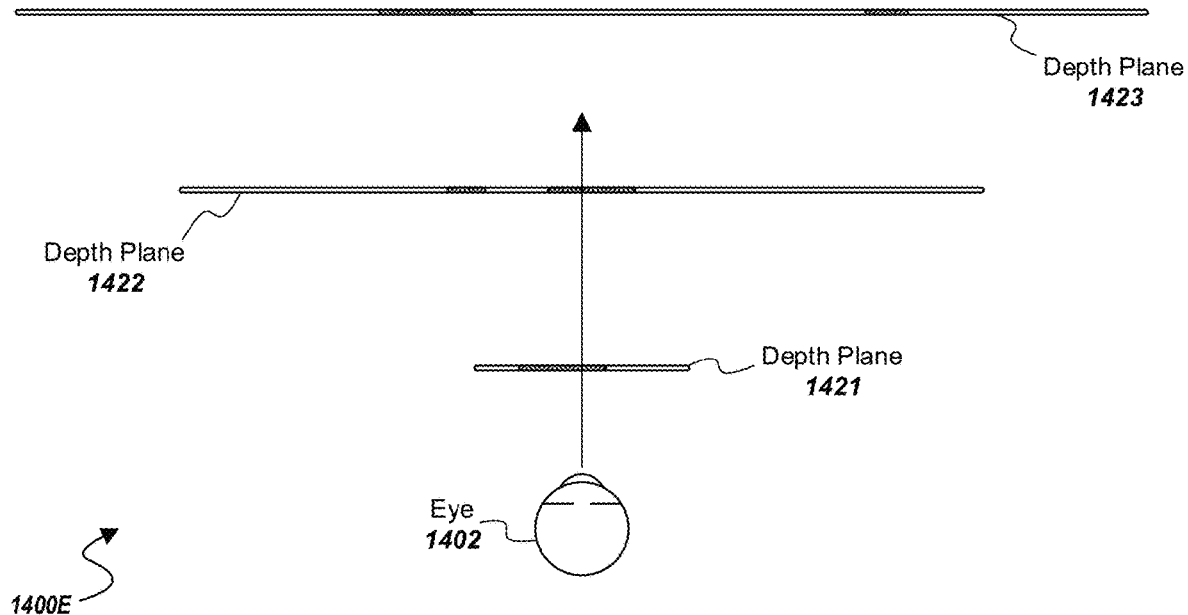
FIGS. 14E and 14F illustrate an example in which a mixed reality system displays virtual objects using two or more depth planes to generate two or more accommodation cues simultaneously.
Figure 14F:
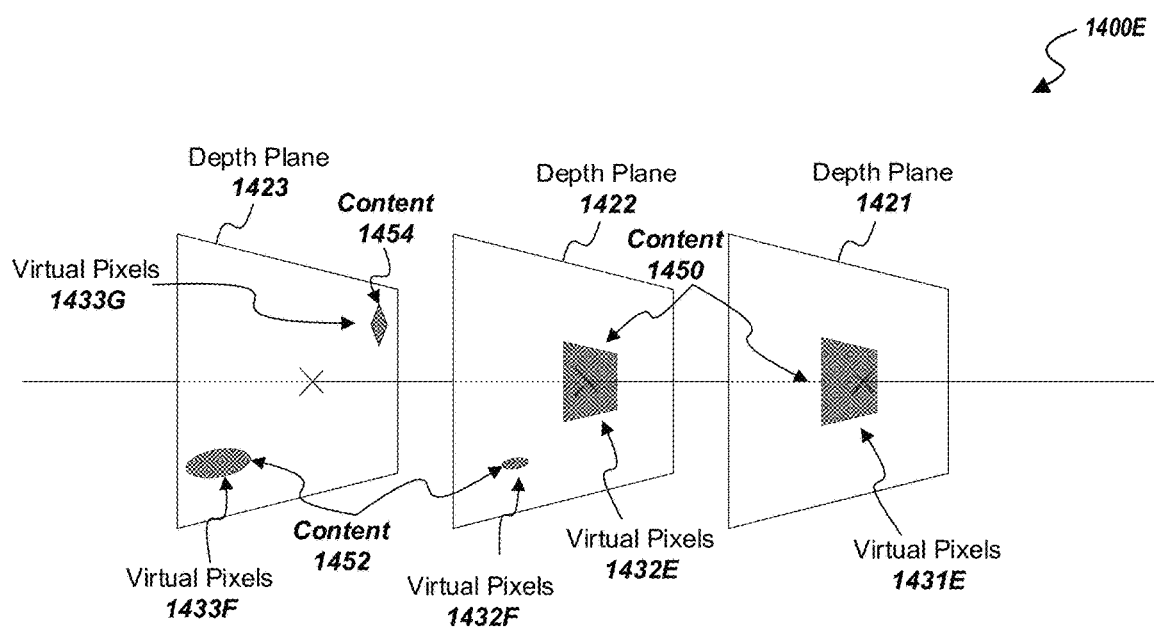

As will be discussed in more detail below, different rendering modes may be employed in a mixed reality system (such as mixed reality system 1300 in FIG. 13) to provide differing eye accommodation cues across a user's field of view, for different content, and/or at different periods of time. As examples, a mixed reality system may employ a discrete vari-focus mode in which virtual objects are displayed using a single depth plane at a time (as shown in FIGS. 14A-14B), may employ a blended vari-focus mode in which virtual objects are displayed using two adjacent depth planes to generate accommodation cues between the two depth planes (as shown in FIGS. 14C-14D), and may employ a multi-focus mode in which virtual objects are displayed using two or more depths planes to generate two or more accommodation cues simultaneously (as shown in FIGS. 14E-14F). In general, a mixed reality system may switch between these and other rendering modes during operation in response to a variety of conditions. As an example, the mixed reality system may utilize a first rendering mode (such as the discrete vari-focus mode) when displaying a first kind of content (such as text that may be provided at a single depth) and may utilize a second, different rendering mode (such as the multi-focus mode) when displaying a second kind of content (such as content that may be provided at a variety of depths simultaneously). In at least some embodiments, light-field render controller 618 of FIG. 6 may be configured to select which rendering mode is employed at any given time, based on a variety of inputs and conditions as discussed herein.

Single Depth Plane Rendering Mode (Discrete Vari-Focus Mode)

As illustrated in FIGS. 14A and 14B, the wearable system described herein can render virtual reality objects using a single depth plane at a time, in mode referred to herein as a single depth plane rendering mode and also referred to as a discrete-vari-focus mode. In the discrete vari-focus mode, the wearable system may utilize a single depth plane, across the entire field-of-view (FOV) of the display, for displaying all of the currently-rendered virtual objects (even if some of those objects are disposed at depths other than those associated with that depth plane). In other words, the wearable system may provide a single focal or accommodation cue across the entire FOV. Of course, the wearable system may switch which depth plane is used to render content over time, thus altering the accommodation cue of rendered virtual content over time (in response to changes in user vergence depth, the depth of virtual content, and other facts as discussed in more detail herein). In general, in the discrete vari-focus mode, only one depth plane is employed by the mixed reality system at any one time.

FIGS. 14A-14B respectively show top and side/isometric views of a mixed reality system 1400A that is operating in discrete vari-focus mode to present content to a user's eye 1402. FIGS. 14A-14B also shows depth planes 1421, 1422, and 1423 onto which virtual content can be projected and converted into virtual pixels. While operating in discrete vari-focus mode, virtual content may only be projected onto one of depth planes 1421-1423 at a given time. In the example of FIGS. 14A-14B, the mixed reality system 1400A has been switched to a state in which virtual content is projected onto depth plane 1422, but is not projected onto either of depth planes 1421 or 1423. As shown, the virtual content that is projected onto depth plane 1422 is converted into virtual pixels 1432A.

As discussed in more detail in connection with FIGS. 4, 6, 7A, 7B, and 12, the choice of which depth to place all the pixels on (e.g., which depth plane virtual content is to be projected onto) and the timing of switching between depth planes may be based on eye tracking and virtual content information. As examples, the wearable system, while operating in a discrete vari-focus mode, may switch which depth plane is active based on a user's vergence depth, based a user's vergence depth but with depth plane switches delayed until a trigger event (e.g., upon user blink or saccade, after a predetermined AVM mismatch timeout as discussed in connection with FIG. 12, etc.), based on the depth of virtual content, and based on the depth of virtual content but with depth plane switches delayed until a trigger event (e.g., upon user blink or saccade, after a predetermined AVM mismatch timeout as discussed in connection with FIG. 12, etc.) or any combination of these. In at least some embodiments, one or more of depth plane selection module 750, hysteresis band crossing detection module 752, and ocular event detection module 754, individually or in combination, may be configured to implement a desired depth plane switching scheme.

Blended Depth Plane Rendering Mode (Blended Vari-Focus Mode)

As illustrated in FIGS. 14C and 14D, the wearable system described herein can render virtual reality objects using two adjacent depth planes to generate accommodation or focal cues that lie between depth planes. In some embodiments, this blended vari-focus mode may enable the wearable system to generate accommodation or focal cues at any distance between, and including, the depths provided by the set of depth planes in the wearable system. In other words, if the system includes three depth planes, a first of which provides an accommodation cue of 1 foot, a second of which provides an accommodation cue of 10 feet, and a third of which provides an accommodation cue of optical infinity, then the wearable system may be able to provide the user with accommodation cues anywhere from the 1 foot depth of the first plane to the optical infinity depth of the third depth plane.

FIGS. 14C-14D show top and side/isometric views of a mixed reality system 1400C that is operating in blended vari-focus mode to present content to the user's eye 1402. The mixed reality system 1400C may, for example, have the same architecture as the mixed reality system 1400A as described above with reference to FIGS. 14A-14B. While operating in blended vari-focus mode, virtual content can be simultaneously projected onto two or more of depth planes 1421-1423 at any given point in time so as to generate an accommodation cue between planes. In the example of FIGS. 14C-14D, the mixed reality system 1400C has been switched to a state in which virtual content is projected onto depth planes 1421 and 1422. As shown, the virtual content that is projected onto depth planes 1421 and 1422 is converted into virtual pixel sets 1431C and 1432C, respectively. Virtual pixel sets 1431C and 1432C may blend together and, based on their relative intensities, provide the user with an accommodation cue somewhere between depth planes 1421 and 1422.

In the blended vari-focus mode, the wearable system may provide the same focal or accommodation cue for all pixels across the display's FOV, and this accommodation cue may be continuously variable between the depths of any pair of adjacent depth planes. The wearable system may achieve continuously variable accommodation cues by blending pixel intensities between two depth planes. As an example, the wearable system may display a virtual object having an accommodation cue between depth planes 1422 and 1421 by rendering the virtual object in both depth planes 1421 and 1421. In the further example in which the virtual object is closer to the depth of depth plane 1421, the wearable system may render the virtual object at a greater light intensity (e.g., brightness) in depth plane 1421 than in depth plane 1422. In such an arrangement, the light from the two depth planes may blend such that the user perceives the virtual object as having an accommodation cue that lies near depth plane 1421 (but still between planes 1421 and 1422).

In the blended vari-focus mode, the wearable system is configured to select which adjacent depth planes to blend, to provide a desired accommodation cue. However, since the accommodation cue can vary continuously between the planes by continuously varying the brightness, the timing of depth plane switches may not be as significant as in the discrete vari-focus mode. Thus, the wearable system may be configured to switch which two depth planes form the pair of adjacent depth planes without waiting for a triggering event such as a user blink, saccade, or AVM timeout. Instead, the wearable system may smoothly vary the provided accommodation cue, and which depth planes are utilized, over time in response to a user's vergence depth, to the depth of virtual content, or to a combination of these and other inputs as desired.

Multiple Depth Plane Rendering Mode (Multi-Focus Mode)

As illustrated in FIGS. 14E and 14F, the wearable system described herein can render virtual reality objects, in a multi-focus mode, using two or more depth planes to generate two or more accommodation cues simultaneously. In other words, virtual content in a given frame may be presented across multiple depths simultaneously. As examples, the multi-focus mode may include using two or more depth planes, in the manner described in connection with the blended vari-focus mode, to provide a first blended accommodation cue; using two or more depth planes to provide a second blended accommodation cue; using a single depth plane to provide a third accommodation cue; using a second single depth plane to provide a fourth accommodation cue; or using combinations of these and other focus modes to provide a variety of accommodation cues.

FIGS. 14E-14F show top and side/isometric views of a mixed reality system 1400E that is operating in multi-focus mode to present content to the user's eye 1402. The mixed reality system 1400E may, for example, have the same architecture as the mixed reality system 1400A and/or 1400C as described above with reference to FIGS. 14A-14D. While operating in multi-focus mode, virtual content can be simultaneously projected onto two or more of depth planes 1421-1423 at any given point in time so as to generate two or more different focus cues. In the example of FIGS. 14E-14F, virtual content is simultaneously projected onto depth planes 1421, 1422, and 1423. As shown, the virtual content that is projected onto depth planes 1421-1423 is converted into virtual pixel sets 1431E-1433E, In general, the wearable system can provide by blended and non-blended accommodation cues while operating in a multi-focus mode (or while operating in a blended vari-focus mode). As shown in FIG. 14F, depth planes 1421 and 1422 may be configured to provide content 1450 with a blended accommodation cue using pixels 1431E on depth plane 1421 and pixels 1432E on depth plane 1422, may be configured to provide content 1452 with a different blended accommodation cue using pixels 1432F on depth plane 1422 and pixels 1433F on depth plane 1423, and may be configured to provide content 1454 with a non-blended accommodation cue using pixels 1433G on depth plane 1423. Blended content 1452 may include content that stretches across the depth dimension of the user's perspective and thus includes portions at a depth associated with depth plane 1423 rendered as virtual pixels 1433F and additional portions at a different depth associated with depth plane 1422 rendered as virtual pixels 1432F. As an example, blended content 1542 may include non-overlapping content, such that virtual pixels 1432F do not overlap, in the planes perpendicular to the depth axis, with the virtual pixels 1433F. In other embodiments, blended content 1452 may include content at depths between planes 1422 and 1423, which is rendered by overlapping and blending virtual pixels 1433F and 1432F. Overlapping and blending pixels 1433F and 1432F may include varying the relative intensities of pixels 1433F and 1432F to shift the apparent depth towards depth plane 1422 or towards depth plane 1422. As an example, dimming pixels 1433F and amplifying or brightening pixels 1432F may have the effect of shifting the user perceived depth towards depth plane 1422. Moreover, overlapped pixels may have a different intensity (which may generally be a lower intensity) than non-overlapped pixels, such that overlapped and blended pixels have a desired intensity (to prevent overlapped pixels from appearing excessively bright due to the contribution of multiple depth planes to light at that position in the display). These are merely illustrative examples and, in general, the wearable system may present any desired combination of blended and non-blended accommodation cues.

As discussed in connection with the blended vari-focus mode, the timing of depth plane switches may not be as significant in modes with variable accommodation cues, such as the blended vari-focus mode and the multi-focus mode, as such switches are in a discrete vari-focus mode. Thus, the wearable system may be configured to switch which depth planes are active in the multi-focus mode without waiting for a triggering event such as a user blink, saccade, or AVM timeout. Instead, the wearable system may smoothly vary the provided accommodation cues, and which depth planes are utilized, over time in response to a user's vergence depth, to the depth of virtual content, or to a combination of these and other inputs as desired. In other implementations, however, triggering events such as a user blink, saccade, or AVM timeout may be utilized.

Effects of Center of Perspective Misalignments in Various Rendering Modes

When projected onto one or more depth planes, it may be desirable to render and view 3D virtual content from a particular center of perspective (CoP), which may be determined for both a render world and the real world. When content is rendered from a proper center of perspective in the render world, the pixels of each virtual screen may accurately appear as 3D virtual content when observed from a proper center of perspective in the real word, which may include a specific position and orientation. However, if the same content is rendered from a different position in the render world or viewed from a different position in the real world, the 3D virtual content may not accurately resemble an image of such 3D virtual content. This rendering framework can be represented using a pinhole camera model, where the CoP is represented as a "virtual" or "render" pinhole camera that is positioned and oriented within the Render World (e.g., 3D render space) in a manner so as to correctly capture the projection of the 3D virtual content. Additional detailed related to the CoP is described below, with respect to FIGS. 22-24B, while FIGS. 15A-15C and corresponding description provided below further demonstrate the impact that CoP accuracy and/or precision may have on mixed reality system performance for each of various example rendering modes.

In operation, a digitized light field that is projected onto the retina of the user's eye may serve to form an image of 3D virtual content containing artifacts or exhibiting other problematic characteristics if the perspective of the virtual pinhole camera (in the Render World frame) and the perspective of the user (in the Real World frame) are misaligned. For a simple scenario in which the one depth plane is employed, a misalignment between the virtual pinhole camera and the perspective of the user may yield a digitized light field that forms an image of 3D virtual content at an incorrect (an unintended) location within the user's FOV. For scenarios in which two or more depth planes are employed, such as scenarios in which any of the focus modes described above with reference to FIGS. 14A-14F are employed, a misalignment between the virtual pinhole camera and the perspective of the user may yield a digitized light field that forms an image of 3D virtual content that appears to jump or pop between locations and/or that includes visual artifacts, such as fractures and/or dislocations. More specifically, an occurrence of such a misalignment in a mixed reality system operating in any one of the above-mentioned focus modes may serve to introduce a parallax shift that causes 3D virtual content having been planarized onto one depth plane (or blended between depth planes) to shift out of place relative to 3D virtual content having been planarized onto another depth plane (or blended between depth planes).

Figure 15A:
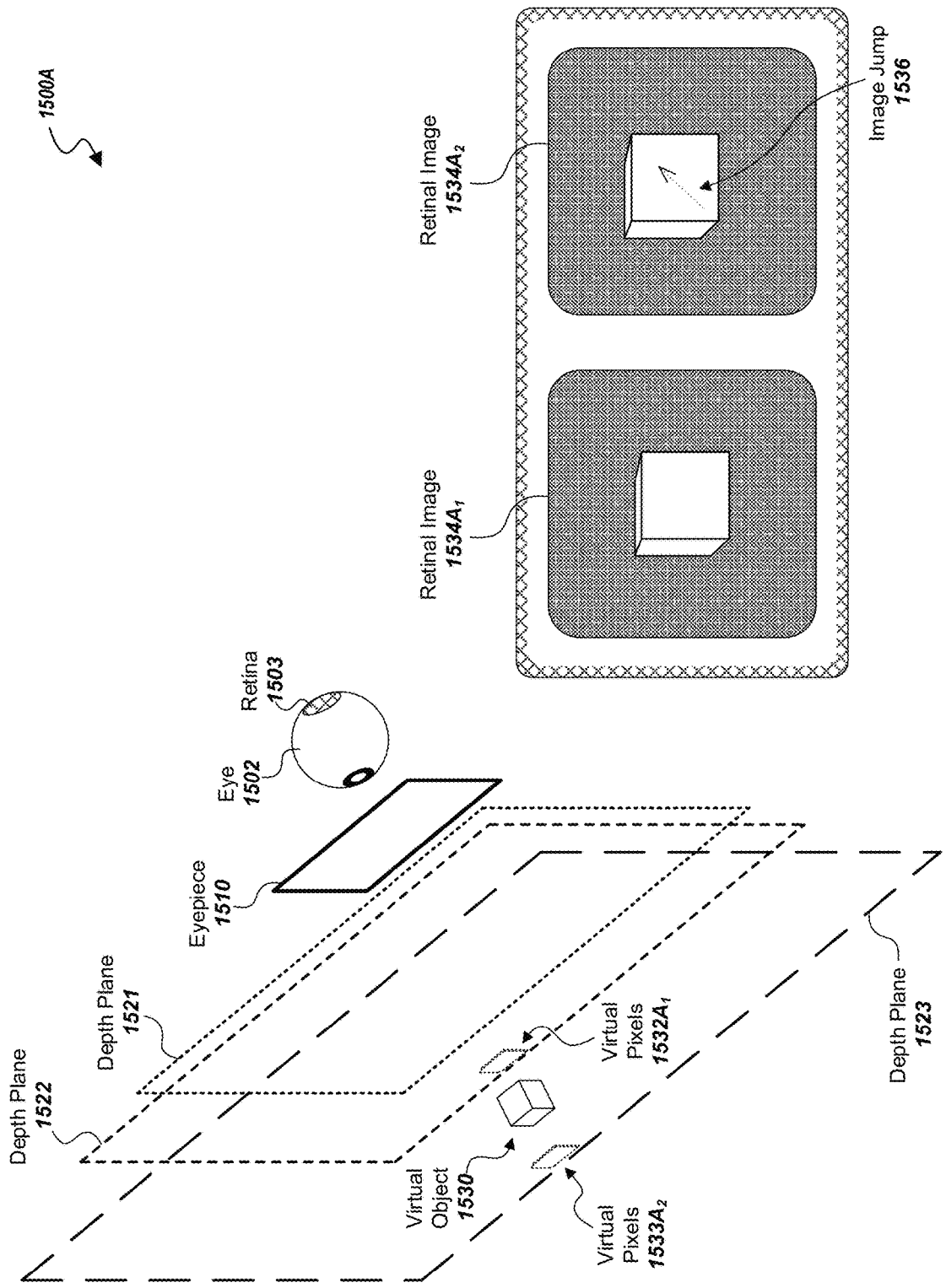
FIG. 15A illustrates an example in which a mixed reality system displays virtual objects in the manner of FIGS. 14A and 14B in the presence of a center of perspective misalignment.

As an example of CoP misalignment, FIG. 15A shows a mixed reality system 1500A that is operating in a discrete vari-focus mode to present content to a user's eye 1502 in the presence of a CoP misalignment. Much like mixed reality system 1300, as described above with reference to FIG. 13, the mixed reality system 1500A includes an eyepiece 1510, which may represent that of a head-worn digital light-field display device or a portion thereof that is configured to project a light-field representative of 15D virtual object 1530 through the eyepiece 1510 and onto the retina 1503 of a user's eye 1502. FIG. 15A also shows depth planes 1521-1523 onto which the virtual object 1530 can be projected and converted into virtual pixels. In the particular example depicted in FIG. 15A, the mixed reality system 1500A operates in a discrete vari-focus mode (e.g., in a manner similar to that having been described above with reference to FIGS. 14A-14B) to switch from projecting virtual object 1530 onto depth plane 1522 at a first point in time to projecting virtual object 1530 onto depth plane 1523 at a second, subsequent point in time. As such, the virtual object 1530 is projected onto depth plane 1522 and converted into virtual pixels $1532A_1$ at the first point in time, and is then projected onto depth plane 1523 and converted into virtual pixels $1533A_2$ at the second point in time. It follows that the mixed reality system 1500A may generate and project a digitized light field representative of the virtual pixels $1532A_1$ through the eyepiece 1510 and onto the retina 1503 of a user's eye 1502 at the first point in time, and may generate and project a digitized light field representative of the virtual pixels $1533A_2$ through the eyepiece 1510 and onto the retina 1503 of a user's eye 1502 at the second point in time.

Although there may be no desire to perceptually change the image of the virtual object 1530 formed on the retina 1503 of the user's eye 1502 between the first and second points in time (other than providing a new accommodation cue), because there is a CoP misalignment in the example of FIG. 15A (e.g., misalignment between the perspective of the virtual camera and the correct perspective of the user's eye 1502), a parallax shift may occur as the mixed reality system 1500A switches depth planes that may serve to change the perceived location of the virtual 1530 within the user's FOV. FIG. 15A further shows example retinal images $1534A_1$ and $1534A_2$ that are representative of images of the virtual object 1530 formed on the retina 1503 of the user's eye 1502 at the first and second points in time, respectively. FIG. 15A demonstrates this shift in its depiction of retinal images $1534A_1$ and $1534A_2$, which are representative of images of the virtual object 1530 formed on the retina 1503 of the user's eye 1502 at the first and second points in time, respectively. As such, when the mixed reality system 1500A switches from using depth plane 1522 to using depth plane 1523, the virtual object 1530 may appear to "jump," "pop," or otherwise rapidly shift locations within the user's FOV. FIG. 15A illustrates this shift as image jump 1536. In particular, FIG. 15A illustrates how retinal image $1534A_2$ may be shifted up and to the right from retinal image $1534A_1$, and thus the user may perceive the virtual object 1530 jumping along jump 1536 during the depth plane switch.

Figure 15B:
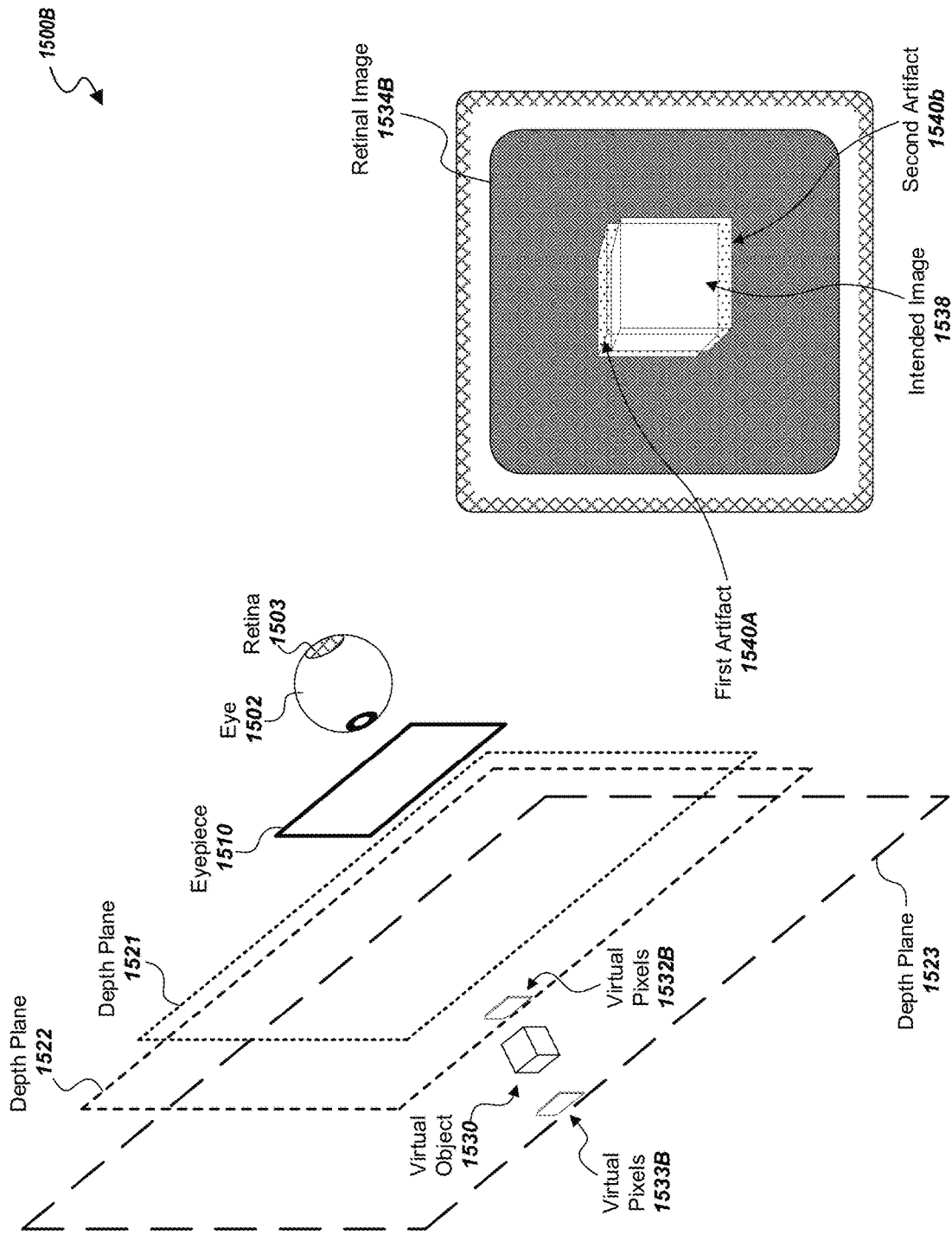
FIG. 15B illustrates an example in which a mixed reality system displays virtual objects in the manner of FIGS. 14C and 14D in the presence of a center of perspective misalignment.

Similarly, FIG. 15B shows a mixed reality system 1500B that is operating in a blended vari-focus mode to present content to a user's eye 1502 in the presence of a CoP misalignment. The mixed reality system 1500B may, for example, have the same architecture as the mixed reality system 1500A as described above with reference to FIG. 15A. In the particular example depicted in FIG. 15B, the mixed reality system 1500C operates in blended vari-focus mode (e.g., in a manner similar to that having been described above with reference to FIGS. 14C-14D) to simultaneously project virtual object 1530 onto depth planes 1522 and 1523 so as to convert virtual object 1530 into virtual pixel sets 1532B and 1533B, respectively. In this way, the intensities of virtual pixel sets 1522B and 1533B may be blended so as to generate an accommodation cue between depth planes 1522 and 1523. The mixed reality system 1500B may generate and project a digitized light field representative of the virtual pixel sets 1532B and 1533B through the eyepiece 1510 and onto the retina 1503 of the user's eye 1502 to form retinal image 1534B. For reasons similar to those described above with reference to FIG. 15A (e.g., parallax shift caused by CoP misalignment), virtual pixel sets 1532B and 1533B are not properly aligned with one another relative to the user's eye 1502 and, as such, the virtual object 1530 is distorted/obscured with visual artifacts in the retinal image 1534B. In particular, FIG. 15B illustrates how virtual content 1530 was supposed to have been perceived, as intended image 1538, and how the CoP misalignment creates first and second image artifacts 1540A and 1540B (e.g., the stippled regions in retinal image 1534B).

Figure 15C:
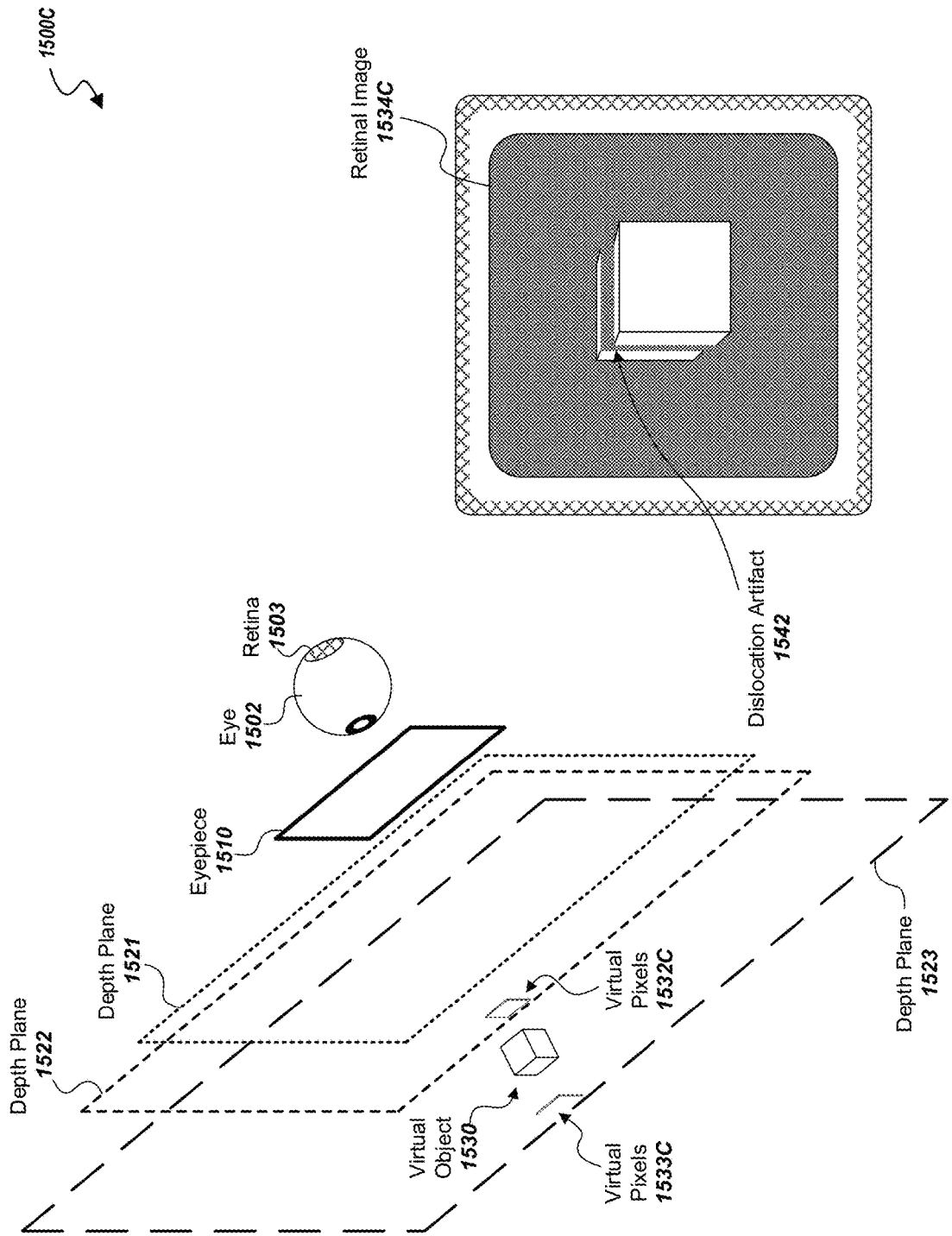
FIG. 15C illustrates an example in which a mixed reality system displays virtual objects in the manner of FIGS. 14E and 14F in the presence of a center of perspective misalignment.

Similarly, FIG. 15C shows a mixed reality system 1500C that is operating in blended vari-focus mode to present content to a user's eye 1502 in the presence of a CoP misalignment. The mixed reality system 1500C may, for example, have the same architecture as the mixed reality system 1500A and/or 1500B as described above with reference to FIGS. 15A-15B. In the particular example depicted in FIG. 15C, the mixed reality system 1500C operates in blended vari-focus mode (e.g., in a manner similar to that having been described above with reference to FIGS. 14E-14F) to simultaneously project one portion of virtual object 1530 onto depth plane 1522 and project another portion of virtual object 1530 onto depth plane 1523. As such, the portion of virtual object 1530 that is projected onto depth plane 1522 is converted into virtual pixel set 1532C, while the portion of virtual object 1530 that is projected onto depth plane 1523 is converted into virtual pixel set 1533C. In this way, virtual pixel sets 1532C and 1533C may provide different focus cues. The mixed reality system 1500C may generate and project a digitized light field representative of the virtual pixel sets 1532C and 1533C through the eyepiece 1510 and onto the retina 1503 of the user's eye 1502 to form retinal image 1534C. For reasons similar to those described above with reference to FIGS. 15A and 15B (e.g., parallax shift caused by CoP misalignment), virtual pixel sets 1532C and 1533C are not properly aligned with one another relative to the user's eye 1502 and, as such, the virtual object 1530 appears fractured (e.g., separated at the seams between the two corresponding portions of the virtual object 1530) in the retinal image 1534C. In particular, the virtual objection 1530 may have a dislocation artifact 1542, as shown in retinal image 1534C.

Indeed, the correct alignment of the perspective of the virtual camera and the perspective of the user's eye (which corresponds to the positional/optical configuration of the user's eye) may be important to a digital light-field display device's ability to present graphics that are of relatively high perceptual quality. In some examples, a particular virtual camera perspective may be leveraged in a digital light-field display device, and may correspond to a perspective in which the virtual camera is positioned at the center of the effective aperture of the display-plus-eye optical system.

The eye perspective position may correspond to the position of the effective entrance pupil of the eye (generally referred to herein as the eye "CoP"), which is about 5.01 millimeters in front of the center of cornea curvature the optical axis. In order to maintain proper alignment between the pinhole of a render camera and such a location, the system may obtain information about the real world and the user's eye perspective. In some examples, such information can be inferred from measurements of the user's eye. Such measurements may be obtained by eye tracking module 614. The position of the eye's CoP may be calculated or otherwise inferred by walking or moving to a location about 5.01 millimeters from the cornea center position such as position 1008 of FIG. 10 (toward the outer surface or cornea of the eye) along the current optical or visual axis. Thus, a user's CoP may change if the wearable device moves relative to the user's face (as such, information from registration observer 620 may be utilized in identifying a user's CoP) and/or may also change as the user looks at different portions of their FOV (changing their optical or visual axis and thus changing their eye's CoP).

Examples of Render Camera Modes in a Mixed Reality System

As illustrated in FIGS. 16A-17B, the wearable system may utilize different render camera modes including a pupil render camera mode, a center of rotation (CoR) render camera mode, and a hybrid pupil-CoR render camera mode. Additionally, each of these render camera modes may be used in conjunction with each of the display focal modes described herein in connection with FIGS. 13-15C. In at least some embodiments, the light-field render controller 618 may be configured to select which render camera mode to utilize at any particular time and may make such selections based on suitable data, such as eye tracking data and, in particular, the quality of eye tracking data. As an example, the light-field render controller 618 or other module in the wearable system may select the pupil render camera mode or may bias the hybrid render camera mode towards the user's CoP whenever the eye tracking data is relatively stable and the wearable system is able to identify the location of the CoP with low jitter or noise. In contrast, if the tracking data is limited or noisy, the light-field render controller 618 may be configured to select the CoR render camera mode or bias the hybrid render camera mode toward the user's CoR. The light-field render controller 618 may determine left and right camera positions in real-time (e.g., by way of render camera controller 758) in accordance with the selected render camera mode and may provide data indicative of the left and right camera positions (and the selected render camera mode) to the render engine 622.

Pupil Render Camera Mode

In the pupil render camera mode, the pinhole camera of a render camera (e.g., a simulated camera position which the render engine 622 may use in generating content for a particular user's perspective) may be slaved to the position of the estimated user's CoP for all time (e.g., as indicated by module 732 described above). In particular, the pinhole camera of a right eye render camera may be slaved to the user's right eye CoP, while the pinhole camera of a left eye render camera may be slaved to the user's left eye CoP. Thus, virtual image content presented by the display has the perspective of the location of the CoP, which is just in front of the pupil (e.g., within the anterior chamber of the eye).

FIGS. 16A-16B show a system 1600A operating in the pinhole camera tracked to live pupil mode (e.g., the pupil render camera mode). The system 1600A includes an eyepiece 1610 through which an eye 1602 can view virtual content projected onto one or more of depth planes 1621, 1622, and 1623. FIGS. 16A-16B further show a render camera 1630 positioned at the CoP of eye 1602. It can be seen that eye 1602 is in a first pose relative to eyepiece 1610 in FIG. 16A, and is in a second, different pose relative to eyepiece 1610 in FIG. 16B. As such, it can further be seen that the render camera 1630 is in one position in FIG. 16A (e.g., a position corresponding to the CoP of eye 1602 in FIG. 16A), and is in another, different position in FIG. 16B (e.g., a position corresponding to the CoP of eye 1602 in FIG. 16B).

With a pinhole render camera tracked to a pupil in real-time, the absolute position (and orientation) of the pinhole camera and the relative position (and relative orientation) between the pinhole render camera and the pupil changes stochastically over time. The visuals in this mode may be jittery if the pupil position from eye tracking is noisy and/or is not sufficiently filtered. Slaving the pinhole of the render camera to the actual position of the eye's CoP for all time attempts to account for all pupil movement with respect to display, e.g., both low frequency changes (like slippage and IPD) as well as high frequency changes from rotation of eye. This may introduce high frequency dynamics into the rendering system and result in undesirable temporal artifacts (jitter/jumping).

Figure 16C:
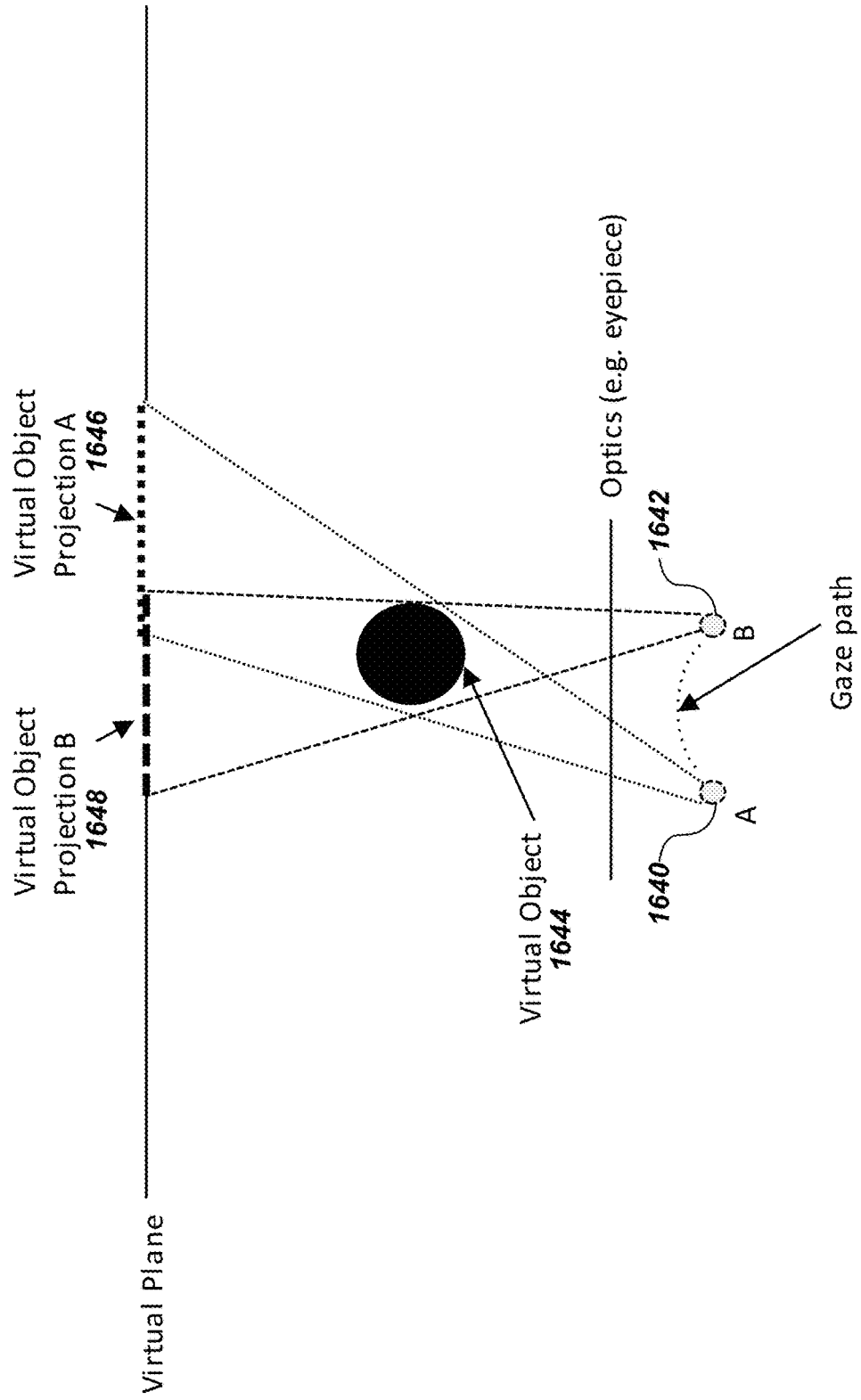
FIG. 16C illustrates another example in which the pinhole of a render camera is aligned with an eye's center of perspective or approximately with an eye's pupil.

FIG. 16C illustrates another example in which the pinhole of a render camera is aligned with an eye's center of perspective or approximately with an eye's pupil. As depicted, a user's pupil for a single eye may move from position A (point 164) to position B (point 1642). For an optical eyepiece displaying a virtual object 1644, given an optical power, a virtual object 1644 that is meant to appear stationary will project in 3D at either position 1646, representing a virtual objection projection A, or position 1648, representing a virtual object projection B, based on the pupil position (assuming the render camera is configured to use a pupil as the coordinate frame). Given that the projections have two locations by which to project, using a pupil coordinate transformed to a head coordinate will cause jitter in a stationary virtual content as the user's eyes move. This render camera protocol may also be referred to as a view dependent display or projection system.

Center of Rotation (CoR) Render Camera Mode

In the CoR render camera mode, the pinhole camera of a render camera (e.g., a simulated camera position which the render engine 622 may use in generating content for a particular user's perspective) may be slaved to the position of the user's center of rotation (e.g., CoR 1010 as shown in FIG. 10). Left and right eye centers of rotation may be estimated through execution of one or more of the operations described above with reference to eye tracking module 614 of FIG. 7A, such as one or more of those described above in association with CoR estimation module 724. By positioning the render camera at the user's CoR, the wearable system may avoid temporal artifacts (jitter resulting from eye tracking lag in the pinhole camera tracked to live pupil mode, which may be especially severe during micro-saccade movement) in exchange for potential spatial artifacts in the periphery (e.g., small parallax-induced magnification/demagnification pops). This approach makes use of the fact that relation between render camera location (eye perspective) and what the eye is foveating on (e.g., focused on) is fixed for all the time while the glasses are stationary relative to the eyeball centers. That is, a scene may be pre-rendered in this mode such that the image is always perfectly correct for the fovea no matter the orientation of the eye or how it is moving, but towards the periphery is generally misregistered. With the render camera anchored to the CoR of the eye, the light field will be correctly presented at the fovea (e.g., there is no registration to world or pop in the fovea), but may include errors at the periphery (e.g., as the Center of Rotation (CoR) is not the Center of Perspective (CoP), and thus is not immune to parallax shifts). Advantageously, such errors at the periphery may be far less noticeable than errors/artifacts elsewhere within an FOV, as eye acuity tapers off rapidly.

Figure 17A:
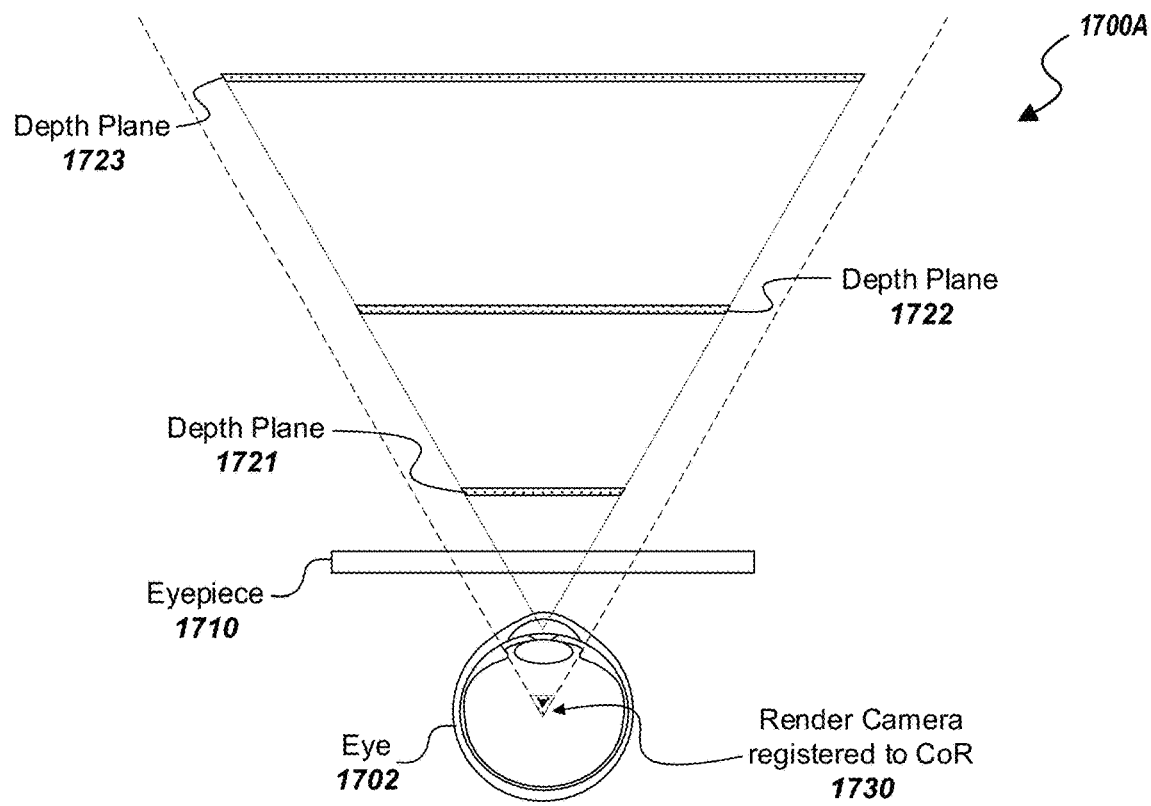
FIGS. 17A and 17B illustrate an example in which the pinhole of a render camera is aligned with an eye's center of rotation.
Figure 17B:
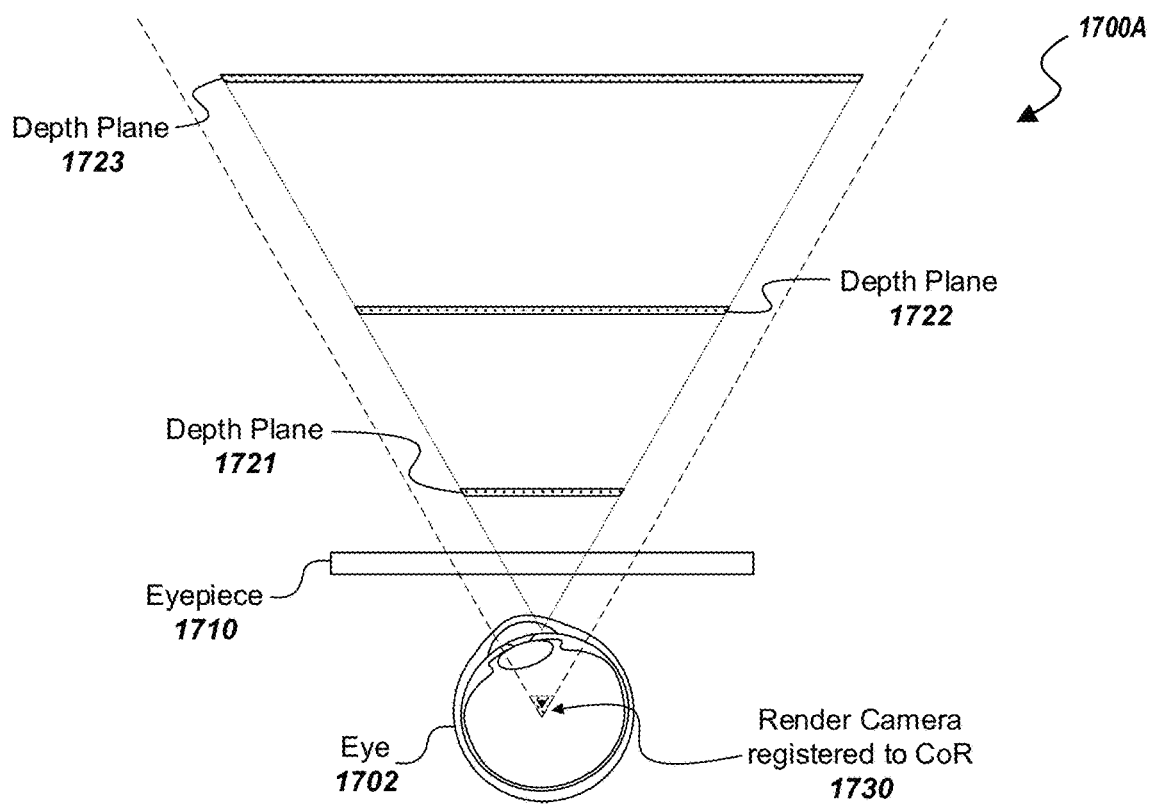

For example, FIGS. 17A-17B show a system 1700A operating in the pinhole camera fixed at CoR mode. Much like system 1600A described above with reference to FIGS. 16A-16B, the system 1700A includes an eyepiece 1710 through which an eye 1702 can view virtual content projected onto one or more of depth planes 1721, 1722, and 1723. FIGS. 17A-17B further shows a render camera 1730 positioned at the estimated CoR of eye 1702. It can be seen that eye 1702 is in a first pose relative to eyepiece 1710 in FIG. 17A, and is in a second, different pose relative to eyepiece 1710 in FIG. 17B. It can be seen that the render camera 1730 is in the same position in each of FIGS. 17A and 17B (e.g., the estimated CoR of the eye 1702), as the CoR does not change with changes in eye pose.

In at least some embodiments, the render camera 1730 may comprise a multi-perspective render camera 1730 which may, for example, comprise an array of render cameras radially-distributed about the center of rotation (CoR) at a distance (e.g., a radius) equal to the distance from the CoP of eye 1702 to the center of rotation of eye 1702. As such, the CoP of eye 1702 may be aligned with or nearly aligned with at least one render camera in the array in each of several different poses. In such embodiments, the light-field render controller 618 may select a particular render camera from the radially-distributed array based on a user's current pose (e.g., the user's current optical axis or pupil location), or may simply employ multiple render cameras in the radially-distributed array (or all render cameras in the radially-distributed array) simultaneously. Thus, the render controller 618 may select a render camera substantially aligned and orientated with a user's CoP.

Figure 17C:
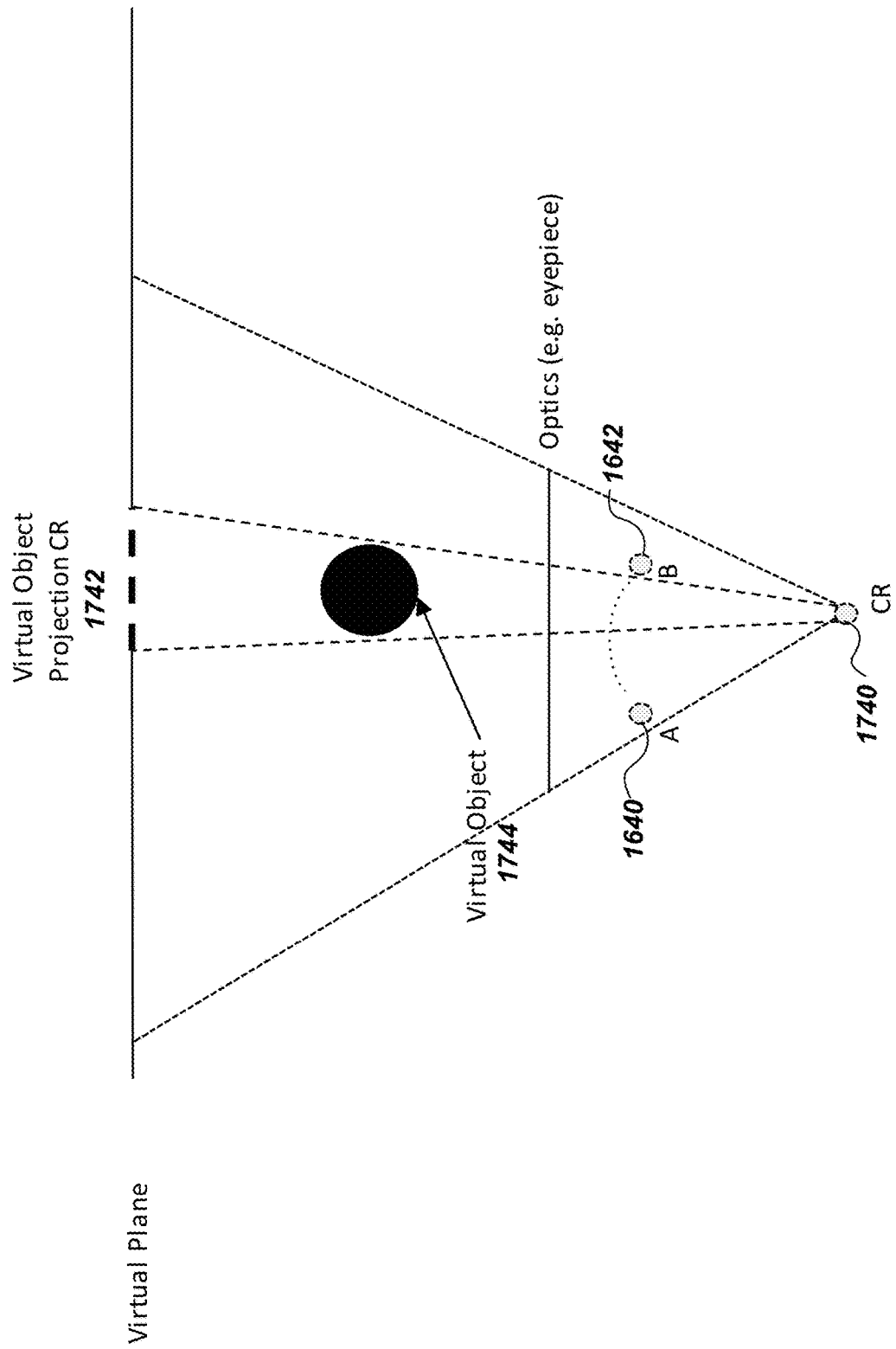
FIG. 17C illustrates another example in which the pinhole of a render camera is aligned with an eye's center of rotation.

FIG. 17C illustrates another example in which the pinhole of a render camera is aligned with an eye's center of rotation. In some embodiments, a camera render frame is positioned at a point 1740 that encompasses all pupil positions, for example at the center of rotation of the eyeball. A virtual object projection camera render area 1742 may be consistent regardless of the pupil position A (point 1640) and position B (point 1642). The head coordinate transforms to the camera render frame. In some embodiments, an image warp may be applied to the image to account for a change in eye position, but as this still renders at the same position, jitter is reduced or minimized. This render camera protocol may also be referred to as a view independent display or projection system.

Hybrid Pupil-CoR Render Camera Mode

In the hybrid pupil-CoR render camera mode, the pinhole camera of a render camera may be located at the pupil (CoP) position, at the CoR position, or at any position on the line between the CoP and CoR positions. The particular position of the render camera along that line may vary over time, in response to changes in eye tracking data. As an example, the light-field render controller 618 may analyze the nature and quality of the eye tracking data, as discussed in more detail below, to determine whether to locate the render camera at the user's CoP, the user's CoR, or somewhere in-between.

In some embodiments, the system may change the location of the pinhole camera based on the determined standard deviation (or other measure of statistical variance) of eye tracking data. For instance, the system may elect to position the pinhole camera at or near the center of rotation (CoR) in response to determining that the eye tracking data being collected is relatively noisy (and thus likely to yield substantial temporal artifacts, such as "jitter"). Positioning the pinhole camera at or near the CoR may help to reduce jitter and other temporal artifacts. Additionally, the system may elect to position the pinhole camera at or near the center of perspective (CoP) in response to determining that the eye tracking data being collected is relatively stable (and thus less likely to yield substantial temporal artifacts, such as jitter). Positioning the pinhole camera at or near the CoP may help to reduce parallax-induced (spatial) artifacts, for example as described below with respect to FIGS. 22-24B. In some examples, the system may simply toggle between these two discrete locations (CoR and CoP); see Appendix (Parts I and II) for additional discussion; see also the description provided above with reference to FIGS. 10 and 15A-17B for relevant discussion. In other examples, the system may position the pinhole camera at any of a range of different locations along the optical axis between the CoR and CoP (which in some implementations may be positioned roughly 9.71 mm away from one another for an average user). In these examples, the system may be seen as "sliding" (or translating the location of) the pinhole camera along the optical axis of the eye in coordination with the determined standard deviation of eye tracking data. When the standard deviation of eye tracking data is relatively high, the system may slide the pinhole camera all the way to the CoR. In contrast, when the standard deviation of eye tracking data is relatively low, the system may slide the pinhole camera all the way to the CoP. The system may position the pinhole of the render camera some distance in front (away from the retina) of the user's CoR in a direction along the optical and/or visual axis. As examples, the pinhole (aperture) of the render camera may be positioned between 6.0 mm and 13.0 mm, between 7.0 mm and 12.0 mm, between 8.0 mm and 11.0 mm, between 9.0 mm and 10.0 mm, between 9.5 mm and 10.0 mm, about 9.7 mm, about 9.71 mm, or other suitable distances in front of the user's CoR.

FIGS. 18A-18D provide an example of illustrative eye tracking data and how the system may relocate the render camera over time in response to the eye tracking data.

Figure 18A:
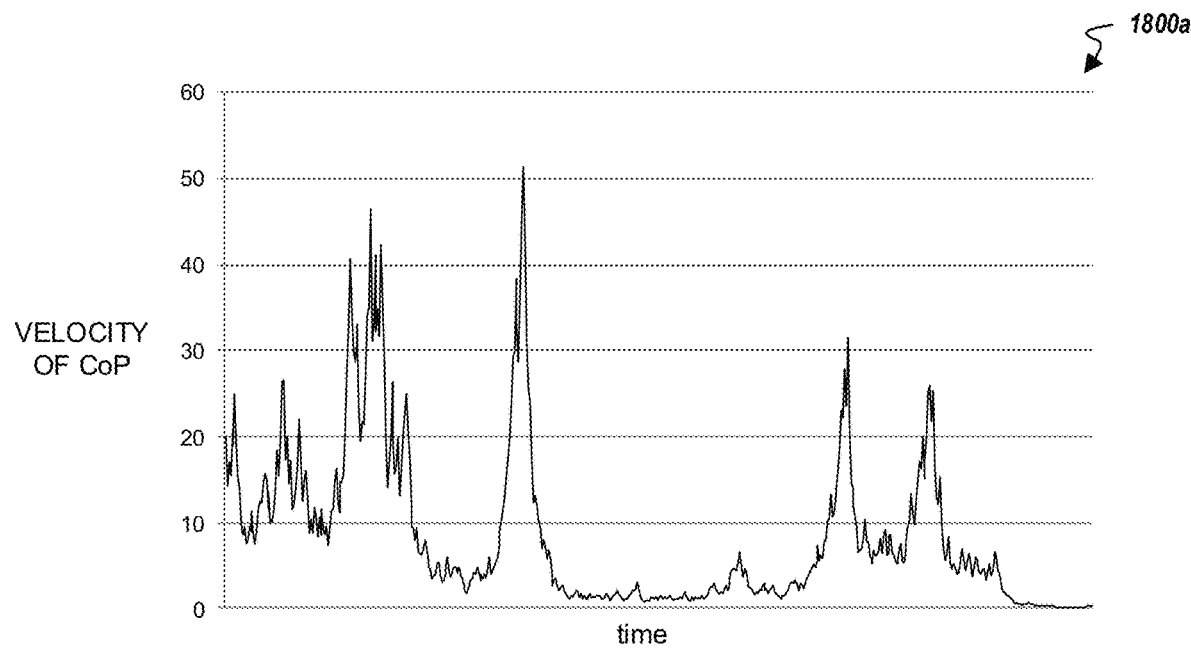
FIGS. 18A and 18B are a set of example graphs illustrating eye tracking data related to a user's center of perspective.

Graph 1800a of FIG. 18A provides an example of raw eye tracking data that may be indicative of the level of noise in the eye tracking system and the speed of movement of a user's eyes. The units of the y-axis may be eye angular velocity in degrees per second (e.g., the change in the user's optical axis direction in degrees per second). As shown in graph 1800a, noise and/or movement of the user's eyes may contribute to movements in the location of a user's CoP with substantially different velocities over time.

Figure 18B:
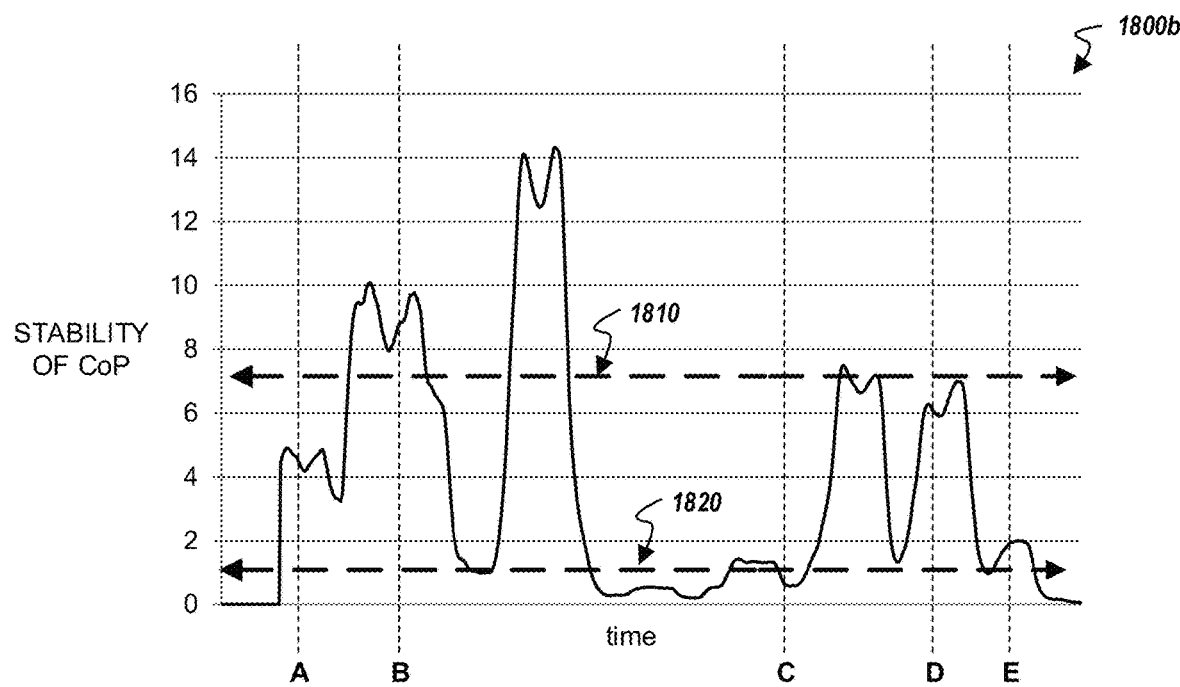

Graph 1800b of FIG. 18B provides an example of the variance of the eye tracking data of FIG. 18A. As an example, graph 1800b may be the exponentially-weighted moving standard deviation of graph 1800a. In general, any measure of variance of the eye tracking data may be used by the render controller 618 in determining where to locate the render camera. As indicated by threshold 1810, whenever the variance (e.g., noise, variability, velocity, etc.) in the position of the user's pupil or CoP is high, the system may position the render camera at the CoR. In contrast and as indicated by threshold 1820, whenever the variance in the position of the user's pupil or CoP is low, the system may position the render camera at the CoP. In the intermediate regions of variance, the system may position the render camera between the CoR and CoP. As examples, the system may place the render camera between CoR and CoP at times A, D, and E, may place the render camera at CoR at time B, and may place the render camera at CoP at time C. In some embodiments, the render camera position may slide between the CoR and CoP positions as a function of the eye tracking data (e.g., as a function of the noise or velocity in the determined CoP data).

Figure 18C:
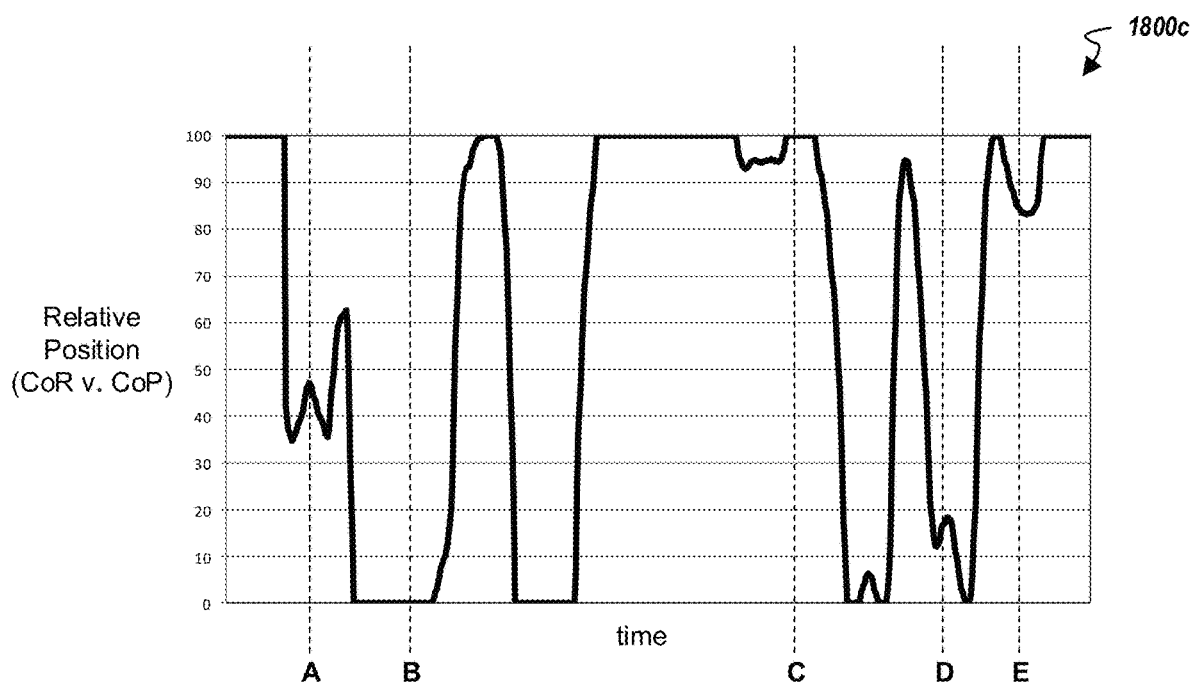
FIG. 18C is an example graph illustrating how render camera position may vary as a function of eye tracking data.

Graph 1800c of FIG. 18C illustrates how the position of the render camera, between CoR and CoP, might vary given the example data of FIGS. 18A and 18B. As shown in graph 1800c, the render camera may be approximately 48% of the way towards the CoP position (and away from the CoR position) along the optical axis at time A, may be located at the CoR position at time B, may be located at the CoP position at time C, may be located near the CoR position (approximately 18% away from the CoR position) at time D, and may be located near the CoP position (approximately 88% away from the CoR position) at time E.

Figure 18D:
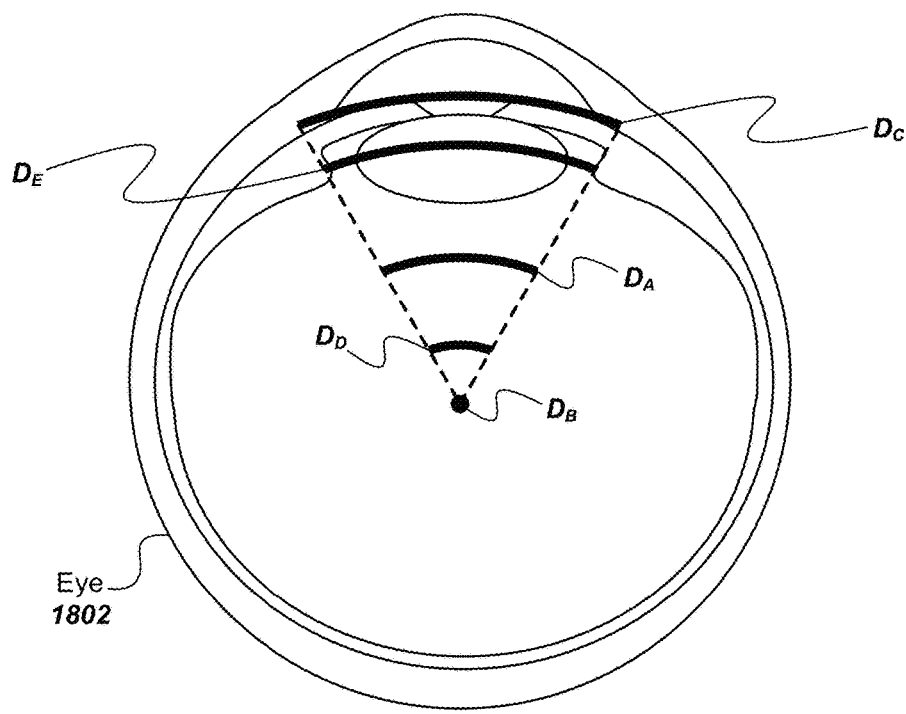
FIG. 18D is a schematic diagram of a user's eye illustrating various render camera positions that may be utilized as a function of eye tracking data.

The positions of the render camera relative to a user's eye 1802 at times A-E are illustrated in the diagram of FIG. 18D. In particular, position $D_B$ may be the CoR and may be used when the CoP location is rapidly moving or noise (e.g., is undesirably jittery), position $D_D$ may be just outside the CoR and may be used when the CoP location data is slightly less jittery, position $D_A$ may be halfway between the CoR and CoP positions and may be used when the CoP location data is slightly improved, position $D_E$ may be nearly to the CoP position and may be used when the CoP data is nearly sufficient to position the render camera at the CoP, and position $D_C$ may be at the CoP and used when the CoP data is sufficiently stable. In general, the render camera may be located at any point between the CoP and CoR and may be smoothly moved between these positions over time in response to varying eye tracking data. In some implementations, the render camera position may be adjusted between the CoP and the CoR based on the user's determined vergence. For example, as a user's vergence or fixation depth shifts from a location in space at which a depth plane is positioned to a location in space at which a hysteresis threshold is positioned, such as that which has been described above with reference to FIG. 12, the system may shift the position of the render camera toward the CoP. In this way, the CoP may be utilized as the render camera location during a depth plane switch, which may be executed by the system in response to determining that the user's vergence has passed the hysteresis threshold, so as to reduce or minimize parallax-induced artifacts. Similarly, in such implementations, as a user's vergence or fixation depth shifts from a location in space at which a hysteresis threshold is positioned to a location in space at which a depth plane is positioned, the system may shift the position of the render camera toward the CoR. As described above, the system may adjust the focal length of a render camera when switching or otherwise adjusting depth planes. As such, in some examples, the system may adjust both the position and the focal length of a render camera as a function of the user's determined vergence.

Determining Center of Rotation Based on Limbus Projections

As described above, for example with respect to at least FIG. 7A as well as elsewhere herein, a center of rotation or 'CoR' may be determined for a user's eye. The center of rotation, as described herein, may indicate a point around which the user's eye rotates. Accordingly, in some cases when the user's eye rotates, there may be a point (e.g., the CoR) within the eye (e.g., eyeball) which is substantially fixed. As discussed above, to determine a CoR, estimates of the location and orientation of optical axes and/or visual axes may be calculated for the eye for different gaze directions using images obtained by an eye tracking camera or other camera. The intersection of these different optical axes or visual axes may be used to estimate the location of a center of rotation for the eye. Alternatively, a module such as described above (e.g., CoR estimation module 724) may utilize estimated eye dimensions. For example, the module may use a center of curvature of a cornea and estimate the CoR as being a particular distance along an optical axis from the center of curvature towards a retina. In some cases, this particular distance may be about 4.7 mm. Other methods of determining estimates of the CoR may possibly be employed.

As discussed above, in various implementations, an eye's CoR may inform, for example, rendering, and presentation, of virtual content to the user. As an example, a rendering engine (e.g., engine 622) may generate virtual content via simulations of cameras positioned at the user's eyes (e.g., as if the camera located at the user's eye generated the virtual content) so that the virtual content is in proper perspective when viewed by the user with the display. To determine these positions, each eye's determined CoR may be utilized. For example, a particular camera may be simulated as a pinhole camera with the pinhole disposed at or near the position of a determined CoR or at a location determined using the location of the CoR. Thus, increasing the accuracy of a determined CoR may provide for technical advantages with respect to the presenting, and correspondingly viewing, of virtual content.

As referenced above, a variety of methods may be utilized to determine an estimate of the location of the center of rotation of the eye. As will be described in more detail below, with respect to FIGS. 19-21D, for example, a limbus of a user's eye may be utilized to accurately determine the eye's CoR. As an example of a limbus, FIG. 5 illustrates curve 512a which indicates a limbic boundary of an example eye 500. Advantageously, the limbic boundary may be rapidly apparent in images of an eye. For example, a boundary of curve 512a may be identified according to edge detection techniques. Since a color associated with the iris may be substantially distinct from that of the sclera, the boundary may be identified due to sudden differences at the curve 512a. As another example, techniques such as RANSAC, machine learning techniques, and so on, may be utilized to determine the curve 512a corresponding to the boundary of the limbus. Additional examples of identifying a limbus, such as identifying a limbic boundary, are described in U.S. Patent Pub. 2018/0018515, which is incorporated by reference herein.

In certain implementations, an ellipse may be projected onto an image of a user's limbus (hereinafter referred to as a 'projection ellipse'). The projection ellipse may thus represent an ellipse that is fit to the boundary of the user's limbus. As described herein, image preprocessing module 710 may obtain images of a user's eye for analysis. These obtained images may thus be utilized to determine respective projection ellipses. Since each image may include a representation of the eye in a unique orientation (e.g., the gaze may be in a different direction), the projection ellipse may, as an example, be accordingly distinct between successive images of the eye. As will be described, for example at least in FIG. 21A-21D, one or more projection ellipses determined from successive images may be used. The difference in the ellipses may be useful in determining (e.g., estimate) the eye's CoR.

Figure 19:
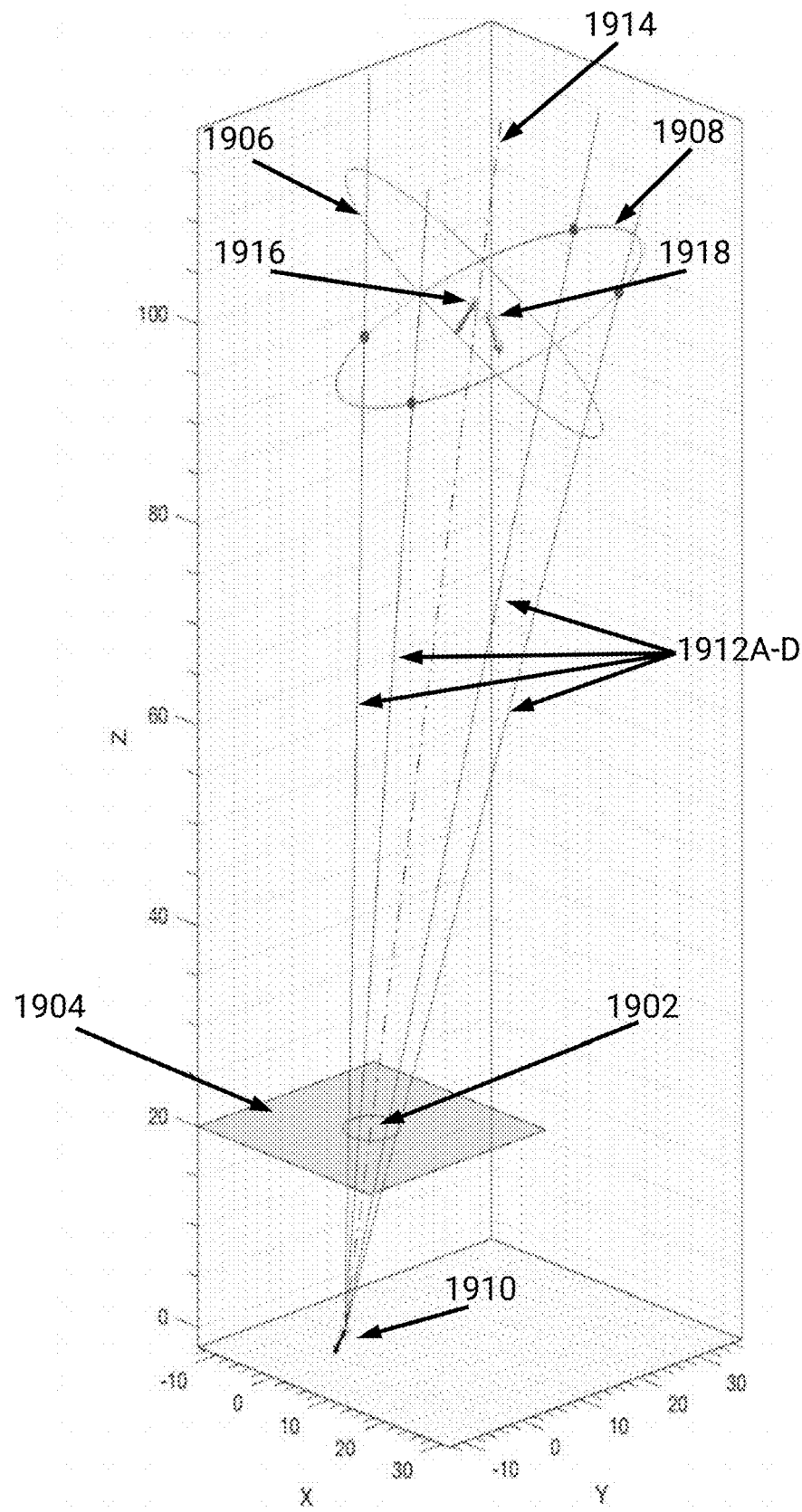
FIG. 19 illustrates a graphical representation of the use of an ellipse projected onto an image of a user's eye (e.g., limbus) used to determine an estimate of the CoR according to various techniques described herein. Rays can be traced through the projection ellipse to form a cone, in which circles are fit. In certain implementations, normals through one or the circles can be used to estimate a CoR.

As an example, a cone such as a cone of rays may be projected as extending from a camera point (e.g., a pinhole camera as described above) through a projection ellipse associated with an image of a user's eye. See, e.g., FIG. 19 as well as FIGS. 21A-21C. Circular cross-sections of the cone may be identified as being associated with the image. An example of these circular cross-sections 1906, 1908, is illustrated in FIG. 19. In some implementations, the circular cross-sections may be determined using an eigenvalue/eigenvector decomposition of the cone although other approaches to identifying the circular cross sections may be used. In some implementations, however, vectors that provide locations of the centers of the circular cross-sections may, for example, be determined.

One of the circular cross-sections may then be selected for the image. For example, one of the circular cross-sections may correspond to a gaze of the user's eye (e.g., towards virtual content). A vector that is normal to the selected circular cross-section (hereinafter referred to as a 'normal vector') may be determined. For example, the normal vector may be normal to the vector also provides a location of the center of the selected circular cross-section.

In the above-described example, two or more images (e.g., successive images) of the eye may be analyzed. Each image of the eye, as described above, may represent the eye in a distinct orientation (e.g., distinct eye pose). A circular cross-section may be selected for each image, and compared to determine the CoR. For example, the CoR may be determined as an intersection of the normal vectors determined for the images. As an example with respect to FIG. 21D, the CoR may be point 2122. In some embodiments, each normal vector may correspond to an optical axis of the eye as determined from a respective image. Thus, and as described in FIG. 7A above, the CoR may be determined as the intersection of optical axes determined for different eye poses.

FIG. 19 illustrates a graphical representation of a projection ellipse 1902 according to the techniques described herein. As described above, a camera may be simulated as being a pinhole camera located at camera point 1910. The camera point 1910 may thus represent an origin of a coordinate system of one or more eye tracking cameras. An image of a user's eye may be obtained (e.g., via module 710), and an image plane 1904 corresponding to the image identified. The image plane 1904 may thus include an imaged representation of the user's eye. A projection ellipse 1902 corresponding to a boundary of the user's limbus may be determined on the image plane 1904.

A cone 1912 formed via extending rays 1912A-D from the camera point 1910 through the boundary of the projection ellipse 1902 may then be identified. In various implementations, circular cross-sections may be determined along a length of the cone 1912. In the example shown, the circular cross-sections have perimeters intersecting with and bounded by the cone of rays. The circular cross-sections, as will be described with reference to FIG. 20, may be uniquely determined based on a specific radius of the circular cross-sections. For example, a first circular cross-section 1906 and a second circular cross-section 1908 with a same radius are illustrated. In some embodiments, and as will be described below with respect to refining a CoR, the limbus radius may not be known, assumed, or taken into account, when determining a two-dimensional CoR. As an example, the radius may represent an average radius of a limbus across a multitude of users, a radius determined for the user based on images of the user's limbus, or may represent an arbitrary constant value. An eigenvector decomposition may optionally be performed, and a principle axis 1914 of the cone 1912 may be identified. As illustrated in FIG. 19, the principle axis 1914 is illustrated as extending through a geometric center of the projection ellipse 1902 to the camera point 1910.

A first vector 1916 may be determined which passes through a center of the first circular cross-section 1906. Similarly, a second vector 1918 may be determined which passes through the second circular cross-section 1908. For examples, these vectors 1916-1918 may be determined based on the eigenvector decomposition of the cone 1912. The circular cross-sections 1906, 1908, may be disambiguated. Thus, one of the circular cross-sections may be identified as better corresponding to a gaze associated with the imaged eye. For example, while either of the circular cross-sections 1906, 1908, may be mathematically allowable for a given radius, one of the circular cross-sections may correspond to an actual gaze of the eye. Thus, one of the circular cross-sections may be selected for utilization in determining an estimate of the eye's CoR.

As will be described in more detail below, with respect to FIG. 20, a normal vector that is normal to the selected circular cross-section may be determined. For example, the normal vector may be normal to either the first circular cross-section 1906 or the second circular cross-section 1908. Normal vectors may be determined for a number of images. An intersection point in three-dimensional space between the normal vectors may then be identified as corresponding to the eye's CoR. An example of an intersection point is illustrated in FIG. 21D, with respect to intersection point 2122. In some cases, a region and associated location where the normal vectors come close together is taken as an estimate of the CoR, for example, if the normal vectors do not intersect at one point. In some implementations, a least-squares approach may be taken to obtain an estimate of such a point of intersection. In such implementations, the system may identify a location at which the sum of the squared distances to the normal vectors is reduced or minimized as the point of intersection.

Advantageously, in some embodiments, one or more techniques may be utilized to refine the estimated CoR described above. For example, a three-dimensional location of the CoR may be refined. In this example, the refined CoR may be a more accurate representation of the eye's CoR. As an example, to refine the CoR, a plane (herein referred to as a 'projection plane') defined by the first vector 1916 and second vector 1918 may be identified. See, e.g., FIG. 19. This projection plane may include the principle axis 1914 of the cone 1912. Thus, the projection plane may include (e.g., pass through) the geometric center of the projection ellipse 1902. Additionally, the projection plane may include (e.g., pass through) the camera point 1910. As will be described, the projection plane may further include (e.g., pass through) the eye's CoR.

Two or more projection planes may be utilized. For example, these projection planes may be determined from successive images of the user's eye. In this example, an intersection between the two or more projection planes may be identified. Since, as described above, each projection plane may include the camera point 1910, the resulting line, formed from the intersection, may thus extend from the camera point 1910. An intersection of the resulting line with the image plane 1904 may therefore represent a two-dimensional location of the CoR on the image plane 1904. To refine the CoR (e.g., the three-dimensional CoR described above), an intersection of the resulting line with the normal vectors may be identified. The intersection may thus be assigned as the refined CoR. Optionally, the refined CoR may be identified as a point along the resulting line based on the point's proximity to the intersection or convergence of the normal vectors. For example, a point on the resulting line which is closest (e.g., according to a root mean squared process) to the normal vectors, or an intersection or convergence thereof, may be assigned as the refined CoR. As mentioned above, in some examples, a least-squares method may also be employed to estimate of such a point.

Figure 20:
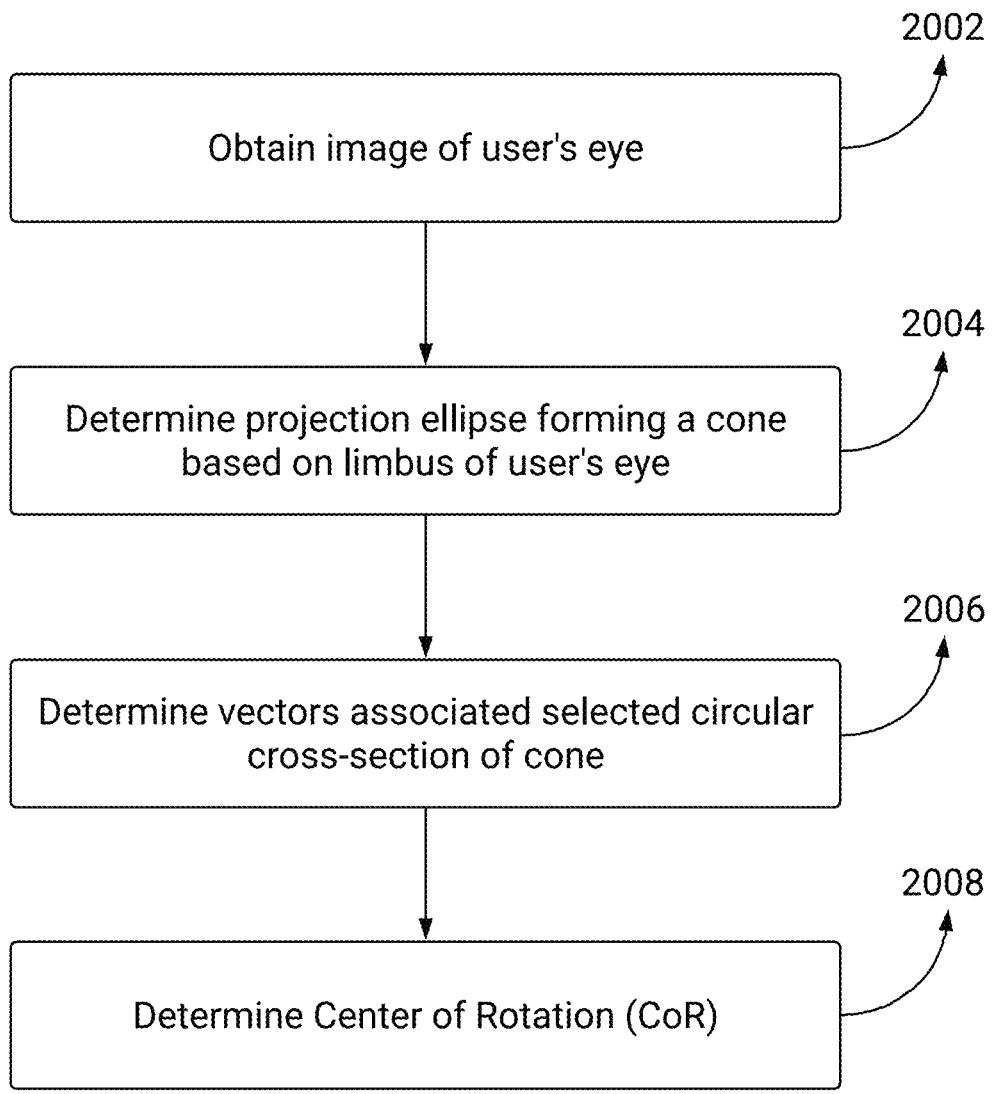
FIG. 20 is a flowchart of an example process for determining an eye's center of rotation based on the eye's limbus.

FIG. 20 is a flowchart of an example process 2000 for determining an eye's center of rotation (CoR) based on the eye's limbus. For convenience, the process 2000 will be described as being performed by a display system of one or more processors or processing elements.

At block 2002, the display system obtains an image of a user's eye. As described above, with respect to at least FIG. 7A, the display system may obtain images of a user's eye via one or more cameras or other imaging systems.

At block 2004, the display system determines a projection ellipse forming a cone based on a limbus of the user's eye. To determine the projection ellipse, the limbus of the user's eye may be identified in the obtained image (e.g. limbic boundary 512 illustrated in FIG. 5). Without being constrained by theory, the limbic boundary may be identified according to different techniques. As an example, an edge detection scheme may be utilized to identify an edge between the sclera and iris. In this example, the edge may represent the limbic boundary. As another example, a machine learning model may be trained to label a limbic boundary (e.g., a neural network). The projection ellipse may in some cases be an ellipse which the display system determines approximates (e.g., substantially approximates) the limbic boundary.

Figure 21A:
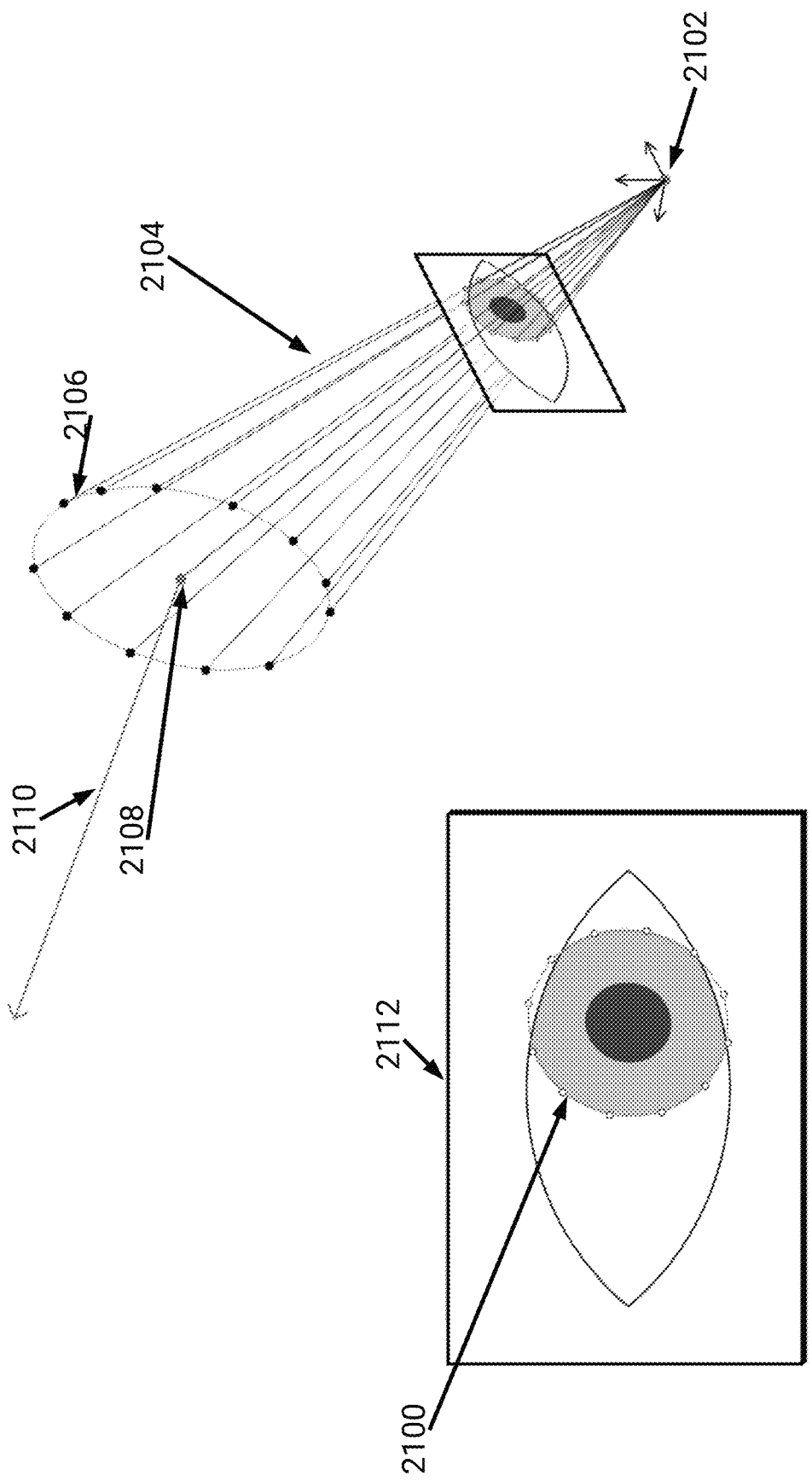
FIG. 21A illustrates a first ellipse projected onto an image of a user's limbus (hereinafter referred to as a 'projection ellipse') determined based on a first gaze of a user. Rays through the projection ellipse are shown that form a cone in a circle is fit.

However, and as illustrated in FIG. 21A, the obtained image may not include the entirety of the limbus. For example, an eyelid of the user's eye may occlude a portion of the limbus. In the example of FIG. 21A, the upper and lower portion of the limbus are occluded. The display system may thus estimate the projection ellipse (e.g., the semi-major and semi-minor axis). Optionally, to estimate the projection ellipse the display system may fit the ellipse based on the visible portions of the limbus. For example, the display system may identify a semi-major axis and semi-minor axis based on the boundary of the limbus visible in the image. Optionally, to estimate the projection ellipse the display system may utilize average information associated with a limbus. For example, if the left and right most portions of the limbic boundary are visible, the display system may utilize average ratios between the semi-major and semi-minor axes of an average limbus. Optionally, the display system may utilize previously obtained images of the user's limbus to identify the dimensions of the limbus.

As described in FIG. 19, rays may be extended from a camera point (e.g., a pinhole camera associated with an imaging system that obtained the image, aperture of camera, etc.) through the projection ellipse boundary. For example, FIG. 21A illustrates 12 example rays being extended from the camera point through respective locations along the projection ellipse boundary. These extended rays may thus form a cone. In some embodiments, the cone may be an elliptical cone. A circular-cross section of the cone may be selected (e.g., as described above) and a normal vector identified based on the circular-cross section. Different techniques to identify such normal vectors, and/or circular cross-sections, may be employed. An example of a technique is described in more detail below.

Without subscribing to any particular scientific or mathematical theories, in some implementations, the projection ellipse described above may be described according to the following equation:

$$ax^2+bxy+cy^2dx+ey+f=0$$

in which the five coefficients (e.g., a, b, c, d, e, f) are defined as follows:

$$a=A^2 \sin^2\phi+B^2 \cos^2\phi$$

$$b=2(B^2-A^2)\sin \phi \cos \phi$$

$$c=A^2 \cos^2\phi+B^2 \sin^2\phi$$

$$d=-2ax_c-by_c$$

$$e=-bx_c-2cy_c$$

$$f=ax_c^2+bx_cy_c+cy_c^2-A^2B^2$$

The projection ellipse equation described above may be written according to homogenous coordinates $\bar{x}=(x\ y\ 1)^T$ as:

$$\bar{x}=C_{2D}\bar{x}=0$$

The conic matrix, $C_{2D}$, identified above may be defined as:

$$C_{2D}=\begin{pmatrix} a & b/2 & d/2 \\ b/2 & c & e/2 \\ d/2 & e/2 & f \end{pmatrix}$$

The display system may adjust the above-identified equation according to intrinsic camera parameters (e.g., an intrinsic camera parameter matrix). Thus, the conic equation may be represented as:

$$C=\Lambda^T C_{2D} \Lambda$$

At block 2006, the display system determines vectors associated with a selected circular cross-section of the cone. As described in block 2004, the cone formed by rays extending from the camera point through the boundary of the projection ellipse may be determined. In some implementations, to determine the vectors associated with the circular cross-sections, the display system may determine eigenvalues and eigenvectors of the cone. For example, the cone 'C' may be decomposed into an orthogonal matrix and a diagonal matrix:

$$C=UDU^T$$

The display system may select an eigenvalue '$\lambda_3$' (e.g., from diagonal matrix 'D') with a sign opposite that of the remaining two eigenvalues. The corresponding eigenvector may then be determined as corresponding to a principle axis of the cone (e.g., principle axis 1914 illustrated in FIG. 19). The principle axis may be represented as being based on the corresponding eigenvector (referred to below as $e_3$):

$$\bar{e}_3=\text{sign}[(\bar{e}_3)_z]\cdot\bar{e}_3$$

The display system may identify, from the two remaining eigenvalues, a smallest eigenvalue according to absolute values of the two remaining eigenvalues. This smallest eigenvalue may be referred to as '$\lambda_2$', and the remaining eigenvalue may be referred to as '$\lambda_1$'

The display system may then determine the following:

$$l_1 = \sqrt{\frac{|\lambda_3| \cdot (|\lambda_1| - |\lambda_2|)}{|\lambda_1| \cdot (|\lambda_1| + |\lambda_3|)}}$$

$$l_2 = \sqrt{\frac{|\lambda_1| \cdot (|\lambda_2| + |\lambda_3|)}{|\lambda_3| \cdot (|\lambda_1| + |\lambda_3|)}}$$

$$l_3 = \sqrt{\frac{|\lambda_1| - |\lambda_2|}{|\lambda_1| + |\lambda_3|}}$$

$$l_4 = \sqrt{\frac{|\lambda_2| + |\lambda_3|}{|\lambda_1| + |\lambda_3|}}$$

As described in FIG. 19, two circular cross-sections of the cone may be determined. For example, in some implementations, the specific two circular cross-sections may be determined based on specified radius. The radius, may, as an example represent a radius associated with a limbus (e.g., as described above).

In some implementations, the circular cross-sections may be defined, at least in part, according to vectors based on the eigenvector decomposition described above. The vectors may represent vectors extending through a center of each of the circular cross-sections. For example, vector $c_1$ and $c_2$ may be determined, along with corresponding normal vectors $n_1$ and $n_2$.

$$\bar{c}_1 = R(-l_1\bar{e}_1 + l_2\bar{e}_3) \quad \bar{n}_1 = l_3\bar{e}_1 + l_4\bar{e}_3$$

$$\bar{c}_2 = R(l_1\bar{e}_1 + l_2\bar{e}_3) \quad \bar{n}_2 = -l_3\bar{e}_1 + l_4\bar{e}_3$$

The display system selects one of the circular-cross sections. For example, the display system may select one of the vector pairs [$c_1$, $n_1$] or [$c_2$, $n_2$] which corresponds to a gaze of the eye. In this example, the display system may determine which associated circular cross-section corresponds to the user looking at a virtual display (e.g., virtual content). As an example, the display system may utilize the corresponding normal vectors to identify which normal vector points at virtual content. Thus, the disambiguation may be performed using the display system. In some embodiments, other schemes such as utilizing a two-dimensional CoR (e.g., as described below) may be utilized to select from among the vector pairs. Other methods, however, may be used to determine any one or more of the projection ellipse, the cone, the circular cross-sections through the cone, the normal vectors for the circular cross-sections, or to select a cross-section and/or associated normal vector. Variations of the mathematical methods discussed above may be used or such mathematical methods need not be used. A variety of other methods may be employed.

As will be described below with respect to block 2008, the display system may utilize the selected vector pair to determine the eye's CoR. For example, the display system may utilize the selected vector pair in combination with other vector pairs, selected from one or more successive images, to determine the CoR.

At block 2008, the display system determines the eye's CoR. As described in blocks 2002-2006 above, the display system may determine a normal vector based on the user's limbus as represented in an image of the user's eye. For example, the normal vector may represent an optical axis of the user's eye. As described in block 2006, the display system may determine a vector pair such as for example a vector pair [$c_x$, $n_x$]. To determine the eye's CoR, the display system may utilize two or more normal vectors determined from respective images of the user's eye. For example, the two or more images may be successive images of the user's eye (e.g., obtained according to a certain periodicity). As another example, the two or more images may represent images taken a threshold time apart. In the example of FIG. 20, the display system may optionally perform block 2008 upon receipt of a threshold number of images. For example, the image described in blocks 2002-2006 may represent a last image of the threshold number of images. Other approaches are possible. Advantageously, the display system may periodically refine, and update, the determined CoR as will be described below.

Similar to the above discussion, for each of the images the display system may determine a vector providing a location of a center of a selected circular cross-section. The display system may also determine a normal vector that is normal to the selected circular cross-section. The normal vector may, as an example, represent an optical axis of the eye. For example, the normal vectors may identify the varying optical axes of the eye according to eye poses represented in the images.

To determine the CoR, the display system may identify a location (e.g., three-dimensional location) at which the normal vectors intersect, converge, or are in close proximity, for example, most of the vectors intersect, converge, or are in close proximity or on average the vectors intersect, converge, or are in close proximity. For example, a root mean squared process may be employed. Thus, and as described in FIG. 7A, the identified location may represent a location at which the optical axes intersect. This intersection point may be assigned as the eye's CoR. In some implementations, the distance from the center of the limbus circle to the CoR may be determined and stored for future use. In at least some of these implementations, the system may store such a distance in association with a particular user, and later rely upon the stored distance to determine the CoR for that particular user (e.g., by identifying a position along the normal vector that is the stored distance away from the center of the limbus). Similarly, in some embodiments, the CoR may be determined by identifying a position along the normal vector that is an assumed distance away from the center of the limbus. In these embodiments, such an assumed distance may correspond to a population average or other predefined value.

As new images of the user's eye are received, the display system may refine the CoR. For example, the display system may determine one or more new CoRs based on respective images (e.g., respective groups of a threshold number of images). The display system may then refine the CoR based on the new CoRs. As an example, the display system may compute a root mean square of the CoRs. Optionally, the display system may utilize all obtained images, or a threshold number, to continually update the CoR. For example, the display system may initially utilize two or more images to determine the CoR. As new images are received, the display system may perform the process 2000 with all, or a threshold number, of the received images. With the increase in the number of images, and thus increase in a number of determined normal vectors, the accuracy of the CoR may be increased. Other approaches are possible.

FIG. 21A illustrates a first projection ellipse 2100 determined based on a first gaze of a user's eye. As described above, an image of the user's eye may be obtained. Based on the image, a boundary of the eye's limbus may be determined. As illustrated, a first projection ellipse 2100 has been determined in an image plane 2112 based on the boundary of the limbus. In the illustrated example, points along the boundary are identified. Rays forming a cone 2104 are illustrated as extending from a camera point 2102 through the points along the boundary. A circular cross-section 2106 has been determined, for example, as described in FIG. 20, with a center 2108 of the circular cross-section 2106 identified in FIG. 21A.

As described in FIGS. 19-20, two circles from the cone 2104 may be determined for a given radius. In the example of FIG. 21A-21D, one of the circles may be selected. For example, and as described above, one of the circles may correspond to a gaze pointing at a virtual display being viewed by a user (e.g., virtual content). Extending from the center 2108 of the circle is a vector 2110. The vector may thus represent one of the normal vectors $n_1$ or $n_2$ described above with respect to FIG. 20.

Figure 21B:
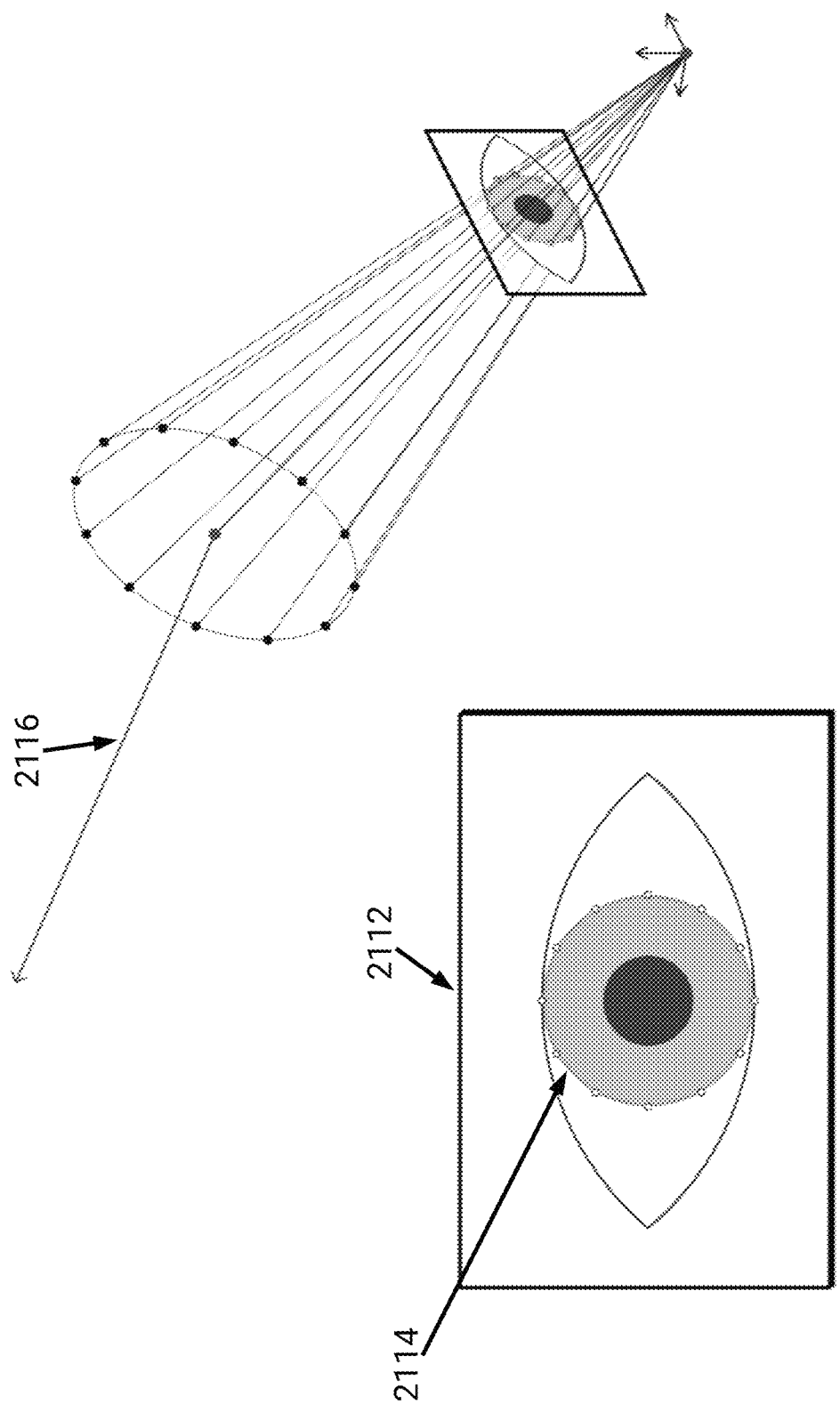
FIG. 21B illustrates a second projection ellipse determined based on a second gaze of the user's eye. A second cone and circle fit thereto are also shown.

FIG. 21B illustrates a second projection ellipse 2114 determined based on a second gaze of the user's eye. In this example, an image subsequent to the image described in FIG. 21A is obtained. Similar to the above, the second projection ellipse 2114 is identified in image plane 2112. Additionally, vector 2116 has been determined.

Figure 21C:
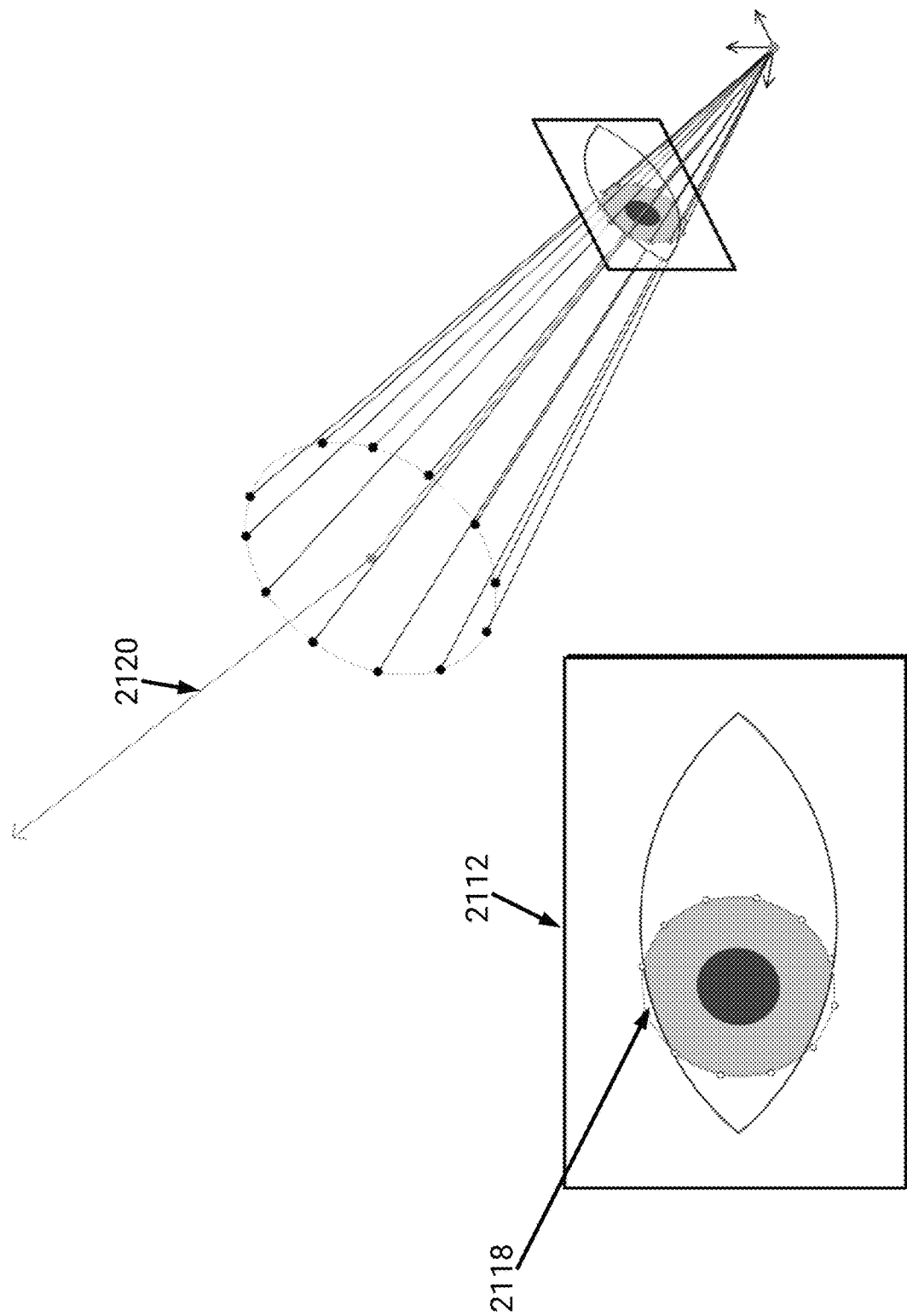
FIG. 21C illustrates a third projection ellipse determined based on a third gaze of the user's eye. A third cone and circle fit thereto are also shown.
Figure 21D:
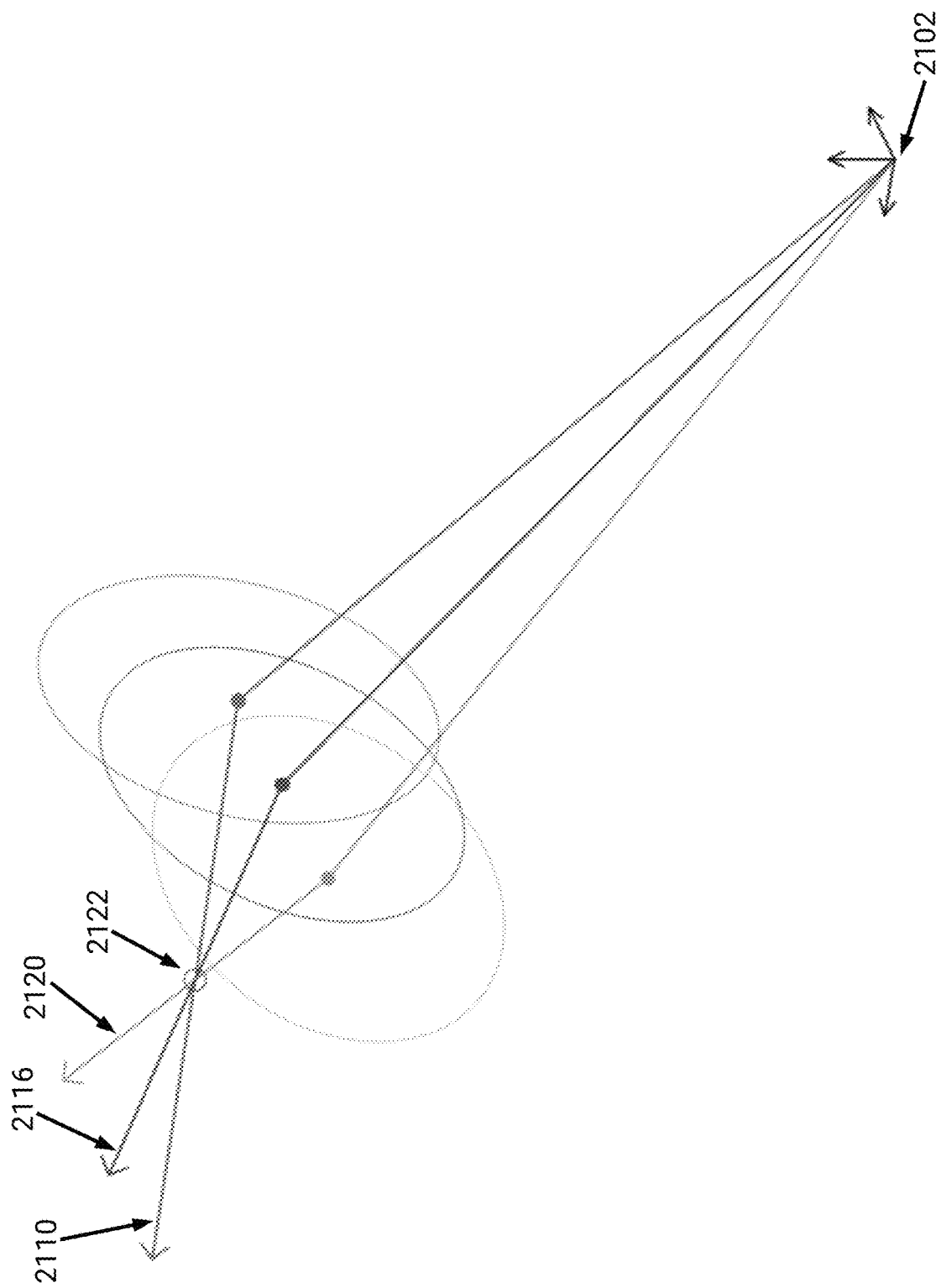
FIG. 21D illustrates determining a center of rotation based on the circles obtained using the projection ellipses as described above.

FIG. 21C illustrates a third projection ellipse 2118 determined based on a third gaze of the user's eye. In this example, an image subsequent to the images described in FIGS. 21A-21B is obtained. Similar to the above, the third projection ellipse 2118 is identified in image plane 2112. Additionally, vector 2120 has been determined.

FIG. 21D illustrates estimating a center of rotation (CoR) based on the determined vectors 2110, 2116, 2120. The display system may utilize the determined vectors to identify a point at which the vectors intersect. For example, the display system has determined that the vectors intersect at point 2122. To determine intersection point 2122, the display system may optionally utilize known physical information. For example, a distance between camera point 2102 and the user's eye may be employed. Alternatively, or in addition, the intersection or location where the normals appear to come in close proximity or converge, for example, where most of the vectors intersect, converge, or are in close proximity or on average the vectors intersect, converge, or are in close proximity, may be determined. The display system may then assign intersection point 2122 or the intersection or location where the normals appear to come in close proximity or converge, for example, where most of the vectors intersect, converge, or are in close proximity or on average the vectors intersect, converge, or are in close proximity, as the eye's CoR.

As described above, with respect to FIGS. 19-21D, images of a user's eye may be utilized to determine an estimate of the eye's CoR. Additional variations and techniques may be employed and fall within the scope of the disclosure. As an example, the display system may determine the eye's CoR based on images of a user's eye during rotation and/or movement of the eye. Through analyzing variations in geometric aspects of the eye the display system may identify the CoR. For example, the display system may identify optical axes of the eye as represented in the images. The display system may utilize the optical axes to determine the CoR. Thus, additional techniques and variations may be employed which utilize geometric aspects of a user's eye to determine an estimate of the eye's CoR.

As an example, the display system may determine an array of positions associated with an image of a user's eye. The array of positions may correspond to spatial locations on the image. Example spatial locations may be associated with a portion of the user's eye (e.g., the limbus, pupil, iris, and so on). Thus, in some implementations, the array of positions may be fit to an extremity of the portion. The extremity of the portion may be associated with a curve (e.g., the projection ellipse described above), which is determined for the portion of the user's eye. In some implementations, the display system may identify linear paths extending from a same point through the array of positions. As described above, the linear paths (e.g., rays) may extend from a camera point. The linear paths may form a cone, and a particular circular cross-section of the cone may be selected. For example, the particular cross-section may have a certain radius (e.g., a radius of an average limbus or of the user's limbus, a radius of an average pupil or the of the user's pupil, and so on). A vector normal to the particular cross-section may be identified. The display system may determine an intersection of multiple of the normal vectors, and then assign the intersection as the CoR. In some implementations, one or more of the techniques for determining 3D points of intersection between two or more optical axes and/or other vectors, as described above with reference to FIG. 7A, may be leveraged to determine 3D points of intersection between the normal vectors described herein with reference to FIGS. 19-21D. Similarly, in some embodiments, one or more of the techniques for averaging and/or applying a filter (e.g., a Kalman-type filter) to a plurality of estimated CoR positions or other 3D positions, as described above with reference to FIG. 7A, may be leveraged to determine and/or refine the CoR estimates described herein with reference to FIGS. 19-21D. Variations and other methods may be employed.

Refining Center of Rotation (CoR) Utilizing Additional Example Techniques

As described in FIGS. 20-21, the display system may determine an eye's CoR as a location (e.g., three-dimensional location) at which multiple vectors intersect, converge, or are in close proximity (e.g., vectors 2110, 2116, 2120). Alternatively, or additionally, the display system may refine the determined CoR according to one or more other techniques. For example, and as described in FIGS. 19-20, vectors $c_1$ and $c_2$ (e.g., vectors 1916, 1918) may be determined from a cone (e.g., cone 1912) formed via rays extending through a projection ellipse (e.g., ellipse 1902). These vectors may form a projection plane. Similar to the above regarding utilizing a plurality of images, the display system may determine projection planes for two or more images.

To refine the determined CoR, the display system may utilize the determined projection planes. For example, in some implementations, the display system may determine intersections of the projection planes (e.g., in three-dimensional space). The intersection of the projection planes may, as an example, result in a line. Additionally, this line may pass through the camera point (e.g., point 1910) from which the cone associated with the projection planes extend. To refine the CoR, the display system may identify a point in the image plane (e.g., image plane 1904) at which this resulting line intersects. The display system may then assign this point as the two-dimensional CoR on the image plane. As described in FIG. 19, the display system may adjust the two-dimensional CoR along the resulting line (e.g., in three-dimensional space). For example, the refined CoR may be assigned as a location along the resulting line close or closest to an intersection of the normal vectors (e.g., vectors 2110, 2116, 2120).

Optionally, the display system may refine the eye's CoR according to the following technique. Different images of the user's eye (e.g., successive images) may be obtained. For each image, the display system may determine an intersection of the vectors $c_1$ and $c_2$ with the image plane (e.g., image plane 1904). The display system may then connect a line between (1) the intersection of vector $c_1$ with the image plane and (2) the intersection of vector $c_2$ with the image plane. Thus, the line may represent the intersection of the projection plane, as defined by vectors $c_1$ and $c_2$, with the image plane. The images may thus be associated with respective lines, and the display system may determine a two-dimensional CoR based on proximity of points in the image plane to the lines. For example, the display system may perform a root mean squared (RMS) process (e.g., based on random sample consensus) to determine the two-dimensional CoR. Similar to the above, the display system may refine the CoR (e.g., as described in FIGS. 20-21) by adjusting the two-dimensional CoR along a line connecting the two-dimensional CoR and camera point.

With respect to the above example, the display system may optionally select one of the vectors $c_1$ or $c_2$ for each of the images. For example, the display system may select one of the vectors $c_1$ or $c_2$ based on a gaze of an eye. As another example, the display may select one of the vectors $c_1$ or $c_2$ based on the respective vectors intersection with the image plane. In this example, the vector which intersects the image plane closer to that of the two-dimensional CoR (e.g., as described above), may be selected. The display system may then determine a point at which each selected vector intersects with the image plane. Similar to the above, the display system may then determine the two-dimensional CoR based on proximity of points in the image plane to the determined intersection points. For example, an RMS process may be utilized.

Determining Center of Rotation (CoR) Based on Pupil Projections

Similar to the above description in FIGS. 19-21D related to utilizing a limbus of an eye, a pupil may alternatively, or additionally, be utilized to determine an eye's CoR. For example, a projection ellipse may be determined for a pupil included in an image of a user's eye. Since the pupil is located behind a surface of the user's cornea, light may be refracted at the surface. However, the main effect of such refraction may be a rotation of a normal vector extending from the pupil with respect to the un-refracted pupil. The refraction effect of the cornea may be considered as discussed herein to determine the refraction based location of the pupil. As a non-limiting example, the refraction based location of the pupil center may also coincide with the projection plane as determined according to the techniques described above. The display system may utilize images of the user's pupil to determine refraction planes as described herein. Thus, the display system may utilize images of the user's pupil to determine projection planes as described herein. For example, a CoR ray (or "eyeball center ray") may be found the same way for the pupil as was described above for the limbus. Including the refraction effect for pupil may, as an example, not change the CoR ray calculation. Then, using a fixed (e.g., average) pupil radius, the display system may find circular sections and their corresponding normal (e.g., as described above).

The display system may then determine the eye's CoR based on the pupil in similar ways as described above for determining the CoR based on the limbus. For example, an ellipse may be fit to the pupil image. A cone of rays may be projected through the ellipse. Circular cross-sections may be fit to the cone. Normals through a plurality of cross-sections obtain using a plurality of images may be used may considered and the intersection or convergence of those normal may be identified. An estimate of the CoR may be obtained therefrom. Other methods, including other methods described herein, such as using projection planes may be employed to determine an estimate of the CoR.

Center of Perspective (CoP) Analysis/Derivation

In the pinhole camera model, the center of perspective (CoP) may be considered as an aperture of a pinhole camera. An example property of this CoP is that it may also be the origin of the object angle space. Thus, and as an example with reference to this origin, objects which are at a same angle from a pinhole will map to the same pixel (e.g., overlap). As another example, if a scene is rigidly rotated about the CoP, then a projected image will translate and the objects in the scene will not experience parallax shifts.

In developing the systems and techniques described herein, two hypotheses were developed and tested. The first hypothesis was that the center of the principal plane is the CoP, and the second hypothesis was that the center of the aperture is the CoP. The principal plane, as an example, may represent a plane where incident light rays may be considered to bend due to refraction. As will be described, it may be determined that the center of aperture is the CoP. For example, FIGS. 22, 23A-23B, and 24A-24B, along with their corresponding descriptions below, may be informative as to the analysis associated with the testing of these two hypotheses.

Figure 22:
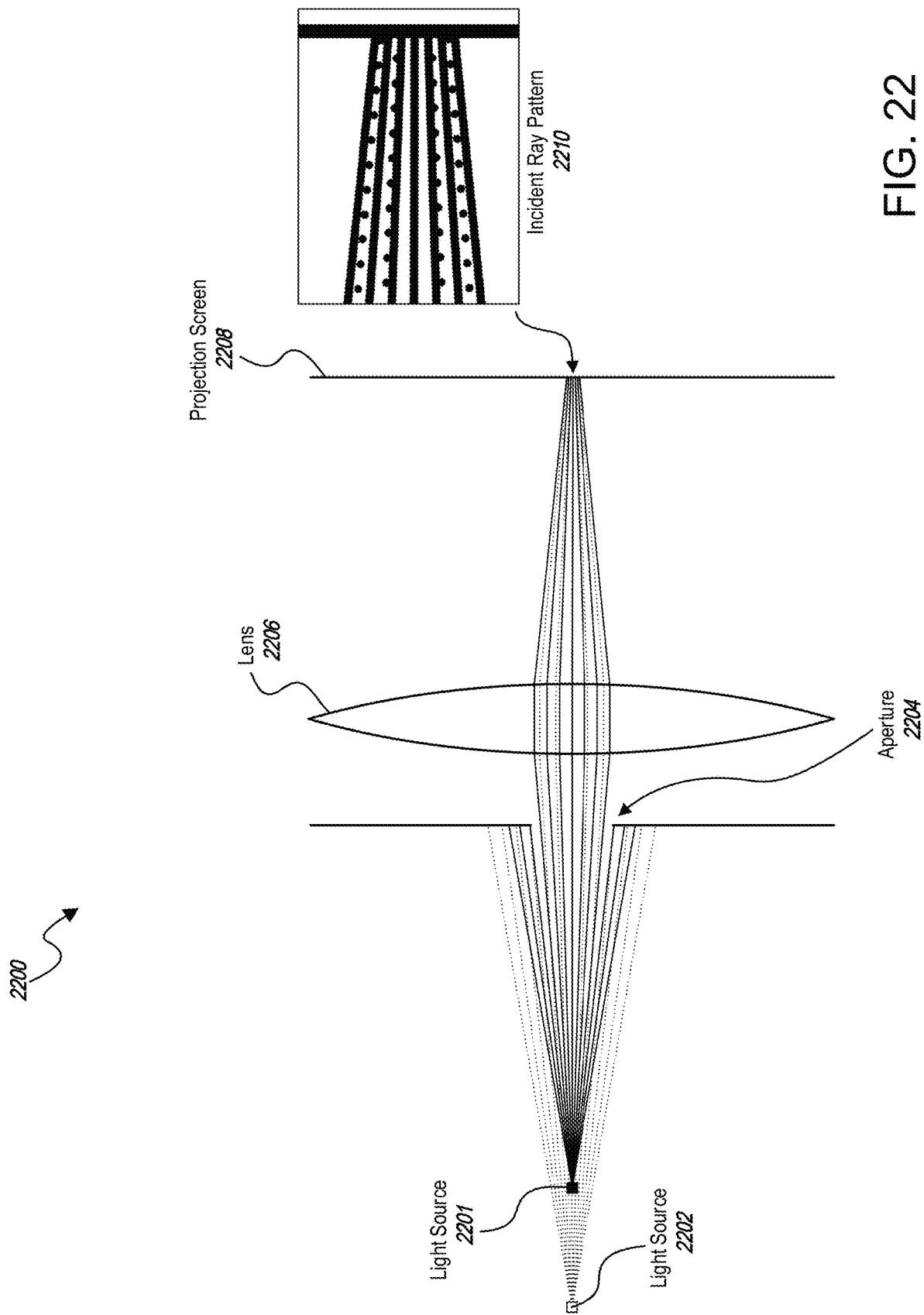
FIG. 22 illustrates an optical system including two point light sources, an aperture, a lens, and a projection screen.

FIG. 22 illustrates an optical system 2200 including two point light sources 2201 and 2202, an aperture 2204, a lens 2206, and a projection screen 2208. In this example, the aperture 2204, lens 2206, and projection screen 2208 of optical system 2200 may be representative of or at least functionally similar to anatomical features of the human eye. For instance, the aperture 2204, lens 2206, and projection screen 2208 of optical system 2200 may correspond to a pupil, lens, and retina, respectively.

In FIG. 22, rays of light emitted by the first point light source 2201 are represented as solid lines extending from the first point light source 2201 toward the projection screen 2208, while rays of light emitted by the second point light source 2202 are represented as dotted lines extending from the second point light source 2202 toward the projection screen 2208. Some of the light emitted from each of the two point light sources 2201 and 2202 may propagate through the aperture 2204 and the lens 2206 and ultimately strike the projection screen 2208 to form an incident ray pattern 2210.

FIG. 23A illustrates an optical system 2300 in a first stage (e.g., stage "A"), which includes two point light sources 2301 and 2302, an aperture 2304, a lens 2306, and a projection screen 2308. Optical system 2300 may, for example, be architecturally and functionally identical or similar to optical system 2200, as described in further detail above with reference to FIG. 22. More specifically, optical system 2300 may represent a particular implementation of optical system 2200, as described in further detail above with reference to FIG. 22, in which the center of the principal plane is defined as the CoP such that the abovementioned first hypothesis may be tested. Since the lens 2306 may serve to define the principal plane in optical system 2300, it follows that the CoP in this example may correspond to lens center 2307.

An evaluation of optical system 2300 for the two abovementioned implications may be informative as to whether the abovementioned first hypothesis is true or false. That is, in order for the abovementioned first hypothesis to be true, the image that is projected onto the projection screen 2308 (e.g., the incident ray pattern) should not undergo any parallax shifts when the two point light sources 2301 and 2302 are rigidly rotated about the lens center 2307 (e.g., rotated along radii of curvature 2311 and 2312, respectively), but merely experience a translation. Referring again to FIG. 22, this means that the image that is projected onto the projection screen 2308 should look like a translated version of the incident ray pattern 2210 (e.g., image is formed at a slightly different location on the projection screen 2308) when the two point light sources 2301 and 2302 are rigidly rotated to any pair of points along radii of curvature 2311 and 2312, respectively.

Figure 23B:
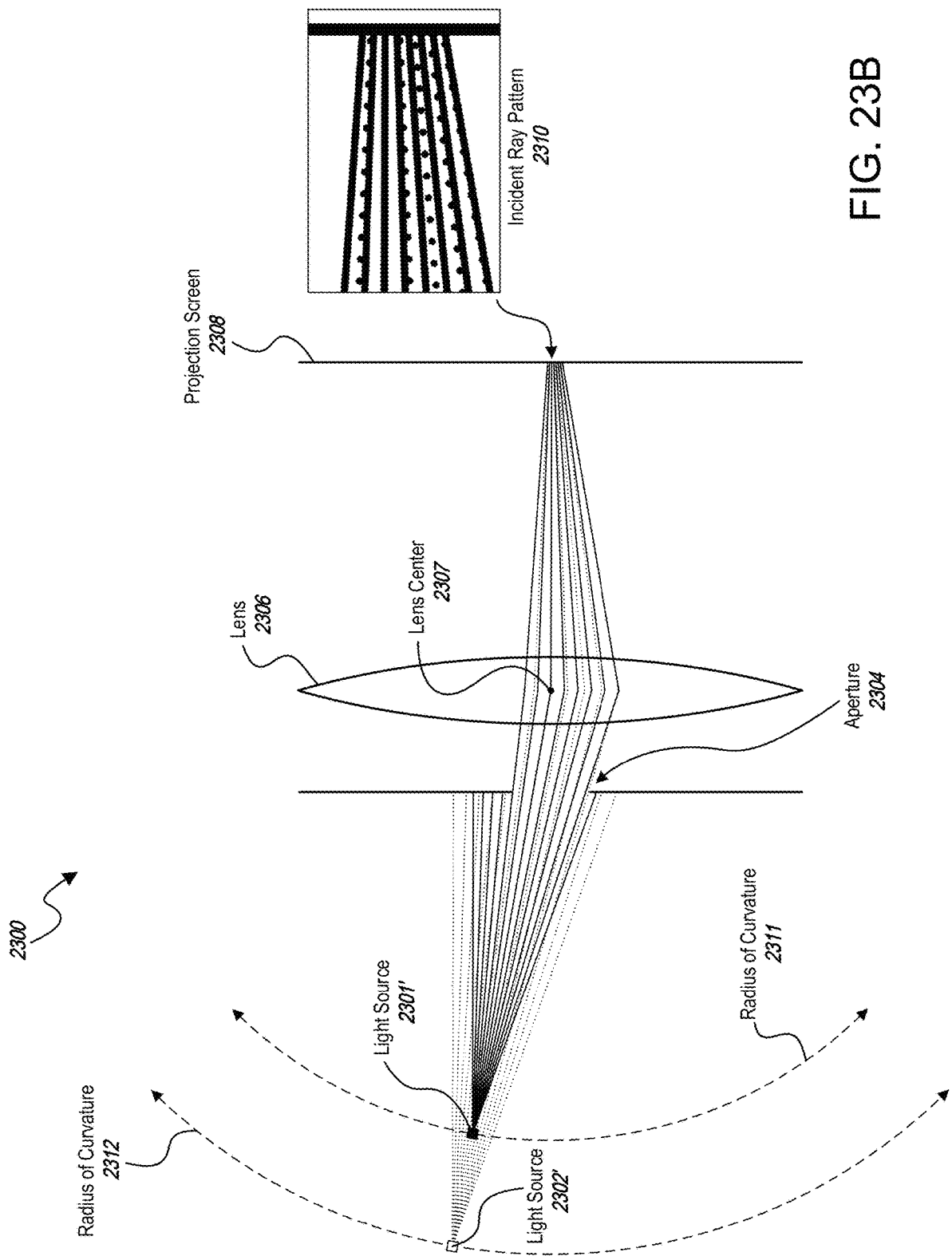
FIG. 23B illustrates the optical system in a second stage.

FIG. 23B illustrates optical system 2300 in a second stage (e.g., stage "B") in which the two point light sources 2301 and 2302 have been rigidly rotated about lens center 2307 along radii of curvature 2311 and 2312, respectively, to become rigidly rotated point light sources 2301' and 2302'. It can be seen that some of the light emitted from each of the two rigidly rotated point light sources 2301' and 2302' propagates through the aperture 2304 and the lens 2306 and ultimately strikes the projection screen 2308 to form an incident ray pattern 2310.

However, upon examination of the incident ray pattern 2310, it can also be seen that the relative position (e.g., on the projection screen 2310) between rays of the incident ray pattern 2310 that originate from the first rigidly rotated light source 2301' and rays of the incident ray pattern 2310 that originate from the second rigidly rotated light source 2302' has shifted. Referring again to FIG. 22, it can be further noted that the incident ray pattern 2310 yielded in FIG. 23B does not appear to resemble a translated version of the incident ray pattern 2210. In other words, rigid rotation of the two point light sources 2301 and 2302 about the lens center 2307 resulted in a parallax shift. For this reason, the lens center 2307 may be seen as an unsuitable location for the CoP. Thus, FIGS. 22, 23A, and 23B and the accompanying analysis thereof can be as effectively demonstrating that the abovementioned first hypothesis is false.

FIG. 24A illustrates an optical system 2400 in a first stage (e.g., stage "A"), which includes two point light sources 2401 and 2402, an aperture 2404, a lens 2406, and a projection screen 2408. Optical system 2400 may, for example, be architecturally and functionally identical or similar to optical system 2200, as described in further detail above with reference to FIG. 22, in much the same way as described above with reference to FIGS. 23A and 23B. More specifically, optical system 2400 may represent a particular implementation of optical system 2200, as described in further detail above with reference to FIG. 22, in which the aperture center 2407 is defined as the CoP such that the abovementioned second hypothesis may be tested.

An evaluation of optical system 2400 similar to evaluation of optical system 2300, as described above with reference to FIGS. 23A and 23B, may be informative as to whether the abovementioned second hypothesis is true or false. That is, in order for the abovementioned second hypothesis to be true, the image that is projected onto the projection screen 2408 (e.g., the incident ray pattern) should not undergo any parallax shifts when the two point light sources 2401 and 2402 are rigidly rotated about the aperture center 2407 (e.g., rotated along radii of curvature 2411 and 2412, respectively), but merely experience a translation.

Figure 24B:
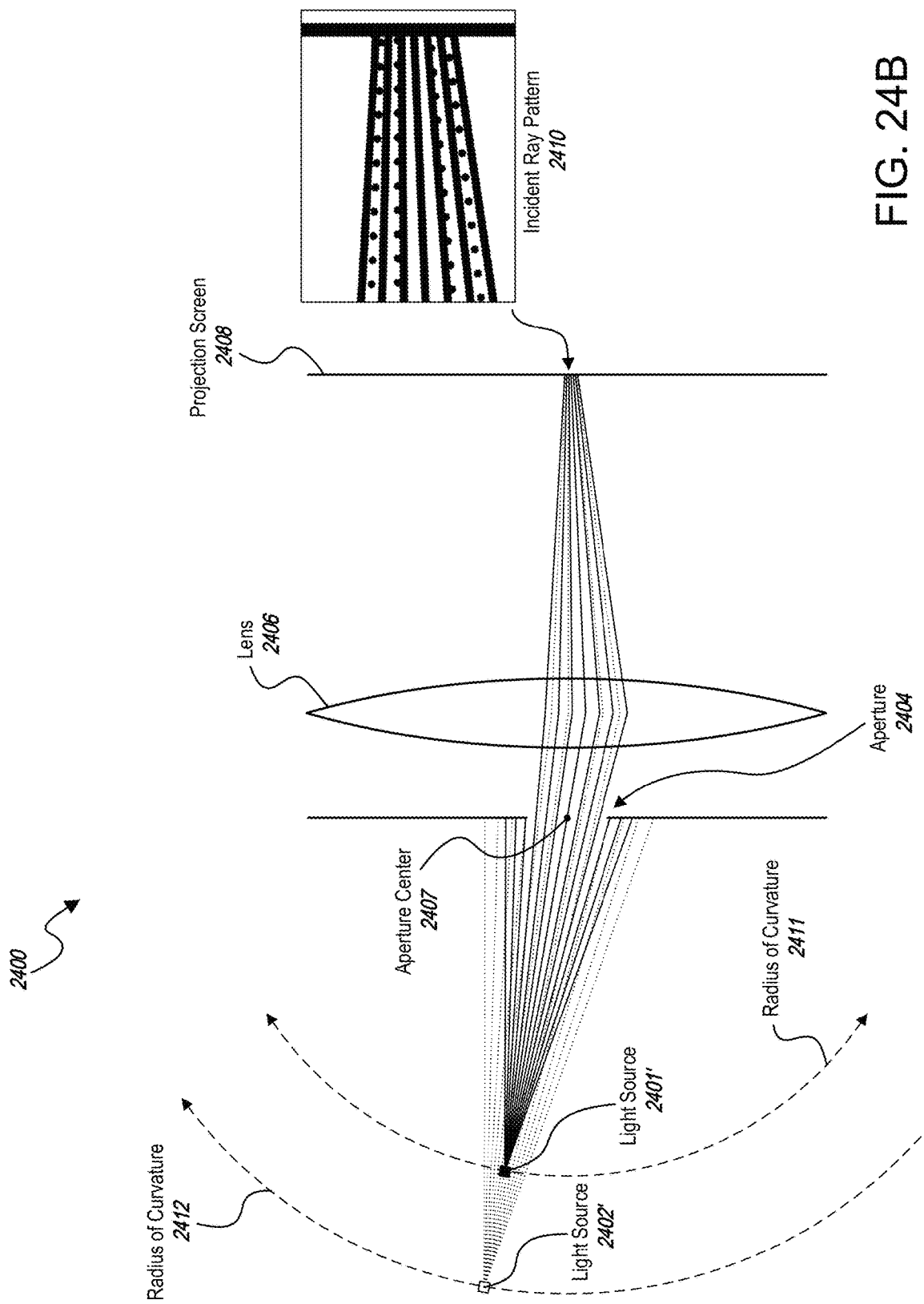
FIG. 24B illustrates the optical system in a second stage.

FIG. 24B illustrates optical system 2400 in a second stage (e.g., stage "B") in which the two point light sources 2401 and 2402 have been rigidly rotated about aperture center 2407 along radii of curvature 2411 and 2412, respectively, to become rigidly rotated point light sources 2401' and 2402'. It may be appreciated that light from the two rigidly rotated point light sources 2401' and 2402' strikes the projection screen 2408 to form an incident ray pattern 2410 that appears to resemble a translated version of the incident ray pattern 2210, as described above with reference to FIG. 22. That is, although the position of the incident ray pattern 2410 with respect to the projection screen 2408 may differ from that of the incident ray pattern 2210 with respect to the projection screen 2208, the relative position (e.g., on the projection screen 2310) between rays of the incident ray pattern 2410 that originate from the first rigidly rotated light source 2401' and rays of the incident ray pattern 2410 that originate from the second rigidly rotated light source 2402' does not appear to have shifted. As such, rigid rotation of the two point light sources 2401 and 2402 about the aperture center 2407 does not appear to yield a parallax shift. Given that the two abovementioned implications appear to have been met in this example, the aperture center 2407 may be seen as a suitable location for the CoP. Thus, FIGS. 22, 24A, and 24B and the accompanying analysis thereof can be as effectively demonstrating that the abovementioned second hypothesis is true.

As such, it may, in some embodiments, be desirable to align the CoP in the Render World (e.g., location of the pinhole of a render camera) with a portion of a user's eye (in the Real World) which is the anatomical equivalent of the aperture center 2407. Because the human eye further includes a cornea (which imparts additional optical power to light propagating toward the retina), the anatomical equivalent of the aperture center 2407 may not correspond to the center of the pupil or iris of a user's eye, but may instead correspond to a region of the user's eye positioned between the outer surface of the cornea of the user's eye and the center of the pupil or iris of the user's eye. For example, the anatomical equivalent of the aperture center 2407 may correspond to a region within the anterior chamber of the user's eye.

Examples for when Eye Tracking is Unavailable

In some embodiments, eye tracking may not be provided or may be temporarily unavailable. As examples, the eye tracking camera 324 or light sources 326 may be obscured, damaged, or disabled by a user, the environmental lighting conditions may make eye tracking prohibitively difficult, the wearable system may be improperly fitted in a manner that prevents eye tracking, the user may be squinting or have eyes that are not easily tracked, etc. At such times, the wearable system may be configured to fall back upon various strategies for positioning the render camera and selecting depth planes in the absence of eye tracking data.

With respect to the render camera, the wearable system may position the render camera to a default position if the user's pupils are not detected for longer than a predetermined threshold, such as a few seconds or longer than a typical blink. The wearable system may move the render camera to the default position in a smooth movement, which may follow an over-damped oscillator model. The default position may be determined as part of a calibration process of the wearable system to a particular user. The default position may be a user's left and right eyes' centers of rotation. These are merely illustrative examples.

With respect to the depth plane, the wearable system may provide accommodation cues based on the depth of virtual content, as opposed to the vergence depth of the user as previously discussed. In some embodiments, the wearable system may receive, obtain, or determine information estimating where the user is likely to be looking and may provide matching accommodation cues. As an example, the wearable system may be displaying content that the user is likely to be focused on, such as a video clip, may assume that the user is looking at the content, and may provide the content on a depth plane (or with blended depth planes) to provide accommodation cues that match the depth of that content.

Computer Vision to Detect Objects in Ambient Environment

As discussed above, the display system may be configured to detect objects in or properties of the environment surrounding the user. The detection may be accomplished using a variety of techniques, including various environmental sensors (e.g., cameras, audio sensors, temperature sensors, etc.), as discussed herein.

In some embodiments, objects present in the environment may be detected using computer vision techniques. For example, as disclosed herein, the display system's forward-facing camera may be configured to image the ambient environment and the display system may be configured to perform image analysis on the images to determine the presence of objects in the ambient environment. The display system may analyze the images acquired by the outward-facing imaging system to perform scene reconstruction, event detection, video tracking, object recognition, object pose estimation, learning, indexing, motion estimation, or image restoration, etc. As other examples, the display system may be configured to perform face and/or eye recognition to determine the presence and location of faces and/or human eyes in the user's field of view. One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques may also be used together with data acquired from other environmental sensors (such as, e.g., microphone) to detect and determine various properties of the objects detected by the sensors.

As discussed herein, the objects in the ambient environment may be detected based on one or more criteria. When the display system detects the presence or absence of the criteria in the ambient environment using a computer vision algorithm or using data received from one or more sensor assemblies (which may or may not be part of the display system), the display system may then signal the presence of the object.

Machine Learning

A variety of machine learning algorithms may be used to learn to identify the presence of objects in the ambient environment. Once trained, the machine learning algorithms may be stored by the display system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of additional images obtained), conditional situations, or other variations. In some embodiments, the display system may be configured to utilize a plurality of techniques to generate models for analysis of the aggregated data. Other techniques may include using predefined thresholds or data values.

The criteria for detecting an object may include one or more threshold conditions. If the analysis of the data acquired by the environmental sensor indicates that a threshold condition is passed, the display system may provide a signal indicating the detection the presence of the object in the ambient environment. The threshold condition may involve a quantitative and/or qualitative measure. For example, the threshold condition may include a score or a percentage associated with the likelihood of the reflection and/or object being present in the environment. The display system may compare the score calculated from the environmental sensor's data with the threshold score. If the score is higher than the threshold level, the display system may detect the presence of the reflection and/or object. In some other embodiments, the display system may signal the presence of the object in the environment if the score is lower than the threshold. In some embodiments, the threshold condition may be determined based on the user's emotional state and/or the user's interactions with the ambient environment.

In some embodiments, the threshold conditions, the machine learning algorithms, or the computer vision algorithms may be specialized for a specific context. For example, in a diagnostic context, the computer vision algorithm may be specialized to detect certain responses to the stimulus. As another example, the display system may execute facial recognition algorithms and/or event tracing algorithms to sense the user's reaction to a stimulus, as discussed herein.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

Other Considerations

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems can include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, animations or video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities can be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto can be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems can generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted can be incorporated in the example methods and processes that are schematically illustrated. For example, one or more additional operations can be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

EXAMPLES of a user to display virtual image content in a vision field of said user are described herein such as the examples enumerated below:

Example 1: A display system configured to project light to an eye of a user to display virtual image content in a vision field of said user, said eye having a cornea, an iris, a pupil, a lens, a retina, and an optical axis extending through said lens, pupil, and cornea, said display system comprising: a frame configured to be supported on a head of the user; a head-mounted display disposed on the frame, said display configured to project light into said user's eye to display virtual image content to the user's vision field at different amounts of at least one of divergence and collimation and thus the displayed virtual image content appears to originate from different depths at different periods of time; one or more eye tracking cameras configured to image the user's eye; and processing electronics in communication with the display and the one or more eye tracking cameras, the processing electronics configured to obtain an estimate of a center of rotation of said eye based on images of said eye obtained with said one or more eye tracking cameras.

Example 2: The display system of Example 1, further comprising one or more light sources disposed on said frame with respect to said user's eye to illuminate said user's eye, said one or more eye tracking cameras forming images of said eye using said light from said one or more light sources.

Example 3: The display system of Example 1 or 2, wherein said one or more light sources comprises at least two light sources disposed on said frame with respect to said user's eye to illuminate said user's eye.

Example 4: The display system of Example 1 or 3, wherein said one or more light sources comprises infrared light emitters.

Example 5: The display system of any of the Examples 1 to 4, wherein one or more light sources form one or more glints on said eye and said processing electronics is configured to determine a location of said cornea based on said one or more glints.

Example 6: The display system of any of the Examples 1 to 5, wherein said cornea has associated therewith a cornea sphere having a center of curvature and said processing electronics is configured to determine a location of said center of curvature of said cornea sphere.

Example 7: The display system of Example 5, wherein said cornea has associated therewith a cornea sphere having a center of curvature and said processing electronics is configured to determine a location of said center of curvature of said cornea sphere based on said one or more glints.

Example 8: The display system of any of the Examples above, wherein said one or more eye tracking camera is configured to image said pupil of said eye.

Example 9: The display system of any of the Examples above, wherein said processing electronics is configured to determine the location of said center of said pupil.

Example 10: The display system of any of the Examples above, wherein said processing electronics is configured to determine at least a portion of a boundary between said iris and said pupil.

Example 11: The display system of Example 10, wherein said processing electronics is configured to determine a center of said boundary between said iris and said pupil.

Example 12: The display system of any of the Examples above, wherein said processing electronics is configured to determine a location of said center of said pupil in three-dimensional space with respect to a center of curvature of said cornea.

Example 13: The display system of any of the Examples above, wherein said processing electronics is configured to determine a location and orientation of said optical axis.

Example 14: The display system of Example 12, wherein said processing electronics is configured to determine a location and orientation of said optical axis based on a location of said center of said pupil in three-dimensional space.

Example 15: The display system of any of the Examples above, wherein said processing electronics is configured to determine said location and orientation of said optical axis based on a location of said center of said pupil in three-dimensional space with respect to a center of curvature of said cornea.

Example 16: The display system of any of the Examples above, wherein said processing electronics is configured to determine a location of said center of rotation of said eye based on a center of curvature of said cornea.

Example 17: The display system of any of the Examples above, wherein said processing electronics is configured to determine a location of said center of rotation of said eye based on a center of curvature of said cornea and a location and orientation of said optical axis.

Example 18: The display system of Example 17, wherein said processing electronics is configured to determine the location of said center of rotation of said eye by translating a particular distance along said optical axis from said center of curvature of said cornea.

Example 19: The display system of Example 18, wherein said particular distance from said center of curvature to said center of rotation is between 4.0 mm and 6.0 mm.

Example 20: The display system of Example 18 or 19, wherein said particular distance from said center of curvature to said center of rotation is about 4.7 mm.

Example 21: The display system of Example 18 or 19, wherein said particular distance is fixed.

Example 22: The display system of Example 18 or 19, wherein said processing electronics is configured to determine the particular distance based at least on one or more images of said eye previously obtained with said one or more eye tracking cameras.

Example 23: The display system of any of the Examples above, wherein said processing electronics is configured to determine a location and orientation of a visual axis, offset from said optical axis, based on said location and orientation of said optical axis.

Example 24: The display system of any of the Examples above, wherein said processing electronics is configured to determine a location and orientation of a visual axis based on an angular rotation with respect to said optical axis.

Example 25: The display system of any of the Examples above, wherein said processing electronics is configured to determine a location and orientation of a visual axis based on an angular rotation of between 4.0° and 6.5° with respect to said optical axis.

Example 26: The display system of any of the Examples above, wherein said processing electronics is configured to determine a location and orientation of a visual axis based on an angular rotation of about 5.2° with respect to said optical axis.

Example 27: The display system of any of the Examples above, wherein said processing electronics are configured to determine a location and orientation of a visual axis based at least on one or more images of said eye previously obtained with said one or more eye tracking cameras.

Example 28: The display system of any of the Examples above, wherein said processing electronics is configured to determine a center of rotation of said eye based multiple determinations of said location of said optical axis or visual axis over a period of time during which said eye is rotating.

Example 29: The display system of any of the Examples above, wherein said processing electronics is configured to determine said center of rotation by identifying a region of intersection of multiple determinations of said location of said optical axis or a visual axis over a period of time during which said eye is rotating.

Example 30: The display system of any of the Examples above, wherein said processing electronics is configured to determine a vergence distance of said user where left and right eyes of a user are gazing based on a determination of the location and orientation of said optical axes for said left and right eyes of the user.

Example 31: The display system of any of the Examples above, wherein said processing electronics is configured to determine a vergence distance of said user where left and right eyes of a user are gazing based on a determination of the location and orientation of said visual axes for said left and right eyes of the user.

Example 32: The display system of any of the Examples above, wherein said processing electronics is configured to determine a vergence distance where left and right eyes of a user are gazing based on identifying a region of intersection of said visual axes for said left and right eyes of the user.

Example 33: The display system of any of the Examples above, wherein said processing electronics is configured to determine a vergence distance where left and right eyes of a user are gazing by projecting the visual axes for said left and right eyes onto a horizontal plane and identifying a region of intersection of said projections of the visual axes for said left and right eyes onto a horizontal plane.

Example 34: The display system of any of the Examples above, wherein said processing electronics is configured to determine the relative amounts of at least one of divergence, and collimation to project image content based on a determination of said vergence distance.

Example 35: The display system of any of the Examples above, wherein said processing electronics includes electronics on said frame.

Example 36: The display system of any of the Examples above, wherein said processing electronics includes electronics on said frame and electronics disposed at a location remote from said frame.

Example 37: The display system of any of the Examples above, wherein said processing electronics includes electronics on said frame and electronics on a belt pack.

Example 38: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 39: The display system of any of the Examples above, wherein said head-mounted display receives light from a portion of the environment in front of the user at a first amount of divergence and transmits the light from the portion of the environment in front of the user to the user's eye with a second amount of divergence that is substantially similar to the first amount of divergence.

Example 40: The display system of any of the Examples above, wherein the processing electronics is configured to obtain the estimate of the center of rotation by filtering, averaging, applying a Kalman filter, or any combinations thereof a plurality of estimated center of rotation positions.

Example 41: The display system of any of the Examples above, wherein said processing electronics is configured to present said virtual image content to said user's eye that is rendered as if captured by a camera having an aperture at the determined position of the center of rotation of said user's eye.

Example 42: The display system of any of the Examples above, wherein said processing electronics is configured to use a render camera at said center of rotation to render virtual images to be presented to said eye.

Example 43: The display system of any of the Examples above, wherein said processing electronics is configured to use a render camera configured to render virtual images to be presented to said eye that are rendered as if captured by a camera having an aperture closer to said the center of rotation than said retina of said eye.

Example 44: The display system of any of the Examples above, wherein said processing electronics is configured to use a render camera configured to render virtual images to be presented to said eye that are rendered as if captured by a camera having an aperture at said the center of rotation of said eye.

Example 45: The display system of any of the Examples above, wherein said processing electronics is configured to use a render camera at said center of rotation to render virtual images to be presented to said eye, said render camera modeled with an aperture at said center of rotation of said eye.

Example 46: A display system configured to project light to an eye of a user to display virtual image content in a vision field of said user, said eye having a cornea, an iris, a pupil, a lens, a retina, and an optical axis extending through said lens, pupil, and cornea, said display system comprising: a frame configured to be supported on a head of the user; a head-mounted display disposed on the frame, said display configured to project light into said user's eye to display virtual image content to the user's vision field at different amounts of at least one of divergence and collimation and thus the displayed virtual image content appears to originate from different depths at different periods of time; one or more eye tracking cameras configured to image the user's eye; and processing electronics in communication with the display and the one or more eye tracking cameras, the processing electronics configured to obtain a position estimate of a center of perspective of said eye based on images of said eye obtained with said one or more eye tracking cameras, said center of perspective being estimated to be proximal said pupil of said eye or between said cornea and said pupil of said eye, wherein said processing electronics is configured to present said virtual image content to said user's eye that are rendered by a render camera located at said center of perspective.

Example 47: The display system of any of the Examples above, wherein said processing electronics is configured to present said virtual image content to said user's eye that are rendered as if captured by a camera having an aperture closer to said center of perspective than said retina.

Example 48: The display system of any of the Examples above, wherein said processing electronics is configured to present said virtual image content to said user's eye that are rendered as if captured by a camera having an aperture closer to said center of perspective than a center of rotation of the eye.

Example 49: The display system of any of the Examples above, wherein said processing electronics is configured to present said virtual image content to said user's eye that are rendered as if captured by a camera having an aperture at said center of perspective.

Example 50: The display system of any of the Examples above, wherein said center of perspective is not located at said pupil of said eye.

Example 51: The display system of any of the Examples above, wherein the processing electronics is configured to obtain an estimate of said user's eye pose over time and wherein the processing electronics adjust the position of the render camera based at least in part upon the user's eye pose.

Example 52: The display system of any of the Examples above, wherein the processing electronics is configured to track said user's eye pose over time and wherein the position of the render camera is adjusted over time in response to changes in said user's eye pose over time.

Example 53: The display system of any of the Examples above, wherein the processing electronics is configured to obtain the estimate of the center of perspective by filtering a plurality of estimated center of perspective positions.

Example 54: The display system of any of the Examples above, wherein the processing electronics is configured to obtain the estimate of the center of perspective by averaging and/or applying a Kalman filter to a plurality of estimated center of perspective positions.

Example 55: The display system of any of the Examples above, wherein the center of perspective comprises a position within the anterior chamber of said user's eye.

Example 56: The display system of any of the Examples above, wherein the center of perspective comprises a position in front of said pupil of said user's eye.

Example 57: The display system of any of the Examples above, wherein the center of perspective comprises a position that is between 1.0 mm and 2.0 mm in front of said pupil of said user's eye.

Example 58: The display system of any of the Examples above, wherein the center of perspective comprises a position that is about 1.0 mm in front of said pupil of said user's eye.

Example 59: The display system of any of the Examples above, wherein the center of perspective comprises a position that is between 0.25 mm and 1.0 mm in front of said pupil of said user's eye.

Example 60: The display system of any of the Examples above, wherein the center of perspective comprises a position that is between 0.5 mm and 1.0 mm in front of said pupil of said user's eye.

Example 61: The display system of any of the Examples above, wherein the center of perspective comprises a position that is between 0.25 mm and 0.5 mm in front of said pupil of said user's eye.

Example 62: The display system of any of the Examples above, wherein the center of perspective lies along the optical axis of said eye and wherein said processing electronics are further configured to obtain the position estimate of the center of perspective by obtaining a position estimate of the optical axis of said eye.

Example 63: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye.

Example 64: The display system of any of the Examples above, wherein the center of perspective lies along the optical axis of said eye at a position between an outer surface of the cornea and the pupil of said eye and wherein said processing electronics are further configured to obtain the position estimate of the center of perspective by obtaining a position estimate of the optical axis of said eye and a position estimate of a center of rotation of said eye, the cornea of said eye, the iris of said eye, the retina of said eye, and the pupil of said eye or any combinations thereof.

Example 65: The display system of any of the Examples above, wherein said processing electronics includes electronics on said frame.

Example 66: The display system of any of the Examples above, wherein said processing electronics includes electronics on said frame and electronics disposed at a location remote from said frame.

Example 67: The display system of any of the Examples above, wherein said processing electronics includes electronics on said frame and electronics on a belt pack.

Example 68: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 69: The display system of any of the Examples above, further comprising one or more light sources disposed on said frame with respect to said user's eye to illuminate said user's eye, said one or more eye tracking cameras capturing images of said eye using said light from said one or more light sources.

Example 70: The display system of any of the Examples above, wherein said one or more light sources comprises at least two light sources disposed on said frame with respect to said user's eye to illuminate said user's eye.

Example 71: The display system of any of the Examples above, wherein said one or more light sources comprises at least three light sources disposed on said frame with respect to said user's eye to illuminate said user's eye.

Example 72: The display system of any of the Examples above, wherein said one or more light sources comprises infrared light emitters.

Example 73: The display system of any of the Examples above, wherein said one or more light sources form one or more glints on said eye and said processing electronics is configured to determine the position of the center of curvature of said cornea based on said one or more glints.

Example 74: The display system of any of the Examples above, wherein said one or more light sources form one or more glints on said eye and said processing electronics is configured to determine a three-dimensional position of the center of curvature of said cornea based on said one or more glints.

Example 75: The display system of any of the Examples above, wherein said one or more eye-tracking cameras are further configured to image said pupil of the user's eye and wherein said processing electronics are further configured to determine the position of said pupil of said eye based at least on the image of said pupil from the one or more eye-tracking cameras.

Example 76: The display system of any of the Examples above, wherein said one or more eye-tracking cameras are further configured to image said pupil of the user's eye and wherein said processing electronics are further configured to determine a three-dimensional position of said pupil of said eye based at least on the image of said pupil from the one or more eye-tracking cameras.

Example 77: The display system of any of the Examples above, wherein said one or more eye-tracking cameras are further configured to image said pupil of the user's eye and wherein said processing electronics are further configured to determine the position of said pupil of said eye based on the position of the center of curvature of said cornea and based on the image of said pupil from the one or more eye-tracking cameras.

Example 78: The display system of any of the Examples above, wherein said processing electronics is configured to determine the optical axis of said eye based on the three-dimensional position of the center of curvature of said cornea and based on the three-dimensional position of said pupil.

Example 79: The display system of any of the Examples above, wherein said processing electronics is configured to determine a visual axis of said eye based on the optical axis.

Example 80: The display system of any of the Examples above, wherein said processing electronics is configured to determine the visual axis of said eye based on the optical axis and the three-dimensional position of at least one of the center of curvature of said cornea, said pupil or both.

Example 81: The display system of any of the Examples above, wherein said processing electronics is configured to determine a three-dimensional position of the center of rotation of said eye based on the three-dimensional position of the center of curvature of said cornea.

Example 82: The display system of any of the Examples above, wherein said processing electronics is configured to determine a three-dimensional position of the center of rotation of said eye based on the three-dimensional position of the center of curvature of said cornea and based on said optical axis.

Example 83: The display system of any of the Examples above, wherein said processing electronics is configured to determine the distance between said eye and the additional eye of said user based at least on the three-dimensional position of the center of rotation of said eye.

Example 84: The display system of any of the Examples above, wherein said processing electronics is configured to determine an interpupillary distance between said eye and the additional eye of said user based at least on the three-dimensional position of the center of rotation of said eye.

Example 85: The display system of any of the Examples above, wherein said processing electronics is configured to determine the vergence distance of said user based at least on the optical axis of said eye.

Example 86: The display system of any of the Examples above, wherein said processing electronics is configured to determine the vergence distance of said user based at least on the optical axis of said eye and on a determined optical axis of the additional eye of said user.

Example 87: The display system of any of the Examples above, wherein said processing electronics is configured to determine the vergence distance of said user based at least on the visual axis of said eye and on a determined visual axis of the additional eye of said user.

Example 88: The display system of any of the Examples above, wherein said display is configured to project collimated light into said user's eye.

Example 89: The display system of any of the Examples above, wherein said display is configured to project collimated light corresponding to an image pixel into said user's eye at a first period of time and divergent light corresponding to said image pixel into said user's eye at a second period of time.

Example 90: The display system of any of the Examples above, wherein said display is configured to project light corresponding to an image pixel having a first amount of divergence into said user's eye at a first period of time and to project light corresponding to said image pixel having a second amount of divergence, greater than the first amount of divergence, into said user's eye at a second period of time.

Example 91: A method of rendering virtual image content in a display system configured to project light to an eye of a user to display the virtual image content in a vision field of said user, said eye having a cornea, an iris, a pupil, a lens, a retina, and an optical axis extending through said lens, pupil, and cornea, said method comprising: with one or more eye tracking cameras configured to image said eye of the user to track movements of said eye, determining a position of a center of rotation of said eye; with a render engine, rendering virtual image content with a render camera at said center of rotation of said eye, said render camera configured to render virtual images to be presented to said eye; and with a head-mounted display, projecting light into said user's eye to display the rendered virtual image content to the user's vision field at different amounts of divergence such that the virtual image content appears to originate from different depths at different periods of time.

Example 92: The method of any of the Examples above, wherein said render camera is configured to render virtual images to be presented to said eye that are rendered as if captured by a camera having an aperture closer to said the center of rotation than said retina of said eye.

Example 93: The method of any of the Examples above, wherein said render camera is configured to render virtual images to be presented to said eye that are rendered as if captured by a camera having an aperture at said the center of rotation.

Example 94: The method of any of the Examples above, wherein said render camera is modeled with an aperture at said center of rotation of said eye.

Example 95: The method of any of the Examples above, wherein said render camera is modeled with an aperture, a lens, and a detector.

Example 96: The method of any of the Examples above, wherein said render camera has an aperture at a position along a line between (i) the determined position of the center of rotation of said eye and (ii) the determined position of the at least one of said iris or pupil.

Example 97: The method of any of the Examples above, further comprising: with the one or more eye tracking cameras, determining a position of a center of perspective of said user's eye, wherein the center of perspective of said user's eye is located less than approximately 1.0 mm from the pupil of said user's eye; and with the render engine, rendering the virtual image content with the render camera, wherein said render camera has an aperture at the determined position of the center of perspective of said user's eye.

Example 98: The method of any of the Examples above, further comprising: with the render engine, rendering the virtual image content with the render camera, wherein said render camera has an aperture at a position along a line between (i) the determined position of the center of rotation of said eye and (ii) the determined position of the center of perspective of said user's eye.

Example 99: The method of any of the Examples above, further comprising: with processing electronics in communication with the one or more eye tracking cameras, determining a measure of change with time of the determined position of the center of perspective of said user's eye; and with the processing electronics, if it is determined that the measure of change with time exceeds a first threshold, directing the render engine to render the virtual content with the render camera, wherein the render camera has an aperture at the determined position of the center of rotation of said eye.

Example 100: The method of any of the Examples above, further comprising: with the processing electronics, if it is determined that the measure of change with time is below a second threshold, directing the render engine to render the virtual content with the render camera, wherein the render camera has an aperture at the determined position of the center of perspective of said eye, and wherein the first threshold is indicative of a higher level change with time in the determined position of the center of perspective of said user's eye than the second threshold.

Example 101: The method of any of the Examples above, further comprising: with the processing electronics, if it is determined that the measure of change with time is below a second threshold, directing the render engine to render the virtual content with the render camera, wherein the render camera has an aperture at the determined position of the center of perspective of said eye.

Example 102: The method of any of the Examples above, further comprising: with the processing electronics, if it is determined that the measure of change with time is between the first and second thresholds, directing the render engine to render the virtual content with the render camera, wherein the render camera has an aperture at a point along a line between (i) the determined position of the center of rotation of said eye and (ii) the determined position of the center of perspective of said eye.

Example 103: The method of any of the Examples above, further comprising: with at least a portion of said display, said portion being transparent and disposed at a location in front of the user's eye when the user wears said head-mounted display, transmitting light from a portion of the environment in front of the user and said head-mounted display to the user's eye to provide a view of said portion of the environment in front of the user and said head-mounted display.

Example 104: The method of any of the Examples above, further comprising: with the one or more eye tracking cameras, determining a position of at least one of said iris, pupil, or lens Example 105: The method of any of the Examples above, further comprising: with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the at least one of said iris or pupil.

Example 106: The method of any of the Examples above, further comprising: with the one or more eye tracking cameras, determining a position of a center of perspective of said user's eye, wherein the center of perspective of said user's eye is located less than approximately 1.0 mm from the pupil of said user's eye; and with the render engine, rendering the virtual image content with the render camera, said render camera configured to present virtual images to said eye images that are rendered as if captured by a camera having an aperture at the determined position of the center of perspective of said user's eye.

Example 107: The method of any of the Examples above, further comprising: with the render engine, rendering the virtual image content with the render camera, said render camera configured to present virtual images to said eye images that are rendered as if captured by a camera having an aperture at a position along a line between (i) the determined position of the center of rotation of said eye and (ii) the determined position of the center of perspective of said user's eye.

Example 108: The method of any of the Examples above, further comprising: with processing electronics in communication with the one or more eye tracking cameras, determining a measure of change with time of the determined position of the center of perspective of said user's eye; and with the processing electronics, if it is determined that the measure of change with time exceeds a first threshold, directing the render engine to render the virtual content with the render camera as if captured by a camera having an aperture at the determined position of the center of rotation of said eye.

Example 109: The method of any of the Examples above, further comprising: with the processing electronics, if it is determined that the measure of change with time is below a second threshold, directing the render engine to render the virtual content with the render camera as if captured by a camera having an aperture at the determined position of the center of perspective of said eye, wherein the first threshold is indicative of a higher level change with time in the determined position of the center of perspective of said user's eye than the second threshold.

Example 110: The method of any of the Examples above, further comprising: with the processing electronics, if it is determined that the measure of change with time is below a second threshold, directing the render engine to render the virtual content with the render camera as if captured by a camera having an aperture at the determined position of the center of perspective of said eye.

Example 111: The method of any of the Examples above, further comprising: with the processing electronics, if it is determined that the measure of change with time is between the first and second thresholds, directing the render engine to render the virtual content with the render camera as if captured by a camera having an aperture at a point along a line between (i) the determined position of the center of rotation of said eye and (ii) the determined position of the center of perspective of said eye.

Example 112: A display system configured to project light to an eye of a user to display virtual image content in a vision field of said user, said eye having a cornea, an iris, a pupil, a lens, and a retina, and an optical axis extending through said lens, pupil, and cornea, said display system comprising: a frame configured to be supported on a head of the user; a head-mounted display disposed on the frame, said display configured to project light into said user's eye to display virtual image content to the user's vision field at different amounts of divergence and thus the displayed virtual image content appears to originate from different depths at different periods of time, wherein said head-mounted display is configured to project light into said user's eye having a first amount of divergence at a first period of time and is configured to project light into said user's eye having a second amount of divergence at a second period of time, wherein the first amount of divergence is different from the second amount of divergence; one or more eye tracking cameras configured to image the user's eye; and processing electronics in communication with the display and the one or more eye tracking cameras, the processing electronics configured to obtain an estimate of a center of rotation of said eye based on images of said eye obtained with said one or more eye tracking cameras, obtain an estimate of a vergence distance of said user based on images of said eye obtained with said one or more eye tracking cameras, and shift from projecting light into said user's eye at the first amount of divergence to projecting light into said user's eye at the second amount of divergence based on the estimated vergence distance of said user.

Example 113: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 114: The display system of any of the Examples above, wherein said processing electronics is further configured to, based on images of said eye obtained with said one or more eye tracking cameras, detect a blink of said eye.

Example 115: The display system of any of the Examples above, wherein said processing electronics is further configured to, based on images of said eye obtained with said one or more eye tracking cameras, detect a saccade of said eye.

Example 116: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected the blink of said eye.

Example 117: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected the saccade of said eye.

Example 118: The display system of any of the Examples above, wherein said processing electronics is configured to shift from projecting light into said user's eye at the first amount of divergence to projecting light into said user's eye at the second amount of divergence based on the determined vergence distance of said user and based on whether the processing electronics have detected at least one of the saccade or the blink of said eye.

Example 119: The display system of any of the Examples above, wherein said first amount of divergence is associated with vergence distances in a first range and wherein said second amount of divergence is associated with vergence distances in a second range.

Example 120: The display system of any of the Examples above, wherein said first amount of divergence is associated with vergence distances in a first range, wherein said second amount of divergence is associated with vergence distances in a second range and wherein the first and second ranges overlap but are not equal.

Example 121: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range.

Example 122: The display system of any of the Examples above, wherein said processing electronics is configured to shift from projecting light into said user's eye at the first amount of divergence to projecting light into said user's eye at the second amount of divergence upon determining the vergence distance of said user lies outside the second range and lies within the first range.

Example 123: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range and also detecting a blink of said eye.

Example 124: The display system of any of the Examples above, wherein said processing electronics is configured to shift from projecting light into said user's eye at the first amount of divergence to projecting light into said user's eye at the second amount of divergence upon determining the vergence distance of said user lies outside the first range and lies within the second range and also detecting a saccade of said eye.

Example 125: The display system of any of the Examples above, wherein said processing electronics is configured to shift from projecting light into said user's eye at the first amount of divergence to projecting light into said user's eye at the second amount of divergence upon determining the vergence distance of said user has been outside the first range and within the second range for longer than a predetermined period of time.

Example 126: The display system of any of the Examples above, wherein said processing electronics is configured to shift from projecting light into said user's eye at the first amount of divergence to projecting light into said user's eye at the second amount of divergence upon determining the vergence distance of said user has been outside the first range and within the second range for longer than a predetermined period of time of at least 10 seconds.

Example 127: The display system of any of the Examples above, wherein said head-mounted display comprises a first display element configured to project light having the first amount of divergence and a second display element configured to project light having the second amount of divergence.

Example 128: The display system of any of the Examples above, wherein said display is configured to project light into said user's eye to display virtual image content in a discrete display mode in which the display is configured to project light associated with a plurality of sequential frames using only one of the first display element.

Example 129: The display system of any of the Examples above, wherein said display is configured to project light into said user's eye to display virtual image content in a blended display mode in which the display is configured to project light associated with a plurality of sequential frames using both of the first and second display elements for each of the frames.

Example 130: The display system of any of the Examples above, wherein said display is configured to project light into said user's eye to display virtual image content in a blended display mode in which the display is configured to project light associated with a plurality of sequential frames using both of the first and second display elements for each of the frames and wherein, in the blended display mode, the display is configured to project light, using the first and second display elements, that is perceived by a user as having a given amount of divergence that is between the first and second amounts of divergence.

Example 131: The display system of any of the Examples above, wherein said display is configured to project light into said user's eye to display virtual image content in a multi-focus display mode in which the display is configured to project light associated with a plurality of sequential frames using both of the first and second display elements for each of the frames, wherein, in the multi-focus display mode, the display is configured to project light associated with first virtual image content at a third amount of divergence and to project light associated with second virtual image content at a fourth amount of divergence, and wherein the third amount of divergence is different from the fourth amount of divergence.

Example 132: The display system of any of the Examples above, wherein third and fourth amounts of divergence are each between the first and second amounts of divergence.

Example 133: The display system of any of the Examples above, wherein at least one of the third and fourth amounts of divergence are between the first and second amounts of divergence.

Example 134: The display system of any of the Examples above, wherein the third and fourth amounts of divergence are respectively equal to the first and second amounts of divergence.

Example 135: The display system of any of the Examples above, wherein the display is configured to project light associated with the first virtual image in a first region of the user's vision field and to project light associated with the second virtual image in a second region of the user's vision field and wherein the first and second regions are different.

Example 136: The display system of any of the Examples above, wherein the display is configured to project light associated with the first virtual image in a first region of the user's vision field and to project light associated with the second virtual image in a second region of the user's vision field and wherein the first and second regions do not overlap.

Example 137: A display system configured to project light to left and right eyes of a user to display virtual image content in a vision field of said user, each of said eyes having a cornea, an iris, a pupil, a lens, a retina, and an optical axis extending through said lens, pupil, and cornea, said display system comprising: a frame configured to be supported on a head of the user; a head-mounted display disposed on the frame, said display configured to project light into said user's left and right eyes to display virtual image content to the user's vision field at different amounts of at least one of divergence and collimation and thus the displayed virtual image content appears to originate from different distances from the user's left and right eyes at different periods of time; a first eye tracking camera configured to image the user's left eye; a second eye tracking camera configured to image the user's right eye; and processing electronics in communication with the display and the first and second eye tracking cameras, the processing electronics configured to obtain an estimate of an interpupillary distance between the user's left and right eyes based on images of said left and right eyes obtained with said first and second eye tracking cameras.

Example 138: The display system of any of the Examples above, further comprising one or more light sources disposed on said frame with respect to said user's eye to illuminate said user's eye, said one or more eye tracking cameras forming images of said eye using said light from said one or more light sources.

Example 139: The display system of any of the Examples above, wherein said one or more light sources comprises at least two light sources disposed on said frame with respect to said user's eye to illuminate said user's eye.

Example 140: The display system of any of the Examples above, wherein said one or more light sources comprises infrared light emitters.

Example 141: The display system of any of the Examples above, wherein one or more light sources form one or more glints on said eye and said processing electronics is configured to determine a location of said cornea based on said one or more glints.

Example 142: The display system of any of the Examples above, wherein said cornea has associated therewith a cornea sphere having a center of curvature and said processing electronics is configured to determine a location of said center of curvature of said cornea sphere.

Example 143: The display system of any of the Examples above, wherein said cornea has associated therewith a cornea sphere having a center of curvature and said processing electronics is configured to determine a location of said center of curvature of said cornea sphere based on said one or more glints.

Example 144: The display system of any of the Examples above, wherein said one or more eye tracking camera is configured to image said pupil of said eye.

Example 145: The display system of any of the Examples above, wherein said processing electronics is configured to determine the location of said center of said pupil.

Example 146: The display system of any of the Examples above, wherein said processing electronics is configured to determine at least a portion of a boundary between said iris and said pupil.

Example 147: The display system of any of the Examples above, wherein said processing electronics is configured to determine a center of said boundary between said iris and said pupil.

Example 148: The display system of any of the Examples above, wherein said processing electronics is configured to determine a location of said center of said pupil in three-dimensional space with respect to a center of curvature of said cornea.

Example 149: The display system of any of the Examples above, wherein said processing electronics is configured to determine a location and orientation of said optical axis.

Example 150: The display system of any of the Examples above, wherein said processing electronics is configured to determine a location and orientation of said optical axis based on a location of said center of said pupil in three-dimensional space.

Example 151: The display system of any of the Examples above, wherein said processing electronics is configured to determine said location and orientation of said optical axis based on a location of said center of said pupil in three-dimensional space with respect to a center of curvature of said cornea.

Example 152: The display system of any of the Examples above, wherein said processing electronics is configured to determine a location of said center of rotation of said eye based on a center of curvature of said cornea.

Example 153: The display system of any of the Examples above, wherein said processing electronics is configured to determine a location of said center of rotation of said eye based on a center of curvature of said cornea and a location and orientation of said optical axis.

Example 154: The display system of any of the Examples above, wherein said processing electronics is configured to determine the location of said center of rotation of said eye by translating a particular distance along said optical axis from said center of curvature of said cornea.

Example 155: A method of rendering virtual image content in a display system configured to project light to left and right eyes of a user to display the virtual image content in a vision field of said user, each of said eyes having a cornea, an iris, a pupil, a lens, a retina, and an optical axis extending through said lens, pupil, and cornea, said method comprising: with one or more eye tracking cameras configured to image said eyes of the user to track movements of said eyes, determining a position of a center of rotation of said left eye and a position of a center of rotation of said right eye; with processing electronics in communication with the one or more eye tracking cameras, estimating said user's interpupillary distance based on the determined positions of the center of rotation of said left and right eyes; with the one or more eye tracking cameras, determining a current left eye pose and a current right eye pose; and with the processing electronics, estimating said user's current vergence distance by comparing said estimated interpupillary distance and said determined current left eye pose and said determined current right eye pose.

Example 156: The method of any of the Examples above, wherein determining said current left and right eye poses comprises, with the one or more eye tracking cameras, estimating a position of said pupil of said user's left eye and a position of said pupil of said user's right eye.

Example 157: The method of any of the Examples above, wherein determining said current left and right eye poses comprises, with the one or more eye tracking cameras, estimating a position of said cornea of said user's left eye and a position of said cornea of said user's right eye.

Example 158: The method of any of the Examples above, wherein determining said current left and right eye poses comprises, with the one or more eye tracking cameras, estimating a position of said iris of said user's left eye and a position of said iris of said user's right eye.

Example 159: The method of any of the Examples above, wherein determining said current left and right eye poses comprises, with the one or more eye tracking cameras, estimating a position of said lens of said user's left eye and a position of said lens of said user's right eye.

Example 160: The method of any of the Examples above, wherein estimating said user's current vergence distance comprises: with processing electronics, estimating a distance between said positions of said irises of said user's left and right eyes; and with the processing electronics, estimating said user's current vergence distance based on a comparison of said estimated interpupillary distance and said estimated distance between said positions of said irises of said user's left and right eyes.

Example 161: The method of any of the Examples above, further comprising: with a head-mounted display, projecting light into said user's eye to display the rendered virtual image content to the user's vision field at different amounts of divergence such that the virtual image content appears to originate from different depths at different periods of time.

Example 162: The method of any of the Examples above, further comprising: with at least a portion of said display, said portion being transparent and disposed at a location in front of the user's eye when the user wears said head-mounted display, transmitting light from a portion of the environment in front of the user and said head-mounted display to the user's eye to provide a view of said portion of the environment in front of the user and said head-mounted display.

Example 163: A display system configured to project light to an eye of a user to display virtual image content in a vision field of said user, said eye having a cornea, an iris, a pupil, a lens, a retina, and an optical axis extending through said lens, pupil, and cornea, said display system comprising: a frame configured to be supported on a head of the user; a head-mounted display disposed on the frame, said display configured to project light into said user's eye to display virtual image content to the user's vision field at different amounts of at least one of divergence and collimation and thus the displayed virtual image content appears to originate from different depths at different periods of time; one or more eye tracking cameras configured to image the user's eye; and processing electronics in communication with the display and the one or more eye tracking cameras, the processing electronics configured to obtain a position estimate of a center of rotation of said eye based on images of said eye obtained with said one or more eye tracking cameras and configured to obtain a direction estimate of the optical axis of said eye based on said images, wherein said processing electronics is configured to present said virtual image content to said user's eye that are rendered as if captured by a camera having an aperture disposed along the optical axis and spaced apart from the estimated position of the center of rotation of said eye by between 6.0 mm and 13.0 mm in a direction away from said retina.

Example 164: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 7.0 mm and 12.0 mm in a direction away from said retina.

Example 165: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 8.0 mm and 11.0 mm in a direction away from said retina.

Example 166: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 9.0 mm and 10.0 mm in a direction away from said retina.

Example 167: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by between 9.5 mm and 10.0 mm in a direction away from said retina.

Example 168: The display system of any of the Examples above, wherein said processing electronics is configured to present said virtual image content to said user's eye that are rendered as if captured by a camera having an aperture disposed along the optical axis and spaced apart from the estimated position of the center of rotation of said eye by approximately 9.7 mm.

Example 169: The display system of any of the Examples above, wherein said processing electronics includes electronics on said frame.

Example 170: The display system of any of the Examples above, wherein said processing electronics includes electronics on said frame and electronics disposed at a location remote from said frame.

Example 171: The display system of any of the Examples above, wherein said processing electronics includes electronics on said frame and electronics on a belt pack.

Example 172: The display system of any of the Examples above, wherein at least a portion of said display is transparent and disposed at a location in front of the user's eye when the user wears said head-mounted display such that said transparent portion transmits light from a portion of the environment in front of the user and said head-mounted display to the user's eye to provide a view of said portion of the environment in front of the user and said head-mounted display.

Example 173: The display system of any of the Examples above, further comprising one or more light sources disposed on said frame with respect to said user's eye to illuminate said user's eye, said one or more eye tracking cameras capturing images of said eye using said light from said one or more light sources.

Example 174: The display system of any of the Examples above, wherein said one or more light sources comprises at least two light sources disposed on said frame with respect to said user's eye to illuminate said user's eye.

Example 175: The display system of any of the Examples above, wherein said one or more light sources comprises at least three light sources disposed on said frame with respect to said user's eye to illuminate said user's eye.

Example 176: The display system of any of the Examples above, wherein said one or more light sources comprises infrared light emitters.

Example 177: A display system configured to project light to an eye of a user to display virtual image content in a vision field of said user, said eye having a cornea, an iris, a pupil, a lens, a retina, and an optical axis extending through said lens, pupil, and cornea, said display system comprising: a frame configured to be supported on a head of the user; a head-mounted display disposed on the frame, said display configured to project light into said user's eye to display virtual image content to the user's vision field at different amounts of at least one of divergence and collimation and thus the displayed virtual image content appears to originate from different depths at different periods of time; one or more eye tracking cameras configured to image the user's eye; and processing electronics in communication with the display and the one or more eye tracking cameras, wherein said processing electronics is configured to present said virtual image content to said user's eye that are rendered by a render camera having an aperture located at the pupil of the eye or between the pupil and the cornea of the eye.

Example 178: The display system of any of the Examples above, wherein the aperture of the render camera is located at a position that is between 1.0 mm and 2.0 mm in front of said pupil of said user's eye.

Example 179: The display system of any of the Examples above, wherein the aperture of the render camera is located a position that is about 1.0 mm in front of said pupil of said user's eye.

Example 180: The display system of any of the Examples above, wherein the aperture of the render camera is located at a position that is between 0.25 mm and 1.0 mm in front of said pupil of said user's eye.

Example 181: The display system of any of the Examples above, wherein the aperture of the render camera is located at a position that is between 0.5 mm and 1.0 mm in front of said pupil of said user's eye.

Example 182: The display system of any of the Examples above, wherein the aperture of the render camera is located at position that is between 0.25 mm and 0.5 mm in front of said pupil of said user's eye.

Example 183: The display system of any of the Examples above, wherein the aperture of the render camera is located at the pupil of the eye.

Example 184: The display system of any of the Examples above, wherein the aperture of the render camera is not located at the pupil of the eye.

Example 185: Any of the claims above, wherein the camera comprises a pinhole camera.

Example 186: Any of the claims above, wherein the aperture comprises a pinhole of a pinhole camera.

Any of the above Examples or Additional Examples can be combined. Additionally, any of the above Examples or Additional Examples can be integrated with a head mounted display. In addition, any of the above Examples or Additional Examples can be implemented with a single depth plane and/or with one or more variable depth planes (e.g., one or more elements with variable focusing power that provide accommodation cues that vary over time).

Furthermore, apparatus and methods for determining a variety of values, parameters, etc., such as, but not limited to, anatomical, optical, and geometric features, locations, and orientations, etc., are disclosed herein. Examples of such parameters include, for example, the center of rotation of the eye, the center of curvature of the cornea, the center of the pupil, the boundary of the pupil, the center of the iris, the boundary of the iris, the boundary of the limbus, the optical axis of the eye, the visual axis of the eye, the center of perspective, but are not limited to these. Determinations of such values, parameters, etc., as recited herein include estimations thereof and need not necessarily coincide precisely with the actual values. For example, determinations of the center of rotation of the eye, the center of curvature of the cornea, the center or boundary of the pupil or iris, the boundary of the limbus, the optical axis of the eye, the visual axis of the eye, the center of perspective, etc., may be estimations, approximations, or values close to, but not the same as, the actual (e.g., anatomical, optical, or geometric) values or parameters. In some cases, for example, root mean square estimation techniques are used to obtain estimates of such values. As an example, certain techniques described herein relate to identifying a location or point at which rays or vectors intersect. Such rays or vectors, however, may not intersect. In this example, the location or point may be estimated. For example, the location or point may be determined based on root mean square, or other, estimation techniques (e.g., the location or point may be estimated to be close to or the closest to the rays or vectors). Other processes may also be used to estimate, approximate or otherwise provide a value that may not coincide with the actual value. Accordingly, the term determining and estimating, or determined and estimated, are used interchangeably herein. Reference to such determined values may therefore include estimates, approximations, or values close to the actual value. Accordingly, reference to determining a parameter or value above, or elsewhere herein should not be limited precisely to the actual value but may include estimations, approximations or values close thereto.

What is claimed is:

1. A display system configured to project light to an eye of a user to display virtual image content in a vision field of said user, said eye having a cornea, an iris, a pupil, a lens, a retina, and an optical axis extending through said lens, pupil, and cornea, said display system comprising:
    a frame configured to be supported on a head of the user;
    a head-mounted display disposed on the frame, said display configured to project light into said user's eye to display virtual image content to the user's vision field, at least a portion of said display being transparent and disposed at a location in front of the user's eye when the user wears the frame such that said transparent portion transmits light from a portion of the environment in front of the user and said head-mounted display to the user's eye to provide a view of said portion of the environment in front of the user and said head-mounted display;
    an inward-facing imaging system configured to image the user's eye; and
    processing electronics in communication with the inward-facing imaging system, the processing electronics configured to obtain an estimate of a three-dimensional (3D) position of a center of rotation (CoR) of said eye based at least partly on a plurality of said eye images obtained with said inward-facing imaging system, wherein obtaining the estimate of the 3D position of the CoR includes:

determining a plurality of potential 3D positions of the CoR, wherein each potential 3D position of the CoR is determined as a particular distance from a center of an estimated corneal sphere that includes the cornea of the eye;

calculating a variation for each of the potential 3D positions of the CoR, wherein the variation is calculated based on an analysis of multiple images of the user's eye captured over a period of time; and determining the estimate of the 3D position of the CoR as the potential 3D position that exhibits the lowest variation among the plurality of potential 3D positions.

2. The display system of claim 1, wherein the plurality of potential 3D positions of the CoR includes an initial value of the distance from the center of an estimated corneal sphere.

3. The display system of claim 2, wherein the initial value is an average of experimentally measured distance values.

4. The display system of claim 2, wherein the initial value is 4.7 mm.

5. The display system of claim 1, wherein the processing electronics are further configured to determine an estimate of the corneal sphere based on analyzing the plurality of said eye images.

6. The display system of claim 1, wherein the CoR is the estimated position about which the eye rotates relative to at least two axes.

7. The display system of claim 1, wherein obtaining the estimate of the 3D position of the CoR is performed during an initial user calibration session of the display system.

8. A method implemented by a display system configured to project light to an eye of a user to display virtual image content in a vision field of said user, said eye having a cornea, an iris, a pupil, a lens, a retina, and an optical axis extending through said lens, pupil, and cornea, said method comprising:

displaying, via the display system, virtual image content to the user's vision field;

with an inward-facing imaging system configured to image said eye of the user to track movements of said eye, obtaining an estimate of a center of rotation of said eye based on a plurality of said eye images obtained with said inward-facing imaging system; and determining an estimate of a three-dimensional (3D) position of a center of rotation (CoR) of said eye based at least partly on a plurality of said eye images obtained with said inward-facing imaging system, wherein obtaining the estimate of the 3D position of the CoR includes:

determining a plurality of potential 3D positions of the CoR, wherein each potential 3D position of the CoR is determined as a particular distance from a center of an estimated corneal sphere that includes the cornea of the eye;

calculating a variation for each of the potential 3D positions of the CoR, wherein the variation is calculated based on an analysis of multiple images of the user's eye captured over a period of time; and determining the estimate of the 3D position of the CoR as the potential 3D position that exhibits the lowest variation among the plurality of potential 3D positions.

9. The method of claim 8, wherein the plurality of potential 3D positions of the CoR includes an initial value of the distance from the center of an estimated corneal sphere.

10. The method of claim 9, wherein the initial value is an average of experimentally measured distance values.

11. The method of claim 9, wherein the initial value is 4.7 mm.

12. The method of claim 8, further comprising determining an estimate of the corneal sphere based on analyzing the plurality of said eye images.

13. The method of claim 8, wherein the CoR is the estimated position about which the eye rotates relative to at least two axes.

14. The method of claim 8, wherein obtaining the estimate of the 3D position of the CoR is performed during an initial user calibration session of the display system.

15. Non-transitory computer storage media storing instructions for execution by a display system of one or more processors, wherein the display system is configured to project light to an eye of a user to display virtual image content in a vision field of said user, said eye having a cornea, an iris, a pupil, a lens, a retina, and an optical axis extending through said lens, pupil, and cornea, and wherein the instructions cause the display system to:

display virtual image content to the user's vision field;

receive a plurality of eye images of said eye of the user, the plurality of eye images captured by an inward-facing imaging system configured to image said eye of the user to track movements of said eye; and obtain an estimate of a three-dimensional (3D) position of a center of rotation (CoR) of said eye based on the plurality of said eye images obtained with said inward-facing imaging system, wherein obtaining the estimate of the 3D position of the CoR includes:

determining a plurality of potential 3D positions of the CoR, wherein each potential 3D position of the CoR is determined as a particular distance from a center of an estimated corneal sphere that includes the cornea of the eye;

calculating a variation for each of the potential 3D positions of the CoR, wherein the variation is calculated based on an analysis of multiple images of the user's eye captured over a period of time; and determining the estimate of the 3D position of the CoR as the potential 3D position that exhibits the lowest variation among the plurality of potential 3D positions.

16. The computer storage media of claim 15, wherein the plurality of potential 3D positions of the CoR includes an initial value of the distance from the center of an estimated corneal sphere.

17. The computer storage media of claim 16, wherein the initial value is an average of experimentally measured distance values.

18. The computer storage media of claim 16, wherein the initial value is 4.7 mm.

19. The computer storage media of claim 15, wherein the instructions further cause the display system to determine an estimate of the corneal sphere based on analyzing the plurality of said eye images.

20. The computer storage media of claim 15, wherein the CoR is the estimated position about which the eye rotates relative to at least two axes.

* * * * *